United States Patent
Bettoun et al.

(10) Patent No.: US 11,891,420 B2
(45) Date of Patent: Feb. 6, 2024

(54) MOLECULES FOR ORGANELLE-SPECIFIC PROTEIN DELIVERY

(71) Applicant: Larimar Therapeutics, Inc., Bala Cynwyd, PA (US)

(72) Inventors: Joan David Bettoun, Elkins Park, PA (US); Rebecca Wissner, Wayne, PA (US)

(73) Assignee: Larimar Therapeutics, Inc., Bala Cynwyd, PA (US)

( * ) Notice: Subject to any disclaimer, the term of this patent is extended or adjusted under 35 U.S.C. 154(b) by 152 days.

(21) Appl. No.: 17/214,757

(22) Filed: Mar. 26, 2021

(65) Prior Publication Data

US 2021/0355177 A1    Nov. 18, 2021

Related U.S. Application Data

(60) Provisional application No. 63/000,138, filed on Mar. 26, 2020.

(51) Int. Cl.
| | |
|---|---|
| *C07K 14/47* | (2006.01) |
| *A61K 47/64* | (2017.01) |
| *C07K 14/005* | (2006.01) |
| *C12N 9/10* | (2006.01) |
| *A61K 38/00* | (2006.01) |

(52) U.S. Cl.
CPC .............. *C07K 14/47* (2013.01); *A61K 47/64* (2017.08); *C07K 14/005* (2013.01); *C12N 9/104* (2013.01); *C12Y 203/02* (2013.01); *A61K 38/00* (2013.01); *C07K 2319/02* (2013.01); *C07K 2319/07* (2013.01); *C07K 2319/50* (2013.01); *C12N 2740/16322* (2013.01)

(58) Field of Classification Search
None
See application file for complete search history.

(56) References Cited

U.S. PATENT DOCUMENTS 11,459,363 B2 * 10/2022 Payne ................ A61K 9/0019
2012/0196328 A1    8/2012 Liu et al.

FOREIGN PATENT DOCUMENTS

WO    2012/050402 A2    4/2012
WO    2012/174452 A1    12/2012

OTHER PUBLICATIONS

Chauhan et al., The taming of the cell penetrating domain of the HIV Tat: myths and realities. J Control Release. Feb. 12, 2007;117(2):148-62.
Stauber et al., Intracellular trafficking and interactions of the HIV-1 Tat protein. Virology. Dec. 5, 1998;252(1):126-36.
Vitte et al., Intracellular delivery of peptides via association with ubiquitin or SUMO-1 coupled to protein transduction domains. BMC Biotechnol. Feb. 29, 2008;8:24, 11 pages.
Vyas et al., A TAT-frataxin fusion protein increases lifespan and cardiac function in a conditional Friedreich's ataxia mouse model. Hum Mol Genet. Mar. 15, 2012;21(6):1230-47.
International Search Report and Written Opinion for Application No. PCT/US2021/024534, dated Oct. 6, 2021, 15 pages.

* cited by examiner

*Primary Examiner* — Manjunath N Rao
*Assistant Examiner* — Jae W Lee
(74) *Attorney, Agent, or Firm* — McCarter & English, LLP; Jill Mello; Yelena Margolin

(57) ABSTRACT

The present disclosure provides a fusion protein useful for treating a non-nuclear organelle associated disorder, such as a genetic disorder, e.g., Friedrich's Ataxia. The fusion protein may comprise a protein of interest to be delivered to a non-nuclear organelle; an organelle targeting sequence (OTS); a cell penetrating peptide (CPP); and a target enhancing sequence (TES); wherein the CPP is capable of interference with delivery of the protein of interest to the non-nuclear organelle; and wherein the TES prevents the interference by the CPP. The fusion protein may also comprise a protein of interest to be delivered to a non-nuclear organelle; a CPP and a TES. The present disclosure also provides methods for treating a non-nuclear organelle associated disorder by administering the fusion protein to a subject in need thereof.

26 Claims, 25 Drawing Sheets
Specification includes a Sequence Listing.

A.

B.

Frataxin and Mitochondrial Protein TOMM20 Immunolocalization Further to Transduction with TAT-GG-hFXN in Rat L6 Myoblasts Frataxin and Mitochondrial Protein TOMM20 Immunolocalization Further to Transfection with hFXN or TAT-GG-hFXN in Rat L6 Myoblasts

General Design of the Novel Variant hFXN Fusion Proteins

Frataxin and Mitochondrial Protein TOMM20 Immunolocalization in Rat L6 Myoblasts Further to Transfection with hFXN, or TAT-GG-hFXN, or a Novel hFXN Fusion Protein Panel a Panel b Panel c Panel d Panel e Panel f Panel g Panel h Panel i Detection of hFXN in Cells Transfected with Novel hFXN Variants MW: ~25KDa MW: ~26KDa MW: ~34KDa MW: ~26KDa

D

Lane 1: hFXN (no TAT fusion)
Lane 2: TAT-GG-hFXN
Lane 3: TAT-GG-SUMO-hFXN
Lane 4: TAT-GG-Ubiquitin-hFXN
Lane 5: TAT-GG-EPLFAERK-hFXN
Lane 6: TAT-hFXN-NES

A

B

Scr-S cells treated with vehicle

LRPPRC KD cells treated with vehicle

LRPPRC KD cells treated with 10 µM TAT-GG-hFXN

LRPPRC KD cells treated with 1 µM TAT-GG-EPLFAERK-hFXN

LRPPRC KD cells treated with 1 µM TAT-GG-Ubiquitin-hFXN

D

MW: ~65 KDa

MW: ~54KDa

MW: ~62KDa

MW: ~55KDa

10 µM CCCP, NO PARKIN

NO CCCP, NO PARKIN 0.5 µM TAT-EPLFAERK-PARKIN, 10 µM CCCP 0.5 µM TAT-EPLFAERK-PARKIN, NO CCCP

MOLECULES FOR ORGANELLE-SPECIFIC PROTEIN DELIVERY

RELATED APPLICATIONS

This application claims priority to U.S. Provisional Patent Application No. 63/000,138, filed on Mar. 26, 2020, the entire contents of which are hereby incorporated herein by reference.

SEQUENCE LISTING

The instant application contains a Sequence Listing which has been submitted electronically in ASCII format and is hereby incorporated by reference in its entirety. Said ASCII copy, created on Jun. 3, 2021, is named SL_130197-00402.txt and is 155,823 bytes in size.

BACKGROUND

Cationic cell penetrating peptides (CPPs) have emerged as a promising means of delivering therapeutic proteins into cells. However, one potential drawback of appending a CPP to a therapeutic protein is that the CPP may interfere with the therapeutic protein's proper subcellular localization or function. For example, certain cell penetrating peptides, such as HIV-TAT, have been shown to direct delivery of therapeutic proteins into the nucleus, which may not be the desired subcellular destination for a therapeutic protein of interest.

Delivery of therapeutic proteins into the mitochondria of mammalian cells has been attempted, for example, with the TAT-FXN fusion protein. TAT-FXN fusion protein contains TAT and Frataxin (FXN), which is a mitochondrial protein associated with the inherited condition Friedreich's Ataxia (FRDA). FRDA patients suffer from progressive damage to the nervous system that results in muscle weakness and eventual loss of motor control. FRDA is caused by transcriptional repression of the FRDA gene, resulting in the lack or minute amounts of hFXN protein in FRDA patients.

The improvement of effective technology for delivering therapeutic proteins into cells, and while maintaining the therapeutic protein's proper subcellular localization or function, including in the context of organelle-specific therapeutic protein delivery, continues to be an area of great demand in medicine.

SUMMARY

The present disclosure provides fusion proteins that are capable of being efficiently delivered to cells, e.g., in greater levels than previously achieved. The present disclosure further provides fusion proteins that are capable of efficiently delivering a therapeutic protein of interest to cells and achieving and maintaining the proper subcellular localization and/or function of the therapeutic protein of interest. For example, the present disclosure provides fusion proteins that are capable of being efficiently delivered to non-nuclear organelles. An exemplary fusion protein provided by the present disclosure comprises, in addition to a protein of interest to be delivered to a cell, a cell penetrating peptide (CPP); and/or a target enhancing sequence (TES). In the fusion protein of the present disclosure, the CPP is capable of interference with delivery of the protein of interest to the protein's proper subcellular localization and/or with its function, and the TES prevents this interference by CPP. Another exemplary fusion protein provided by the present disclosure comprises, in addition to a protein of interest to be delivered to a non-nuclear organelle, an organelle targeting sequence (OTS); a cell penetrating peptide (CPP); and/or a target enhancing sequence (TES). In said fusion protein of the present disclosure, the CPP is capable of interference with delivery of the protein of interest to the non-nuclear organelle, and the TES prevents this interference by CPP.

The present disclosure also is based, at least on part, on the surprising discovery that including certain amino acid sequences (i.e., TES) in a fusion protein that also comprises a protein of interest and a CPP, facilitated effective delivery of the protein of interest to the cell, e.g., resulted in increased levels of the protein of interest in cells treated with the fusion protein, and allowed for proper subcellular localization and/or function of the protein of interest. In particular, the present inventors have discovered that cells treated with fusion proteins comprising a protein of interest, CPP and TES contained significantly higher amounts of the protein of interest than cells treated with a fusion protein comprising a protein of interest and CPP, but lacking TES. Thus, the present inventors have surprisingly discovered that introducing TES into a fusion protein comprising CPP and a protein of interest can significantly increase the amount of protein of interest in a cell that has been contacted with the fusion protein. The present inventors also surprisingly discovered that fusion proteins comprising a protein of interest, CPP and TES were correctly processed by the cellular machinery, achieved proper cellular localization, e.g., were targeted to a non-nuclear organelle, and possessed the desired activity of the protein of interest when delivered to cells.

In some exemplary fusion proteins provided by the present disclosure, the TES comprises an amino acid sequence cleavable by an endogenous intracellular protease. In some embodiments, this TES is located immediately adjacent to the CPP, which, in turn, is located at the N-terminal end of the fusion protein. Upon entry of the fusion protein into the cell cytoplasm, the TES is cleaved by an intracellular nuclease. Without wishing to be bound by a specific theory, it is believed that cleavage of the TES facilitates removal of the CPP from the fusion protein and prevents the CPP from facilitating diffusion of the protein of interest across the plasma membrane and out of the cell. This allows the protein of interest to accumulate in the cell. The present disclosure is further based, at least on part, on the surprising discovery that including certain amino acid sequences (i.e., TES) in a fusion protein that also comprises a protein of interest, a CPP and an OTS, facilitated effective delivery of the protein of interest to a non-nuclear organelle, such as mitochondria. In particular, the present inventors have discovered that fusion proteins comprising a protein of interest, CPP and an organelle targeting sequence (OTS), e.g. a mitochondrial targeting sequence (MTS), but not TES, localized to the cell nucleus instead of the mitochondria upon entry into the cell, due to the interference of the CPP with mitochondrial delivery of the protein of interest. The present inventors further discovered that including certain amino acid sequences, such as TES, in fusion proteins also comprising a protein of interest, a CPP and an OTS, e.g., an MTS, facilitated delivery of the protein of interest to the mitochondria upon entry of the fusion protein into the cell.

In exemplary fusion proteins provided by the present disclosure, the TES comprises an amino acid sequence cleavable by an endogenous intracellular protease. In some embodiments, this TES is located immediately adjacent to the CPP, which, in turn, is located at the N-terminal end of the fusion protein. Upon entry of the fusion protein into the cell cytoplasm, the TES is cleaved by an intracellular nuclease. Cleavage of the TES facilitates removal of the CPP from the fusion protein and prevents interference of the CPP with delivery of the fusion protein to the mitochondria. In other exemplary fusion proteins of the present disclosure, the TES comprises a nuclear export signal peptide (NES), which prevents CPP-facilitated delivery of the fusion protein to the nucleus and, instead, facilitates delivery of the fusion protein to non-nuclear organelles, such as mitochondria.

In other exemplary fusion proteins of the present disclosure, the TES comprises a nuclear export signal peptide (NES), which prevents accumulation of the protein of interest in the nucleus.

In some aspects, the present disclosure provides a fusion protein, comprising: a protein of interest to be delivered to a cell; a cell penetrating peptide (CPP); and a target enhancing sequence (TES).

In some embodiments, the CPP is located at the N-terminus of the fusion protein and wherein the TES is fused at the C-terminus of the CPP. In some embodiments, the fusion proteins comprises, or consists of, starting at the N-terminus: CPP; TES; and a protein of interest.

In some embodiments, the CPP is located at the C-terminus of the fusion protein and wherein the TES is fused at the N-terminus of the CPP.

In some embodiments, the fusion protein comprises, or consistes of, starting at the C-terminus: a protein of interest; TES; and CPP.

In some embodiments, the protein of interest lacks an OTS.

In other embodiments, the fusion protein further comprises an organelle targeting sequence (OTS) exogenous to the protein of interest.

In some embodiments, the protein of interest comprises an OTS.

In some embodiments, the OTS is heterologous to the protein of interest. In some embodiments, the OTS is endogenous to the protein of interest.

In some embodiments, the protein of interest is selected from the group consisting of Frataxin (FXN), Tafazin, Pyruvate Dehydrogenase (PDH), SLIRP, LRPPC, PARK2 protein, PARK6 protein, PARK7 protein, Phospholipase A2, Group VI and a variant or derivative thereof. In some embodiments, the protein of interest comprises Frataxin (FXN) or PARK2 protein (PARKIN), or a variant or derivative thereof.

In some embodiments, the CPP comprises a peptide selected from the group of CPPs listed in the Database of Cell-Penetrating Peptides CPPsite 2.0. In some embodiments, the CPP comprises a peptide selected from the group consisting of HIV-TAT, galanin, mastoparan, transportan, penetratin, polyarginine, VP22, and a variant or derivative thereof. In some embodiments, the CPP comprises HIV-TAT or a variant or derivative thereof.

In some embodiments, the TES is a nuclear export signal peptide. In some embodiments, the nuclear export signal peptide comprises a sequence having at least 85% sequence identity to any one of SEQ ID NOs. 36-43. In some embodiments, the nuclear export signal peptide comprises a peptide selected from the group consisting of NES1, NES2, NES3, NES4, NES5, NES6, NES7, NES8, and a variant or derivative thereof. In some embodiments, the nuclear export signal peptide comprises a peptide selected from the group consisting of NES1 and NES2, or a variant or derivative thereof.

In some embodiments, the TES is a protease sensitive peptide. In some embodiments, the protease sensitive peptide comprises a ubiquitin-like modifier. In some embodiments, the protease sensitive peptide comprises a sequence having at least 85% sequence identity to any one of SEQ ID NOs. 18-31.

In some embodiments, the protease sensitive peptide comprises a peptide selected from the group consisting of ubiquitin, a caspase cleavage domain, a calpain cleavage domain, SUMO1, SUMO2, SUMO3, SUMO4, ISG15, Atg8, Atg12, NEDD8, and a variant or derivative thereof.

In some embodiments, the fusion protein comprises an amino acid sequence having at least 85%, 90%, or 95% sequence identity to any of SEQ ID NOs. 55-61, 69-71, and 81.

In some aspects, the present disclosure provides a fusion protein, comprising: a protein of interest to be delivered to a non-nuclear organelle; an organelle targeting sequence (OTS); a cell penetrating peptide (CPP); and a target enhancing sequence (TES); wherein the CPP is capable of interference with delivery of the protein of interest to the non-nuclear organelle; and wherein the TES prevents said interference by the CPP.

In some embodiments, the CPP is located at the N-terminus of the fusion protein and wherein the TES is fused at the C-terminus of the CPP.

In some embodiments, the fusion protein comprises, or consists of, starting at the N-terminus: CPP; TES; OTS; and a protein of interest.

In some embodiments, the CPP is located at the C-terminus of the fusion protein and wherein the TES is fused at the N-terminus of the CPP. In some embodiments, the non-nuclear organelle is selected from the group consisting of mitochondria, cytosol, lysosome, endoplasmic reticulum (ER), peroxisome and Golgi apparatus. In some embodiments, the protein of interest in its naturally occurring form is localized to mitochondria, cytosol, lysosome, endoplasmic reticulum (ER), peroxisome or Golgi apparatus.

In some embodiments, the protein of interest is selected from the group consisting of Frataxin (FXN), Tafazin, Pyruvate Dehydrogenase (PDH), SLIRP, LRPPC, PARK2 protein, PARK6 protein, PARK7 protein, Phospholipase A2, Group VI and a variant or derivative thereof. In some embodiments, the protein of interest is Frataxin (FXN) or a variant or derivative thereof. In some embodiments, the protein of interest is Pyruvate Dehydrogenase (PDH) or a variant or derivative thereof.

In some embodiments, the CPP comprises a peptide selected from the group of CPPs listed in the Database of Cell-Penetrating Peptides CPPsite 2.0. In some embodiments, the CPP comprises a peptide selected from the group consisting of HIV-TAT, galanin, mastoparan, transportan, penetratin, polyarginine, VP22, and a variant or derivative thereof. In some embodiments, the CPP comprises HIV-TAT or a variant or derivative thereof.

In some embodiments, the TES is a nuclear export signal peptide. In some embodiments, the nuclear export signal peptide comprises a sequence having at least 85% sequence identity to any one of SEQ ID NOs. 36-43. In some embodiments, the nuclear export signal peptide comprises a peptide selected from the group consisting of NES1, NES2, NES3, NES4, NES5, NES6, NES7, NES8, and a variant or derivative thereof. In some embodiments, the nuclear export signal peptide comprises a peptide selected from the group consisting of NES1, NES2 and a variant or derivative thereof.

In some embodiments, the TES is a protease sensitive peptide. In some embodiments, the protease sensitive peptide comprises a ubiquitin-like modifier. In some embodiments, the protease sensitive peptide comprises a sequence having at least 85% sequence identity to any one of SEQ ID NOs. 18-31. In some embodiments, the protease sensitive peptide comprises a peptide selected from the group consisting of ubiquitin, a caspase cleavage domain, a calpain cleavage domain, SUMO1, SUMO2, SUMO3, SUMO4, ISG15, Atg8, Atg12, NEDD8, and a variant or derivative thereof.

In some embodiments, the fusion protein of the present disclosure further comprises a secretion signal (SS).

In some embodimehts, the fusion protein of the present disclosure further comprises an extracellular proteolytic site (EPS).

In some embodiments, the fusion protein delivers the protein of interest to a non-nuclear organelle. In some embodiments, the fusion protein delivers the protein of interest to mitochondria.

In some embodiments, the fusion protein comprises an amino acid sequence having at least 85%, 90% or 95% sequence identity to any of SEQ ID NOs. 55-61, 69-71 and 81.

In some aspects, the present disclosure also provides nucleic acids encoding the fusion proteins of the present disclosure.

In some aspects, the present disclosure also provides an expression vector for introducing a fusion protein into a cell comprising the nucleic acid of the disclosure. In some embodiments, the expression vector is selected from the group consisting of a retroviral vector, a DNA vector, a plasmid, an RNA vector, an adenoviral vector, an adenovirus associated vector, a lentiviral vector, a phagemid, a baculovirus and a combination thereof.

In some aspects, the present disclosure provides a conjugate for intracellular delivery of proteins to non-nuclear organelles comprising the fusion protein of the disclosure and a moiety linked to said fusion protein, wherein said moiety is selected from a group consisting of a radioactive label, a fluorescent label, a small molecule, and a polymeric molecule. In some embodiments, the polymeric molecule is polyethylene glycol (PEG).

In some aspects, the present disclosure provides a cell comprising the fusion protein of the disclosure, the nucleic acid the disclosure, the expression vector of the disclosure, the conjugate of the disclosure, or a combination thereof.

In some embodiments, the cell is a stem cell or an iPS cell. In some embodiments, the cell is selected from the group consisting of a muscle progenitor cell, a neuron progenitor cell, a bone marrow stem cell, a bacterial cell line, or an yeast cell line.

In some aspects, the present disclosure also provides a pharmaceutical composition comprising the fusion protein of the disclosure, a conjugate of the disclosure, or a combination thereof and a pharmaceutically acceptable diluent, carrier, additive or excipient.

In some aspects, the present disclosure provides a method of delivery of a protein of interest to a cell, said method comprising contacting the cell with a fusion protein of the disclosure, the nucleic acid of the disclosure, the vector of the disclosure or the conjugate of the disclosure.

In some aspects, the present disclosure also provides a method of intracellular delivery of a protein of interest to a non-nuclear organelle in a cell, the method comprising contacting said cell with a fusion protein of the disclosure, the nucleic acid of the disclosure, the vector of any one of the disclosure or the conjugate of the disclosure. In some embodiments, the non-nuclear organelle is mitochondria.

In some aspects, the present disclosure also provides a therapeutic compound for treating a non-nuclear organelle associated disorder, the compound comprising the fusion protein the disclosure, the nucleic acid of the disclosure, the vector of the disclosure or the conjugate of the disclosure. In some embodiments, the non-nuclear organelle associated disorder is selected from the group consisting of Friedreich's ataxia (FDRA), Barth Syndrome, Parkinson's Disease, Wilson's Disease, Leigh Syndrome, Fibrosis, and PLA2G6-associated neurodegeneration (PLAN). In some embodiments, the non-nuclear organelle associated disorder is FDRA. In some embodiments, the non-nuclear organelle associated disorder is Parkinson's Disease.

In some aspects, the present disclosure also provides a method for treating a non-nuclear organelle associated disorder, the method comprising administering to a subject in need thereof the fusion protein of the disclosure, the nucleic acid of the disclosure, the vector of the disclosure, the conjugate of the disclosure or the pharmaceutical composition of the disclosure, such that the non-nuclear organelle associated disorder is treated.

In some embodiments, the non-nuclear organelle associated disorder is selected from the group consisting of Friedreich's ataxia (FDRA), Barth Syndrome, Parkinson's Disease, Wilson's Disease, Leigh Syndrome and Fibrosis. In some embodiments, the non-nuclear organelle associated disorder is FDRA. In some embodiments, the non-nuclear organelle associated disorder is Parkinson's Disease.

In some embodiments, the subject is a human.

In some aspects, the present disclosure also provides a method for increasing an amount of a protein of interest delivered to a cell, the method comprising: modifying a sequence of a fusion protein comprising the protein of interest and a cell penetrating peptide (CPP) by introducing into the fusion protein a target enhancing sequence (TES), thereby producing a modified fusion protein; and contacting a cell with the modified fusion protein, thereby increasing the amount of the protein of interest delivered to the cell relative to the amount of the protein of interest delivered to the cell by the fusion protein lacking the TES.

In some embodiments, the modified fusion protein, the CPP is located at the N-terminus of the fusion protein and wherein the TES is fused at the C-terminus of the CPP.

In some embodiments, the modified fusion protein comprises, starting at the N-terminus: CPP; TES; and a protein of interest.

In some embodiments, the modified fusion protein comprises, starting at the N-terminus: CPP; TES; OTS; and a protein of interest.

In some embodiments, the modified fusion protein the CPP is located at the C-terminus of the fusion protein and wherein the TES is fused at the N-terminus of the CPP. In some embodiments, the amount of the protein of interest delivered to an organelle targeted by the OTS is increased relative to the amount of the protein of interest delivered to the organelle by the fusion protein lacking the TES.

In some embodiments, the protein of interest is selected from the group consisting of
Frataxin (FXN), Tafazin, Pyruvate Dehydrogenase (PDH), SLIRP, LRPPC, PARK2 protein, PARK6 protein, PARK7 protein, and Phospholipase A2, Group VI, or a variant or derivative thereof. In some embodiments, the protein of interest is Frataxin (FXN) or a variant or derivative thereof. In some embodiments, the protein of interest is PARK2 protein or a variant or derivative thereof.

In some embodiments, the CPP comprises a peptide selected from the group of CPPs listed in the Database of Cell-Penetrating Peptides CPPsite 2.0. In some embodiments, the CPP comprises a peptide selected from the group consisting of HIV-TAT, galanin, mastoparan, transportan, penetratin, polyarginine, VP22, and a variant or derivative thereof. In some embodiments, the CPP comprises HIV-TAT or a variant or derivative thereof.

In some embodiments, the TES is a nuclear export signal peptide. In some embodiments, the nuclear export signal peptide comprises a sequence having at least 85% sequence identity to any one of SEQ ID NOs. 36-43. In some embodiments, the nuclear export signal peptide comprises a peptide selected from the group consisting of NES1, NES2, NES3, NES4, NES5, NES6, NES7, NES8, and a variant or derivative thereof. In some embodiments, the nuclear export signal peptide comprises a peptide selected from the group consisting of NES1, NES2 and a variant or derivative thereof.

In some embodiments, the TES is a protease sensitive peptide. In some embodiments, the protease sensitive peptide comprises a ubiquitin-like modifier. In some embodiments, the protease sensitive peptide comprises a sequence having at least 85% sequence identity to any one of SEQ ID NOs. 18-31. In some embodiments, the protease sensitive peptide comprises a peptide selected from the group consisting of ubiquitin, a caspase cleavage domain, a calpain cleavage domain, SUMO1, SUMO2, SUMO3, SUMO4, ISG15, Atg8, Atg12, NEDD8, and a variant or derivative thereof.

In some embodiments, the modified fusion protein comprises an amino acid sequence having at least 85% sequence identity to any of SEQ ID NOs. 55-61, 69-71 and 81.

In one aspect, the present disclosure provides a fusion protein, comprising: a protein of interest to be delivered to a non-nuclear organelle; an organelle targeting sequence (OTS); a cell penetrating peptide (CPP); and a target enhancing sequence (TES); wherein the CPP is capable of interference with delivery of the protein of interest to the non-nuclear organelle; and wherein the TES prevents said interference by the CPP.

In some embodiments, the CPP is located at the N-terminus of the fusion protein and the TES is fused at the C-terminus of the CPP. In some embodiments, the present disclosure provides a fusion protein that comprises, starting at the N-terminus: CPP; TES; OTS; and a protein of interest.

In some embodiments, the CPP is located at the C-terminus of the fusion protein and the TES is fused at the N-terminus of the CPP.

In some embodiments, the non-nuclear organelle is selected from the group consisting of mitochondria, cytosol, lysosome, endoplasmic reticulum (ER), peroxisome and Golgi apparatus.

In some embodiments, the protein of interest in its naturally occurring form is localized to mitochondria, cytosol, lysosome, endoplasmic reticulum (ER), peroxisome or Golgi apparatus.

In some embodiments, the protein of interest is selected from the group consisting of Frataxin (FXN), Tafazin, Pyruvate Dehydrogenase (PDH), LRPPC, PARK2 protein, PARK6 protein, PARK7 protein, an A2 phospholipase Group VI, a transcription factor, and a variant or derivative thereof. In one embodiment, the protein of interest is Frataxin (FXN) or a variant or derivative thereof. In one embodiment, the protein of interest is pyruvate dehydrogenase (PDH) or a variant or derivative thereof.

In some embodiments, the CPP comprises a peptide selected from the group of CPPs listed in the Database of Cell-Penetrating Peptides CPPsite 2.0. In further embodiments, the CPP comprises a peptide selected from the group consisting of HIV-TAT, galanin, mastoparan, transportan, penetratin, polyarginine, VP22, and a variant or derivative thereof. In some embodiments, the CPP comprises HIV-TAT or a variant or derivative thereof.

In some embodiments, the TES is a nuclear export signal peptide. In further embodiments, the nuclear export signal peptide comprises a sequence having at least 85% sequence identity to any one of SEQ ID NOs. 36-43. In some embodiments, the nuclear export signal peptide comprises a peptide selected from the group consisting of NES1, NES2, NES3, NES4, NES5, NES6, NES7, NES8, and a variant or derivative thereof. In some embodiments, the nuclear export signal peptide comprises a peptide selected from the group consisting of NES1, NES2 and a variant or derivative thereof.

In some embodiments, the TES is a protease sensitive peptide. In some embodiments, the protease sensitive peptide comprises a ubiquitin-like modifier. In some embodiments, the ubiquitin-like modifier comprises a sequence having at least 85% sequence identity to any one of SEQ ID NOs. 18-31.

In some embodiments, the protease sensitive peptide comprises a peptide selected from the group consisting of ubiquitin, a caspase cleavage domain, a calpain cleavage domain, SUMO1, SUMO2, SUMO3, SUMO4, ISG15, Atg8, Atg12, NEDD8, and a variant or derivative thereof.

In some embodiments, the fusion protein provided by the present disclosure comprises a secretion signal (SS). In some embodiments, the fusion protein comprises an extracellular proteolytic site (EPS).

In some embodiments, the fusion protein delivers the protein of interest to a non-nuclear organelle. In a specific embodiment, the fusion protein delivers the protein of interest to mitochondria.

In some embodiments, the fusion protein comprises a sequence having at least 85% sequence identity to any of SEQ ID NOs. 55-61.

In another aspect, the present disclosure provides a nucleic acid encoding the fusion protein of the disclosure.

In a related aspect, the present disclosure provides an expression vector comprising a nucleic acid of the disclosure for introducing a fusion protein into a cell.

In some embodiments, the expression vector is selected from the group consisting of a retroviral vector, a DNA vector, a plasmid, an RNA vector, an adenoviral vector, an adenovirus associated vector, a lentiviral vector, a phagemid, a baculovirus and a combination thereof.

In another aspect, the present disclosure provides a protein conjugate for intracellular delivery of proteins to non-nuclear organelles that comprises a fusion protein of the disclosure and a moiety linked to the fusion protein, wherein the moiety is selected from the group consisting of a radioactive label, a fluorescent label, a small molecule, and a polymeric molecule. In one embodiment, the polymeric molecule is polyethylene glycol (PEG).

In another aspect, the present disclosure provides a cell comprising a fusion protein, a nucleic acid, an expression vector or a conjugate of the disclosure, or a combination thereof. The cell may be a transformed cell, e.g., a cell which has been transformed with a fusion protein, a nucleic acid, an expression vector or a conjugate of the disclosure, or a combination thereof. In some aspects, the cell is stem cell or an iPS cell. In some aspects, a cell may be selected from the group consisting of a muscle progenitor cell, a neuron progenitor cell, a bone marrow stem cell, a bacterial cell, or a yeast cell.

In another aspect, the present disclosure provides a pharmaceutical composition comprising a fusion protein or a protein conjugate of the disclosure, or a combination thereof, and a pharmaceutically acceptable diluent, carrier, additive or excipient.

In another aspect, the present disclosure provides a method of intracellular delivery of a protein of interest to a non-nuclear organelle in a cell, comprising contacting the cell with a fusion protein, a nucleic acid, a vector or a protein conjugate of the disclosure. In one aspect, the non-nuclear organelle is mitochondria.

In another aspect, the present disclosure provides a therapeutic compound for treating a non-nuclear organelle associated disorder, which comprises a fusion protein, a nucleic acid, a vector or a protein conjugate of the disclosure. In some, the non-nuclear organelle associated disorder is selected from the group consisting of Friedreich's ataxia (FDRA), Barth Syndrome, Parkinson's Disease, Wilson's Disease, Leigh Syndrome,Fibrosis and PLA2G6-associated neurodegeneration (PLAN). In one embodiment, PLAN may comprise a disorder selected from the group consisting of infantile neuroaxonal dystrophy (INAD), atypical neuroaxonal dystrophy (ANAD), Parkinsonian Syndrome which contains adult onset dystonia parkinsonism (DP) and autosomal recessive early-onset parkinsonism (AREP),In one aspect, the non-nuclear organelle associated disorder is FDRA.

In a related aspect, the present disclosure provides a method for treating a non-nuclear organelle associated disorder, comprising administering to a subject in need thereof a fusion protein, a nucleic acid, a vector, a protein conjugate, or a pharmaceutical composition of the disclosure, such that the non-nuclear organelle associated disorder is treated. In some embodiments, the non-nuclear organelle associated disorder is selected from the group consisting of Friedreich's ataxia (FDRA), Barth Syndrome, Parkinson's Disease, Wilson's Disease, Leigh Syndrome and Fibrosis. In one specific embodiment, the non-nuclear organelle associated disorder is FDRA.

In some embodiments, the subject is a human.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

Non-limiting examples of embodiments of the disclosure are described below with reference to figures attached hereto that are listed following this paragraph. Identical features that appear in more than one figure are generally labeled with a same label in all the figures in which they appear. A label labeling an icon representing a given feature of an embodiment of the disclosure in a figure may be used to reference the given feature. Dimensions of features shown in the figures are chosen for convenience and clarity of presentation and are not necessarily shown to scale.

FIG. 9, Panel B is a high magnification image of cells treated with TAT-GG-Ubiquitin-hFXN. This image shows the details of hFXN stain and its localization to mitochondria.

FIG. 9, Panel C is a bar graph showing the ratios of mean hFXN stain signal to the mean nuclear stain signal for cells treated with various concentrations of TAT-GG-hFXN, TAT-GG-EPLFAERK-hFXN and TAT-GG-Ubiquitin-hFXN FIG. 9, Panel D is a picture of a nitrocellulose membrane following transfer from an SDS-PAGE gel loaded with samples of TAT-GG-hFXN, TAT-GG-EPLFAERK-hFXN, TAT-GG-Ubiquitin-hFXN used for transduction experiments and stained for total protein. The picture demonstrates lack of fusion protein degradation and that the same amount of each fusion protein was used in transduction experiments.

FIG. 10, Panel B presents the ratio of the mean anti-FXN stain signal to the mean anti-mitochondrial stain signal graphed as a function of hFXN fusion protein concentration in Schwann cells treated with TAT-GG-hFXN, TAT-GG-EPLFAERK-hFXN and TAT-GG-Ubiquitin-hFXN.

FIG. 10, Panel C presents the ratio of the mean anti-FXN stain signal to the mean anti-mitochondrial stain signal graphed as a function of hFXN fusion protein concentration in H9C2 cells treated with TAT-GG-hFXN, TAT-GG-EPLFAERK-hFXN and TAT-GG-Ubiquitin-hFXN.

FIG. 10, Panel D presents the ratio of the mean anti-FXN stain signal to the mean anti-mitochondrial stain signal graphed as a function of hFXN fusion protein concentration in Schwann cells treated with TAT-GG-hFXN, TAT-GG-EPLFAERK-hFXN, TAT-GG-Ubiquitin-hFXN and TAT-GG-hFXN-NES1.

FIG. 12, Panel B is a series of photographs of LRPPRC KD and Scr-5 control cells treated with the highest tested concentration of each hFXN fusion protein or vehicle.

FIG. 12, Panel C is a graph showing the amount of CYR61 in the media of LRPPRC KD cells treated with hFXN fusion proteins.

FIG. 12, Panel D is a graph showing the amount of lactate in the media of LRPPRC KD cells treated with hFXN fusion proteins.

DETAILED DESCRIPTION

Figure 1:
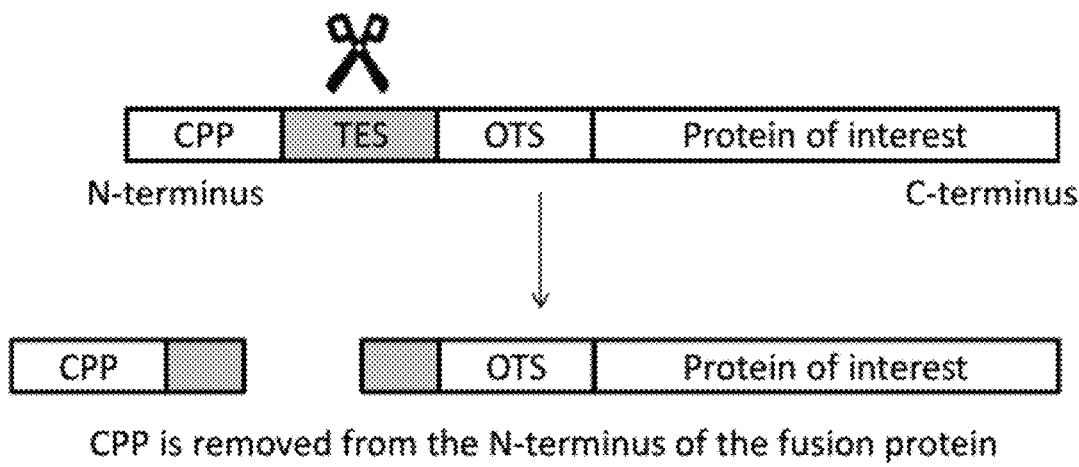
FIG. 1 is a schematic illustrating certain fusion proteins of the disclosure comprising a target enhancing sequence (TES) with a protease cleavage site.
Figure 1:
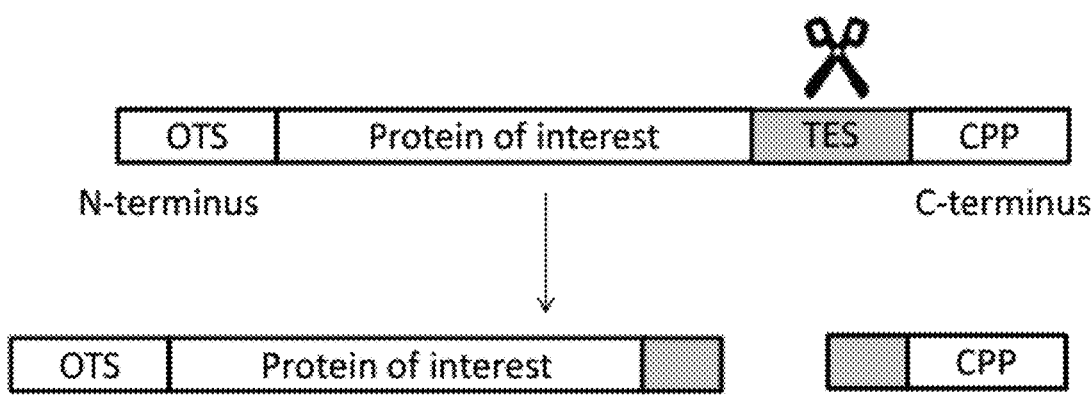

An aspect of the disclosure relates to providing a fusion protein comprising a protein of interest to be delivered to a cell. In some embodiments, the fusion protein comprises a protein of interest to be delivered to a particular organelle, e.g., a non-nuclear organelle, such as the mitochondria. The fusion protein also comprises at least one cell penetrating peptide (CPP), at least one target enhancing sequence (TES) and, optionally, at least one organelle-targeting signal (OTS).

In certain aspects of the present disclosure, the CPP is capable of interfering with delivery of the protein of interest to an organelle, such as a non-nuclear organelle. For example, as demonstrated by certain experimental data included in the present disclosure, a CPP, e.g., HIV-TAT, may interfere with delivery of the protein of interest, e.g., FXN, to the mitochondria. Specifically, HIV-TAT facilitates delivery of FXN to the nucleus instead of the mitochondria. Accordingly, a fusion protein of the present disclosure comprises a TES which prevents or attenuates the interference of CPP with the delivery of the protein of interest to an appropriate cellular (e.g., non-nuclear) organelle.

For example, in some embodiments, a CPP may be located at the N-terminus of the fusion protein and the TES may be fused at the C-terminus of the CPP. Alternatively, the CPP may be located at the C-terminus of the fusion protein and the TES may be fused at the N-terminus of the CPP. The TES may comprise an intracellular protease recognition sequence which facilitates cleavage of the fusion protein at the TES upon entry to the cell, thereby removing CPP from the remainder of the fusion protein and preventing it from directing the fusion protein to the nucleus.

Alternatively, the TES may comprise a nuclear export signal, e.g., a signal that facilitates export of the fusion protein from the nucleus after it has been delivered to the nucleus mediated by the CPP.

Another aspect of the disclosure also relates to providing a fusion protein comprising a protein of interest to be delivered to cell. The fusion protein comprises at least one cell penetrating peptide (CPP), at least one target enhancing sequence (TES) and a protein of interest.

In some embodiments of the present disclosure, the CPP is capable of interfering with delivery of a protein of interest to a cell. For example, as demonstrated by certain experimental data included in the present disclosure, cells treated with fusion proteins comprising a protein of interest, CPP and TES contained significantly higher amounts of the protein of interest than cells treated with a fusion protein comprising a protein of interest and CPP, but not TES. Thus, it was unexpectedly discovered that introducing TES into a fusion protein comprising CPP and a protein of interest can significantly increase the amount of protein of interest delivered to a cell.

Without wishing to be bound by a specific theory, it is believed that cleavage of TES by endogenous proteases in a cell facilitates removal of the CPP from the fusion protein and prevents the CPP from facilitating diffusion of the protein of interest across the plasma membrane and out of the cell. This allows the protein of interest to accumulate in the cell. Removal of the CPP from the fusion protein also prevents the CPP from interfering with proper subcellular localization of the protein of interest. Accordingly, a fusion protein of the present disclosure comprises a TES which prevents or attenuates the interference of CPP with the delivery of the protein of interest to a cell. In some embodimetns, a fusion protein of the present disclosure comprises a TES which prevents or attenuates the interference of CPP with the proper subcellular localization of the protein of interest in the cell.

In some embodiments, a CPP may be located at the N-terminus of the fusion protein and the TES may be fused at the C-terminus of the CPP. Alternatively, the CPP may be located at the C-terminus of the fusion protein and the TES may be fused at the N-terminus of the CPP. The TES may comprise an intracellular protease recognition sequence which facilitates cleavage of the fusion protein at the TES upon entry to the cell, thereby removing CPP from the remainder of the fusion protein and preventing it from directing the fusion protein out of the cell.

Alternatively, the TES may comprise a nuclear export signal peptide (NES). Without wishing to be bound by a specific theory, it is believed that CPP facilitates transport of the fusion protein into the nucleus, and NES, when present in the fusion protein, prevents accumulation of the fusion protein in the nucleus. By preventing accumulation of the fusion protein in the nucleus, NES facilitates proper subcellular localization of the protein of interest comprised in the fusion protein outside of the nucleus, e.g., in the mitochondria.

In some embodiments, removal of CPP through cleavage of the TES by an endogenous protease facilitates proper subcellular localization of the protein of interest. In some cases, a protein of interest, e.g., NFkappa b, androgen receptor, estrogen receptor or aconitase, may typically be localized in more than one cellular compartment, such as nucleus and mitochondria. Removal of CPP through cleavage of TES by an endogenous protease prevents interference of the CPP with proper subcellular localization of the protein of interest in response to endogenous stimuli.

Protein of Interest

The fusion protein provided by the present disclosure comprises a protein of interest to be delivered to a cell. In some embodiments, the fusion protein provided by the present disclosure comprises a protein of interest to be delivered to a particular organelle within the cell, e.g., a non-nuclear organelle. The protein of interest comprised in the fusion protein of the disclosure may be associated with a non-nuclear organelle, e.g., the protein of interest may be an intra-cellular, non-nuclear organelle-specific protein. For example, the protein of interest may localize to a non-nuclear organelle and/or may be capable of, or facilitate, an intracellular function that is effected in a non-nuclear organelle. Exemplary non-nuclear organelles include cytosol, mitochondria, lysosomes, endoplasmic reticulum, Golgi apparatus and peroxisomes. In some embodiments, the protein of interest comprised in the fusion protein of the disclosure may alternatively be associated with the nucleus, and in some embodiments, associated with the nucleus and one or more non-nuclear organelles, e.g., the protein of interest may be an intra-cellular protein that is localized both in the nucleus and in other, non-nuclear organelles (e.g., the cytosol, mitochondria, lysosomes, endoplasmic reticulum, Golgi apparatus and peroxisomes).

The protein of interest may be associated with a pathological condition in a subject. Such pathological condition may result, for example, from a deficiency in the protein of interest in the subject, e.g., when the protein of interest may be mutated in a way to reduce or eliminate the natural activity of the protein of interest, or when the protein of interest may be absent altogether.

In some aspects of the disclosure, the protein of interest may be associated with mitochondria. Exemplary proteins of interest that are associated with mitochondria may include, e.g., frataxin (FXN), tafazzin, pyruvate dehydrogenase beta2 (PDHB), leucine-rich PPR motif-containing protein (LRP-PRC protein), SLIRP, Parkin RBR E3 ubiquitin protein ligase (PARK2 protein or PARKIN), PTEN-induced kinase 1 (PINK1 or PARK6 protein),Protein deglycase DJ-1 (PARK7 protein) and A2 phospholipase Group VI.

In some embodiments, the protein of interest comprises an OTS. In some embodiments, the OTS is endogenous to the protein of interest. In some embodiments, the OTS is exogenous to the protein of interest.

In some embodiments, the protein of interest lacks an OTS. In some embodiments, the protein of interest lacks an OTS in its native form, i.e., it does not contain an OTS in nature. In some embodiments, the protein of interest lacking an OTS is a mature form of a protein wherein the endogenous OTS has been removed.

In one specific embodiment, the protein of interest that is associated with mitochondria may be frataxin (FXN), e.g., human FXN, which is associated with a pathological condition Friedreich's Ataxia (FRDA). FRDA is a genetic, progressive neurodegenerative disorder caused by a mutation in a gene encoding FXN. The FXN is an essential and phylogenetically conserved protein that is found in cells throughout the body, with the highest levels in the heart, spinal cord, liver, pancreas, and skeletal muscle. FXN is encoded in the nucleus, expressed in the cytoplasm and imported into the mitochondria where it is processed to the mature form. In humans, the 210-amino acid full-length hFXN (hFXN$_{1-210}$, 23.1 kDa) contains a typical mitochondrial targeting sequence (MTS) at the amino terminus that is processed in a 2-step cleavage by the mitochondrial matrix processing peptidase (MPP) as it is imported into the mitochondrial matrix. The resulting protein is a 130-amino acid, 14.2 kDa mature hFXN protein (hFXN$_{81-210}$). Sequences of the full-length hFXN and mature hFXN are shown in Table 1 below.

TABLE 1

Sequences of the full-length hFXN and mature hFXN.

| SEQ ID NO. | Protein | Amino Acid Sequence |
|---|---|---|
| 1 | Full-length hFXN hFXN$_{1-210}$ | MWTLGRRAVAGLLASPSPA QAQTLTRVPRPAELAPLCG RRGLRTDIDATCTPRRASS NQRGLNQIWNVKKQSVYLM NLRKSGTLGHPGSLDETTY ERLAEETLDSLAEFFEDLA DKPYTFEDYDVSFGSGVLT VKLGGDLGTYVINKQTPNK QIWLSSPSSGPKRYDWTGK NWVYSHDGVSLHELLAAEL TKALKTKLDLSSLAYSGKD A |
| 2 | Mature hFXN hFXN$_{81-210}$ | SGTLGHPGSLDETTYERLA EETLDSLAEPEEDLADKPY TFEDYDVSFGSGVLTVKLG GDLGTYVINKQTPNKQIWL SSPSSGPKRYDWTGKNWVY SHDGVSLHELLAAELTKAL KTKLDLSSLAYSGKDA |

Accordingly, in some aspects, the fusion protein provided by the present disclosure may comprise the full length hFXN (hFXN$_{1-210}$), i.e., including MTS as an organelle targeting sequence (OTS). In some aspects, the fusion protein may comprise an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of the full length hFXN, e.g., SEQ ID NO: 1 as listed in Table 1.

In some aspects, the fusion protein provided by the present disclosure may comprise the mature hFXN (hFXN$_{81-210}$). In some aspects, the fusion protein may comprise an amino acid sequence having at least 85%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of the mature hFXN, e.g., SEQ ID NO: 2 as listed in Table 1.

In other aspects, exemplary proteins of interest which may be comprised in the fusion protein of the present disclosure include tafazzin, pyruvate dehydrogenase beta2 (PDHB), leucine-rich PPR motif-containing protein (LRP-PRC protein), SLIRP, Parkin RBR E3 ubiquitin protein ligase (PARK2 protein or PARKIN), PTEN-induced kinase 1 (PINK1 or PARK6 protein),Protein deglycase DJ-1 (PARK7 protein) and A2 phospholipase Group VI.

Table 2 below lists exemplary proteins of interest, corresponding human sequences, and associated pathological conditions that may be treated with a fusion protein of the present disclosure comprising said protein of interest.

TABLE 2

Exemplary proteins of interest, corresponding human sequences and associated pathological conditions. The underlined portions of the sequences for PDHB protein, LRPPRC protein, SLIRP protein and PINK1 protein are the predicted mitochondrial targeting sequences identified using MitoProt II (M. G. Claros, P. Vincens. Computational method to predict mitochondrially imported proteins and their targeting sequences. *Eur. J. Biochem.* 241, 770-786, the entire contents of which are hereby incorporated herein by reference).

| SEQ ID NO. | Protein | Amino Acid Sequence | Associated Disorder |
|---|---|---|---|
| 3 | Tafazzin | MPLHVKWPFPAVPPLTWTLASSVVMGLVGTY SCFWTKYMNHLTVHNREVLYELIEKRGPATP LITVSNHQSCMDDPHLWGILKLRHIWNLKLM RWTPAAADICFTKELHSHFFSLGKCVPVCRG AEFFQAENEGKGVLDTGRHMPGAGKRREKGD GVYQKGMDFILEKLNHGDWVHIFPEGKVNMS SEFLRFKWGIGRLIAECHLNPIILPLWHVGM NDVLPNSPPYFPRFGQKITVLIGKPFSALPV LERLRAENKSAVEMRKALTDFIQEEFQHLKT QAEQLHNHLQPGR | Barth Syndrome and Familial Isolated Dilated Cardiomyopathy |
| 4 | Pyruvate Dehydrogenase Beta2 (PDHB) | MAAVSGLVRRPLREVSGLLKRRFHWTAPAAL QVTVRDAINQGMDEELERDEKVFLLGEEVAQ YDGAYKVSRGLWKKYGDKRIIDTPISEMGFA GIAVGAAMAGLRPICEFMTFNFSMQAIDQVI NSAAKTYYMSGGLQPVPIVFRGPNGASAGVA AQHSQCFAAWYGHCPGLKVVSPWNSEDAKGL IKSAIRDNNPVVVLENELMYGVPFEFPPEAQ SKDFLIPIGKAKIERQGTHITVVSHSRPVGH CLEAAAVLSKEGVECEVINMKTIRPMDMETI EASVMKTNHLVTVEGGWPQFGVGAEICARIM EGPAFNFLDAPAVRVTGADVPMPYAKILEDN SIPQVKDIIFAIKKTLNI | Pyruvate Dehydrogenase E1-Beta Deficiency |
| 5 | Leucine-rich PPR Motif-Containing Protein (LRPPRC protein) | MAALLRSARWLLRAGAAPRLPLSLRLLPGGP GRLHAASYLPAARAGPVAGGLLSPARLYAIA AKEKDIQEESTFSSRKISNQFDWALMRLDLS VRRTGRIPKKLLQKVFNDTCRSCiGLGGSII ALLLLRSCGSLLPELKLEERTEFAIIRIWDT LQKLGAVYDVSHYNALLKVYLQNEYKFSPTD FLAKMEEANIQPNRVTYQRLIASYCNVGDIE GASKILGFMKTKDLPVTEAVFSALVTGHARA GDMENAENILTVMRDAGIEPGPDTYLALLNA YAEKGDIDHVKQTLEKVEKSELHLMDRDLLQ IIFSFSKAGYPQYVSEILEKVTCERRYIPDA MNLILLLVTEKLEDVALQILLACPVSKEDGP SVFGSFFLQHCVTMNTPVEKLTDYCKKLKEV QMHSFPLQFTLHCALLANKTDLAKALMKAVK EEGFPIRPHYFWPLLVGRRKEKNVQGIIEIL KGMQELGVHPDQETYTDYVIPCFDSVNSARA ILQENGCLSDSDMFSQAGLRSEAANGNLDFV LSFLKSNTLPISLQSIRSSLLLGFRRSMNIN LWSEITELLYKDGRYCQEPRGPTEAVGYFLY NLIDSMSDSEVQAKEEHLRQYFHQLEKMNVK IPENIYRGIRNLLESYHVPELIKDAHLLVES KNLDFQKTVQLTSSELESTLETLKAENQPIR DVLKQLILVLCSEENMQKALELKAKYESDMV TGGYAALINLCCRHDKVEDALNLKEEFDRLD SSAVLDTGKYVGLVRVLAKHGKLQDAINILK EMKEKDVLIKDTTALSFFHMLNGAALRGEIE TVKQLHEAIVTLGLAEPSTNISFPLVTVHLE KGDLSTALEVAIDCYEKYKVLPRIHDVLCKL VEKGETDLIQKAMDFVSQEQGEMVMLYDLFF AFLQTGNYKEAKKIIETPGIRARSARLQWFC DRCVANNQVETLEKLVELTQKLFECDRDQMY YNLLKLYKINGDWQRADAVWNKIQEENVIPR EKTLRLLAEILREGNQEVPFDVPELWYEDEK HSLNSSSASTTEPDFQKDILIACRLNQKKGA YDIFLNAKEQNIVFNAETYSNLIKLLMSEDY FTQAMEVKAFAETHIKGFTLNDAANSRLHTQ VRRDYLKEAVTTLKTVLDQQQTPSRLAVTRV IQALAMKGDVENIEVVQKMLNGLEDSIGLSK MVFINNIALAQIKNNNIDAAIENIENMLTSE NKVIEPQYFGLAYLFRKVIEEQLEPAVEKIS IMAERLANQFAIYKPVTDFFLQLVDAGKVDD | Leigh Syndrome, French Canadian Type |

TABLE 2-continued

Exemplary proteins of interest, corresponding human sequences and associated pathological conditions. The underlined portions of the sequences for PDHB protein, LRPPRC protein, SLIRP protein and PINK1 protein are the predicted mitochondrial targeting sequences identified using MitoProt II (M. G. Claros, P. Vincens. Computational method to predict mitochondrially imported proteins and their targeting sequences. *Eur. J. Biochem.* 241, 770-786, the entire contents of which are hereby incorporated herein by reference).

| SEQ ID NO. | Protein | Amino Acid Sequence | Associated Disorder |
|---|---|---|---|
| | | ARALLQRCGAIAEQTPILLLFLLRNSRKQGK ASTVKSVLELIPELNEKEEAYNSLMKSYVSE KDVTSAKALYEHLTAKNTKLDDLFLKRYASL LKYAGEPVPFIEPPESFEFYAQQLRKLRENS S | |
| 6 | SLIRP | MAASAARGAAALRRSINQPVAFVRRIPWTAA SSQLKEHFAQFGHVRRCILPFDKETGFHRGL GWVQFSSEEGLRNALQQENHIIDGVKVQVHT RRPKLPQTSDDEKKDF | Leigh Syndrome, French Canadian Type |
| 7 | Parkin RBR E3 ubiquitin protein ligase (PARK2 protein or PARKIN) | MIVFVRFNSSHGFPVEVDSDTSIFQLKEVVA KRQGVPADQLRVIFAGKELRNDWTVQNCDLD QQSIVHIVQRPWRKGQEMNATGGDDPRNAAG GCEREPQSLTRVDLSSSVLPGDSVGLAVILH TDSRKDSPPAGSPAGRSIYNSFYVYCKGPCQ RVQPGKLRVQCSTCRQATLTLTQGPSCWDDV LIPNRMSGECQSPHCPGTSAEFFFKCGAHPT SDKETSVALHLIATNSRNITCITCTDVRSPV LVFQCNSRHVICLDCFHLYCVTRLNDRQFVH DPQLGYSLPCVAGGPNSLIKELHHFRILGEE QYNRYQQYGAEECVLQMGGVLCPRPGCGAGL LPEPDQRKVTCEGGNGLGCGFAFCRECKEAY HEGECSAVFEASGTTTQAYRVDERAAEQARW EAASKETIKKTTKPCPRCHVPVEKNGGCMHM KCPQPQCRLEWCWNCGCEWNRVCMGDHWFDV | Parkinson's Disease and autosomal recessive juvenile Parkinson's Disease |
| 8 | PTEN-induced kinase 1 (PINK1 or PARK6 protein) | MAVRQALGRGLQLGRALLLRFTGKPGRAYGL GRPGPAAGCVRGERPGWAAGPGAEPRRVGLG LPNRLRFFRQSVAGLAARLQRQFVVRAWGCA GPCGRAVFLAFGLGLGLIEEKQAESRRAVSA CQEIQAIFTQKSKPGPDPLDTRRLQGFRLEE YLIGQSIGKGCSAAVYEATMPTLPQNLEVTK STGLLPGRGPGTSAPGEGQERAPGAPAFPLA IKMMWNISAGSSSEAILNTMSQELVPASRVA LAGEYGAVTYRKSKRGPKQLAPHPNIIRVLR AFTSSVPLLPGALVDYPDVLPSRLHPEGLGH GRTLFLVMKNYPCTLRQYLCVNTPSPRLAAM MLLQLLEGVDHLVQQGIAHRDLKSDNILVEL DPDGCPWLVIADFGCCLADESIGLQLPFSSW YVDRGGNGCLMAPEVSTARPGPRAVIDYSKA DAWAVGAIAYEIFGLVNPFYGQGKAHLESRS YQEAQLPALPESVPPDVRQLVRALLQREASK RPSARVAANVLHLSLWGEHILALKNLKLDKM VGWLLQQSAATLLANRLTEKCCVETKMKMLF LANLECETLCQAALLLCSWRAAL | Parkinson's Disease |
| 9 | Protein deglycase DJ-1 (PARK7 protein) | MASKRALVILAKGAEEMETVIPVDVMRRAGI KVTVAGLAGKDPVQCSRDVVICPDASLEDAK KEGPYDVVVLPGGNLGAQNLSESAAVKEILK EQENRKGLIAAICAGPTALLAHEIGFGSKVT THPLAKDKMMNGGHYTYSENRVEKDGLILTS RGPGTSFEFALAIVEALNGKEVAAQVKAPLV LKD | Parkinson's Disease |
| 72 | Phospholipase A2, Group VI (variant 1) | MQFFGRLVNTFSGVTNLFSNPFRVKEVAVAD YTSSDRVREEGQLILFQNTPNRTWDCVLVNP RNSQSGFRLFQLELEADALVNFHQYSSQLLP FYESSPQVLHTEVLQHLTDLIRNHPSWSVAH LAVELGIRECFHHSRIISCANCAENEEGCTP LHLACRKGDGEILVELVQYCHTQMDVTDYKG ETVPHYAVQGDNSQVLQLLGRNAVAGLNQVN NQGLTPLHLACQLGKQEMVRVLLLCNARCNI MGPNGYPIHSAMKFSQKGCAEMIISMDSSQI HSKDPRYGASPLHWAKNAEMARMLLKRGCNV NSTSSAGNTALHVAVMRNRFDCAIVLLTHGA NADARGEHGNTPLHLAMSKDNVEMIKALIVF | PLA2G6-associated neurodegeneration (PLAN) |

TABLE 2-continued

Exemplary proteins of interest, corresponding human sequences and associated pathological conditions. The underlined portions of the sequences for PDHB protein, LRPPRC protein, SLIRP protein and PINK1 protein are the predicted mitochondrial targeting sequences identified using MitoProt II (M. G. Claros, P. Vincens. Computational method to predict mitochondrially imported proteins and their targeting sequences. *Eur. J. Biochem.* 241, 770-786, the entire contents of which are hereby incorporated herein by reference).

| SEQ ID NO. | Protein | Amino Acid Sequence | Associated Disorder |
|---|---|---|---|
| | | GAEVDTPNDFGETPTFLASKIGRLVTRKAIL TLLRTVGAEYCFPPIHGVPAEQGSAAPHHPF SLERAQPPPISLNNLELQDLMHISRARKPAF ILGSMRDEKRTHDHLLCLDGGGVKGLIIIQL LIAIEKASGVATKDLFDWVAGTSTGGILALA ILHSKSMAYMRGMYFRMKDEVFRGSRPYESG PLEEFLKREFGEHTKMTDVRKPKVMLTGTLS DRQPAELHLFRNYDAPETVREPRFNQNVNLR PPAQPSDQLVWRAARSSGAAPTYFRPNGRFL DGGLLANNPTLDAMTEIHEYNQDLIRKGQAN KVKKLSIVVSLGTGRSPQVPVTCVDVFRPSN PWELAKTVFGAKELGKMVVDCCTDPDGRAVD RARAWCEMVGIQYFRLNPQLGTDIMLDEVSD TVLVNALWETEVYIYEHREEFQKLIQLLLSP | |
| 73 | Phospholipase A2, Group VI (variant 2) | MQFFGRLVNTFSGVTNLFSNPFRVKEVAVAD YTSSDRVREEGQLILFQNTPNRTWDCVLVNP RNSQSGFRLFQLELEADALVNFHQYSSQLLP FYESSPQVLHTEVLQHLTDLIRNHPSWSVAH LAVELGIRECFHHSRIISCANCAENEEGCTP LHLACRKGDGEILVELVQYCHTQMDVTDYKG ETVFHYAVQGDNSQVLQLLGRNAVAGLNQVN NQGLTPLHLACQLGKQEMVRVLLLCNARCNI MGPNGYPIHSAMKFSQKGCAEMIISMDSSQI HSKDPRYGASPLHWAKNAEMARMLLKRGCNV NSTSSAGNTALHVAVMRNRFDCAIVLLTHGA NADARGEHGNTPLHLAMSKDNVEMIKALIVF GAEVDTPNDFGETPTFLASKIGRQLDLMHI SRARKPAFILGSMRDEKRTHDHLLCLDGGGV KGLIIIQLLIAIEKASGVATKDLFDWVAGTS TGGILALAILHSKSMAYMRGMYFRMKDEVFR GSRPYESGPLEEFLKREFGEHTKMTDVRKPK VMLTGTLSDRQPAELHLFRNYDAPETVREPR FNQNVNLRPPAQPSDQLVWRAARSSGAAPTY FRPNGRFLDGGLLANNPTLDAMTEIHEYNQD LIRKGQANKVKKLSIVVSLGTGRSPQVPVTC VDVFRPSNPWELAKTVFGAKELGKMVVDCCT DPDGRAVDRARAWCEMVGIQYFRLNPQLGTD IMLDEVSDTVLVNALWETEVYIYEHREEFQK LIQLLLSP | PLA2G6- associated neuro- degeneration (PLAN) |
| 74 | Phospholipase A2, Group VI (variant 3) | MQFFGRLVNTFSGVTNLFSNPFRVKEVAVAD YTSSDRVREEGQLILFQNTPNRTWDCVLVNP RNSQSGFRLFQLELEADALVNFHQYSSQLLP FYESSPQVLHTEVLQHLTDLIRNHPSWSVAH LAVELGIRECFHHSRIISCANCAENEEGCTP LHLACRKGDGEILVELVQYCHTQMDVTDYKG ETVFHYAVQGDNSQVLQLLGRNAVAGLNQVN NQGLTPLHLACQLGKQEMVRVLLLCNARCNI MGPNGYPIHSAMKFSQKGCAEMIISMDSSQI HSKDPRYGASPLHWAKNAEMARMLLKRGCNV NSTSSAGNTALHVAVMRNRFDCAIVLLTHGA NADARGEHGNTPLHLAMSKDNVEMIKALIVF GAEVDTPNDFGETPTFLASKIGRQLDLMHI SRARKPAFILGSMRDEKRTHDHLLCLDGGGV KGLIIIQLLIAIEKASGVATKDLFDWVAGTS TGGILALAILHSKSMAYMRGMYFRMKDEVFR GSRPYESGPLEEFLKREFGEHTKMTDVRKPK VMLTGTLSDRQPAELHLFRNYDAPETVREPR FNQNVNLRPPAQPSDQLVWRAARSSGAAPTY FRPNGRFLDGGLLANNPTLDAMTEIHEYNQD LIRKGQANKVKKLSIVVSLGTGRSPQVPVTC VDVFRPSNPWELAKTVFGAKELGKMVVDCCT DPDGRAVDRARAWCEMVGIQYFRLNPQLGTD IMLDEVSDTVLVNALWETEVYIYEHREEFQK LIQLLLSP | PLA2G6- associated neuro- degeneration (PLAN) |

TABLE 2-continued

Exemplary proteins of interest, corresponding human sequences and associated pathological conditions. The underlined portions of the sequences for PDHB protein, LRPPRC protein, SLIRP protein and PINK1 protein are the predicted mitochondrial targeting sequences identified using MitoProt II (M. G. Claros, P. Vincens. Computational method to predict mitochondrially imported proteins and their targeting sequences. *Eur. J. Biochem.* 241, 770-786, the entire contents of which are hereby incorporated herein by reference).

| SEQ ID NO. | Protein | Amino Acid Sequence | Associated Disorder |
|---|---|---|---|
| 75 | Phospholipase A2, Group VI (variant 4) | MQFFGRLVNTFSGVTNLFSNPFRVKEVAVAD YTSSDRVREEGQLILFQNTPNRTWDCVLVNP RNSQSGFRLFQLELEADALVNFHQYSSQLLP FYESSPQVLHTEVLQHLTDLIRNHPSWSVAH LAVELGIRECFHHSRIISCANCAENEEGCTP LHLACRKGDGEILVELVQYCHTQMDVTDYKG ETVFHYAVQGDNSQVLQLLGRNAVAGLNQVN NQGLTPLHLACQLGKQEMVRVLLLCNARCNI MGPNGYPIHSAMKFSQKGCAEMIISMDSSQI HSKDPRYGASPLHWAKNAEMARMLLKRGCNV NSTSSAGNTALHVAVMRNRFDCAIVLLTHGA NADARGEHGNTPLHLAMSKDNVEMIKALIVF GAEVDTPNDFGETPTFLASKIGRLVTRKAIL TLLRTVGAEYCFPPIHGVPAEQGSAAPHHPF SLERAQPPPISLNNLELQDLMHISRARKPAF ILGSMRDEKRTHDHLLCLDGGGVKGLIIIQL LIAIEKASGVATKDLFDWVAGTSTGGILALA ILHSKSMAYMRGMYFRMKDEVFRGSRPYESG PLEEFLKREFGEHTKMTDVRKPKVMLTGTLS DRQPAELHLFRNYDAPETVREPRFNQNVNLR PPAQPSDQLVWRAARSSGAAPTYFRPNGRFL DGGLLANNPTLDAMTEIHEYNQDLIRKGQAN KVKKLSIVVSLGTGRSPQVPVTCVDVFRPSN PWELAKTVFGAKELGKMVVDCCTDPDGRAV DRARAWCEMVGIQYFRLNPQLGTDIMLDEVS DTVLVNALWETEVYIYEHREEFQKLIQLLLS P | PLA2G6-associated neuro-degeneration (PLAN) |
| 76 | Phospholipase A2, Group VI (variant 5) | MQFFGRLVNTFSGVTNLFSNPFRVKEVAVAD YTSSDRVREEGQLILFQNTPNRTWDCVLVNP RNSQSGFRLFQLELEADALVNFHQYSSQLLP FYESSPQVLHTEVLQHLTDLIRNHPSWSVAH LAVELGIRECFHHSRIISCANCAENEEGCTP LHLACRKGDGEILVELVQYCHTQMDVTDYKG ETVFHYAVQGDNSQVLQLLGRNAVAGLNQVN NQGLTPLHLACQLGKQEMVRVLLLCNARCNI MGPNGYPIHSAMKFSQKGCAEMIISMDSSQI HSKDPRYGASPLHWAKNAEMARMLLKRGCNV NSTSSAGNTALHVAVMRNRFDCAIVLLTHGA NADARGEHGNTPLHLAMSKDNVEMIKALIVF GAEVDTPNDFGETPTFLASKIGRQLQDLMHI SRARKPAFILGSMRDEKRTHDHLLCLDGGGV KGLIIIQLLIAIEKASGVATKDLFDWVAGTS TGGILALAILHSKSMAYMRGMYFRMKDEVFR GSRPYESGPLEEFLKREFGEHTKMTDVRKPK VMLTGTLSDRQPAELHLFRNYDAPETVREPR FNQNVNLRPPAQPSDQLVWRAARSSGAAPTY FRPNGRFLDGGLLANNPTLDAMTEIHEYNQD LIRKGQANKVKKLSIVVSLGTGRSPQVPVTC VDVFRPSNPWELAKTVFGAKELGKMVVDCCT DPDGRAVDRARAWCEMVGIQYFRLNPQLGTD IMLDEVSDTVLVNALWETEVYIYEHREEFQK LIQLLLSP | PLA2G6-associated neuro-degeneration (PLAN) |
| 77 | Phospholipase A2, Group VI (variant 6) | MQFFGRLVNTFSGVTNLFSNPFRVKEVAVAD YTSSDRVREEGQLILFQNTPNRTWDCVLVNP RNSQSGFRLFQLELEADALVNFHQYSSQLLP FYESSPQVLHTEVLQHLTDLIRNHPSWSVAH LAVELGIRECFHHSRIISCANCAENEEGCTP LHLACRKGDGEILVELVQYCHTQMDVTDYKG ETVFHYAVQGDNSQVLQLLGRNAVAGLNQVN NQGLTPLHLACQLGKQEMVRVLLLCNARCNI MGPNGYPIHSAMKFSQKGCAEMIISMDSSQI HSKDPRYGASPLHWAKNAEMARMLLKRGCNV NSTSSAGNTALHVAVMRNRFDCAIVLLTHGA NADARGEHGNTPLHLAMSKDNVEMIKALIVF GAEVDTPNDFGETPTFLASKIGRQLQDLMHI SRARKPAFILGSMRDEKRTHDHLLCLDGGGV | PLA2G6-associated neuro-degeneration (PLAN) |

TABLE 2-continued

Exemplary proteins of interest, corresponding human sequences and associated pathological conditions. The underlined portions of the sequences for PDHB protein, LRPPRC protein, SLIRP protein and PINK1 protein are the predicted mitochondrial targeting sequences identified using MitoProt II (M. G. Claros, P. Vincens. Computational method to predict mitochondrially imported proteins and their targeting sequences. *Eur. J. Biochem.* 241, 770-786, the entire contents of which are hereby incorporated herein by reference).

| SEQ ID NO. | Protein | Amino Acid Sequence | Associated Disorder |
|---|---|---|---|
| | | KGLIIIQLLIAIEKASGVATKDLFDWVAGTS TGGILALAILHSKSMAYMRGMYFRMKDEVFR GSRPYESGPLEEFLKREFGEHTKMTDVRKPK VMLTGTLSDRQPAELHLFRNYDAPETVREPR FNQNVNLRPPAQPSDQLVWRAARSSGAAPTY FRPNGRFLDGGLLANNPTLDAMTEIHEYNQD LIRKGQANKVKKLSIVVSLGTGRSPQVPVTC VDVFRPSNPWELAKTVFGAKELGKMVVDCCT DPDGRAVDRARAWCEMVGIQYFRLNPQLGTD IMLDEVSDTVLVNALWETEVYIYEHREEFQK LIQLLLSP | |
| 78 | Phospholipase A2, Group VI (variant 7) | MDVTDYKGETVFHYAVQGDNSQVLQLLGRNA VAGLNQVNNQGLTPLHLACQLGKQEMVRVLL LCNARCNIMGPNGYPIHSAMKFSQKGCAEMI ISMDSSQIHSKDPRYGASPLHWAKNAEMARM LLKRGCNVNSTSSAGNTALHVAVMRNRFDCA IVLLTHGANADARGEHGNTPLHLAMSKDNVE MIKALIVFGAEVDTPNDFGETPTFLASKIGR LVTRKAILTLLRTVGAEYCFPPIHGVPAEQG SAAPHHPFSLERAQPPPISLNNLELQDLMHI SRARKPAFILGSMRDEKRTHDHLLCLDGGGV KGLIIIQLLIAIEKASGVATKDLFDWVAGTS TGGILALAILHSKSMAYMRGMYFRMKDEVFR GSRPYESGPLEEFLKREFGEHTKMTDVRKPK VMLTGTLSDRQPAELHLFRNYDAPETVREPR FNQNVNLRPPAQPSDQLVWRAARSSGAAPTY FRPNGRFLDGGLLANNPTLDAMTEIHEYNQD LIRKGQANKVKKLSIVVSLGTGRSPQVPVTC VDVFRPSNPWELAKTVFGAKELGKMVVDCCT DPDGRAVDRARAWCEMVGIQYFRLNPQLGTD IMLDEVSDTVLVNALWETEVYIYEHREEFQK LIQLLLSP | PLA2G6-associated neuro-degeneration (PLAN) |
| 79 | Phospholipase A2, Group VI (variant 8) | MGRSWWSWCSTATLRWMSPTTRERPSSIMLS RVTILRCCRCAEMIISMDSSQIHSKDPRYGA SPLHWAKNAEMARMLLKRGCNVNSTSSAGNT ALHVAVMRNRFDCAIVLLTHGANADARGEHG NTPLHLAMSKDNVEMIKALIVFGAEVDTPND FGETPTFLASKIGRLVTRKAILTLLRTVGAE YCFPPIHGVPAEQGSAAPHHPFSLERAQPPP ISLNNLELQDLMHISRARKPAFILGSMRDEK RTHDHLLCLDGGGVKGLIIIQLLIAIEKASG VATKDLFDWVAGTSTGGILALAILHSKSMAY MRGMYFRMKDEVFRGSRPYESGPLEEFLKRE FGEHTKMTDVRKPKVMLTGTLSDRQPAELHL FRNYDAPETVREPRFNQNVNLRPPAQPSDQL VWRAARSSGAAPTYFRPNGRFLDGGLLANNP TLDAMTEIHEYNQDLIRKGQANKVKKLSIVV SLGTGRSPQVPVTCVDVFRPSNPWELAKTVF GAKELGKMVVDCCTDPDGRAVDRARAWCEMV GIQYFRLNPQLGTDIMLDEVSDTVLVNALWE TEVYIYEHREEFQKLIQLLLSP | PLA2G6-associated neuro-degeneration (PLAN) |
| 80 | Phospholipase A2, Group VI (variant 9) | MDVTDYKGETVFHYAVQGDNSQVLQLLGRNA VAGLNQVNNQGLTPLHLACQLGKQEMVRVLL LCNARCNIMGPNGYPIHSAMKFSQKGCAEMI ISMDSSQIHSKDPRYGASPLHWAKNAEMARM LLKRGCNVNSTSSAGNTALHVAVMRNRFDCA IVLLTHGANADARGEHGNTPLHLAMSKDNVE MIKALIVFGAEVDTPNDFGETPTFLASKIGR QLQDLMHISRARKPAFILGSMRDEKRTHDHL LCLDGGGVKGLIIIQLLIAIEKASGVATKDL FDWVAGTSTGGILALAILHSKSMAYMRGMYF RMKDEVFRGSRPYESGPLEEFLKREFGEHTK MTDVRKPKVMLTGTLSDRQPAELHLFRNYDA PETVREPRFNQNVNLRPPAQPSDQLVWRAAR SSGAAPTYFRPNGRFLDGGLLANNPTLDAMT | PLA2G6-associated neuro-degeneration (PLAN) |

TABLE 2-continued

Exemplary proteins of interest, corresponding human sequences and associated pathological conditions. The underlined portions of the sequences for PDHB protein, LRPPRC protein, SLIRP protein and PINK1 protein are the predicted mitochondrial targeting sequences identified using MitoProt II (M. G. Claros, P. Vincens. Computational method to predict mitochondrially imported proteins and their targeting sequences. *Eur. J. Biochem.* 241, 770-786, the entire contents of which are hereby incorporated herein by reference).

| SEQ ID NO. | Protein | Amino Acid Sequence | Associated Disorder |
|---|---|---|---|
| | | EIHEYNQDLIRKGQANKVKKLSIVVSLGTGR SPQVPVTCVDVFRPSNPWELAKTVFGAKELG KMVVDCCTDPDGRAVDRARAWCEMVGIQYFR LNPQLGTDIMLDEVSDTVLVNALWETEVYIY EHREEFQKLIQLLLSP | |

In some embodiments, the protein of interest comprised in the fusion protein of the present disclosure may comprise of consist of any sequence as listed in Table 2, e.g., any one of SEQ ID NOS. 3-9 or 72-80. In some embodiments, the protein of interest comprised in the fusion protein of the present disclosure may comprise or consist of an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of the amino acid sequences listed in Table 2, e.g., any of SEQ ID NOS. 3-9 or 72-80.

In some embodiments, the protein of interest comprised in the fusion protein of the present disclosure comprises or consists of any sequence as listed in Table 2, e.g., any one of SEQ ID NOS. 3-9 or 72-80, and lacks the endogenous OTS, i.e., wherein the endogenous OTS has been removed. An OTS of a particular protein would be easily recognized by one of skill in the relevant art.

In some aspects of the disclosure, the protein of interest may be associated with lysosomes. In some aspects of the disclosure, the protein of interest may be associated with endoplasmic reticulum (ER). In some aspects of the disclosure, the protein of interest may be associated with Golgi apparatus.

In some embodiments, the protein of interest can be a protein that is localized to the nucleus. In some embodiments, the protein of interest can be a protein that is localized to the nucleus and one or more other cellular organelles. The skilled artisan will appreciate that, by introducing a TES to fusion proteins comprising a CPP and such a protein of interest, interference by CPP with localization of the protein of interest will be removed, e.g., aberrant localization to the nucleus will be prevented or reduced, thereby allowing the natural regulatory pathway to dictate the proper cellular localization of the protein in response to endogenous signals, and thereby improve the propensity to relocalize to the appropriate subcellular location. Such proteins may include, e.g., NFKbeta, STAT3, androgen receptor, estrogen receptor, and p53.

In some embodiments, the fusion protein provided by the present disclosure may comprise a protein of interest as described herein, or a functional analogue, derivative or a fragment of the protein of interest. The term "derivative", as used herein, encompasses amino acid sequences (polypeptides) which differ from the polypeptides specifically defined in the present disclosure, e.g., SEQ ID NOS. 3-9 or 72-80, by insertions, deletions, substitutions and modifications of amino acids that do not alter the activity of the original polypeptide. It should be appreciated that by the terms "insertion(s)", "deletion(s)" or "substitution(s)", as used herein, encompasses any addition, deletion or replacement, respectively, of between 1 and 50 amino acid residues of a polypeptide, e.g., between 1 and 5 amino acid residues, between 1 and 10 amino acid residues, between 5 and 15 amino acid residues, between 10 and 20 amino acid residues, between 25 and 40 amino acid residues or between 30 and 50 amino acid residues. More particularly, insertion(s), deletion(s) or substitution(s) may be of any one of 1, 2, 3, 4, 5, 6, 7, 8, 9, or 10 amino acid residues. It should be noted that the insertion(s), deletion(s) or substitution(s) may occur in any position of the modified peptide, as well as in any of the N' or C' termini thereof. In one embodiment, the protein of interest is a derivative of FXN, e.g., human FXN. In one embodiment, the protein of interest is a derivative of Tafazzin. In one embodiment, the protein of interest is a derivative of PDHB. In one embodiment, the protein of interest is a derivative of LRPPRC. In one embodiment, the protein of interest is a derivative of SLIRP. In one embodiment, the protein of interest is a derivative of PARK2 protein. In one embodiment, the protein of interest is a derivative of PINK1 (or PARK6 protein). In one embodiment, the protein of interest is a derivative of PARK7. In one embodiment, the protein of interest is a derivative of Phospholipase A2, Group VI (e.g., variant 1, 2, 3, 4, 5, 6, 7, 8 or 9).

In some embodiments, the amino acid sequence of a protein of interest within the context of the present disclosure may differ from the amino acid sequence of a naturally occurring protein associated with any pathological condition as described above. In some embodiments, the amino acid sequence of a protein of interest as compared to the amino acid sequence of a naturally occurring protein associated with any pathological condition may include a conservative amino acid substitution, i.e., substitution with a structurally-similar amino acid. For instance, structurally similar amino acids include: (isoleucine (I), leucine (L) and valine (V)); (phenylalanine (F) and tyrosine (Y)); (lysine (K) and arginine (R)); (glutamine (Q) and asparagine (N)); (aspartic acid (D) and glutamic acid (E)); and (glycine (G) and alanine (A)).

The term "derivative", as used herein, encompasses homologues, variants and analogues of the original polypeptide, as well as covalent modifications of the original polypeptide. A derivative, a variant and an analogue of any one of the proteins or the peptides comprised in the fusion protein provided in the present disclosure will have the same biological activity as its native form. In one specific embodiment, the protein of interest is a homologue, variant or analogue of FXN, e.g., human FXN.

In some embodiments, a protein of interest which may be comprised in the fusion protein of the present disclosure may be a naturally occurring in a subject. The subject may be a mammal, e.g., a mouse, a rat, a monkey or a human.

Organelle Targeting Sequence (OTS)

In some embodiments, the fusion proteins of the present disclosure may also comprise an organelle targeting sequence (OTS). The term "organelle targeting sequence", or "OTS", as used herein, refers to any amino acid sequence, e.g., a protein, a peptide or a consensus domain, which facilitates delivery of a protein of interest to a specific non-nuclear organelle. For example, an OTS may be a mitochondrial targeting sequence (MTS) that facilitates delivery of a protein of interest to mitochondria. An MTS may be a peptide of about 10-70 amino acids comprising an alternating pattern of hydrophobic and positively charged amino acids that forms an amphipathic helix.

An OTS may also be an endoplasmic reticulum (ER) targeting sequence. An ER targeting sequence may be a peptide of about 16-30 amino acids comprising a hydrophilic region, a hydrophobic domain, and a C-terminal region containing a cleavage site for an ER-specific signal peptidase.

An OTS may also comprise a HEAT motif, which may be present in naturally occurring proteins that localize to the Golgi and endoplasmic reticulum (ER). HEAT is a protein tandem repeat structural motif composed of two alpha helices linked by a short loop. HEAT repeats can form alpha solenoids, a type of solenoid protein domain found in a number of cytoplasmic proteins.

An OTS may also be a peroxisomal targeting signal (PTS) which may be located either at the N-terminus or at the C-terminus of the protein of interest. The N-terminal peroxisomal targeting signal may have a consensus sequence of Arg-Leu-X-X-X-X-X-His/Gln-Leu, where X may be any amino acid. The C-terminal peroxisomal targeting signal may be short and comprised of Ser-Lys-Leu, but other variations exist, such as PTS2 and mPTS (membrane PTS). mPTS may consist of a cluster of basic amino acids (arginines and lysines) within a loop of protein (i.e., between membrane spans).

An OTS may also be a lysosomal targeting motif, e.g., comprising a sequence Tyr-X-XO, where X may be any amino acid and O may be a bulky hydrophobic amino acid or a dileucine motif (Leu-Leu).

In a fusion protein of the present disclosure, an OTS may be a native sequence, i.e., the OTS may be naturally found within, or be naturally associated with, a protein of interest also present in the fusion protein. For example, the OTS and the protein of interest may be parts of the same naturally occurring polypeptide sequence. In one specific example, a fusion protein of the present disclosure may comprise mature hFXN and an MTS sequence MWTLGRRAVAGLLASPSPAQAQTLTRVPRPAEL-APLCGRRGLRTDIDATCTPRR ASSNQR-GLNQIWNVKKQSVYLMNLRK (SEQ ID NO: 10), which are both parts of the same naturally occurring polypeptide sequence corresponding to full-length hFXN (SEQ ID NO: 1). Following synthesis in a cell, the naturally occurring polypeptide sequence SEQ ID NO: 1 is processed in a two-step cleavage by the mitochondrial matrix processing peptidase (MPP) as the polypeptide sequence is imported into the mitochondrial matrix. As a result, mature hFXN (SEQ ID NO: 2) which does not comprise MTS is generated.

In other embodiments, an OTS comprised in a fusion protein of the present disclosure may be a heterologous sequence, i.e., not naturally associated with the protein of interest also comprised in the fusion protein. An OTS which is a heterologous sequence may be derived from a protein that is different from the protein of interest comprised in a fusion protein. For example, a fusion protein of the present disclosure may comprise FXN, e.g., mature hFXN, as a protein of interest and an MTS derived from citrate synthase or lipoamide dehydrogenase (LAD), as described in U.S. Pat. No. 8,912,147, the entire contents of which are incorporated herein by reference. A heterologous OTS may be a fragment from another protein, produced by cleavage, by recombinant technology, or it may be chemically synthesized, and further fused to the protein of interest.

In some embodiments, an OTS may comprise an amino acid sequence that has at least 85%, e.g., at least 90%, at least 95%, at least 96%, at least 97%, at least 98%, at least 99% or 100% sequence identity to a naturally occurring OTS domain of a native protein or a heterologous protein.

In some embodiments, a fusion protein of the present disclosure comprises an MTS, e.g., MWTLGRRAVAGL-LASPSPAQAQTLTRVPRPAELAPLCGRRGLRTDI-DATCTPRRASSNQ RGLNQIWNVKKQSVYLMNLRK (SEQ ID NO: 10). In other examples, the fusion protein of the present disclosure comprises an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 10. In some embodiments, a fusion protein may comprise a functional analogue, derivative or a fragment of SEQ ID NO: 10, as defined above.

In some embodiments, an OTS may be naturally associated with a protein of interest, e.g., a protein of interest in its naturally occurring form may comprise an OTS as a part of its sequence. One example of such protein of interest is full length hFXN (SEQ ID NO: 1), which comprises, as parts of its sequence, an MTS (SEQ ID NO: 10) and a mature hFXN (SEQ ID NO: 2). When a protein of interest comprising OTS as a part of its sequence is included in a fusion protein of the present disclosure, the fusion protein does not include another OTS, in addition to the OTS present as a part of the protein of interest.

In other embodiments, an OTS naturally associated with a protein of interest may be substituted with an OTS that does not occur naturally together with the protein of interest. For example, an MTS that is a part of full length hFXN and that is naturally associated with hFXN (SEQ ID NO: 10) may be substituted with a different OTS, e.g., an MTS derived from citrate synthase or lipoamide dehydrogenase (LAD), as described in U.S. Pat. No. 8,912,147. Thus, a fusion protein of the present disclosure may comprise mature hFXN (SEQ ID NO: 2) and an MTS that is different from SEQ ID NO: 10, such as an MTS derived from LAD.

In some embodiments, an OTS may be absent from a fusion protein of the present disclosure. For example, a fusion protein of the present disclosure may comprise a protein of interest, a CPP, e.g., HIV-TAT, and a TES, and lack an OTS. In some embodiments, a fusion protein of the present disclosure consists of a protein of interest, a CPP, e.g., HIV-TAT, and a TES.

Cell Penetrating Peptide (CPP)

The fusion proteins provided by the present disclosure also comprise a cell penetrating peptide (CPP). Cell penetrating peptides (CPPs) are short peptide sequences, typically between 5 and 30 amino acids long, that can facilitate cellular intake of various molecular cargo, such as proteins. CPPs may be polycationic, i.e., have an amino acid composition that either contains a high relative abundance of positively charged amino acids, such as lysine or arginine. CCPs may also be amphipathic, i.e., have sequences that contain an alternating pattern of polar/charged amino acids and non-polar, hydrophobic amino acids. CPPs may also be hydrophobic, i.e., contain only apolar residues with low net charge, or have hydrophobic amino acid groups that are crucial for cellular uptake.

A CPP useful in the context of the present disclosure may be any CPP known to a person skilled in the art. For example, a CPP comprised in the fusion protein of the present disclosure may be any CPP listed in the Database of Cell-Penetrating Peptides CPPsite 2.0, the entire contents of which are hereby incorporated herein by reference. For examples, CPPs useful in the context of the present disclosure may be selected from the group consisting of HIV-TAT (which may also be referred to herein as "TAT"), galanin, mastoparan, transportan, penetratin, polyarginine, or VP22. In one specific embodiment, the CPP is HIV-TAT. Table 4 below lists amino acid sequences of the exemplary CPPs.

In some embodiments, and without wishing to be bound by a specific theory, it is believed that a CPP comprised in the fusion protein of the present disclosure may be capable of interference with delivery of the protein of interest, also comprised in the fusion protein, to an organelle, e.g., a non-nuclear organelle. For example, as illustrated in Example 1 of the present disclosure, the TAT-GG-hFXN fusion protein is localized primarily in the cytosol and in the nucleus, but not in the mitochondria.

Target Enhancing Sequence (TES)

A fusion protein of the present disclosure also comprises a target enhancing sequence (TES). The term "target enhancing sequence" (TES), as used herein, refers to an amino acid sequence that, when present in a fusion protein comprising a CPP, prevents or attenuates interference by the CPP with delivery of the protein of interest to its appropriate subcellular location. For example, in some embodiments the TES, as used herein, refers to an amino acid sequence that facilitates the effective delivery of the protein of interest to the intended organelle (e.g., a non-nuclear organelle, such as mitochondria) by removing or attenuating interference with delivery of the protein of interest to the intended organelle-

TABLE 4

Exemplary CPPs and corresponding sequences

| SEQ ID NO. | CPP | Amino Acid Sequence |
| --- | --- | --- |
| 11 | HIV-TAT | YGRKKRRQRRR |
| 12 | Galanin | GWTLNSAGYLLGPHAVGNHRSFSDKNGLTS |
| 13 | Mastoparan | INLKALAALAKKIL-NH$_2$ |
| 14 | Transportan | GWTLNSAGYLLGKINLKALAALAKKIL |
| 15 | Penetratin | RQIKIWFQNRRMKWKK |
| 16 | Polyarginine | RRRRRRRRR |
| 17 | VP22 | DAATATRGRSAASRPTERPRAPARSASRPRRPVE |
| 83 | HIV-TAT (with N-terminal methionine) | MYGRKKRRQRRR |

In some examples, fusion proteins of the present disclosure may comprise an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of the amino acid sequences listed in Table 4, i.e., SEQ ID NO: 11, SEQ ID NO: 12, SEQ ID NO: 13, SEQ ID NO: 14, SEQ ID NO: 15, SEQ ID NO: 16, SEQ ID NO: 17 or SEQ ID NO: 83. In some examples, fusion proteins of the present disclosure may comprise a functional analogue, derivative or a fragment of the protein of interest of any one of the amino acid sequences listed in Table 4, i.e., SEQ ID NO: 11, SEQ ID NO: 12, SEQ ID NO: 13, SEQ ID NO: 14, SEQ ID NO: 15, SEQ ID NO: 16, SEQ ID NO: 17 or SEQ ID NO: 83.

In one embodiment, CPP comprised in the fusion protein of the present disclosure is HIV-TAT, e.g., SEQ ID NO: 11. In another specific example, CPP comprised in the fusion protein of the present disclosure is HIV-TAT (with N-terminal methionine), e.g., SEQ ID NO: 83. In another example, the fusion protein of the present disclosure comprises full-length FXN, e.g., SEQ ID NO: 1 and HIV-TAT as CPP. In another further example, the fusion protein of the present disclosure comprises mature FXN, e.g., SEQ ID NO: 2, as the protein of interest and HIV-TAT as CPP.

brought about by the CPP. Exemplary TES may include a protease sensitive sequence, also referred herein as "protease cleavable domain", "protease sensitive domain", "protease sensitive protein" or "protease sensitive peptide". Exemplary TES may also include a nuclear export signal peptide.

A protease-sensitive peptide may be also referred to as a "protease cleavage site". A protease-sensitive peptide or protease cleavage site refers to a specific amino acid motif within an amino acid sequence which is recognized and cleaved by a specific intracellular cytosolic protease.

As mentioned above, in some embodiments, in the fusion proteins of the present disclosure, CPP may be capable of interference with delivery to a non-nuclear organelle of the protein of interest comprised in the fusion protein. TES comprising a protease cleavage site facilitates removal of the CPP from the fusion protein, thereby preventing the interference by CPP. For example, as illustrated in FIG. 1, panel A, in some exemplary fusion proteins of the present disclosure, CPP may be located at the N-terminus of the fusion protein and TES may be fused at the C-terminal side of the CPP. When the fusion protein is exposed to an endogenous protease, the endogenous protease may cleave TES at the protease cleavage site, facilitating removal of the CPP from the N-terminus of the fusion protein. Similarly, as illustrated in FIG. 1, panel B, in other exemplary fusion proteins of the present disclosure, CPP may be located at the C-terminus of the fusion protein and TES may be fused at the N-terminal side of the CPP. When the fusion protein is exposed to an endogenous protease, the endogenous protease may cleave TES at the protease cleavage site, thereby removing the CPP from the C-terminus of the fusion protein.

Non-limiting examples of protease sensitive peptide or proteins that may be comprised in the TES include ubiquitin-like modifiers, such as ubiquitin, caspase cleavage domains, calpain cleavage domains, SUMO1, SUMO2, SUMO3, SUMO4, ISG15, Atg8, Atg12, and NEDD8.

Ubiquitin is highly conserved through eukaryote organisms, and the sequence of the human ortholog is:

(SEQ ID NO. 18)
MQIFVKTLTGKTITLEVEPSDTIENVKAKIQDKEGIPPDQQRLIFAGKQ

LEDGRTLSDYNIQKESTLHLVLRLRGG.

An exemplary caspase cleavage domain may comprise DEVD (SEQ ID NO. 19).

Nonlimiting examples of calpain cleavage domains are EPLFAERK (SEQ ID NO. 20) or LLVY (SEQ ID NO. 21).

Other exemplary protease cleavage sites may include any cleavage site described in Waugh, *Protein Expr. Purif.* 2011, 80(2):283-293, the entire contents of each of which are hereby incorporated herein by reference.

Exemplary proteases with specific protease cleavage sites may include ubiquitinase, caspase, calpain, enterokinase (light chain), enteropeptidase, prescission protease, human rhinovirus protease (HRV 3C), TEV (Tobacco Etch Virus) protease, TVMV (tobacco vein mottling virus) protease, Factor Xa protease, thrombin, and other proteases known to the person skilled in the art. Table 5 below includes some examples of amino acid sequences of protease cleavage sites and their respective proteases.

TABLE 5

Exemplary protease cleavage sites and corresponding proteases

| SEQ ID NO. | Protease | Cleavage Site Sequence |
| --- | --- | --- |
| 22 | Enterokinase (light chain)/ Enteropeptidase | DDDDK |
| 23 | PreScission Protease/human Rhinovirus protease (HRV 3C) | LEVLFQP |
| 24 | TEV protease | LEVLFGP |
| 25 | TEV protease | ENLYFQS |
| 26, 84 | TEV protease | Modified motifs based on the EXXYXQG (SEQ ID NO: 26) and EXXYXQS (SEQ ID NO: 84), where X may be any amino acid. |
| 27 | TVMV protease | ETVRFQS |
| 28 | Factor Xa protease | IEGR |
| 29 | Factor Xa protease | IDGR |
| 30 | Thrombin | LVPRS |
| 31 | Thrombin | LVPGS |

SUMO (Small Ubiquitin-like Modifier) proteins are a family of small proteins (about 100 amino acids in length and about 12 kDa in molecular weight) that are covalently attached to and detached from other proteins in cells to modify their function. The exact length and molecular weight vary between SUMO family members and depend on the organism from which the protein is derived. Examples of SUMO proteins are SUMO1, SUMO2, SUMO3 and SUMO4 with amino acid sequences as listed in Table 6 below.

TABLE 6

Amino acid sequences of SUMO proteins.

| SEQ ID NO. | SUMO Protein | Amino Acid Sequence |
| --- | --- | --- |
| 32 | SUMO1 | MSDQEAKPSTEDLGDKKEGEYIKLKVIGQDSSEIHFK VKMTTHLKKLKESYCQRQGVPMNSLRFLFEGQRIAD NHTPKELGMEEEDVIEVYQEQTGG |
| 33 | SUMO2 | MADEKPKEGVKTENNDHINLKVAGQDGSVVQFKIKR HTPLSKLMKAYCERQGLSMRQIRFRFDGQPINETDTP AQLEMEDEDTIDVFQQQTGGVY |
| 34 | SUMO3 | MSEEKPKEGVKTENDHINLKVAGQDGSVVQFKIKRH TPLSKLMKAYCERQGLSMRQIRPRFDGQPINETDTPA QLEMEDEDTIDVFQQQTGGVPESSLAGHSF |
| 35 | SUMO4 | MANEKPTEEVKTENNNHINLKVAGQDGSVVQFKIKR QTPLSKLMKAYCEPRGLSMKQIRFRFGGQPISGTDKP AQLEMEDEDTIDVFQQPTGGVY |

In some embodiments, TES comprised in a fusion protein of the present disclosure may comprise a protease sensitive peptide or protein. In some examples, the TES may comprise a sequence described herein, e.g., any one of SEQ ID NOS. listed in Table 5 (SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31 or SEQ ID NO: 84), or a sequence having at least 85%, e.g., at least 90% or at least 95% sequence identity with any one of SEQ ID NOS. listed in Table 5 (SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30,SEQ ID NO: 31, or SEQ ID NO: 84). In some examples, fusion proteins of the present disclosure may comprise a functional analogue, derivative or a fragment of the protein of interest of any one of SEQ ID NOS. listed in Table 5 (SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31 or SEQ ID NO: 84).

In other embodiments, TES comprised in a fusion protein of the present disclosure may comprise a ubiquitin-like modifier. In some examples, the TES may comprise a sequence described herein, e.g., any one of SEQ ID NOS. listed in Table 6 (SEQ ID NO: 32, SEQ ID NO: 33, SEQ ID NO: 34 or SEQ ID NO: 35), or a sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98% or at least 99% sequence identity with any one of SEQ ID NOS. listed in Table 6 (SEQ ID NO: 32, SEQ ID NO: 33, SEQ ID NO: 34 or SEQ ID NO: 35). In some examples, fusion proteins of the present disclosure may comprise a functional analogue, derivative or a fragment of the protein of interest of any one of SEQ ID NOS. listed in Table 6 (SEQ ID NO: 32, SEQ ID NO: 33, SEQ ID NO: 34 or SEQ ID NO: 35).

Amino acid sequences having at least 85% sequence identity to any of SEQ ID NOS. 22-31 or any of SEQ ID NOS. 32-35 may be found in one or more of the following databases: GenBank, Protein Data Bank (PDB), SwissProt, Protein Information Resource (PIR), or Protein Research Foundation (PRF).

In some examples, TES comprised in a fusion protein of the present disclosure may comprise a nuclear export signal (NES). NES, when present in a protein, targets the protein for export from the cell nucleus into the cytoplasm. The export of the protein occurs through the nuclear pore complex via nuclear transport. Accordingly, in the context of the present disclosure, when a CPP present in a fusion protein facilitates delivery of the protein of interest to nucleus, TES counteracts said action by the CPP by facilitating export of the protein of interest from the nucleus into cytoplasm. In this manner, TES increases the likelihood that the protein of interest will be delivered to a non-nuclear organelle of interest, i.e., to mitochondria.

In some examples, NES may be a peptide comprising four hydrophobic residues which may not necessarily be in tandem. For example, NES may be a peptide comprising an amino acid sequence LXXXLXXLXL, where "L" is a hydrophobic residue (often leucine) and "X" is any amino acid other than leucine. Without wishing to be bound by a specific theory, it is believed that the spacing of the hydrophobic residues in an NES may be explained by examining known structures that contain an NES, as the critical residues usually lie in the same face of adjacent secondary structures within a protein, which allows them to interact with the exportin.

Any NES known to one of ordinary skill in the art is encompassed by the present disclosure, including NES listed in the NESbase version 1.0, a database of nuclear export signals, the entire contents of which are hereby incorporated herein by reference. Table 7 lists certain exemplary NESs and their corresponding sequences.

TABLE 7

Exemplary NESs and corresponding sequences.

| SEQ ID NO. | SUMO Protein | Amino Acid Sequence |
| --- | --- | --- |
| 36 | NES1 | LALKLAGLDL |
| 37 | NES2 | LQKKLEELEL |

TABLE 7-continued

Exemplary NESs and corresponding sequences.

| SEQ ID NO. | SUMO Protein | Amino Acid Sequence |
|---|---|---|
| 38 | NES3 | MQELSNILNL |
| 39 | NES4 | LPPLERLTL |
| 40 | NES5 | LCQAFSDVIL |
| 41 | NES6 | RTFDMHSLESSLIDIMR |
| 42 | NES7 | TNLEALQKKLEELELDE |
| 43 | NES8 | RSFEMTEFNQALEEIKG |

In some embodiments of the present disclosure, TES may comprise a sequence described herein, e.g., any one of SEQ ID NOS. listed in Table 7 (SEQ ID NO: 36, SEQ ID NO: 37, SEQ ID NO: 38, SEQ ID NO: 39, SEQ ID NO: 40, SEQ ID NO: 41, SEQ ID NO: 42 or SEQ ID NO: 43), or a sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98% or at least 99% sequence identity with any one of SEQ ID NOS. listed in Table 7 (SEQ ID NO: 36, SEQ ID NO: 37, SEQ ID NO: 38, SEQ ID NO: 39, SEQ ID NO: 40, SEQ ID NO: 41, SEQ ID NO: 42 or SEQ ID NO: 43). In some examples, fusion proteins of the present disclosure may comprise a functional analogue, derivative or a fragment of the protein of interest of any one of SEQ ID NOS. listed in Table 7 (SEQ ID NO: 36, SEQ ID NO: 37, SEQ ID NO: 38, SEQ ID NO: 39, SEQ ID NO: 40, SEQ ID NO: 41, SEQ ID NO: 42 or SEQ ID NO: 43).

Amino acid sequences having at least 85% sequence identity to any of SEQ ID NOS. 36-43 may be found in one or more of the following databases: GenBank, Protein Data Bank (PDB), SwissProt, Protein Information Resource (PIR), or Protein Research Foundation (PRF).

Fusion Protein

In an embodiment of the disclosure a fusion protein provided herein may comprise a protein of interest to be delivered to a non-nuclear organelle, an organelle targeting sequence (OTS), a cell penetrating peptide (CPP), and a target enhancing sequence (TES), wherein the CPP is capable of interference with delivery of the protein of interest to the non-nuclear organelle and wheren the TES prevents said interference by the CPP. In some examples, the protein of interest, OTS, CPP and TES may be directly fused to each other directly to form a single polypeptide chain. In other examples, the protein of interest, OTS, CPP and TES may be fused to each other via a spacer to form a single polypeptide chain.

In one specific embodiment, the protein of interest is FXN, e.g., SEQ ID NO: 2. In one specific embodiment, the OTS is MTS, e.g., SEQ ID NO: 10. In one specific embodiment, the CPP is HIV-TAT, e.g., SEQ ID NO: 11. In one specific embodiment, the TES may be a protease sensitive peptide or proteins, e.g., SUMO 1 (e.g., SEQ ID NO: 32); ubiquitin (e.g., SEQ ID NO: 18); a caspase cleavage site, e.g., DEVD (SEQ ID NO: 19) or a calpain cleavage site, e.g., EPLFAERK (SEQ ID NO: 20) or LLVY (SEQ ID NO: 21). In one specific embodiment, the TES may be an NES, e.g., NES1 (SEQ ID NO: 36) or NES2 (SEQ ID NO: 37).

In an embodiment of the disclosure a fusion protein provided herein may comprise a protein of interest to be delivered to a cell, a cell penetrating peptide (CPP) and a target enhancing sequence (TES). In some embodiments, the CPP is capable of interference with the delivery of the protein of interest to a cell and/or to a cellular organelle, and the TES prevents said interference by the CPP. In some examples, the protein of interest, CPP and TES may be directly fused to each other directly to form a single polypeptide chain. In other examples, the protein of interest, CPP and TES may be fused to each other via a spacer to form a single polypeptide chain.

In one specific embodiment, the protein of interest is PARKIN, e.g., SEQ ID NO: 7. In one specific embodiment, the CPP is HIV-TAT, e.g., SEQ ID NO: 11. In one specific embodiment, the TES may be a protease sensitive peptide or proteins, e.g., SUMO 1 (e.g., SEQ ID NO: 32); ubiquitin (e.g., SEQ ID NO: 18); a caspase cleavage site, e.g., DEVD (SEQ ID NO: 19), or a calpain cleavage site, e.g., EPLFAERK (SEQ ID NO: 20), or LLVY (SEQ ID NO: 21). In one specific embodiment, the TES may be an NES, e.g., NES1 (SEQ ID NO: 36) or NES2 (SEQ ID NO: 37).

Figure 2:
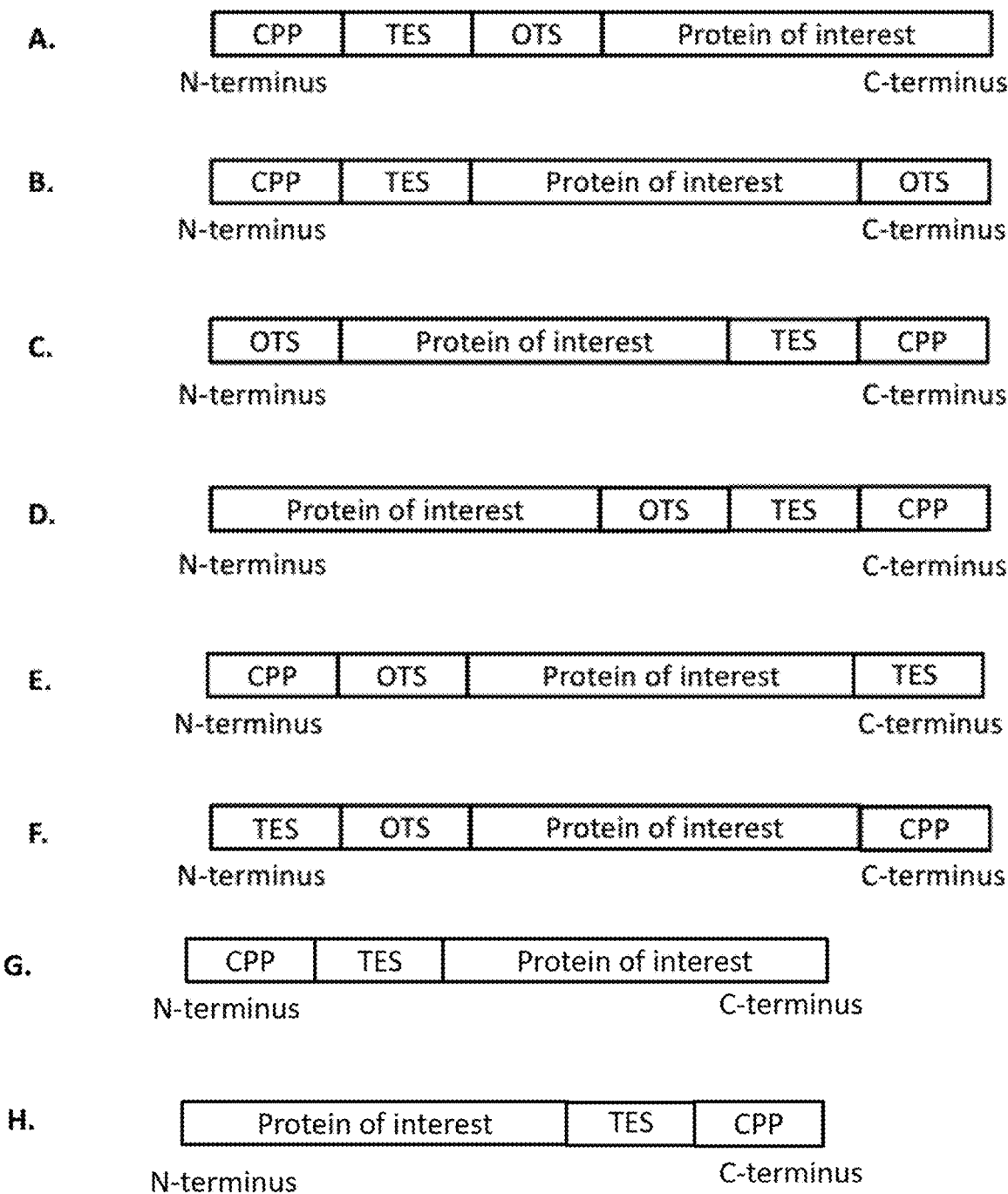
FIG. 2 is a schematic illustrating configurations of various domains in the fusion proteins of the present disclosure.

In the fusion proteins provided by the present disclosure, the positions of protein of interest, OTS (if present), CPP and TES relative to each other and the N-terminus and the C-terminus may vary. Exemplary fusion proteins comprising different relative configurations of the protein of interest, OTS, CPP and TES are shown in FIG. 2. For example, as illustrated in FIG. 2, Panel A, an exemplary fusion protein may comprise, starting from the N-terminus, CPP, followed by TES, followed by OTS, followed by protein of interest at the C-terminus. In another example illustrated in FIG. 2, Panel B, a fusion protein may comprise, starting from the N-terminus, CPP, followed by TES, followed by the protein of interest, followed by OTS at the C-terminus. In another example illustrated in FIG. 2, Panel C, an exemplary fusion protein may comprise, starting from the N-terminus, OTS, followed by the protein of interest, followed by TES, followed by CPP at the C-terminus. In another example illustrated in FIG. 2, Panel D, a fusion protein may comprise, starting from the N-terminus, protein of interest, followed by OTS, followed by TES, followed by CPP at the C-terminus. In another example illustrated in FIG. 2, Panel E, a fusion protein may comprise, starting from the N-terminus, CPP, followed by OTS, followed by protein of interest, followed by TES. In yet another example illustrated in FIG. 2, Panel F, a fusion protein may comprise, starting at the N-terminus, TES, followed by OTS, followed by protein of interest, followed by CPP. In yet another example illustrated in FIG. 2, Panel G, a fusion protein may comprise, starting at the N-terminus, CPP, followed by TES, followed by protein of interest. In yet another example illustrated in FIG. 2, Panel H, a fusion protein may comprise, starting at the N-terminus, protein of interest, followed by TES, followed by CPP.

In some examples, in fusion proteins of the present disclosure, various domains (i.e., protein of interest, CPP, OTS, if present, and TES) may be fused to each other directly to form a single polypeptide chain. As used herein, the term "directly" means that there are no interfering amino acids between the C-terminal amino acid of the first domain and the N-terminal amino acid of the second domain that are directly fused to each other. That is, the (first or last) amino acid at the terminal end (N or C-terminal end) of the first domain may fused to the (first or last) amino acid at the terminal end (N or C-terminal end) of the second domain, forming a single polypeptide. In other words, in this embodiment, the last amino acid of the C-terminal end of a first domain is linked directly by a covalent bond to the first amino acid of the N-terminal end of the second domain, or the first amino acid of the N-terminal end of the fist domain is directly linked by a covalent bond to the last amino acid of the C-terminal end of to form a single polypeptide.

In other examples, in fusion proteins of the present disclosure, various domains (i.e., protein of interest, CPP, OTS, if present, and TES) may be fused together via a spacer to form a single polypeptide chain. As used herein, the term "spacer", which may be used interchangeably with the term "linker", refers to a sequence of at least one amino acid that links together two domains to form a single polypeptide chain. When included in a fusion protein, a spacer may prevent steric hindrances. In some example, length of a spacer or a linker may vary from 2 to 31 amino acids, e.g., from 2-10 amino acids, from 5 to 15 amino acids, from 10 to 25 amino acids or from 12 to 31 amino acids. One of ordinary skill in the art would be able to determine an appropriate linker or spacer length for each specific fusion protein, such that the linker or spacer does not impose any constraints on the conformation of the fusion protein, or interactions of the domains of the fusion protein with each other. A linker or a spacer may be a previously described endogenous and naturally occurring linker or spacer that plays a role in separating domains within a protein or for the formation of dimers. Alternatively a linker or a spacer may be an artificially designed linker or a spacer useful in recombinant technology for the generation of fusion proteins. Examples of linkers or spacers useful within the context of the present disclosure are shown in Table 8 below.

TABLE 8

Exemplary linkers or spacers.

| SEQ ID NO. | Amino Acid Sequence |
| --- | --- |
| 44 | GGGGSLVPRGSGGGGS |
| 45 | GSGSGS |
| 46 | GSGSGSGSGSGSGSGS |

TABLE 8-continued

Exemplary linkers or spacers.

| SEQ ID NO. | Amino Acid Sequence |
| --- | --- |
| 47 | GGSGGHMGSGG |
| 48 | GGSGGSGGSGG |
| 49 | GGSGG |
| 50 | GGGSEGGGSEGGGSEGGG |
| 51 | AAGAATAA |
| 52 | GGGGG |
| 53 | GGSSG |
| 54 | GSGGGTGGGSG |
|  | GT |
|  | GG |

In some embodiments, a fusion protein of the present disclosure may comprise a GG (Gly-Gly) linker. For example, a fusion protein of the present disclosure may comprise a GG linker connecting a CPP domain to the TES domain, e.g., a protease cleavage site. In another example, a fusion protein of the present disclosure may comprise a GG linker connecting a CPP domain to the OTS domain, e.g., MTS. In one specific embodiment, TAT-CPP is connected to MTS-FXN via a GG linker.

Exemplary fusion proteins of the present disclosure and their corresponding sequences are listed in Table 9 below.

TABLE 9

Exemplary fusion proteins.

| SEQ ID NO. | Fusion Protein | Sequence |
| --- | --- | --- |
| 55 | TAT-GG-SUMO1-hFXN | MYGRKKRRQRRRGGMSDQEAKPSTEDLGDKKEGEYIKLKVI GQDSSEIHFKVKMTTHLKKLKESYCQRQGVPMNSLRFLFEGQ RIADNHTPKELGMEEEDVIEVYQEQTGGMWTLGRRAVAGLL ASPSPAQAQTLTRVPRPAELAPLCGRRGLRTDIDATCTPRRASS NQRGLNQIWNVKKQSVYLMNLRKSGTLGHPGSLDETTYERL AEETLDSLAEFFEDLADKPYTIAEDYDVSFGSGVLTVKLGGDLG TYVINKQTPNKQIWLSSPSSGPKRYDWTGKNWVYSHDGVSLH ELLAAELTKALKTKLDLSSLAYSGKDA |
| 81 | TAT-GG-SUMO-hFXN | MYGRKKRRQRRRGGSDSEVNQEAKPEVKPEVKPETHINLKVS DGSSEIFFKIKKTTPLRRLMEAFAKRQGKEMDSLRFLYDGIRIQ ADQTPEDLDMEDNDIIEAHREQIGGMWTLGRRAVAGLLASPS PAQAQTLTRVPRPAELAPLCGRRGLRTDIDATCTPRRASSNQR GLNQIWNVKKQSVYLMNLRKSGTLGHPGSLDETTYERLAEET LDSLAEFFEDLADKPYTIAEDYDVSFGSGVLTVKLGGDLGTYVI NKQTPNKQIWLSSPSSGPKRYDWTGKNWVYSHDGVSLHELL AAELTKALKTKLDLSSLAYSGKDA |
| 56 | TAT-GG-Ubiquitin-hFXN | MYGRKKRRQRRRGGMQIFVKTLTGKTITLEVEPSDTIENVKA KIQDKEGIPPDQQRLIFAGKQLEDGRTLSDYNIQKESTLHLVLR LRGGMWTLGRRAVAGLLASPSPAQAQTLTRVPRPAELAPLCG RRGLRTDIDATCTPRRASSNQRGLNQIWNVKKQSVYLMNLRK SGTLGHPGSLDETTYERLAEETLDSLAEFFEDLADKPYTFEDY DVSFGSGVLTVKLGGDLGTYVINTKQTPNKQIWLSSPSSGPKRY DWTGKNWVYSHDGVSLHELLAAELTKALKTKLDLSSLAYSG KDA |
| 57 | TAT-GG-DEVD-hFXN | MYGRKKRRQRRRGGDEVDMWTLGRRAVAGLLASPSPAQAQ TLTRVPRPAELAPLCGRRGLRTDIDATCTPRRASSNQRGLNQI WNVKKQSVYLMNLRKSGTLGHPGSLDETTYERLAEETLDSLA EFFEDLADKPYTIAEDYDVSFGSGVLTVKLGGDLGTYVINKQTP NKQIWLSSPSSGPKRYDWTGKNWVYSHDGVSLHELLAAELT KALKTKLDLSSLAYSGKDA |

TABLE 9-continued

Exemplary fusion proteins.

| SEQ ID NO. | Fusion Protein | Sequence |
|---|---|---|
| 58 | TAT-GG-EPLFAERK-hFXN | MYGRKKRRQRRRGGEPLFAERKMWTLGRRAVAGLLASPSPA QAQTLTRVPRPAELAPLCGRRGLRTDIDATCTPRRASSNQRGL NQIWNVKKQSVYLMNLRKSGTLGHPGSLDETTYERLAEETLD SLAEFFEDLADKPYTIAEDYDVSFGSGVLTVKLGGDLGTYVINK QTPNKQIWLSSPSSGPKRYDWTGKNWVYSHDGVSLHELLAAE LTKALKTKLDLSSLAYSGKDA |
| 59 | TAT-GG-LLVY-hFXN | MYGRKKRRQRRRGGLLVYMWTLGRRAVAGLLASPSPAQAQ TLTRVPRPAELAPLCGRRGLRTDIDATCTPRRASSNQRGLNQI WNVKKQSVYLMNLRKSGTLGHPGSLDETTYERLAEETLDSLA EFFEDLADKPYTIAEDYDVSFGSGVLTVKLGGDLGTYVINKQTP NKQIWLSSPSSGPKRYDWTGKNWVYSHDGVSLHELLAAELT KALKTKLDLSSLAYSGKDA |
| 60 | TAT-GG-hFXN-NES1 | MYGRKKRRQRRRGGMWTLGRRAVAGLLASPSPAQAQTLTR VPRPAELAPLCGRRGLRTDIDATCTPRRASSNQRGLNQIWNVK KQSVYLMNLRKSGTLGHPGSLDETTYERLAEETLDSLAEFFED LADKPYTIAEDYDVSFGSGVLTVKLGGDLGTYVINKQTPNKQI WLSSPSSGPKRYDWTGKNWVYSHDGVSLHELLAAELTKALK TKLDLSSLAYSGKDALALKLAGLDL |
| 61 | TAT-GG-hFXN-NES2 | MYGRKKRRQRRRGGMWTLGRRAVAGLLASPSPAQAQTLTR VPRPAELAPLCGRRGLRTDIDATCTPRRASSNQRGLNQIWNVK KQSVYLMNLRKSGTLGHPGSLDETTYERLAEETLDSLAEFFED LADKPYTIAEDYDVSFGSGVLTVKLGGDLGTYVINKQTPNKQI WLSSPSSGPKRYDWTGKNWVYSHDGVSLHELLAAELTKALK TKLDLSSLAYSGKDALQKKLEELEL |
| 69 | TAT-GG-Ubiquitin-PARKIN | MYGRKKRRQRRRGGMQIFVKTLTGKTITLEVEPSDTIENVKA KIQDKEGIPPDQQRLIFAGKQLEDGRTLSDYNIQKESTLHLVLR LRGGMIVFVRFNSSHGFPVEVDSDTSIFQLKEVVAKRQGVPAD QLRVIFAGKELRNDWTVQNCDLDQQSIVHIVQRPWRKGQEM NATGGDDPRNAAGGCEREPQSLTRVDLSSSVLPGDSVGLAVIL HTDSRKDSPPAGSPAGRSIYNSFYVYCKGPCQRVQPGKLRVQ CSTCRQATLTLTQGPSCWDDVLIPNRMSGECQSPHCPGTSAEF FFKCGAHPTSDKETSVALHLIATNSRNITCITCTDVRSPVLVFQ CNSRHVICLDCFHLYCVTRLNDRQFVHDPQLGYSLPCVAGCP NSLIKELHHFRILGEEQYNRYQQYGAEECVLQMGGVLCPRPG CGAGLLPEPDQRKVTCEGGNGLGCGFAFCRECKEAYHEGECS AVIALASGTTTQAYRVDERAAEQARWEAASKETIKKTTKPCPR CHVPVEKNGGCMHMKCPQPQCRLEWCWNCGCEWNRVCMG DHWFDV |
| 70 | TAT-GG-EPLFAERK-PARKIN | MYGRKKRRQRRRGGEPLFAERKMIVFVRFNSSHGFPVEVDSD TSIFQLKEVVAKRQGVPADQLRVIFAGKELRNDWTVQNCDLD QQSIVHIVQRPWRKGQEMNATGGDDPRNAAGGCEREPQSLTR VDLSSSVLPGDSVGLAVILHTDSRKDSPPAGSPAGRSIYNSFYV YCKGPCQRVQPGKLRVQCSTCRQATLTLTQGPSCWDDVLIPN RMSGECQSPHCPGTSAEFFFKCGAHPTSDKETSVALHLIATNS RNITCITCTDVRSPVLVFQCNSRHVICLDCFHLYCVTRLNDRQF VHDPQLGYSLPCVAGCPNSLIKELHHFRILGEEQYNRYQQYGA EECVLQMGGVLCPRPGCGAGLLPEPDQRKVTCEGGNGLGCGF AFCRECKEAYHEGECSAVFEASGTTTQAYRVDERAAEQARW EAASKETIKKTTKPCPRCHVPVEKNGGCMHMKCPQPQCRLE WCWNCGCEWNRVCMGDHWFDV |
| 71 | TAT-GG-PARKIN-NES1 | MYGRKKRRQRRRGGMIVFVRFNSSHGFPVEVDSDTSIFQLKE VVAKRQGVPADQLRVIFAGKELRNDWTVQNCDLDQQSIVHIV QRPWRKGQEMNATGGDDPRNAAGGCEREPQSLTRVDLSSSV LPGDSVGLAVILHTDSRKDSPPAGSPAGRSIYNSFYVYCKGPC QRVQPGKLRVQCSTCRQATLTLTQGPSCWDDVLIPNRMSGEC QSPHCPGTSAEFFFKCGAHPTSDKETSVALHLIATNSRNITCITC TDVRSPVLVFQCNSRHVICLDCFHLYCVTRLNDRQFVHDPQL GYSLPCVAGCPNSLIKELHHFRILGEEQYNRYQQYGAEECVLQ MGGVLCPRPGCGAGLLPEPDQRKVTCEGGNGLGCGFAFCREC KEAYHEGECSAVIALASGTTTQAYRVDERAAEQARWEAASKE TIKKTTKPCPRCHVPVEKNGGCMHMKCPQPQCRLEWCWNCG CEWNRVCMGDHWFDVLALKLAGLDL |

In some embodiments, the fusion protein provided by the present disclosure comprises or consists of any one sequence as listed in Table 9, i.e., any of SEQ ID NOS: 55-61, 69-71 or 81 (SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 69, SEQ ID NO: 70, SEQ ID NO: 71 or SEQ ID NO: 81). In some embodiments, the fusion protein provided by the present disclosure comprises or consists of an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one sequence listed in Table 9, e.g., any of SEQ ID NOS. 55-61, 69-71 or 81 (SEQ ID NO: 55, SEQ ID NO: 56, SEQ ID NO: 57, SEQ ID NO: 58, SEQ ID NO: 59, SEQ ID NO: 60,SEQ ID NO: 61, SEQ ID NO: 69, SEQ ID NO: 70, SEQ ID NO: 71 or SEQ ID NO: 81). In some embodiments, the fusion protein of the present disclosure may comprise or consist of a functional analogue, derivative or a fragment of any one sequence listed in Table 9, i.e., any of SEQ ID NOS: 55-61 (SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 69, SEQ ID NO: 70, SEQ ID NO: 71 or SEQ ID NO: 81).

In one embodiment, the fusion protein comprises or consists of TAT-GG-SUMO1-hFXN having an amino acid sequence as set forth in SEQ ID NO: 55. In one embodiment, the fusion protein comprises or consists of TAT-SS_SUMO-hFXN having an amino acid sequence as set forth in SEQ ID NO: 81. In one embodiment, the fusion protein comprises or consists of TAT-GG-Ubiquitin-hFXN having an amino acid sequence as set forth in SEQ ID NO: 56. In one embodiments, the fusion protein comprises or consists of TAT-GG-DEVD-hFXN having an amino acid sequence as set forth in SEQ ID NO: 57. In one embodiment, the fusion protein comprises or consists of TAT-GG-EPLFAERK-hFXN having an amino acid sequence as set forth in SEQ ID NO: 58. In one embodiment, the fusion protein comprises or consists of TAT-GG-LLVY-hFXN having an amino acid sequence as set forth in SEQ ID NO: 59. In one embodiment, the fusion protein comprises or consists of TAT-GG-hFXN-NES1 having an amino acid sequence as set forth in SEQ ID NO: 60. In one embodiment, the fusion protein comprises or consists of TAT-GG-hFXN-NES2 having an amino acid sequence as set forth in SEQ ID NO: 61. In one embodiment, the fusion protein comprises or consists of TAT-GG-Ubiquitin-PARKIN having an amino acid sequence as set forth in SEQ ID NO: 69. In one embodiment, the fusion protein comprises or consists of TAT-GG-EPLFAERK-PARKIN having an amino acid sequence as set forth in SEQ ID NO: 70. In one embodiment, the fusion protein comprises or consists of TAT-PARKIN-NES1 having an amino acid sequence as set forth in SEQ ID NO: 71.

In some embodiments, the fusion protein provided by the present disclosure comprises: 1) an amino acid sequence having at least 85%, at least 90%, at least 95%, or at least 99% sequence identity to full-length hFXN (SEQ ID NO: 1) as protein of interest; 2) any CPP as described herein; and 3) any TES as described herein.

In some embodiments, the fusion protein provided by the present disclosure comprises: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11 or SEQ ID NO: 83); and 3) any TES as described herein.

For example, the fusion protein of the present disclosure may comprise 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11 or SEQ ID NO: 83); and 3) an amino acid sequence having at least 85%, at least 90%, at least 95% or at least 99% to Ubiquitin (SEQ ID NO: 18).

For example, the fusion protein of the present disclosure may comprise 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to a calpain cleavage domain of SEQ ID NO: 20.

For example, the fusion protein of the present disclosure may comprise 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11 or SEQ ID NO: 83); and 3) an amino acid sequence having at least 85%, at least 90%, at least 95% or at least 99% to any one of SEQ ID NO 19, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, or SEQ ID NO: 31, SEQ ID NO: 32, SEQ ID NO: 33, SEQ ID NO: 34 and SEQ ID NO: 35.

In some embodiments, the fusion protein provided by the present disclosure comprises: 1) an amino acid sequence having at least 85%, at least 90%, at least 95%, or at least 99% sequence identity to PARKIN (SEQ ID NO: 7) as protein of interest; 2) any CPP as described herein; and 3) any TES as described herein.

In some embodiments, the fusion protein provided by the present disclosure comprises: 1) an amino acid sequence having at least 85%, at least 90%, at least 95%, or at least 99% sequence identity to PARKIN (also referred to herein as "PARK2 protein", SEQ ID NO: 7) as protein of interest; 2) an amino acid sequence having at least 85%, at least 90%, at least 95% or at least 99% to TAT-HIV (SEQ ID NO: 11); and 3) any TES as described herein.

For example, the fusion protein of the present disclosure may comprise 1) an amino acid sequence having at least 85%, at least 90%, at least 95%, or at least 99% sequence identity to PARKIN (SEQ ID NO: 7) as protein of interest; 2) an amino acid sequence having at least 85%, at least 90%, at least 95% or at least 99% to TAT-HIV (SEQ ID NO: 11 or SEQ ID NO: 83); and 3) an amino acid sequence having at least 85%, at least 90%, at least 95% or at least 99% to Ubiquitin (SEQ ID NO: 18).

For example, the fusion protein of the present disclosure may comprise 1) an amino acid sequence having at least 85%, at least 90%, at least 95%, or at least 99% sequence identity to PARKIN (SEQ ID NO: 7) as protein of interest; 2) an amino acid sequence having at least 85%, at least 90%, at least 95% or at least 99% to TAT-HIV (SEQ ID NO: 11 or SEQ ID NO: 83); and 3) an amino acid sequence having at least 85%, at least 90%, at least 95% or at least 99% to a calpain cleavage domain of SEQ ID NO: 20.

For example, the fusion protein of the present disclosure may comprise 1) an amino acid sequence having at least 85%, at least 90%, at least 95%, or at least 99% sequence identity to PARKIN (SEQ ID NO: 7) as protein of interest; 2) an amino acid sequence having at least 85%, at least 90%, at least 95% or at least 99% to TAT-HIV (SEQ ID NO: 11 or SEQ ID NO: 83); and 3) an amino acid sequence having at least 85%, at least 90%, at least 95% or at least 99% to any one of SEQ ID NO 19, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, or SEQ ID NO: 31, SEQ ID NO: 32, SEQ ID NO: 33, SEQ ID NO: 34 and SEQ ID NO: 35.

In some embodiments, one or more of the fusion proteins provided by the present disclosure may also include a post-translational modification characteristic of eukaryotic cells, e.g., mammalian cells, e.g., human cells. In some embodiments, the fusion protein may comprise one or more (e.g., 2, 3, 4, 5, 6, 7, 8, 9, 10, or more) post-translational modifications, such as glycosylation, phosphorylation, acetylation, or combinations thereof. In some embodiments, glycosylation may include the addition of a glycosyl group to arginine, asparagine, cysteine, hydroxylysine, serine, threonine, tyrosine, or tryptophan. The glycosylation may comprise, e.g., O-linked glycosylation or N-linked glycosylation. Levels of glycosylation of a fusion protein of the disclosure may be assessed in vitro using SDS-PAGE gels and a Western Blot using a modification of Periodic acid-Schiff (PAS) methods. Cellular localization of a fusion protein that may comprise glycosylation may be accomplished by utilizing lectin fluorescent conjugates known in the art. Phosphorylation that may be present in a fusion protein of the present disclosure may be assessed by Western blot using phospho-specific antibodies.

Post-translation modifications that may be present in fusion protein of the present disclosure may also include conjugation to a hydrophobic group (e.g., myristoylation, palmitoylation, isoprenylation, prenylation, or glypiation), conjugation to a cofactor (e.g., lipoylation, flavin moiety (e.g., FMN or FAD), heme C attachment, phosphopantetheinylation, or retinylidene Schiff base formation), diphthamide formation, ethanolamine phosphoglycerol attachment, hypusine formation, acylation (e.g. O-acylation, N-acylation, or S-acylation), formylation, acetylation, alkylation (e.g., methylation or ethylation), amidation, butyrylation, gamma-carboxylation, malonylation, hydroxylation, iodination, nucleotide addition such as ADP-ribosylation, oxidation, phosphate ester (O-linked) or phosphoramidate (N-linked) formation, (e.g., phosphorylation or adenylylation), propionylation, pyroglutamate formation, S-glutathionylation, S-nitrosylation, succinylation, sulfation, IS Gylation, SUMOylation, ubiquitination, neddylation, or a chemical modification of an amino acid (e.g., citrullination, deamidation, eliminylation, or carbamylation), formation of a disulfide bridge, racemization (e.g., of proline, serine, alanine, or methionine).

Nucleic Acids

The present disclosure also provides a nucleic acid encoding a fusion protein as described above, or any variants thereof.

As used herein, the term "nucleic acid(s)" is interchangeable with the term "polynucleotide(s)" and generally refers to any polyribonucleotide or poly-deoxyribonucleotide, which may be unmodified RNA or DNA or modified RNA or DNA or any combination thereof. The term "nucleic acid(s)" include, without limitation, single- and double-stranded nucleic acids.

The present disclosure provides fusion proteins as described herein, or variants thereof. Variants provided by the present disclosure may include conservatively substituted variants that apply to both amino acid and nucleic acid sequences. With respect to nucleic acid sequences, conservatively modified variants refer to those nucleic acids which encode identical or essentially identical amino acid sequences. Specifically, degenerate codon substitutions may be achieved by generating sequences in which the third position of one or more selected (or all) codons is substituted with mixed base and/or deoxyinosine residues. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are silent variations, which are one species of conservatively modified variations. Every nucleic acid sequence described herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to encode a functionally identical polypeptide. Accordingly, each silent variation of a nucleic acid which encodes a polypeptide is implicit in each described sequence.

With regard to conservative substitution of amino acid sequences, an ordinary artisan may recognize that individual substitution(s), deletion(s) or addition(s) to a nucleic acid, peptide, polypeptide, or protein sequence which alters, adds or deletes a single amino acid or a small percentage of amino acids in the encoded sequence is a conservatively modified variant where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following groups each contain amino acids that are conservative substitutions for one another:

1) alanine (A), glycine (G);
2) serine (S), threonine (T);
3) aspartic acid (D), glutamic acid (E);
4) asparagine (N), glutamine (Q);
5) cysteine (C), methionine (M);
6) arginine (R), lysine (K), histidine (H);
7) isoleucine (I), leucine (L), valine (V); and
8) phenylalanine (F), tyrosine (Y), tryptophan (W).

Listed in Table 10 below are certain exemplary nucleic acids encoding fusion proteins of the present disclosure.

TABLE 10

Nucleic acids encoding fusion proteins of the disclosure.

| SEQ ID NO. | Fusion Protein | Sequence |
|---|---|---|
| 62 | TAT-GG-SUMO1-hFXN | ATGTACGGCCGCAAGAAGCGGAGACAGAGGCGCCGGGGAGGA ATGTCCGACCAGGAGGCCAAGCCCTCTACCGAGGACCTGGGCG ATAAGAAGGAGGGCGAGTACATCAAGCTGAAAGTGATCGGCC AGGATAGCTCCGAGATCCACTTCAAGGTGAAGATGACCACACA CCTGAAGAAGCTGAAGGAGTCTTATTGCCAGCGGCAGGGCGTG CCAATGAACAGCCTGAGATTCCTGTTTGAGGGCCAGAGGATCG CCGACAATCACACCCCCAAGGAGCTGGGCATGGAGGAGGAGG ATGTGATCGAGGTGTATCAGGAGCAGACCGGCGGCATGTGGAC ACTGGGCAGAAGGGCAGTGGCCGGCCTGCTGGCATCCCCATCT CCTGCACAGGCACAGACCCTGACACGCGTGCCACGGCCCGCAG AGCTGGCACCACTGTGCGGCCGGAGAGGCCTGAGGACAGACAT CGATGCCACCTGTACACCTAGAAGGGCCTCTAGCAACCAGCGG GGCCTGAACCAGATCTGGAATGTGAAGAAGCAGTCCGTGTACC TGATGAATCTGAGAAAGAGCGGCACCCTGGGACACCCTGGCTC CCTGGACGAGACAACATATGAGAGGCTGGCCGAGGAGACACTG GATTCTCTGGCCGAGTTCTTTGAGGACCTGGCCGATAAGCCATA CACCTTCGAGGACTATGATGTGAGCTTTCCGGCGTGCTGA CAGTGAAGCTGGGAGGCGACCTGGGCACCTACGTGATCAACAA GCAGACACCTAATAAGCAGATCTGGCTGTCCTCTCCTAGCTCCG GCCCAAAGCGGTACGACTGGACCGGCAAGAACTGGGTGTATTC TCACGATGGCGTGAGCCTGCACGAGCTGCTGGCAGCAGAGCTG ACCAAGGCCCTGAAGACAAAGCTGGACCTGTCTAGCCTGGCCT ATAGCGGCAAGGATGCCTGA |
| 63 | TAT-GG-Ubiquitin-hFXN | ATGTACGGCCGGAAGAAGCGGAGACAGAGGCGCCGGGGAGGA ATGCAGATCTTCGTGAAGACCCTGACAGGCAAGACCATCACAC TGGAGGTGGAGCCCTCTGACACCATCGAGAACGTGAAGGCCAA GATCCAGGACAAGGAGGGCATCCCCCCTGATCAGCAGCGCCTG ATCTTTGCAGGCAAGCAGCTGGAGGACGGACGGACCCTGTCTG ATTATAATATCCAGAAGGAGAGCACACTGCACCTGGTGCTGAG GCTGAGGGGAGGAATGTGGACCCTGGGCAGAAGGGCAGTGGC AGGCCTGCTGGCCTCTCCAAGCCCAGCACAGGCACAGACCCTG ACAAGAGTGCCTAGGCCAGCAGAGCTGGCACCACTGTGCGGCC GGAGAGGCCTGAGAACAGACATCGATGCCACCTGTACACCCAG AAGGGCCAGCTCCAACCAGAGGGGCCTGAACCAGATCTGGAAT GTGAAGAAGCAGAGCGTGTACCTGATGAATCTGAGGAAGTCCG GCACCCTGGGACACCCTGGCTCTCTGGACGAGACAACATATGA GCGGCTGGCCGAGGAGACACTGGATTCCCTGGCCGAGTTCTTT GAGGACCTGGCCGATAAGCCATACACCTTCGAGGACTATGACG TGAGCTTCGGCTCTGGCGTGCTGACAGTGAAGCTGGGCGGCGA TCTGGGCACCTACGTGATCAACAAGCAGACACCTAATAAGCAG ATCTGGCTGTCTAGCCCCTCCTCTGGCCCTAAGAGATACGACTG GACCGGCAAGAACTGGGTGTATAGCCACGATGGCGTGTCCCTG CACGAGCTGCTGGCAGCAGAGCTGACCAAGGCCCTGAAGACAA AGCTGGACCTGAGCTCCCTGGCCTATTCCGGCAAGGATGCCTG A |
| 64 | TAT-GG-DEVD-hFXN | ATGTACGGCAGAAAGAAGAGGCGGCAGAGACGCAGGGGAGGC GACGAGGTGGATATGTGGACCCTGGGCCGGAGAGCAGTGGCAG GACTGCTGGCCTCTCCCAGCCCTGCCCAGGCCCAGACCCTGACA CGCGTGCCAAGGCCAGCAGAGCTGGCACCACTGTGCGGCCGCA GGGGCCTGCGGACAGACATCGATGCCACCTGTACACCTCGGAG AGCCAGCTCCAACCAGAGAGGCCTGAACCAGATCTGGAATGTG AAGAAGCAGTCCGTGTACCTGATGAATCTGAGGAAGTCGGCA CCCTGGGACACCCAGGCAGCCTGGACGAGACCACATACGAGAG GCTGGCCGAGGAGACACTGGATTCTCTGGCCGAGTTCTTTGAG GACCTGGCCGATAAGCCCTACACCTTCGAGGACTACGACGTGA GCTTCGGCTCTGGCGTGCTGACAGTGAAGCTGGGCGGCGACCT GGGCACCTACGTGATCAACAAGCAGACACCTAATAAGCAGATC TGGCTGTCTAGCCCTTCCTCTGGCCCAAAGAGGTACGACTGGAC CGGCAAGAACTGGGTGTACAGCCACGATGGCGTGTCCCTGCAC GAGCTGCTGGCAGCAGAGCTGACCAAGGCCCTGAAGACAAAGC TGGACCTGAGCTCCCTGGCCTACAGCGGCAAGGATGCCTGA |
| 65 | TAT-GG-EPLFAERK-hFXN | ATGTATGGAAGGAAGAAGAGACGGCAGAGACGGAGAGGAGGC GAGCCCCTGTTTGCTGAGCGGAAGATGTGGACCCTGGGAAGGC GGGCAGTGGCCAGGCCTGCTGGCAAGCCCATCCCCTGCACAGGC ACAGACCCTGACAAGGGTGCCACGGCCCGCAGAGCTGGCACCA CTGTGCGGCAGGCGGGGCCTGAGAACCGACATCGATGCCACCT GTACACCTAGAAGGGCCAGCTCCAACCAGAGGGGCCTGAACCA GATCTGGAATGTGAAGAAGCAGTCCGTGTACCTGATGAATCTG AGGAAGAGCGGCACCCTGGGACACCCAGGCTCCCTGGACGAGA CAACATACGAGAGGCTGGCCGAGGAGACACTGGATTCCCTGGC CGAGTTCTTTGAGGACCTGGCCGATAAGCCCTACACCTTCGAGG ACTACGACGTGAGCTTCGGCAGCGGCGTGCTGACAGTGAAGCT GGGAGGCGACCTGGGCACCTACGTGATCAACAAGCAGACACCT |

TABLE 10-continued

Nucleic acids encoding fusion proteins of the disclosure.

| SEQ ID NO. | Fusion Protein | Sequence |
| --- | --- | --- |
|  |  | AATAAGCAGATCTGGCTGTCTAGCCCTTCCTCTGGCCCAAAGCG GTACGACTGGACCGGCAAGAACTGGGTGTACTCCCACGATGGC GTGTCTCTGCACGAGCTGCTGGCAGCAGAGCTGACAAAAGCAC TGAAAACAAAACTGGACCTGTCATCACTGGCATACTCTGGAAA GGACGCATAA |
| 66 | TAT-GG-LLVY-hFXN | ATGTACGGCAGAAAGAAGAGGCGGCAGAGACGCAGGGGAGGA CTGCTGGTGTACATGTGGACCCTGGGCCGGAGAGCAGTGGCAG GACTGCTGGCCTCTCCCAGCCCTGCCCAGGCCCAGACCCTGACA CGCGTGCCAAGGCCAGCAGAGCTGGCACCACTGTGCGGCCGCA GGGGCCTGCGGACAGACATCGATGCCACCTGTACACCTCGGAG AGCCAGCTCCAACCAGAGAGGCCTGAACCAGATCTGGAATGTG AAGAAGCAGTCCGTGTACCTGATGAATCTGAGGAAGTCTGGCA CCCTGGGACACCCAGGCAGCCTGGACGAGACCACATACGAGAG GCTGGCCGAGGAGACACTGGATTCTCTGGCCGAGTTCTTTGAG GACCTGGCCGATAAGCCCTACACCTTCGAGGACTACGACGTGA GCTTCGGCTCTGGCGTGCTGACAGTGAAGCTGGGCGGCGACCT GGGCACCTACGTGATCAACAAGCAGACACCTAATAAGCAGATC TGGCTGTCTAGCCCTTCCTCTGGCCCAAAGAGGTACGACTGGAC CGGCAAGAACTGGGTGTACAGCCACGATGGCGTGTCCCTGCAC GAGCTGCTGGCAGCAGAGCTGACCAAGGCCCTGAAGACAAAGC TGGACCTGAGCTCCCTGGCCTACAGCGGCAAGGATGCCTGA |
| 67 | TAT-GG-hFXN-NES1 | ATGTATGGAAGGAAGAAGAGACGGCAGAGACGGAGAGGAGGC GAGCCCCTGTTTGCTGAGCGGAAGATGTGGACCCTGGGAAGGC GGGCAGTGGCAGGCCTGCTGGCAAGCCCATCCCCTGCACAGGC ACAGACCCTGACAAGGGTGCCACGGCCCGCAGAGCTGGCACCA CTGTGCGGCAGGCGGGGCCTGAGAACCGACATCGATGCCACCT GTACACCTAGAAGGGCCAGCTCCAACCAGAGGGGCCTGAACCA GATCTGGAATGTGAAGAAGCAGTCGTGTACCTGATGAATCTG AGGAAGAGCGGCACCCTGGGACACCCAGGCTCCCTGGACGAGA CAACATACGAGAGGCTGGCCGAGGAGACACTGGATTCCCTGGC CGAGTTCTTTGAGGACCTGGCCGATAAGCCCTACACCTTCGAGG ACTACGACGTGAGCTTCGGCAGCGGCGTGCTGACAGTGAAGCT GGGAGGCGACCTGGGCACCTACGTGATCAACAAGCAGACACCT AATAAGCAGATCTGGCTGTCTAGCCCTTCCTCTGGCCCAAAGCG GTACGACTGGACCGGCAAGAACTGGGTGTACTCCCACGATGGC GTGTCTCTGCACGAGCTGCTGGCAGCAGAGCTGACAAAAGCAC TGAAAACAAAACTGGACCTGTCATCACTGGCATACTCTGGAAA GGACGCATAA |
| 68 | TAT-GG-hFXN-NES2 | ATGTACGGCAGAAAGAAGAGGCGGCAGAGACGCAGGGGAG GAATGTGGACCCTGGGCCGGAGAGCAGTGGCAGGACTGCTGGC CTCTCCCAGCCCTGCCCAGGCCCAGACCCTGACACGCGTGCCA AGGCCAGCAGAGCTGGCACCACTGTGCGGCCGCAGGGGCCTGC GGACAGACATCGATGCCACCTGTACACCTCGGAGAGCCAGCTC CAACCAGAGAGGCCTGAACCAGATCTGGAATGTGAAGAAGCA GTCCGTGTACCTGATGAATCTGAGGAAGTCTGGCACCCTGGGA CACCCAGGCAGCCTGGACGAGACCACATACGAGAGGCTGGCCG AGGAGACACTGGATTCTCTGGCCGAGTTCTTTGAGGACCTGGCC GATAAGCCCTACACCTTCGAGGACTACGACGTGAGCTTCGGCT CTGGCGTGCTGACAGTGAAGCTGGGCGGCGACCTGGGCACCTA CGTGATCAACAAGCAGACACCTAATAAGCAGATCTGGCTGTCT AGCCCTTCCTCTGGCCCAAAGAGGTACGACTGGACCGGCAAGA ACTGGGTGTACAGCCACGATGGCGTGTCCCTGCACGAGCTGCT GGCAGCAGAGCTGACCAAGGCCCTGAAGACAAAGCTGGACCTG AGCTCCCTGGCCTACAGCGGCAAGGATGCCCTGCAGAAGAAGC TGGAGGAGCTGGAGCTGTGA |
| 86 | TAT-GG-Ubiquitin-PARKIN | ATGTACGGCCGGAAGAAGCGGCGGCAGCGTCGGAGAGGCGGC ATGCAGATCTTCGTGAAAACATTAACCGGCAAGACCATCACCC TGGAAGTGGAACCTAGCGACACCATCGAGAACGTGAAGGCCAA GATCCAGGACAAGGAAGGCATCCCTCCTGATCAGCAGCGACTG ATTTTCGCTGGAAAGCAGCTGGAAGATGGCAGAACCCTGAGCG ACTACAACATCCAGAAGGAGAGCACACTGCACCTGGTGCTGAG GCTGCGGGGCGGCATGATCGTGTTCGTGAGATTCAACAGCAGC CACGGCTTCCCCGTCGAGGTGGATTCTGACACCAGCATCTTTCA ACTGAAGGAAGTGGTGGCAAAGAGACAGGGCGTGCCCGCCGAT CAACTGCGGGTAATCTTCGCCGGAAAAGAGCTGAGAAATGACT GGACAGTGCAGAACTGCGACCTGGATCAGCAAAGCATTGTGCA CATCGTGCAGCGGCCTTGGCGGAAAGGCCAGGAGATGAACGCC ACCGGCGGAGATGATCCTAGAAATGCTGCTGGCGGCTGCGAGC GGGAACCCCAGAGCCTGACCAGAGTGGACCTGTCCAGCTCTGT GCTACCAGGCGACAGCGTGGGCCTGGCCGTGATCCTGCACACA GATTCCAGAAAGGACAGCCCACCTGCCGGCAGCCCGGCCGGAA GGTCCATCTACAACTCCTTCTACGTGTACTGCAAGGGCCCCTTGC |

TABLE 10-continued

Nucleic acids encoding fusion proteins of the disclosure.

| SEQ ID NO. | Fusion Protein | Sequence |
| --- | --- | --- |
|  |  | CAGAGAGTGCAACCTGGCAAACTGAGAGTTCAGTGCTCTACAT
GTAGACAAGCCACACTGACACTGACCCAGGGCCCCAGCTGTTG
GGACGACGTGCTGATCCCCAACAGAATGAGCGGCGAGTGCCAA
AGCCCCCACTGCCCTGGCACCAGCGCCGAGTTCTTCTTTAAGTG
TGGAGCTCACCCCACCTCCGACAAGGAAACCAGCGTGGCCCTG
CATCTGATCGCCACCAACAGCAGAAACATCACCTGTATCACAT
GCACCGACGTCAGAAGCCCTGTGCTTGTGTTTCAGTGTAATAGC
CGGCACGTGATCTGCCTGGACTGCTTCCACCTGTACTGCGTGAC
CAGACTGAACGACAGACAGTTTGTGCACGACCCTCAGCTGGGC
TACTCGCTGCCTTGTGTGGCCGGCTGTCCTAACTCTCTGATCAA
GGAACTGCATCACTTCAGAATCCTGGGCGAGGAACAGTACAAC
CGGTACCAGCAGTACGGCGCCGAGGAATGCGTGCTGCAGATGG
GCGGAGTGCTGTGCCCTAGACCCGGATGTGGAGCCGGACTGCT
GCCTGAGCCCGACCAGCGGAAAGTGACCTGCGAGGGAGGCAAC
GGCCTCGGCTGCGGTTTCGCCTTCTGCAGAGAATGTAAAGAAG
CTTACCACGAGGGGGAGTGTTCTGCCGTGTTCGAGGCCTCTGGC
ACAACCACCCAGGCTTATAGAGTGGACGAGAGAGCCGCCGAGC
AGGCCAGATGGGAGGCCGCCAGCAAGGAGACAATCAAGAAGA
CCACAAAGCCTTGCCCACGCTGCCACGTGCCTGTGGAAAAGAA
CGGCGGCTGTATGCACATGAAGTGCCCTCAGCCTCAGTGCAGA
CTGGAATGGTGCTGGAACTGCGGCTGCGAGTGGAATAGAGTCT
GCATGGGCGATCACTGGTTCGACGTT |
| 87 | TAT-GG-
EPLFAERK-
PARKIN | ATGTACGGCAGAAAGAAAAGACGCCAGAGACGGCGGGGCGGC
GAGCCTCTGTTCGCCGAAAGAAAGATGATTGTGTTTGTCAGATT
TAATTCTTCACACGGATTTCCCGTCGAAGTGGATTCAGACACCA
GTATTTTTCAGCTTAAGGAGGTCGTAGCCAAGCGGCAGGGCGT
GCCCGCCGACCAATTGAGAGTGATCTTTGCTGGAAAAGAATTG
AGGAATGATTGGACTGTCCAGAACTGCGATTTGGATCAGCAGT
CTATCGTGCATATAGTTCAGCGACCATGGCGCAAGGGACAGGA
GATGAATGCAACCGGAGGCGACGACCCACGGAATGCAGCCGG
AGGGTGTGAGAGAGAGCCCCAGAGTTTGACTCGGGTCGATCTG
AGCTCTAGCGTACTCCCAGGGGATTCAGTGGGACTCGCAGTTAT
CCTGCATACTGACTCCAGAAAGGACTCACCGCCCGCCGGGAGT
CCGGCCGGAAGATCAATTTATAATAGCTTTTACGTTTATTGTAA
GGGACCCTGTCAGAGAGTACAGCCCGGCAAGTTGAGGGTGCAA
TGTAGTACCTGCCGCCAGGCCACGCTGACACTCACACAGGGAC
CATCCTGTTGGGACGACGTGCTTATCCCCAACAGGATGTCCGGT
GAGTGTCAATCCCCTCACTGCCCTGGGACAAGCGCCGAATTCTT
CTTCAAATGTGGTGCCCACCCCACATCCGACAAGGAGACTTCCG
TCGCCCTGCACCTGATCGCAACTAACAGCCGGAATATCACGTGC
ATCACCTGCACGGATGTGCGGTCCCCTGTGCTGGTCTTTCAGTG
TAATTCTCGGCACGTGATCTGCCTTGACTGCTTCCACCTGTACT
GCGTTACACGACTGAACGACAGGCAGTTCGTGCATGACCCTCA
GCTTGGGTACTCTCTTCCATGTGTTGCCGGGTGTCCTAACTCATT
GATCAAGGAGCTCCACCACTTCAGGATTTTGGGGAGGAGCAA
TATAACCGATACCAGCAGTACGGCGCCGAGGAGTGTGTGCTGC
AGATGGGAGGAGTACTTTGTCCACGCCCGGGATGTGGAGCAGG
CCTGCTCCCAGAACCAGATCAACGCAAGGTGACGTGTGAGGGA
GGAAATGGGCTCGGCTGCGGGTTCGCCTTTTGCAGGGAGTGTA
AGGAGGCCTATCATGAAGGTGAATGCTCCGCTGTGTTCGAGGC
CTCTGGTACTACCACTCAGGCCTATAGGGTCGACGAGAGAGCT
GCTGAGCAAGCCCGATGGGAGGCTGCAAGCAAAGAAACCATCA
AGAAAACTACGAAGCCATGCCCTCGCTGCCATGTGCCCGTCGA
GAAGAACGGTGGCTGCATGCACATGAAGTGTCCACAGCCCCAG
TGCCGGTTGGAATGGTGTTGGAATTGCGGATGCGAATGGAACC
GCGTCTGCATGGGCGATCACTGGTTCGACGTT |
| 88 | TAT-GG-
PARKIN-NES1 | ATGTACGGAAGAAAAAAGCGGAGACAGAGAAGAAGAGGCGGG
ATGATCGTGTTCGTGCGGTTCAACAGCAGCCACGGCTTTCCAGT
CGAGGTGGACTCTGACACCTCCATCTTCCAGCTGAAGGAGGTG
GTGGCCAAGCGGCAGGGCGTGCCCTGCCGATCAGCTGAGGGTGA
TCTTTGCCGGGAAGGAGCTGCGGAATGACTGGACCGTACAGAA
CTGCGACCTGGACCAGCAATCTATCGTGCACATCGTGCAGCGA
CCCTTGGCGGAAGGGCCAGGAGATGAACGCTACAGGCGGCGAC
GACCCTAGAAATGCCGCCGGCGGATGTGAACGGGAACCTCAAT
CTCTGACACGGGTGGATCTGAGCTCTAGCGTGCTCCCCGGAGAC
TCTGTGGGCCTGGCCGTGATCCTGCACACCGACAGCAGGAAGG
ACAGCCCCCCGCCGGAAGTCCTGCCGGCAGATCCATCTACAA
CTCTTTCTACGTGTACTGCAAAGGCCCTTGCCAGCGCGTGCAGC
CTGGCAAGCTGAGAGTGCAATGTAGCACCTGTAGACAGGCCAC
ACTGACACTGACCCAGGGACCTAGCTGCTGGGATGATGTGCTG
ATTCCTAACAGAATGAGCGGCGAGTGCCAGAGCCCTCACTGCC
CCGGCACAAGCGCCGAATTCTTCTTCAAGTGCGGCGCCCACCCT
ACCAGCGACAAGGAGACAAGCGTGGCCCTGCATCTAATCGCCA
CTAACAGCAGAAACATCACCTGTATCACCTGCACCGACGTCAG |

TABLE 10-continued

Nucleic acids encoding fusion proteins of the disclosure.

| SEQ ID NO. | Fusion Protein | Sequence |
|---|---|---|
| | | AAGCCCAGTGCTCGTGTTTCAGTGCAACAGCCGGCACGTGATCT |
| | | GCCTGGATTGCTTCCACCTGTACTGTGTCACCAGACTGAACGAT |
| | | AGACAGTTCGTGCATGATCCACAGCTGGGCTACAGCCTGCCCTG |
| | | CGTTGCCGGCTGTCCTAACTCCCTGATCAAGGAACTGCACCACT |
| | | TCCGGATCCTGGGCGAGGAACAGTACAACCGCTACCAGCAGTA |
| | | CGGCGCCGAGGAATGCGTGCTGCAGATGGGAGGAGTGCTGTGC |
| | | CCCAGACCTGGATGCGGTGCTGGACTGCTGCCTGAGCCCGACC |
| | | AAAGAAAGGTGACCTGCGAGGGCGGCAACGGCCTGGGCTGTGG |
| | | CTTCGCCTTCTGCAGAGAGTGCAAGGAAGCCTATCACGAGGGC |
| | | GAATGCAGCGCCGTGTTTGAGGCTTCTGGCACCACCACCCAGG |
| | | CTTATAGAGTCGACGAGCGGGCCGCTGAGCAGGCCAGATGGGA |
| | | GGCTGCCAGCAAGGAAACCATCAAGAAAACAACAAAGCCCTGC |
| | | CCTAGATGTCACGTGCCAGTTGAGAAGAACGGCGGCTGCATGC |
| | | ACATGAAATGTCCTCAGCCTCAGTGCAGACTGGAATGGTGCTG |
| | | GAATTGCGGCTGTGAATGGAATCGGGTGTGCATGGGCGACCAC |
| | | TGGTTCGATGTGCTGGCCCTGAAACTGGCAGGCCTGGACCTG |

In some embodiments, nucleic acid sequences encoding fusion proteins of the present disclosure comprises any one sequence as listed in Table 10, i.e., any of SEQ ID NOS: 62-68 (SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 86, SEQ ID NO: 87 or SEQ ID NO: 88). In some embodiments, a nucleic acid sequence encoding a fusion protein provided by the present disclosure comprises a sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any of SEQ ID NOS. 62-68 (SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 86, SEQ ID NO: 87 or SEQ ID NO: 88).

In one embodiment, the nucleic acid sequence encoding a fusion protein TAT-GG-SUMO1-hFXN has a sequence as set forth in SEQ ID NO: 62. In one embodiment, the nucleic acid sequence encoding a fusion protein TAT-GG-Ubiquitin-hFXN has a sequence as set forth in SEQ ID NO: 63. In one embodiments, the nucleic acid sequence encoding a fusion protein TAT-GG-DEVD-hFXN has a sequence as set forth in SEQ ID NO: 64. In one embodiment, the nucleic acid sequence encoding a fusion protein TAT-GG-EPLFAERK-hFXN has a sequence as set forth in SEQ ID NO: 65. In one embodiment, the nucleic acid sequence encoding a fusion protein TAT-GG-LLVY-hFXN has a sequence as set forth in SEQ ID NO: 66. In one embodiment, the nucleic acid sequence encoding a fusion protein TAT-GG-hFXN-NES1 has a sequence as set forth in SEQ ID NO: 67. In one embodiment, the nucleic acid sequence encoding a fusion protein TAT-GG-hFXN-NES2 has a sequence as set forth in SEQ ID NO: 68. In one embodiment, the nucleic acid sequence encoding a fusion protein TAT-GG-Ubiquitin-PARKIN has a sequence as set forth in SEQ ID NO: 86. In one embodiment, the nucleic acid sequence encoding a fusion protein TAT-GG-EPLFAERK-PARKIN has a sequence as set forth in SEQ ID NO: 87. In one embodiment, the nucleic acid sequence encoding a fusion protein TAT-GG-PARKIN-NES1 has a sequence as set forth in SEQ ID NO: 88.

The present disclosure also provides an expression vector for producing a fusion protein as defined herein in a cell, e.g., a mammalian cell, a bacterial cell or a fungal cell. The expression vector of the present disclosure may comprise a nucleic acid encoding a fusion protein of the present disclosure, e.g., any one of SEQ ID NOS. 62-68. By way of example, the expression vector may be a retroviral vector, a DNA vector, a plasmid, an RNA vector, an adenoviral vector, an adenovirus associated vector, a lentiviral vector, a phagemid, a baculovirus, or any combination thereof.

Vectors

Vectors may enable the integration of DNA fragments or nucleic acid sequences into the genome of the host or enable expression of genetic elements that are not integrated. Vectors are typically self-replicating DNA or RNA constructs containing the desired nucleic acid sequences, and operably linked genetic control elements that are recognized in a suitable host cell and effect the translation of the desired spacers. Generally, the genetic control elements may include a prokaryotic promoter system or a eukaryotic promoter expression control system. Such system typically includes a transcriptional promoter and transcription enhancers to elevate the level of RNA expression. Vectors usually contain an origin of replication that allows the vector to replicate independently of the host cell. Accordingly, the term control and regulatory elements include promoters, terminators and other expression control elements. Such regulatory elements are described in the art and known to the skilled artisan. For instance, any of a wide variety of expression control sequences that control the expression of a DNA sequence when operatively linked to it may be used in these vectors to express DNA sequences encoding any desired fusion protein as described herein.

A vector may additionally include appropriate restriction sites, antibiotic resistance or other markers for selection of vector-containing cells. Plasmids are the most commonly used form of vector but other forms of vectors which serve an equivalent function, and which are, or become, known in the art are suitable for use herein.

A vector may also be referred to as a construct, or as recombinant nucleic acid. As referred to herein, the term "recombinant DNA", "recombinant nucleic acid sequence" or "recombinant gene" refers to a nucleic acid comprising an open reading frame (ORF) encoding a fusion protein as described herein. A construct comprising an ORF encoding a fusion protein as described herein may optionally further comprise additional elements such as promoters, regulatory and control elements, translation, expression and other signals, operably linked to the nucleic acid sequence described herein. The term "operatively-linked", as used herein, is intended to mean attached in a manner which allows for transgene transcription. The term "encoding", as used herein, is intended to mean that the subject nucleic acid may be transcribed and translated into either the desired polypeptide or the subject protein in an appropriate expression system, e.g., when the subject nucleic acid is linked to appropriate control sequences such as promoter and enhancer elements in a suitable vector (e.g., an expression vector) and when the vector is introduced into an appropriate system or cell.

According to some embodiments, recombinant DNA encoding a fusion protein of the present disclosure may be cloned into a vector, e.g., lentiviral vector plasmid capable of integration into a cell. According to some embodiments, recombinant DNA encoding the one or more fusion proteins may be cloned into a plasmid DNA construct encoding a selectable trait, such as an antibiotic resistance gene. According to some embodiments, recombinant DNA encoding the fusion proteins may be cloned into a plasmid construct that is adapted to stably express a fusion protein in a cell.

Conjugate

The present disclosure also provides a conjugate for intracellular delivery of a protein of interest to a non-nuclear organelle. The conjugate of the disclosure may comprise a fusion protein as defined in the disclosure, and at least one of a label, for example a radioactive, fluorescent, chromophore, enzymatic, peptide or protein label, a small molecule, or a polymer (such as polyethylene glycol, PEG, for example).

Cell

The present disclosure also provides a cell comprising any one of a fusion protein, a nucleic acid, a vector, a conjugate, or any combination thereof, as described herein. In some aspects, the cell may be a stem cell or an iPS cell. In other aspects, a cell may be selected from the group consisting of a muscle progenitor cell, a neuron progenitor cell, a bone marrow stem cell, a bacterial cell, or a yeast cell. By way of example, a cell may be any one of a muscle or muscle progenitor cell, a fibroblast, an epidermal cell, a cardiac cell, a stem cell, an embryonic stem cell, a pluripotent cell, a neuron, a bone marrow stem cell, and including yeast or bacteria cell lines.

In certain embodiments, the cell comprising a fusion protein, a nucleic acid, a vector, a conjugate, or any combination thereof, may be selected from the group consisting of a long term hematopoietic stem cell, a short term hematopoietic stem cell, a multipotent progenitor cell, a lineage restricted progenitor cell, a lymphoid progenitor cell, a myeloid progenitor cell, a common myeloid progenitor cell, an erythroid progenitor cell, a megakaryocyte erythroid progenitor cell, a retinal cell, a photoreceptor cell, a rod cell, a cone cell, a retinal pigmented epithelium cell, a trabecular meshwork cell, a cochlear hair cell, an outer hair cell, an inner hair cell, a pulmonary epithelial cell, a bronchial epithelial cell, an alveolar epithelial cell, a pulmonary epithelial progenitor cell, a striated muscle cell, a cardiac muscle cell, a muscle satellite cell, a neuron, a neuronal stem cell, a mesenchymal stem cell, an induced pluripotent stem (iPS) cell, an embryonic stem cell, a fibroblast, a monocyte-derived macrophage or dendritic cell, a megakaryocyte, a neutrophil, an eosinophil, a basophil, a mast cell, a cell, a B cell, e.g., a progenitor B cell, a Pre B cell, a Pro B cell, a memory B cell, a plasma cell, a gastrointestinal epithelial cell, a biliary epithelial cell, a pancreatic ductal epithelial cell, an intestinal stem cell, a hepatocyte, a liver stellate cell, a Kupffer cell, an osteoblast, an osteoclast, an adipocyte, a preadipocyte, a pancreatic islet cell (e.g., a beta cell, an alpha cell, a delta cell), a pancreatic exocrine cell, a Schwann cell and an oligodendrocyte.

In some embodiments, the cell comprising the fusion protein is a dividing cell. In other embodiments, the cell comprising the fusion protein is a non-dividing cell.

In some embodiments, the cell comprising the fusion protein of the present disclosure may be in a subject, such as a subject who is administered the fusion protein, e.g., for treating a pathological condition, e.g., a genetic disorder. In some examples, the pathological condition may be a non-nuclear organelle associated disorder. In one specific example, the pathological condition is Friedrich's Ataxia.

In one specific example, the subject may be administered a fusion protein of the present disclosure, e.g., any of SEQ ID NOS. 55-61, for treating Friedrich's Ataxia. In other examples, the subject may be administered a fusion protein of the present disclosure for treating a mitochondrial disorder, e.g., mitochondrial myopathy, diabetes mellitus and deafness, Leber's hereditary optic neuropathy, neuropathy, retinitis pigmentosa, ptosis (NARP), myoneurogenic gastrointestinal encephalopathy, myoclonic epilepsy, Alzheimer's disease, muscular dystrophy, Lou Gehrig's disease, and cancer. In yet other examples, the subject may be administered the fusion protein of the present disclosure for treating a lysosomal disorder, such as a lipid storage disease of the group of sphingolipoidoses disease (e.g., a Niemann-Pick disease, Fabry disease, Krabbe disease, Gaucher disease, Tay—Sachs disease or metachromatic leukodystrophy), Hunter syndrome, I-cell disease, multiple sulfatase deficiency, mucolipidosis type II and IIIA, galactosialidosis, GM2-AP deficiency, SAP deficiency and Salla disease. In yet other examples, the subject may be administered the fusion protein provided by the present disclosure, e.g., any of SEQ ID NOS. 69-71, for treating Parkinson's Disease.

In other embodiments, the cell comprising the fusion protein of the present disclosure may be a cell that has been engineered to express the fusion protein. In some examples, such engineered cell may be obtained, e.g., isolated, from a subject. Methods for engineering a cell to express fusion protein of the disclosure are known to one of ordinary skill in the art and include methods described herein below, in a section entitled "Method for Intracellular Delivery".

Pharmaceutical Composition

Also provided by the present disclosure is a pharmaceutical composition comprising a fusion protein or a conjugate as described above, and a pharmaceutically acceptable diluent, carrier, additive and/or excipient.

Preparation of pharmaceutical compositions is discussed in, for example, in Hoover, John E.(eds.) Remington's Pharmaceutical Sciences, Mack Publishing Co., Easton, Pennsylvania 18$^{th}$ edition (1990), and in Liberman, H. A. and Lachman, L. (eds.) Pharmaceutical Dosage Forms, Marcel Decker, New York, New York (1989), the entire contents of each of which are hereby incorporated herein by reference.

A pharmaceutical composition may be delivered to cells in vitro, for example by contacting the cells with the pharmaceutical composition. Alternatively, for delivery in vivo, the pharmaceutical composition provided in the present disclosure may be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques.

Injectable pharmaceutical compositions, for example, sterile injectable aqueous or oleaginous suspensions, may be formulated according to the techniques known in the art using suitable dispersing or wetting agents and suspending agents. The sterile injectable pharmaceutical composition may also be a sterile injectable solution or a suspension in a nontoxic parenterally acceptable diluent or solvent, for example, 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids, such as oleic acid, are useful in the preparation of injectables. Dimethyl acetamide, surfactants including ionic and non-ionic detergents, and polyethylene glycols can be used. Mixtures of solvents and wetting agents such as those discussed above are also useful.

Pharmaceutical compositions for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The fusion proteins or compositions can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration may include pharmaceutically acceptable emulsions, solutions, suspensions, syrups, and elixirs containing inert diluents commonly used in the art, such as water. Such pharmaceutical compositions may also comprise adjuvants, such as wetting agents, emulsifying and suspending agents, and sweetening, flavoring, and perfuming agents.

Solid dosage forms for oral administration may include capsules, tablets, pills, powders, and granules. In such solid dosage forms, a fusion protein may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as can be provided in a dispersion of active compound in hydroxypropylmethyl cellulose. In the case of capsules, tablets, and pills, the dosage forms may also comprise buffering agents such as sodium citrate, or magnesium or calcium carbonate or bicarbonate. Tablets and pills may additionally be prepared with enteric coatings.

Suppositories for rectal administration of the fusion proteins discussed herein can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

The fusion protein of the present disclosure may be administered by a variety of methods, including, for example, orally, enterally, mucosally, percutaneously, or parenterally. Parenteral administration is preferred, especially by intravenous, intramuscular, subcutaneous, intracutaneous, intraarticular, intrathecal, and intraperitoneal infusion or injection, including continuous infusions or intermittent infusions with pumps available to those skilled in the art. Alternatively, the fusion protein may be administered by means of micro-encapsulated preparations, for example based on liposomes.

Methods for Intracellular Delivery

In some embodiments, the present disclosure also provides methods for intracellular delivery of a protein of interest to a non-nuclear organelle in a cell. The method comprises contacting the cell with a fusion protein, a nucleic acid, a vector or a conjugate as described herein above. In one example, the non-nuclear organelle is mitochondria. In one example, the protein of interest is FXN, e.g., human FXN.

Contacting the cell with a fusion protein of the present disclosure may occur in the context of administering a fusion protein, a nucleic acid, a vector, a conjugate, a pharmaceutical composition for the present disclosure, or any combination thereof, to a subject, e.g., a human. The subject may have a pathological condition, e.g., a genetic disorder, such as a non-nuclear organelle associated disorder. In one specific example, the pathological condition is Friedrich's Ataxia.

In some embodiments, the method for intracellular delivery of a protein of interest to a non-nuclear organelle may comprise contacting a cell, e.g., an isolated cell, by contacting the cell with a nucleic acid encoding a fusion protein of the present disclosure or with a vector comprising the nucleic acid of the present disclosure. In some aspects, the cell is stem cell or an iPS cell. In other aspects, a cell may be selected from the group consisting of a muscle progenitor cell, a neuron progenitor cell, a bone marrow stem cell, a bacterial cell, or a yeast cell. In some aspects, the cell may be a muscle progenitor cell, a neuron progenitor cell, a bone marrow stem cell, a bacterial cell line, or a yeast cell line, with a nucleic acid encoding a fusion protein of the disclosure. The methods may further comprise additional steps for facilitating delivery of a nucleic acid or a vector of the present disclosure into the cell, e.g., electroporation, chemical or polymeric transfection, viral transduction, mechanical membrane disruption, or other method know to a skilled artisan.

In some embodiments, the present disclosure also provides methods for increasing an amount of protein of interest delivered to a cell. As demonstrated by certain experimental data included in the present disclosure, e.g., in Example 6, cells treated with fusion proteins comprising a protein of interest, CPP and TES contained significantly higher amounts of the protein of interest than cells treated with a fusion protein comprising a protein of interest and CPP, but not TES. Thus, the experimental data indicates that TES facilitates delivery to and/or accumulation of a protein of interest in a cell. Accordingly, introducing TES into a fusion protein comprising CPP and a protein of interest can significantly increase the amount of protein of interest in a cell.

Without wishing to be bound by a specific theory, it is believed that cleavage of TES by endogenous proteases in a cell facilitates removal of the CPP from the fusion protein and prevents the CPP from facilitating diffusion of the protein of interest across the plasma membrane and out of the cell. This allows the protein of interest to accumulate in the cell, resulting in increased amounts of protein of interest delivered to a cell.

In some embodiments, the cell may be in a subject, e.g., a human. Thus, methods for increasing an amount of protein of interest delivered to a cell may allow to decrease a dose of a fusion protein to be delivered to a subject as a part of therapy, e.g., for treating a non-nuclear organelle associated disorder.

In some embodiments, the protein of interest may be FXN. Therefore, in some embodiments, the fusion protein may comprise CPP (e.g., SEQ ID NO: 11 or SEQ ID NO: 83), TES and FXN (e.g., SEQ ID NO: 1 or SEQ ID NO: 2), and the subject may have a disorder associated with FXN deficiency, e.g., Friedreich's Ataxia. In other embodiments, the fusion protein may comprise CPP (e.g., SEQ ID NO: 11 or SEQ ID NO: 83), TES and FXN (e.g., SEQ ID NO: 1 or SEQ ID NO: 2), and the subject may have a disorder that is not associated with FXN deficiency, e.g., Leigh Syndrome, French Canadian Type.

In some embodiments, the protein of interest may be PARKIN. Therefore, in some embodiments, the fusion protein may comprise CPP (e.g., SEQ ID NO: 11 or SEQ ID NO: 83), TES and PARKIN (e.g., SEQ ID NO: 7), and the subject may have Parkinson's disease associated with a mutation in PARK2 gene encoding PARKIN. In other embodiments, the fusion protein may comprise CPP (e.g., SEQ ID NO: 11 or SEQ ID NO: 83), TES and PARKIN (e.g., SEQ ID NO: 7), and the subject may have Parkinson's disease not associated with a mutation in PARK2 gene encoding PARKIN, e.g., Parkinson's disease associated with a mutation in PINK1 (PARK6) gene.

In some aspects, methods for increasing an amount of protein of interest delivered to a cell provided by the present disclosure comprise modifying sequence of a fusion protein comprising the protein of interest and a cell penetrating peptide (CPP) by introducing into the fusion protein a target enhancing sequence (TES), thereby producing a modified fusion protein; and contacting a cell with the modified fusion protein, thereby increasing the amount of the protein of interest delivered to the cell.

The CPP may be located at the N-terminus of the modified fusion protein and the TES may be fused at the C-terminus of the CPP. For example, the modified fusion protein may comprise, starting at the N-terminus: CPP; TES and a protein of interest. In another example, the modified fusion protein may comprise, starting at the N-terminus: CPP, TES, OTS and a protein of interest.

The CPP may also be located at the C-terminus of the modified fusion protein and the TES may be fused at the N-terminus of the CPP. For example, the modified fusion protein may comprise, starting at the N-terminus: protein of interest, TES and CPP. In another example, the modified fusion protein may comprise, starting at the N-terminus: protein of interest, OTS, TES and CPP. In yet another example, the modified fusion protein may comprise, starting at the N-terminus: OTS, protein of interest, TES and CPP.

In some embodiments, the protein of interest may be any protein of interest as described herein, e.g., any protein of interest listed in Table 2 herein. For example, the protein of interest may be selected from the group consisting of Frataxin (FXN), Tafazin, Pyruvate Dehydrogenase (PDH), SLIRP, LRPPC, PARK2 protein, PARK6 protein, PARK7 protein, and a variant or derivative thereof. In one example, the protein of interest is Frataxin (FXN) or a variant or derivative thereof. In another example, the protein of interest is PARK2 protein (PARKIN) or a variant or derivative thereof.

In some embodiments, the CPP may be any CPP as described herein, e.g., any CPP listed in Table 4 herein. For example, the CPP may comprise a peptide selected from the group of CPPs listed in the Database of Cell-Penetrating Peptides CPPsite 2.0. For example, the CPP may comprise a peptide selected from the group consisting of HIV-TAT, galanin, mastoparan, transportan, penetratin, polyarginine, VP22, and a variant or derivative thereof. In one embodiment, the CPP may comprise HIV-TAT or a variant or derivative thereof.

In some embodiments, the TES included in the modified fusion protein may be any TES described herein. For example, the TES may be a nuclear export signal peptide, e.g., comprising a sequence having at least 85%, at least 90%, at least 95% or at least 99% sequence identity to any one of SEQ ID NOs. 36-43. In some examples, the nuclear export signal peptide may comprise a peptide selected from the group consisting of NES1, NES2, NES3, NES4, NES5, NES6, NES7, NES8, and a variant or derivative thereof. In one example, the nuclear export signal peptide may comprise NES1 or a variant or derivative thereof. In another example, the nuclear export signal peptide may comprise NES or a variant or derivative thereof.

The TES included in the modified fusion protein may also be a protease sensitive peptide. For example, the TES may comprise a ubiquitin-like modifier, e.g., may comprise a sequence having at least 85%, at least 90%, at least 95%, or at least 99% sequence identity to any one of SEQ ID NOs. 18-31.

In other examples, the TES may comprise a protease sensitive peptide selected from the group consisting of ubiquitin, a caspase cleavage domain, a calpain cleavage domain, SUMO1, SUMO2, SUMO3, SUMO4, ISG15, Atg8, Atg12, NEDD8, and a variant or derivative thereof.

In some examples, the modified fusion protein may comprise an amino acid sequence having at least 85%, at least 90%, at least 95% or at least 99% sequence identity to any of SEQ ID NOs. 55-61 and 69-71.

Methods of Treatment

Provided herein is a therapeutic compound for treating a non-nuclear organelle associated disorder in a subject in need thereof. The therapeutic compound, in some embodiments, may comprise a fusion protein, a nucleic acid, a vector, or a conjugate of the present disclosure. Non-limiting examples of a non-nuclear organelle associated disorder may include, in some embodiments, a mitochondrial disorder and a lysosomal disorder. In some embodiments, the non-nuclear organelle associated disorder is a genetic disorder.

Also provided in the present disclosure are methods for treating a non-nuclear organelle associated disorder that comprise administering to a subject in need thereof a fusion protein, a nucleic acid, a vector, a conjugate, a cell, or a pharmaceutical composition as described herein. In some embodiments, the non-nuclear organelle associated disorder is a mitochondrial disorder. In one specific example, the mitochondrial disorder is Friedrich's Ataxia.

In some examples, the non-nuclear organelle associated disorder may be a lysosomal disorder, i.e., a disorder associated with a dysfunction of lysosomes.

In some embodiments, the non-nuclear organelle associated disorder may be selected from the group consisting of Friedreich's Ataxia (FRDA), Barth Syndrome, Parkinson's Disease, Leigh Syndrome, such as Leigh Syndrome, French Canadian Type, and Pyruvate Dehydrogenase Deficiency.

Subjects suffering from or who may be at risk of developing any one or more of the disorders disclosed herein may be selected for treatment based on multiple factors, including symptom presentation, and/or the identification of a marker that predisposes the subject to the disease or disorder (such as a genetic mutation).

As used herein, the term "subject" includes a human or non-human animal, preferably a vertebrate, and more preferably a mammal. A subject may also include a transgenic organism. Most preferably, the subject is a human, such as a human suffering from or predisposed to developing a non-nuclear organelle associated disorder, such as Friedrich's Ataxia or Parkinson's Disease.

As used herein, the term "treating a non-nuclear organelle associated disorder" comprises reducing, ameliorating, or eliminating one or more symptom(s) associated with the non-nuclear organelle associated disorder, e.g., Friedreich's Ataxia or Parkinson's Disease. The term "treating a non-nuclear organelle associated disorder" also comprises achieving, partially or substantially, one or more of the following: ameliorating or improving a symptom or an indicator associated with a non-nuclear organelle associated disorder; arresting the progression or worsening of at least one symptom of the non-nuclear organelle associated disorder. The term "treating a non-nuclear organelle associated disorder" also comprises preventing the development or delaying the appearance of at least one symptom of a non-nuclear organelle associated disorder, or developing at least one symptom of the non-nuclear organelle associated disorder that is of a lesser severity than the same symptom that would develop without treatment.

Methods of Treating Friedreich's Ataxia (FRDA)

In one embodiment, the present disclosure provides methods for treating Friedreich's Ataxia (FRDA) that comprise administering to a subject in need thereof a fusion protein of the disclosure. For example, the present disclosure provides methods for treating FRDA that comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) any CPP as described herein; and 3) any TES as described herein.

In some embodiments, methods for treating FRDA comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) any TES as described herein.

In some embodiments, methods for treating FRDA comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to Ubiquitin (SEQ ID NO: 18).

In some embodiments, methods for treating FRDA comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to a calpain cleavage domain of SEQ ID NO: 20.

In some embodiments, methods for treating FRDA comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to any one of SEQ ID NO 19, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, or SEQ ID NO: 31, SEQ ID NO: 32, SEQ ID NO: 33, SEQ ID NO: 34 and SEQ ID NO: 35.

In some embodiments, methods for treating FRDA comprise administering to a subject in need thereof a fusion protein comprising or consisting of an amino acid sequence selected from the group consisting of SEQ ID NO: 56, SEQ ID NO: 57, SEQ ID NO: 58, SEQ ID NO: 59, SEQ ID NO: 60, SEQ ID NO: 61 and SEQ ID NO: 81.

In one embodiment, methods for treating FRDA comprise administering to a subject in need thereof a fusion protein comprising or consisting of an amino acid sequence having at least about 85%, about 90%, about 95% or about 99% sequence identity to SEQ ID NO: 56.

In one embodiment, methods for treating FRDA comprise administering to a subject in need thereof a fusion protein comprising or consisting of an amino acid sequence having at least about 85%, about 90%, about 95% or about 99% sequence identity to SEQ ID NO: 57.

In one embodiment, methods for treating FRDA comprise administering to a subject in need thereof a fusion protein comprising or consisting of an amino acid sequence having at least about 85%, about 90%, about 95% or about 99% sequence identity to SEQ ID NO: 58.

In one embodiment, methods for treating FRDA comprise administering to a subject in need thereof a fusion protein comprising or consisting of an amino acid sequence having at least about 85%, about 90%, about 95% or about 99% sequence identity to SEQ ID NO: 59.

In one embodiment, methods for treating FRDA comprise administering to a subject in need thereof a fusion protein comprising or consisting of an amino acid sequence having at least about 85%, about 90%, about 95% or about 99% sequence identity to SEQ ID NO: 60.

In one embodiment, methods for treating FRDA comprise administering to a subject in need thereof a fusion protein comprising or consisting of an amino acid sequence having at least about 85%, about 90%, about 95% or about 99% sequence identity to SEQ ID NO: 61.

In one embodiment, methods for treating FRDA comprise administering to a subject in need thereof a fusion protein comprising or consisting of an amino acid sequence having at least about 85%, about 90%, about 95% or about 99% sequence identity to SEQ ID NO: 81.

The term "FRDA", as used herein, encompasses any disease, disorder or condition associated with a frataxin deficiency. The term "FRDA-associated disease, disorder or condition", as used herein, encompasses a disease, disorder or condition secondary to and/or caused by FRDA, i.e., when present in a subject, it accompanies FRDA and is not present in a subject in the absence of FRDA. Non-limiting examples of an FRDA-associated disease, disorder, or condition, include FRDA-associated pneumonia, FRDA-associated hypertrophic cardiomyopathy and FRDA-associated diabetes. Other non-limiting examples of an FRDA-associated disease, disorder or condition include an FRDA-associated disease, disorder or condition characterized by, without limitation:

(1) a neurological deficiency including, without limitation, one or more of the following: loss of proprioception, loss of reflexes, loss of ability to walk, loss of ability to hold gaze with eyes;
(2) impaired swallowing and/or a progressive loss of the ability to swallow; progressive loss of hearing;
(3) progressive loss of vision due to retinal degeneration from lack of FXN;
(4) progressive loss of speech;
(5) metabolic syndrome including, without limitation, elevated triglycerides, low high-density lipoprotein (HDL) cholesterol, and elevated low-density lipoprotein (LDL) cholesterol;
(6) scoliosis that requires surgery to correct; and/or combinations thereof.

In some embodiments, administration of a fusion protein of the present disclosure to a subject may treat FRDA, including, e.g., an FRDA-associated disease, disorder or condition. "Treating FRDA", as used herein, encompasses ameliorating, improving or achieving a reduction in the severity of FRDA, including, e.g., an FRDA-associated disease, disorder or condition. For example, "treating FRDA" encompasses ameliorating, improving or achieving a reduction in at least one symptom or indicator associated with FRDA. "Treating FRDA", as used herein, also encompasses delaying progression of FRDA, including, e.g., an FRDA-associated disease disorder or condition, e.g., delaying appearance of at least one symptom or indicator associated with FRDA or preventing an increase in the severity of at least one symptom or indicator associated with FRDA, in a subject.

In some embodiments, the term "treating FRDA" also encompasses achieving increased survival (e.g., survival time) of a subject, e.g., a human, with FRDA, including, e.g., an FRDA-associated disease, disorder or condition. For example, treatment of FRDA may result in an increased life expectancy of a subject, e.g., a human, with FRDA, including, e.g., an FRDA-associated disease disorder or condition. In some embodiments, treatment of FRDA in the context of the present disclosure may result in an increased life expectancy of a subject of greater than about 10%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, greater than about 150%, greater than about 160%, greater than about 170%, greater than about 180%, greater than about 190%, or greater than about 200% or more, as compared to the average life expectancy of one or more control individuals with similar disease without treatment.

In some embodiments, treatment of FRDA, including, e.g., an FRDA-associated disease, disorder or condition, in the context of the present disclosure may result in an increased life expectancy of a subject by greater than about 6 months, greater than about 8 months, greater than about 10 months, greater than about 12 months, greater than about 2 years, greater than about 4 years, greater than about 6 years, greater than about 8 years, or greater than about 10 years or more, as compared to the average life expectancy of one or more control individuals with similar disease without treatment. In some embodiments, treatment of FRDA, including, e.g., an FRDA-associated disease, disorder or condition in the context of the present disclosure may result in a long-term survival of a subject, e.g., a human, with FRDA, including, e.g., an FRDA-associated disease, disorder or condition. The term "long-term survival", as used herein, refers to a survival time or life expectancy longer than about 40 years, 45 years, 50 years, 55 years, 60 years, or longer.

Clinical assessments known to one of ordinary skill in the art may be used to assess FRDA, including, e.g., an FRDA-associated disease, disorder or condition, to determine the severity of the FRDA and/or to determine the effect of administration to a subject of a fusion protein of the present disclosure. Examples of methods of clinical assessment of FRDA, including assessments of the severity of FRDA, are described, e.g., in Paap et al., "Standardized Assessment of Hereditary Ataxia Patients in Clinical Studies", *Mov Disord Clin Pract.* 2016, 3(3):230-240 and Patel et al., "Progression of Friedreich ataxia: quantitative characterization over 5 years", *Ann Clin Transl Neurol* 2016, 3(9):684-694, the entire contents of each of which are hereby incorporated herein by reference.

Timed 25-Foot Walk (T25-FW) is a quantitative mobility and leg function performance test that measures the time needed to complete a 25-foot walk. In some embodiments, administration to a subject of a fusion protein of the present disclosure may result in a decrease in the severity of FRDA as measured, e.g., by the time needed to complete a 25-foot walk. For example, administration to a subject of a fusion protein of the disclosure may result in a decrease in the time needed to complete a 25-foot walk, e.g., a decrease of at least about 5%, at least about 10%, at least about 25%, or at least about 50% in the time needed to complete a 25-foot walk, as compared to the time needed to complete a 25-foot walk measured in the subject prior to administration of a fusion protein of the disclosure, or as compared to a baseline value. A baseline value may be the time needed to complete a 25-food walk measured prior to administration of a fusion protein of the present disclosure.

In other embodiments, administration to a subject of a fusion protein of the present disclosure may delay progression of FRDA in the subject as measured, e.g., by the time needed to complete a 25-foot walk. For example, administration to a subject of a fusion protein of the present disclosure may result in a substantially similar time needed to complete a 25-foot walk, or a lack of a substantial increase in the time needed to complete a 25-foot walk (e.g., less than a 20%, less than a 10%, or less than a 5% increase in the time needed to complete a 25-foot walk), as compared to the baseline value, i.e., time needed to complete a 25-foot walk measured in the subject prior to administration of a fusion protein of the present disclosure.

The Modified Friedreich's Ataxia Rating Scale (mFARS) is an examination-based rating scale for assessing the severity of FRDA as described, e.g., in Burk et al., "Monitoring progression in Friedreich ataxia (FRDA): the use of clinical scales", *J of Neurochemistry* 2013, 126(suppl. 1):118-124 and Rummey et al., "Psychometric properties of the Friedreich's Ataxia Rating Scale", *Neurol Genet* 2019, 5:e371, the entire contents of each of which are hereby incorporated herein by reference.

In some embodiments, the mFARS score may comprise at least one of the following subscores: a) a score based on the Functional Disability Rating Scale (FARS-FDS; 0-6 scale; assessment usually made by a neurologist; b) a score based on the Activities of Daily Living Scale (FARS-ADL, 0-36 scale; assessment made by a patient or caregiver); and c) a score based on the Neurological Rating Scale (FARS-neuro) 0-125 scale; assessment made by a neurologist). In some examples, the FARS_ADL score is a FARS rating scale assessing subject ability to complete ADLs (e.g., speech, cutting food, dressing, and personal hygiene), with scores ranging from 0 to 36 points. The respondent may be the subject; a combination of the subject and family; or a family member, spouse or caregiver for those subjects unable to complete the test.

In some embodiments, the score based on the Neurological Rating Scale may include modified scoring of the neurological rating scale involving direct subject participation and targeting specific areas impacted by FRDA, such as bulbar, upper limb, lower limb, and upright stability (mFARS-neuro, 0-99 scale). The mFARS-neuro excludes subscale D (peripheral nervous system) and the first 2 questions of subscale A (bulbar) from the neurological rating scale of the FARS questionnaire.

In some embodiments, the mFARS score may be based on two subscores derived from the full FARS questionnaire: mFARS-neuro as described above and the FARS_ADL as described above.

In some embodiments, administration to a subject of a fusion protein of the present disclosure may result in a decrease in the severity of FRDA as measured, e.g., by an mFARS score, or at least one mFARS subscore as described herein. For example, administration to a subject of a fusion protein of the present disclosure may result in a decrease in an mFARS score or at least one mFARS subscore, as compared to a baseline value, i.e., the mFARS score or the at least one mFARS subscore measured in the subject prior to administration of a fusion protein of the present disclosure.

In other embodiments, administration to a subject of a fusion protein of the present disclosure may delay progression of FRDA in the subject as measured, e.g., by an mFARS score or at least one mFARS subscore as disclosed herein. For example, administration to a subject of a fusion protein of the present disclosure may result in a substantially similar mFARS score or at least one mFARS subscore, or a substantial lack of an increase in an mFARS score or at least one mFARS subscore, as compared to a baseline value, i.e., the mFARS score or the at least one mFARS subscore measured in the subject prior to administration of a fusion protein of the present disclosure, or as compared to a baseline value.

The Nine-Hole Peg Test (9HPT) may be used to measure finger dexterity in subjects with FRDA. In this test, a subject is asked to take pegs from a container, one by one, and place them into the nine holes on the board as quickly as possible. The subject must then remove the pegs from the holes, one by one, and replace them back into the container. Scores are based on the time taken to complete the test activity, recorded in seconds.

In some embodiments, administration to a subject of a fusion protein of the present disclosure may result in a decrease in the severity of FRDA as measured, e.g., by a 9HPT score. For example, administration to a subject of a fusion protein of the present disclosure may result in an decrease in a 9HPT score expressed as time to complete the test activity (e.g., at least an about 5%, 10%, 25%, or 50% decrease in a 9HPT score expressed as time to complete the test activity), as compared to a baseline value, i.e., the 9HPT score measured in the subject prior to administration of a fusion protein of the present disclosure.

In other embodiments, administration to a subject of a fusion protein of the present disclosure may delay progression of FRDA in the subject as measured, e.g., by a 9HPT score. For example, administration to a subject of a fusion protein of the present disclosure may result in a substantially similar 9HPT score, or a lack of a substantial increase in a 9HPT score expressed as time to complete the test activity, as compared to a baseline value, i.e., the 9HPT score measured in the subject prior to administration of a fusion protein of the present disclosure.

In some embodiments, administration to a subject of a fusion protein of the present disclosure results in an increase in the level of hFXN in at least one tissue or biological fluid of the subject, as compared to a baseline level, i.e., the hFXN level in the at least one tissue or biological fluid of the subject prior to administration of a fusion protein of the present disclosure. In some embodiments, the increase in the level of hFXN in the at least one tissue or biological fluid of a subject resulting from administration of a fusion protein of the present disclosure to the subject is sufficient to have a therapeutic effect, i.e., sufficient to treat FRDA in the subject.

In some embodiments, administration of a fusion protein of the present disclosure to a subject with FRDA may result in a level of hFXN in at least one tissue or biological fluid of the subject that is lower than the level of hFXN in the at least one tissue or biological fluid of a subject who does not have FRDA (e.g., a normal, healthy subject), but is still sufficient to have a therapeutic effect, i.e., sufficient to treat FRDA in the subject. For example, after administration of a fusion protein of the present disclosure to a subject with FRDA, the level of hFXN in at least one tissue or a biological fluid of the subject may be about 10% to about 50%, about 20% to about 60%, or about 30% to about 80% of the level of hFXN in the at least one tissue or a biological fluid of a subject who does not have FRDA (e.g., a normal, healthy subject), but the level of hFXN is still sufficient to have a therapeutic effect, i.e., sufficient to treat FRDA in the subject.

In some embodiments, administration to a subject with FRDA of a fusion protein of the present disclosure may result in an increase of at least about 5%, about 10%, about 25%, about 50%, about 100%, about 150%, about 200%, about 300%, about 400%, about 500%, or about 600% in the level of hFXN in at least one tissue or biological fluid of the subject, as compared to the hFXN level in the at least one tissue or biological fluid of the subject prior to administration of a fusion protein of the present disclosure, or as compared to a baseline level.

In some embodiments, administration to a subject with FRDA of a fusion protein of the present disclosure may result in an increase of about 5% to about 30%, about 10% to about 50%, about 25% to about 100%, about 50% to about 150%, about 100% to about 300%, about 50% to about 250%, about 150% to about 500% or about 200% to about 700% in the level of hFXN in at least one tissue or biological fluid of the subject, as compared to the hFXN level in the at least one tissue or biological fluid of the subject prior to administration of a fusion protein of the present disclosure, or as compared to a baseline level. In some embodiments, administration to a subject of a fusion protein of the present disclosure may result in an increase of at least about 2-fold, about 3-fold, about 4-fold, about 5-fold in the level of hFXN in at least one tissue or biological fluid of the subject, as compared to the hFXN level in the at least one tissue or biological fluid of the subject prior to administration of a fusion protein of the present disclosure, or as compared to a baseline level. In some embodiments, administration to a subject of the disclosed TAT-FXN fusion polypeptide and/or a pharmaceutical composition comprising the disclosed TAT-FXN fusion polypeptide may result in an increase of between about 2-fold and about 5-fold, or between about 2-fold and about 10-fold, in the level of hFXN in at least one tissue or biological fluid of the subject, as compared to the hFXN level in the at least one tissue or biological fluid of the subject prior to administration of a fusion protein of the present disclosure, or as compared to a baseline level.

In some embodiments, the tissue of a subject in which the level of hFXN may be measured and/or increased may be any tissue that is capable of being biopsied. In some embodiments, the tissue may comprise bronchoalveolar tissue (which may be sampled by, e.g., bronchoalveolar brushing), a mucous membrane (e.g., nasal mucous membrane, which may be sampled by, e.g., nose brushing), a hair follicle, skin tissue, or buccal tissue. In some embodiments, the tissue comprises skin tissue or buccal tissue.

In some embodiments, the biological fluid of a subject in which the level of hFXN may be measured and/or increased may be blood or a component thereof (e.g., serum, plasma, platelets, or any other blood component), urine, or saliva.

FRDA-Associated Pneumonia

Subjects diagnosed with FRDA suffer neurodegeneration of the dorsal root ganglia causing progressive ataxia. This typically leads to the progressive loss of an ability to walk, feed oneself, talk, swallow, and pulmonary aspiration. The event of pulmonary aspiration can lead to pneumonia, frequent hospitalizations, and, eventually, death over a period of 10-15 years from the date of diagnosis.

Accordingly, administration of a fusion protein of the present disclosure can be effective as a protein replacement therapy in FXN-deficient subjects diagnosed with FRDA to prevent pulmonary aspiration, thereby preventing the pneumonia that follows pulmonary aspiration. Accordingly, the present disclosure provides methods of treating an FRDA-associated pneumonia in a subject, comprising administering to a subject in need thereof a fusion protein of the present disclosure, thereby treating the FRDA-associated pneumonia in the subject.

FRDA-Associated Hypertrophic Cardiomyopathy

Hypertrophic cardiomyopathy is a condition in which the muscles of the heart thicken, making it difficult for the heart to pump blood through the circulatory system. It can be caused by a deficiency in FXN in the mitochondria of the heart cells. In subjects diagnosed with FRDA, progressive hypertrophic cardiomyopathy about 50% of the time progresses to heart failure and death. Protein replacement therapy with a fusion protein of the present disclosure can replace the FXN deficiency underlying hypertrophic cardiomyopathy.

Administration of a fusion protein of the present disclosure can, therefore, be effective as a protein replacement therapy in FXN-deficient subjects diagnosed with both FRDA and hypertrophic cardiomyopathy. Accordingly, the present disclosure provides methods of treating an FRDA-associated hypertrophic cardiomyopathy in a subject, comprising administering to a subject in need thereof a fusion protein of the present disclosure, thereby treating the FRDA-associated hypertrophic cardiomyopathy in the subject.

Diabetes

The hallmark of diabetes is an inability to properly regulate blood levels of glucose, resulting in elevated blood glucose levels. In subjects diagnosed with FRDA, diabetes often shows up as a consequence of FXN-deficient mitochondria in the pancreas. Protein replacement therapy with a fusion protein of the present disclosure can replace the FXN deficiency underlying diabetes.

Administration of a fusion protein of the present disclosure, can, therefore, be effective as a protein replacement therapy in FXN-deficient subjects diagnosed with diabetes. Accordingly, the present disclosure provides methods of treating an FRDA-associated diabetes in a subject, comprising administering to a subject in need thereof a fusion protein of the present disclosure, thereby treating the FRDA-associated diabetes in the subject.

Other FRDA-Associated Diseases/Disorders

Subjects diagnosed with FRDA often experience other disorders associated with FXN deficiency. Such FRDA-associated disorders can include, without limitation: neurological disorders including, without limitation, loss of proprioception, loss of reflexes, loss of ability to walk, loss of ability to hold gaze with eyes; impaired swallowing and/or a progressive loss of the ability to swallow; progressive loss of hearing; progressive loss of vision due to retinal degeneration from lack of FXN; progressive loss of speech; metabolic syndrome including, without limitation, elevated triglycerides, low high-density lipoprotein (HDL) cholesterol, and elevated low-density lipoprotein (LDL) cholesterol; scoliosis that requires surgery to correct; and/or combinations thereof. Protein replacement therapy with a fusion protein of the present disclosure can replace the FXN deficiency underlying these FRDA-associated diseases/disorders.

Administration of a fusion protein of the present disclosure can, therefore, be effective as a protein replacement therapy in FXN-deficient subjects diagnosed with FRDA and experiencing neurological disorders including, without limitation, loss of proprioception, loss of reflexes, loss of ability to walk, loss of ability to hold gaze with eyes; impaired swallowing and/or a progressive loss of the ability to swallow; progressive loss of hearing; progressive loss of vision due to retinal degeneration from lack of FXN; progressive loss of speech; metabolic syndrome including, without limitation, elevated triglycerides, low HDL cholesterol, and elevated LDL cholesterol; scoliosis that requires surgery to correct; and/or combinations thereof.

Accordingly, the present disclosure provides methods of treating an FRDA-associated disease, disorder or condition, comprising administering to a subject in need thereof a fusion protein of the present disclosure, wherein the FRDA-associated disease, disorder or condition is selected from: neurological disorders including, without limitation, loss of proprioception, loss of reflexes, loss of ability to walk, loss of ability to hold gaze with eyes; impaired swallowing and/or a progressive loss of the ability to swallow; progressive loss of hearing; progressive loss of vision due to retinal degeneration from lack of FXN; progressive loss of speech; metabolic syndrome including, without limitation, elevated triglycerides, low HDL cholesterol, and elevated LDL cholesterol; and scoliosis that requires surgery to correct.

In certain embodiments, treatment of a subject in need thereof with a fusion protein, a pharmaceutical composition or a therapeutic compound of the present disclosure, e.g., a fusion protein comprising FXN, increases cellular levels of FXN in a subject. In some embodiments, the methods of the present disclosure increase the cellular levels of FXN by at least about 10%, e.g., about 20%, about 25%, about 30%, about 40%, about 50%, about 60%, about 70%, about 75%, about 80%, about 85%, about 90%, about 95%, or more, relative to the levels of FXN in the subject prior to treatment. In another embodiment, the methods of the present disclosure increase the cellular levels of FXN by at least about two-fold, at least about three-fold, at least about four-fold, at least about five-fold, at least about six-fold, at least about seven-fold, at least about eight-fold, at least about nine-fold, or at least about ten-fold. In some embodiments, the increase is measured by comparing the cellular levels of FXN in a subject before and after administration of the fusion protein of the disclosure.

Before, during, and after the administration of the fusion protein, pharmaceutical composition and/or therapeutic compound of the disclosure, the cellular levels of FXN in the subject may be measured in a biological sample, such as blood, serum, plasma, urine, peritoneal fluid, cerebrospinal fluid, fecal matter, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods may include administration of a fusion protein disclosed herein to increase the cellular levels of FXN in a subject. In some embodiments, the methods may include administration of the fusion protein disclosed herein to increase the cellular levels of FXN by more than about 1%, 2%, 5%, 10%, 20%, 25%, 30%, 40%, 50%, 60%, 70%, 75%, 80%, 85%, 90%, or 95% of the subject's cellular levels of FXN prior to treatment. Cellular levels of FXN may be measured by methods known in the art. For example, cellular levels of FXN may be measured by collecting samples, such as skin biopsies (punch) buccal swab, platelets and analyzing them for FXN using ELISA, Hybrid LBA-LC-MS/MS or other mass spectrometry related methods.

Methods for Treating Leigh Syndrome, French Canadian Type (LSFC)

The present disclosure also provides methods of treating Leigh Syndrome, French Canadian Type (LSFC) that comprise administering to a subject in need thereof a fusion protein of the disclosure, such that the LSFC in the subject is treated. It was surprisingly discovered that the mitochondrial impairment in LRPPRC-deficient cells, as evidenced by acidification of cell growth media, is reduced by treatment of the cells with hFXN fusion proteins of the present disclosure. It was also surprisingly discovered that the amount of CYR61 protein secreted by the LRPPRC-deficient cells into the cell growth media is reduced by treatment of the cells with hFXN fusion proteins of the present disclosure. Further, it was also surprisingly discovered that the hFXN fusion proteins of the present disclosure comprising TES are more potent in reducing acidification of the media and secretion of CYR61 from LRPPRC-deficient cells than the hFXN fusion protein that does not comprise TES.

The above described discoveries indicate that certain molecular and cellular changes associated with deficiencies in LRPPRC may be mitigated and/or reversed by administering a hFXN fusion protein of the present disclosure. The above described discoveries also indicate that LSFC, which is associated with a deficiency in LRPPRC, may be treated by administering a hFXN fusion protein of the present disclosure. Further, the above described discoveries indicate that hFXN fusion proteins of the present disclosure comprising TES are more potent in treating LSFC and/or lactic acidosis in a subject with LSFC than hFXN fusion proteins that do not comprise TES.

In some embodiments, the present disclosure provides methods for treating LSFC in a subject in need theref that comprise administering to the subject a fusion protein comprising: 1) an amino acid sequence having at least 85%, at least 90%, at least 95%, or at least 99% sequence identity to full-length hFXN (SEQ ID NO: 1) as protein of interest; 2) any CPP as described herein; and 3) any TES as described herein.

In some embodiments, methods for treating LSFC comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) any TES as described herein.

In some embodiments, methods for treating LSFC comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to Ubiquitin (SEQ ID NO: 18).

In some embodiments, methods for treating LSFC comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to a calpain cleavage domain of SEQ ID NO: 20.

In some embodiments, methods for treating LSFC comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to any one of SEQ ID NO 19, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, or SEQ ID NO: 31, SEQ ID NO: 32, SEQ ID NO: 33, SEQ ID NO: 34 and SEQ ID NO: 35.

In some embodiments, methods for treating LSFC comprise administering to a subject in need thereof a fusion protein comprising or consisting of an amino acid sequence selected from the group consisting of SEQ ID NO: 56, SEQ ID NO: 57, SEQ ID NO: 58, SEQ ID NO: 59, SEQ ID NO: 60, SEQ ID NO: 61 and SEQ ID NO: 83.

In one embodiment, methods for treating LSFC comprise administering to a subject in need thereof a fusion protein comprising or consisting of an amino acid sequence having at least about 85%, about 90%, about 95% or about 99% sequence identity to SEQ ID NO: 56.

In one embodiment, methods for treating LSFC comprise administering to a subject in need thereof a fusion protein comprising an amino acid sequence having at least about 85%, about 90%, about 95% or about 99% sequence identity to SEQ ID NO: 57.

In one embodiment, methods for treating LSFC comprise administering to a subject in need thereof a fusion protein comprising or consisting of an amino acid sequence having at least about 85%, about 90%, about 95% or about 99% sequence identity to SEQ ID NO: 58.

In one embodiment, methods for treating LSFC comprise administering to a subject in need thereof a fusion protein comprising or consisting of an amino acid sequence having at least about 85%, about 90%, about 95% or about 99% sequence identity to SEQ ID NO: 59.

In one embodiment, methods for treating LSFC comprise administering to a subject in need thereof a fusion protein comprising or consisting of an amino acid sequence having at least about 85%, about 90%, about 95% or about 99% sequence identity to SEQ ID NO: 60.

In one embodiment, methods for treating LSFC comprise administering to a subject in need thereof a fusion protein comprising or consisting of an amino acid sequence having at least about 85%, about 90%, about 95% or about 99% sequence identity to SEQ ID NO: 61.

In one embodiment, methods for treating LSFC comprise administering to a subject in need thereof a fusion protein comprising or consisting of an amino acid sequence having at least about 85%, about 90%, about 95% or about 99% sequence identity to SEQ ID NO: 83.

In some embodiments, the present disclosure provides methods for lactic acidosis in a subject with LSFC that comprise administering to a subject in need thereof a fusion protein of the disclosure, such that lactic acidosis in the subject is treated. For example, the present disclosure provides methods for treating lactic acidosis in a subject with LSFC that comprise administering to the subject a fusion protein comprising: 1) an amino acid sequence having at least 85%, at least 90%, at least 95%, or at least 99% sequence identity to full-length hFXN (SEQ ID NO: 1) as protein of interest; 2) any CPP as described herein; and 3) any TES as described herein.

In some embodiments, methods for treating lactic acidosis in a subject with LSFC comprise administering to the subject a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) any TES as described herein.

In some embodiments, methods for treating lactic acidosis in a subject with LSFC comprise administering to the subject a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to Ubiquitin (SEQ ID NO: 18).

In some embodiments, methods for treating lactic acidosis in a subject with LSFC comprise administering to the subject a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to a calpain cleavage domain of SEQ ID NO: 20.

In some embodiments, methods for treating lactic acidosis in a subject with LSFC comprise administering to the subject a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to any one of SEQ ID NO 19, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, or SEQ ID NO: 31, SEQ ID NO: 32, SEQ ID NO: 33, SEQ ID NO: 34 and SEQ ID NO: 35.

In some embodiments, methods for treating lactic acidosis in a subject with LSFC comprise administering to the subject a fusion protein comprising or consisting of an amino acid sequence selected from the group consisting of SEQ ID NO: 56, SEQ ID NO: 57, SEQ ID NO: 58, SEQ ID NO: 59, SEQ ID NO: 60, SEQ ID NO: 61 and SEQ ID NO: 83.

In one embodiment, for treating lactic acidosis in a subject with LSFC comprise administering to the subject a fusion protein comprising or consisting of an amino acid sequence having at least about 85%, about 90%, about 95% or about 99% sequence identity to SEQ ID NO: 56.

In one embodiment, methods for treating lactic acidosis in a subject with LSFC comprise administering to the subject a fusion protein comprising or consisting of an amino acid sequence having at least about 85%, about 90%, about 95% or about 99% sequence identity to SEQ ID NO: 57.

In one embodiment, methods for treating lactic acidosis in a subject with LSFC comprise administering to the subject a fusion protein comprising or consisting of an amino acid sequence having at least about 85%, about 90%, about 95% or about 99% sequence identity to SEQ ID NO: 58.

In one embodiment, methods for treating lactic acidosis in a subject with LSFC comprise administering to the subject a fusion protein comprising or consisting of an amino acid sequence having at least about 85%, about 90%, about 95% or about 99% sequence identity to SEQ ID NO: 59.

In one embodiment, methods for treating lactic acidosis in a subject with LSFC comprise administering to the subject a fusion protein comprising or consisting of an amino acid sequence having at least about 85%, about 90%, about 95% or about 99% sequence identity to SEQ ID NO: 60.

In one embodiment, methods for treating lactic acidosis in a subject with LSFC comprise administering to the subject a fusion protein comprising or consisting of an amino acid sequence having at least about 85%, about 90%, about 95% or about 99% sequence identity to SEQ ID NO: 61.

In one embodiment, methods for treating lactic acidosis in a subject with LSFC comprise administering to the subject a fusion protein comprising or consisting of an amino acid sequence having at least about 85%, about 90%, about 95% or about 99% sequence identity to SEQ ID NO: 83.

The term "treating LSFC", as used herein, encompasses ameliorating, improving or achieving a reduction in the severity of LSFC, e.g., ameliorating, improving or achieving a reduction in at least one symptom or indicator associated with LSFC in a subject. "Treating LSFC", as used herein, also encompasses delaying progression of LSFC, e.g., delaying appearance of at least one symptom or indicator associated with LSFC, or preventing an increase in the severity of at least one symptom or indicator associated with LSFC in a subject. In some embodiments, the at least one symptom or indicator associated with LSFC may be selected from the group consisting of developmental delay, ataxia, hypotonia, brain lesions, coma, abnormal breathing patterns, seizures, stroke-like episodes and lactic acidosis.

Methods of Treating Parkinson's Disease

In one embodiment, the present disclosure provides methods for treating Parkinson's Disease (PD) that comprise administering to a subject in need thereof a fusion protein of the disclosure. For example, the present disclosure provides methods for treating Parkinson's Disease that comprise administering to a subject in need thereof a fusion protein of the disclosure. For example, the present disclosure provides methods for treating Parkinson's Disease that comprise administering to a subject in need thereof a fusion protein comprising: 1) an amino acid sequence having at least 85%, at least 90%, at least 95%, or at least 99% sequence identity to PINK1 (SEQ ID NO: 8) as protein of interest; 2) any CPP as described herein; and 3) any TES as described herein.

In some embodiments, methods for treating Parkinson's Disease comprise administering to a subject in need thereof a fusion protein comprising: 1) an amino acid sequence having at least 85%, at least 90%, at least 95%, or at least 99% sequence identity to PINK1 (SEQ ID NO: 8) as protein of interest; 2) an amino acid sequence having at least 85%, at least 90%, at least 95% or at least 99% to TAT-HIV (SEQ ID NO: 11); and 3) any TES as described herein, e.g., Ubiquitin (SEQ ID NO: 18) or calpain cleavage domain (SEQ ID NO: 20).

In some embodiments, methods for treating Parkinson's Disease comprise administering to a subject in need thereof a fusion protein comprising: 1) an amino acid sequence having at least 85%, at least 90%, at least 95%, or at least 99% sequence identity to PINK1 (SEQ ID NO: 8) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to Ubiquitin (SEQ ID NO: 18).

In one embodiment, the present disclosure provides methods for treating Parkinson's Disease that comprise administering to a subject in need thereof a fusion protein comprising: 1) an amino acid sequence having at least 85%, at least 90%, at least 95%, or at least 99% sequence identity to PARKIN (SEQ ID NO: 7) as protein of interest; 2) any CPP as described herein; and 3) any TES as described herein.

In some embodiments, methods for treating Parkinson's Disease comprise administering to a subject in need thereof a fusion protein comprising: 1) an amino acid sequence having at least 85%, at least 90%, at least 95%, or at least 99% sequence identity to PARKIN (SEQ ID NO: 7) as protein of interest; 2) an amino acid sequence having at least 85%, at least 90%, at least 95% or at least 99% to TAT-HIV (SEQ ID NO: 11); and 3) any TES as described herein.

In some embodiments, methods for treating Parkinson's Disease comprise administering to a subject in need thereof a fusion protein comprising: 1) an amino acid sequence having at least 85%, at least 90%, at least 95%, or at least 99% sequence identity to PARKIN (SEQ ID NO: 7) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to Ubiquitin (SEQ ID NO: 18).

In some embodiments, methods for treating Parkinson's Disease comprise administering to a subject in need thereof a fusion protein comprising: 1) an amino acid sequence having at least 85%, at least 90%, at least 95%, or at least 99% sequence identity to PARKIN (SEQ ID NO: 7) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to a calpain cleavage domain of SEQ ID NO: 20.

In some embodiments, methods for treating Parkinson's Disease comprise administering to a subject in need thereof a fusion protein comprising: 1) an amino acid sequence having at least 85%, at least 90%, at least 95%, or at least 99% sequence identity to PARKIN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to any one of SEQ ID NO 19, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, or SEQ ID NO: 31, SEQ ID NO: 32, SEQ ID NO: 33, SEQ ID NO: 34 and SEQ ID NO: 35.

In some embodiments, methods for treating Parkinson's Disease comprise administering to a subject in need thereof a fusion protein comprising or consisting of an amino acid sequence selected from the group consisting of SEQ ID NO: 69, SEQ ID NO: 70 and SEQ ID NO: 71.

In one embodiment, methods for treating Parkinson's Disease comprise administering to a subject in need thereof a fusion protein comprising or consisting of an amino acid sequence having at least about 85%, about 90%, about 95% or about 99% sequence identity to SEQ ID NO: 69.

In one embodiment, methods for treating Parkinson's Disease comprise administering to a subject in need thereof a fusion protein comprising or consisting of an amino acid sequence having at least about 85%, about 90%, about 95% or about 99% sequence identity to SEQ ID NO: 70.

In one embodiment, methods for treating Parkinson's Disease comprise administering to a subject in need thereof a fusion protein comprising or consisting of an amino acid sequence having at least about 85%, about 90%, about 95% or about 99% sequence identity to SEQ ID NO: 71.

As used herein, the term "Parkinson's Disease" encompasses both sporadic form of Parkinson's Disease and familial form of Parkinson's Disease. Familial form of Parkinson's Disease account for about 5-10% of Parkinson's Disease cases, and mutations in approximately 20 genes are implicated in Parkinson's Disease. In some embodiments, familial form of Parkinson's Disease may be associated with mutations in one or more genes selected from the group consisting of PARK2 (PRKN), PINK1 (PRKN6), PARK7, SNCA and LRRK2. In one embodiment, the familial form of Parkinson's Disease may be associated with a mutation in PARK2 (PRKN). In another embodiment, the familial form of Parkinson's Disease may be associated with a mutation in PINK1 (PRKN6). In one embodiment, the Parkinson's Disease is not a sporadic form of Parkinson's Disease.

In one embodiment, the present disclosure provides methods for treating Parkinson's Disease associated with a mutation in PARK2 gene that comprises administering to a subject in need thereof a fusion protein of the present disclosure comprising PARKIN (SEQ ID NO: 7), e.g., a fusion protein comprising an amino acid sequence having at least about 85%, about 90%, about 95% or about 99% sequence identity to any one of SEQ ID NO: 69, SEQ ID NO: 70 or SEQ ID NO: 71.

In one embodiment, the present disclosure provides methods for treating Parkinson's Disease associated with a mutation in PINK1 (PRKN6) gene that comprises administering to a subject in need thereof a fusion protein of the present disclosure comprising PARKIN (SEQ ID NO: 7), e.g., a fusion protein comprising an amino acid sequence having at least about 85%, about 90%, about 95% or about 99% sequence identity to any one of SEQ ID NO: 69, SEQ ID NO: 70 or SEQ ID NO: 71.

In some embodiments, Parkinson's Disease is characterized by at least one symptoms selected from of the following:
  a) a tremor, or shaking, which usually begins in a limb, often hand or fingers. The tremor associated with Parkinson's Disease may include a back-and-forth rubbing of the thumb and forefinger, known as a pill-rolling tremor, and a tremor of the hand when it is relaxed (at rest);
b) slowed movement (bradykinesia);
c) rigid muscles;
d) impaired posture and balance;
e) loss of automatic movements;

In addition, "non-motor symptoms" or "dopamine-non-responsive" signs or symptoms, are also common in subjects with Parkinson's Disease and may include any of the following:
f) cognitive impairment;
g) mood disorders, e.g., depression and anxiety;
h) sleeping problems, including REM Sleep Disorder, where individuals act out their dreams;
i) low blood pressure when standing;
j) constipation;
k) speech and swallowing problems; and
l) unexplained pains, drooling and smell loss.

The term "treating Parkinson's Disease", as used herein, encompasses reduction, alleviation or amelioration of one or more signs or symptoms of Parkinson's Disease as described above; diminishing the extent of Parkinson's Disease, maintaining stability (i.e., not worsening) of Parkinson's Disease, amelioration or palliation of the disease state. Treatment of Parkinson's Disease may include one or more of reduction, alleviation or amelioration of the cardinal or non-motor symptoms of PD as described above, e.g., reduction, alleviation or amelioration of tremor, bradykinesia, muscle rigidity, reduction in speech and swallowing problems, etc. In one embodiment, the treatment may also include inhibiting and slowing the progression of Parkinson's Disease.

Treatment does not need to be curative. Treatment outcomes need not be determined quantitatively. However, in certain embodiments, treatment outcomes can be quantitated by following the longitudinal course of Parkinson's Disease, using, e.g., the Unified Parkinson's Disease Rating Scale (UPDRS), or a revised UPDRS, knowns as MDS-UPDRS. The UPDRS is a scoring system most commonly used for clinical evaluation of Parkinson's disease. It contains 42 items that are evaluated by interview with the subject and clinical observation. A total of 199 point are possible on the UPDRS scale, with 199 representing the worst disability and 0 representing no disability. UPDRS comprises the following sections:

Part I: evaluation of mentation, behavior, and mood;
Part II: self-evaluation of the activities of daily life (ADLs) including speech, swallowing, handwriting, dressing, hygiene, falling, salivating, turning in bed, walking, and cutting food;
Part III: clinician-scored monitored motor evaluation;
Part IV: complications of therapy;
Part V: Hoehn and Yahr staging of severity of Parkinson's disease; and
Part VI: Schwab and England ADL scale.

These are evaluated by interview and clinical observation. Some sections require multiple grades assigned to each extremity. The revised UPDRS retains the four-scale structure of the original UPDRS, with a reorganization of the various subscales. The scales are titled; (1) nonmotor experiences of daily living (13 items), (2) motor experiences of daily living (13 items), (3) motor examination (18 items), and (4) motor complications (six items). Each subscale has 0-4 ratings, where 0=normal, 1=slight, 2=mild, 3=moderate, and 4=severe.

The UPDRS or MDS-UPDRS may be used to follow the progression of a person's Parkinson's disease or to measure benefits from a therapy, e.g., a therapy that comprises administering a fusion protein of the present disclosure.

In some embodiments, administering a fusion protein of the present disclosure to a subject in accordance with the methods described herein results in inhibition or in slowing down the Parkinson's Disease progression in the subject. Specifically, in some embodiments, administering a fusion protein of the present disclosure to a subject results in a substantially no increase of the UPDRS score in the subject over a period of time, e.g., over 1 week, 2 weeks, 3 weeks, 1 month, 2 months, 3 months, 6 months, 9 months, 1 year, 2 years, 3 years or 5 years. In some embodiments, administering of fusion protein of the disclosure to a subject results in a decrease of the UPDRS score in the subject over a period of time, e.g., over 1 week, 2 weeks, 3 weeks, 1 month, 2 months, 3 months, 6 months, 9 months, 1 year, 2 years, 3 years or 5 years.

Methods for Treating Barth Syndrome and Familial Isolated Dilated Cardiomyopathy In one embodiment, the present disclosure provides methods for treating Barth Syndrome and Familial Isolated Dilated Cardiomyopathy that comprise administering to a subject in need thereof a fusion protein of the disclosure. For example, the present disclosure provides methods for treating Barth Syndrome and Familial Isolated Dilated Cardiomyopathy that comprise administering to a subject in need thereof a fusion protein comprising: 1) an amino acid sequence having at least 85%, at least 90%, at least 95%, or at least 99% sequence identity to Tafazzin (SEQ ID NO: 3) as protein of interest; 2) any CPP as described herein; and 3) any TES as described herein.

In some embodiments, methods for treating Barth Syndrome and Familial Isolated Dilated Cardiomyopathy comprise administering to a subject in need thereof a fusion protein comprising: 1) an amino acid sequence having at least 85%, at least 90%, at least 95%, or at least 99% sequence identity to Tafazzin (SEQ ID NO: 3) as protein of interest; 2) an amino acid sequence having at least 85%, at least 90%, at least 95% or at least 99% to TAT-HIV (SEQ ID NO: 11); and 3) any TES as described herein, e.g., Ubiquitin (SEQ ID NO: 18) or calpain cleavage domain (SEQ ID NO: 20).

Methods for Treating Pyruvate Dehydrogenase E1-Beta Deficiency

In one embodiment, the present disclosure provides methods for treating Pyruvate Dehydrogenase E1-Beta Deficiency that comprise administering to a subject in need thereof a fusion protein of the disclosure. For example, the present disclosure provides methods for treating Pyruvate Dehydrogenase E1-Beta Deficiency that comprise administering to a subject in need thereof a fusion protein comprising: 1) an amino acid sequence having at least 85%, at least 90%, at least 95%, or at least 99% sequence identity to PDHB (SEQ ID NO: 4) as protein of interest; 2) any CPP as described herein; and 3) any TES as described herein.

In some embodiments, methods for treating Pyruvate Dehydrogenase E1-Beta Deficiency comprise administering to a subject in need thereof a fusion protein comprising: 1) an amino acid sequence having at least 85%, at least 90%, at least 95%, or at least 99% sequence identity to PDHB (SEQ ID NO: 4) as protein of interest; 2) an amino acid sequence having at least 85%, at least 90%, at least 95% or at least 99% to TAT-HIV (SEQ ID NO: 11); and 3) any TES as described herein, e.g., Ubiquitin (SEQ ID NO: 18) or calpain cleavage domain (SEQ ID NO: 20).

Methods for Treating Leigh Syndrome, French Canadian Type

In one embodiment, the present disclosure provides methods for treating Leigh Syndrome, French Canadian Type that comprise administering to a subject in need thereof a fusion protein of the disclosure. For example, the present disclosure provides methods for treating Leigh Syndrome, French Canadian Type that comprise administering to a subject in need thereof a fusion protein comprising: 1) an amino acid sequence having at least 85%, at least 90%, at least 95%, or at least 99% sequence identity to LRPPRC (SEQ ID NO: 5) or SLIRP (SEQ ID NO: 6) as protein of interest; 2) any CPP as described herein; and 3) any TES as described herein.

In some embodiments, methods for treating Leigh Syndrome, French Canadian Type comprise administering to a subject in need thereof a fusion protein comprising: 1) an amino acid sequence having at least 85%, at least 90%, at least 95%, or at least 99% sequence identity to LRPPRC (SEQ ID NO: 5) or SLIRP (SEQ ID NO: 6) as protein of interest; 2) an amino acid sequence having at least 85%, at least 90%, at least 95% or at least 99% to TAT-HIV (SEQ ID NO: 11); and 3) any TES as described herein, e.g., Ubiquitin (SEQ ID NO: 18) or calpain cleavage domain (SEQ ID NO: 20).

Methods for Treating PLA2G6-Associated Neurodegeneration (PLAN)

In one embodiment, the present disclosure provides methods for treating PLA2G6-associated neurodegeneration (PLAN). In some embodiments, the term "PLA2G6-associated neurodegeneration (PLAN)" may comprise one or more of the following disorders: infantile neuroaxonal dystrophy (INAD), atypical neuroaxonal dystrophy (ANAD), Parkinsonian Syndrome which contains adult onset dystonia parkinsonism (DP) and autosomal recessive early-onset parkinsonism (AREP).

In some embodiments, the methods for treating PLAN comprise administering to a subject in need thereof a fusion protein comprising: 1) an amino acid sequence having at least 85%, at least 90%, at least 95%, or at least 99% sequence identity to any variant 1-9 of Phospholipase A2, Group VI as described in Table 2 (SEQ ID NOS: 72-80) as protein of interest; 2) any CPP as described herein; and 3) any TES as described herein.

In some embodiments, the methods for treating PLAN comprise administering to a subject in need thereof a fusion protein comprising: 1) an amino acid sequence having at least 85%, at least 90%, at least 95%, or at least 99% sequence identity to any variant 1-9 of Phospholipase A2, Group VI as described in Table 2 (SEQ ID NOS: 72-80) as protein of interest; 2) an amino acid sequence having at least 85%, at least 90%, at least 95% or at least 99% to TAT-HIV (SEQ ID NO: 11); and 3) any TES as described herein, e.g., Ubiquitin (SEQ ID NO: 18) or calpain cleavage domain (SEQ ID NO: 20). Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The terms "administer", "administering" or "administration", as used herein, include any method of delivery of a fusion protein, a pharmaceutical composition or a therapeutic compound of the disclosure. In certain embodiments, the fusion protein, the pharmaceutical composition or a therapeutic compound of the present disclosure may be administered parenterally, e.g., intravenously, intramuscularly or subcutaneously. In one specific embodiment, the fusion protein, the pharmaceutical composition or a therapeutic compound of the present disclosure may be administered subcutaneously. Administering a fusion protein, a pharmaceutical composition or a therapeutic compound can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, etc.

EXAMPLES

Example 1

Comparison of Subcellular Localizations of hFXN and TAT-GG-hFXN Fusion Protein

Determining the Subcellular Localization of hFXN in Rat L6 Myoblasts Following Treatment with TAT-GG-hFXN Fusion Protein by Immunofluorescence Staining.

The human frataxin protein ($hFXN_{1-210}$) is encoded in the nucleus and is synthesized as a 210 amino acid precursor protein, having the amino acid sequence as indicated in SEQ ID NO. 1 (Table 1). Following its expression, full-length $hFXN_{1-210}$ is directed to the mitochondria by its N-terminal 80 aa mitochondrial targeting sequence (MTS), where it is actively imported and proteolytically processed to yield the 130 aa mature form, or active fragment, of the protein ($hFXN_{81-210}$), with a predicted molecular weight of 14.2 kDa and a sequence as provided in SEQ ID NO. 2 (Table 1). The FXN mature form ultimately resides in the mitochondrial matrix.

```
SEQ ID NO. 1:
MWTLGRRAVA GLLASPSPAQ AQTLTRVPRP

AELAPLCGRR GLRTDIDATC TPRRASSNQR

GLNQIWNVKK QSVYLMNLRK SGTLGHPGSL

DETTYERLAE ETLDSLAEFF EDLADKPYTF

EDYDVSFGSG VLTVKLGGDL GTYVINKQTP

NKQIWLSSPS SGPKRYDWTG KNWVYSHDGV

SLHELLAAEL TKALKTKLDL SSLAYSGKDA

SEQ ID NO. 2:
SGTLGHPGSL DETTYERLAE ETLDSLAEFF

EDLADKPYTF EDYDVSFGSG VLTVKLGGDL

GTYVINKQTP NKQIWLSSPS SGPKRYDWTG

KNWVYSHDGV SLHELLAAEL TKALKTKLDL

SSLAYSGKDA
```

A TAT-GG-hFXN fusion protein was developed for use in a protein replacement therapy for the treatment of Friedreich's Ataxia (FRDA). The TAT-GG-hFXN fusion protein has been shown to rescue disease phenotypes associated with FRDA in cells and animals. It is believed that the TAT-GG-hFXN fusion protein, when inside a cell, is localized to mitochondria.

Figure 3:
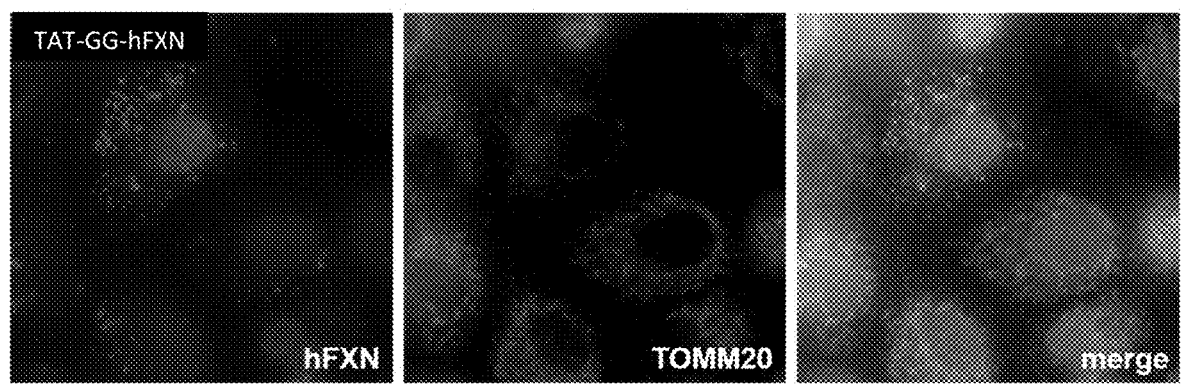
FIG. 3 is a panel of photographs of rat L6 myoblasts after treatment with a TAT-GG-hFXN fusion protein (5 µM) and immunofluorescent labeling with anti-hFXN antibodies (left panel) or mitochondria-specific anti-TOMM20 antibodies (middle panel). The right panel shows the merge of the anti-hFXN and anti-TOMM20 labels.

Subcellular localization of hFXN in rat L6 myoblasts following treatment with TAT-GG-hFXN fusion protein was evaluated through immunofluorescence microscopy (FIG. 3). Briefly, rat L6 myoblasts were treated with TAT-GG-hFXN fusion protein (5 µM) in serum-free medium for 2 hours. After 2 hours, the serum-free medium containing TAT-GG-hFXN fusion protein was replaced with complete medium, and the cells were incubated. As shown in FIG. 3, hFXN was strongly detected within small punctate intracellular vesicles as well as within the nucleus (FIG. 3, see panels "hFXN" and "merge"). The observed intracellular vesicles containing hFXN do not significantly overlap with the mitochondrial membrane marker TOMM20 (shown in FIG. 3, panel "merge"). These vesicles may represent trafficking of the TAT-GG-hFXN fusion protein through the endosomal/lysosomal system following its uptake by the cells, but further studies are required to prove this hypothesis. Together, these data demonstrate that hFXN can be detected in cells and that hFXN is strongly detected in the nucleus following treatment with the TAT-GG-hFXN fusion protein. Although low levels of hFXN may be present in the mitochondria following treatment with the TAT-GG-hFXN fusion protein under the described conditions, mitochondrial hFXN is practically undetectable in rat L6 myoblasts by immunofluorescence staining.

Figure 4:
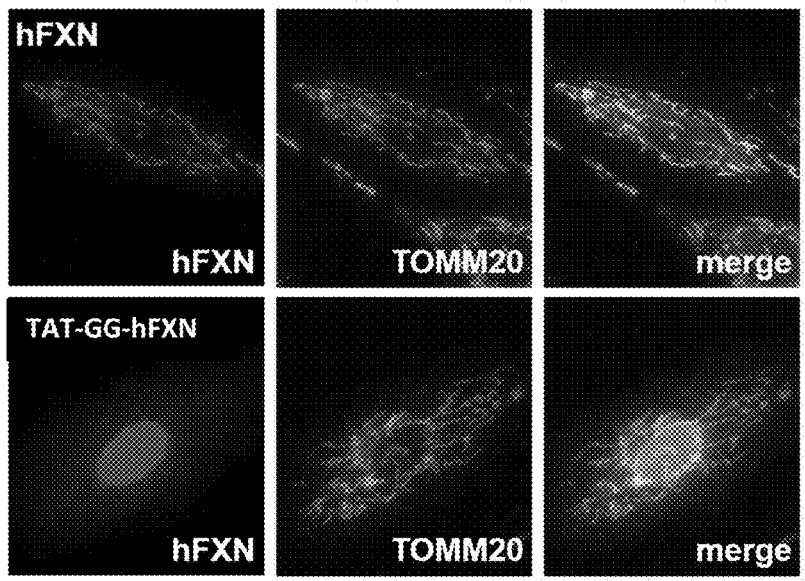
FIG. 4 is a panel of photographs of rat L6 myoblasts transfected with plasmids encoding hFXN (top panel) or a TAT-GG-hFXN fusion protein (bottom panel) after immunofluorescent labelling. The myoblasts were labelled with anti-hFXN antibodies (left panels) or anti-TOMM20 antibodies (middle panels). The right panels shows the merge of the two labels.

Comparison Between Subcellular Localization of hFXN in Rat L6 Myoblasts Following Transfection with hFXN or TAT-GG-hFXN Fusion Protein Under the above-described conditions, hFXN was detected mostly in the nucleus of rat L6 myoblasts following treatment with TAT-GG-hFXN fusion protein (FIG. 3). It is possible that the N-terminal TAT-GG sequence appended to full-length hFXN may direct the therapeutic protein into the nucleus following its internalization into cells. To more carefully assess this effect of TAT-GG on hFXN, subcellular localization of intracellularly expressed TAT-GG-hFXN fusion protein compared to hFXN in rat L6 myoblasts was detected and compared by immunofluorescence microscopy. Rat L6 myoblasts were transfected with expression plasmids containing genetic constructs encoding TAT-GG-hFXN fusion protein or hFXN$_{1-210}$ using lipid-based transfection reagents known to the person skilled in the art of transfections, such as for example the L6 Cell Avalanche system (from EZ Biosystems). After 24 hours, transfected cells were fixed using 4% paraformaldehyde and stained using antibodies against hFXN or the mitochondrial membrane marker TOMM20, as well as the Hoechst 33342 nuclear stain. As expected, rat L6 myoblasts transfected with the hFXN$_{1-210}$ construct were positive for the presence of mitochondrial hFXN, as evidenced by clear co-localization with the mitochondrial membrane marker TOMM20 (FIG. 4, top panel, "merge"). In contrast, rat L6 myoblasts transfected with TAT-GG-hFXN fusion protein stained positively for hFXN throughout the cell cytosol and strongly within the nucleus (FIG. 4, bottom panel, "merge"). In a very low percentage of cells transfected with TAT-GG-hFXN fusion protein, hFXN was detected in the mitochondria as well (very scarce co-localization staining in FIG. 4, bottom panel, "merge"). Taken together, these data demonstrate that TAT-GG-hFXN fusion protein subcellular localization is different from hFXN's native subcellular localization, going from predominantly mitochondrial (hFXN) to cytosolic and strongly nuclear (TAT-GG-hFXN fusion protein).

Example 2

Design of Novel TAT-GG-hFXN Constructs for Enhanced Delivery of hFXN to the Mitochondria The described fluorescence co-localization results shown in Example 1, FIG. 3 and FIG. 4 indicate that the great majority of TAT-GG-hFXN fusion protein molecules in the cells do not specifically localize to the mitochondria, and this may be due to the presence of the appended TAT-GG sequence at the amino-terminus of the molecule. In order to overcome this hurdle, several novel frataxin fusion proteins were designed and tested for their mitochondria delivery yields. Improved yields of mitochondrial delivery of therapeutic fusion proteins which act in the mitochondria will also provide better treatment of mitochondrial diseases, such as, for example, FRDA. To achieve this goal, novel fusion proteins were designed, and a schematic of the proteins is presented in FIG. 5, panels a-c.

One group of proteins was designed to include protease-cleavable domains, and a library of constructs encoding "protease activatable" cell-permeant hFXN fusion proteins was generated. These constructs comprised a sequence encoding a cell penetrating peptide (CPP), such as HIV-TAT (YGRKKRRQRRR; SEQ ID NO. 11) peptide, fused to an amino acid sequence that can be cleaved by an endogenous intracellular protease, and immediately followed by the protein of interest, in the present case full-length precursor hFXN. A di-peptide GG was used as a linker between the CPP and the proteolytic cleavage domain. Cleavage of TAT-GG from the fusion protein in the cytosol will result in a TAT-free hFXN protein which can then be imported into the mitochondria by virtue of its endogenous MTS. By way of example, cleavable intracellular protease-sensitive proteins used were SUMO-1 (cleaved by SUMO protease) and ubiquitin (cleaved by ubiquitinase), and proteolytically-sensitive peptides were DEVD (caspase cleavage site, SEQ ID NO: 19), EPLFAERK (SEQ ID NO: 20), and LLVY (calpain cleavage sites, SEQ ID NO: 21).

An alternative group of proteins was designed to include a nuclear exportation signal (NES), and in that way avoid accumulation of the protein of interest in the cellular nucleus. Thus, constructs were designed to include a CPP, linked to the protein of interest, linked to a NES. By way of example, the carboxyl-terminus of TAT-GG-hFXN fusion constructs was directly fused to a nuclear exportation signal (NES), such as NES domains derived from PKIa (NES1) and MAPKK (NES2).

Figure 5:
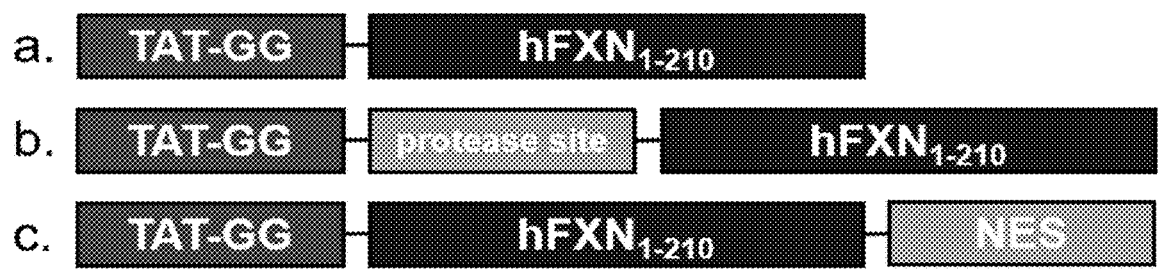
FIG. 5, Panels A-C present a schematic illustrating the design of the exemplary fusion proteins of the present disclosure comprising hFXN. Panel A shows TAT-GG fused to the amino-terminus of $hFXN_{1-210}$ (a TAT-GG-hFXN fusion protein). Panel B shows TAT-GG fused to a proteolytically-sensitive amino acid sequence followed by $hFXN_{1-210}$ Panel C shows TAT-GG fused to $hFXN_{1-210}$ and followed by a nuclear exportation signal (NES); in accordance with an embodiment of the disclosure.

A schematic of the fusion proteins is provided in FIG. 5, panels a-c, and a summary of the fusion protein constructs is provided in Table 11.

TABLE 11

Novel TAT-FNX fusion proteins.

| Fusion Protein | SEQ ID NO. | CPP | Protease cleavable domain or NES | Protease responsible for cleavage | Protein of interest |
|---|---|---|---|---|---|
| TAT-GG-SUMO1-hFXN | 55 | TAT | Sumo1 | SUMO | FXN |
| TAT-GG-Ubiquitin-hFXN | 56 | TAT | Ubiquitin | Deubiquitinase | FXN |

TABLE 11-continued

Novel TAT-FNX fusion proteins.

| Fusion Protein | SEQ ID NO. | CPP | Protease cleavable domain or NES | Protease responsible for cleavage | Protein of interest |
|---|---|---|---|---|---|
| TAT-GG-DEVD-hFXN | 57 | TAT | DEVD (SEQ ID NO: 19) | Caspase | FXN |
| TAT-GG-EPLFAERK-hFXN | 58 | TAT | EPLFAERK (SEQ ID NO: 20) | Calpain1 | FXN |
| TAT-GG-LLVY-hFXN | 59 | TAT | LLVY (SEQ ID NO: 21) | Calpain | FXN |
| TAT-GG-hFXN-NES1 | 60 | TAT | NES1 | not relevant | FXN |
| TAT-GG-hFXN-NES2 | 61 | TAT | NES2 | not relevant | FXN |

Example 3

Intracellular Expression of hFXN Fusion Proteins—Preliminary Screen for Mitochondrial Transport Genetic constructs encoding the various hFXN variants hFXN, TAT-GG-hFXN (TAT-hFXN fusion protein), TAT-GG-SUMO1-hFXN, TAT-GG-Ubiquitin-hFXN, TAT-GG-DEVD-hFXN, TAT-GG-EPLFAERK-hFXN, TAT-GG-LLVY-hFXN, TAT-GG-hFXN-NES1 and TAT-GG-hFXN-NES2 were cloned into expression vectors. By way of example, plasmid vector pcDNA3.1(+) (Genscript®, Piscataway, New Jersey) was used. All protein-encoding sequences were codon optimized for mammalian (human) expression Amino acid sequences of the variants and their respective encoding nucleic acid sequences are provided in Tables 9 and 10 elsewhere in this disclosure.

Rat L6 myoblasts were transfected with the expression plasmids using lipid-based transfection reagents known to the person skilled in the art of transfections, e.g., using the L6 Cell Avalanche™ system (from EZ Biosystems). hFXN subcellular localization was detected by immunofluorescence microscopy, performed as described in Example 1. Transfected cells were cultured for 24 hours, after which cells were fixed using 4% paraformaldehyde and stained using antibodies against hFXN and the mitochondrial membrane marker TOMM20. In addition, the nuclei of the cells were stained using the Hoechst 33342 nuclear stain.

Figure 6:
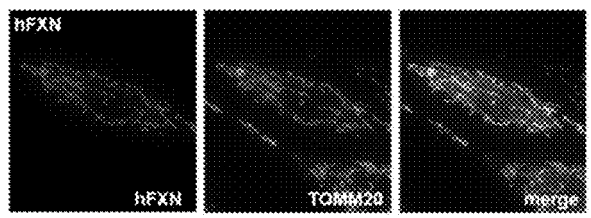
FIG. 6, Panels A-I are photographs of immunofluorescently labeled rat L6 myoblasts transfected with plasmids encoding hFXN (FIG. 4A), a TAT-GG-hFXN fusion protein (FIG. 4B), TAT-GG-SUMO1-hFXN (FIG. 4C), TAT-GG-LLVY-hFXN (FIG. 4D), TAT-GG-hFXN-NES1 (FIG. 4E), TAT-GG-hFXN-NES2 (FIG. 4F), TAT-GG-Ubiquitin-hFXN (FIG. 4G), TAT-GG-DEVD-hFXN (FIG. 4H), and TAT-GG-EPLFAERK-hFXN (FIG. 4I). For immunofluorescent labeling, the L6 myoblasts were stained with antibodies against hFXN (left panel) and TOMM20 (middle panel). The right panel shows the merge of the two labels.
Figure 6:
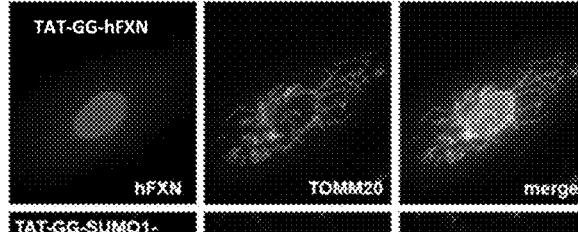
Figure 6:
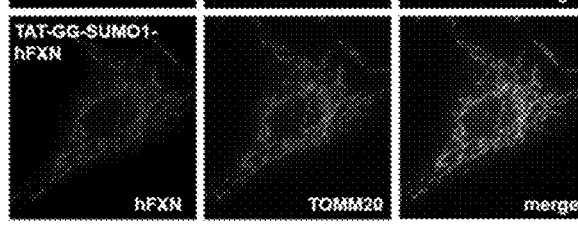
Figure 6:
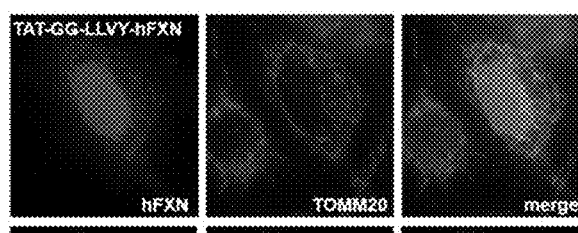
Figure 6:
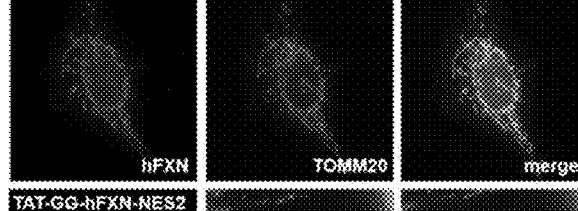
Figure 6:
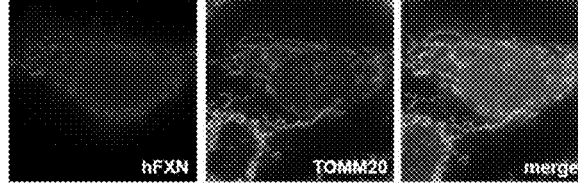
Figure 6:
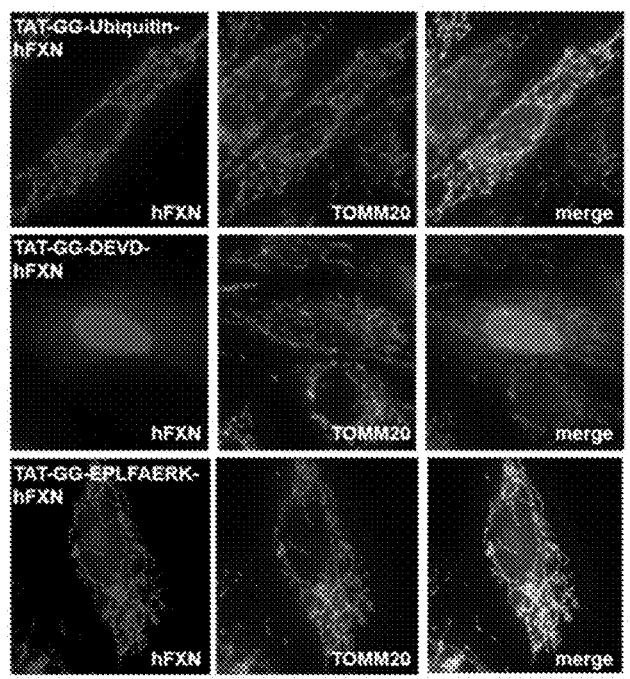

The results of the immunolabelling are presented in FIG. 6, Panels a-i and summarized in Table 12.

TABLE 12

Localication of hFXN and FXN fusion protein variants.

| Construct | Intracellular Localization |
|---|---|
| hFXN | Mitochondria |
| TAT-GG-hFXN fusion protein | Nucleus (mostly) |
| TAT-GG-SUMO1-hFXN | Mitochondria |
| TAT-GG-Ubiquitin-hFXN | Mitochondria |
| TAT-GG-DEVD-hFXN | Cytosol and nucleus |
| TAT-GG-EPLFAERK-hFXN | Mitochondria, cytosol and nucleus |
| TAT-GG-LLVY-hFXN | Mitochondria, cytosol and nucleus |
| TAT-GG-hFXN-NES1 | Mitochondria, cytosol and nucleus |
| TAT-GG-hFXN-NES2 | Mitochondria, cytosol and nucleus |

As demonstrated in Example 1, when expressed in rat L6 myoblasts, hFXN localized to the mitochondria, whereas TAT-GG-hFXN fusion protein was predominantly detected in the cytosol and nucleus. In cells transfected with TAT-GG-SUMO1-hFXN and TAT-GG-Ubiquitin-hFXN, hFXN was detected in the mitochondria. In cells transfected with TAT-GG-DEVD-hFXN, hFXN was detected in the cytosol and nucleus, and no significant mitochondrial localization was observed. In cells transfected with TAT-GG-EPLFAERK-hFXN and TAT-GG-LLVY-hFXN, hFXN was detected in the mitochondria as well as within the cytosol and nucleus. Taken together, these data demonstrate that intracellular SUMO proteases, deubiquitinases, as well as intracellular calpains were able to cleave the fusion proteins at their respective cleavage sites and to yield a variant of hFXN that localizes to the mitochondria. Similar to TAT-GG-hFXN fusion protein, TAT-GG-DEVD-hFXN was not detected in mitochondria, suggesting that caspase-mediated cleavage of DEVD (SEQ ID NO: 19) was inefficient under the current conditions.

In cells transfected with TAT-GG-hFXN-NES1 and TAT-GG-hFXN-NES2, hFXN was detected in the mitochondria as well as within the cytosol and nucleus. Together, these data demonstrate that nuclear exportation of hFXN fusion proteins results in improved mitochondrial import of hFXN.

Example 4

Assessment of hFXN Maturation by Western Blot Analysis

In its native state, full-length $hFXN_{1-210}$ is directed to the mitochondria by its N-terminal mitochondrial targeting sequence (MTS), where it is imported and proteolytically processed in two steps to yield the mature form of the protein, the $hFXN_{81-210}$ fragment. In order to evaluate the extent of hFXN maturation by proteolytic processing of the novel hFXN variants, Western blot analysis was performed in hFXN variants generated in rat L6 myoblasts transfected with the respective expression plasmids containing genes encoding hFXN, TAT-GG-hFXN fusion protein, TAT-GG-SUMO1-hFXN, TAT-GG-Ubiquitin-hFXN, TAT-GG-EPLFAERK-hFXN, TAT-GG-LLVY-hFXN, TAT-GG-hFXN-NES1, and TAT-GG-hFXN-NES2. Cells were harvested 72 hours after transfection, lysed in ice-cold radioimmunoprecipitation assay (RIPA) buffer supplemented with protease inhibitors and EDTA. The cell lysates were separated by SDS-PAGE (sodium dodecyl sulfate polyacrylamide gel electrophoresis), transferred onto a nitrocellulose membrane, and analyzed by Western Blot using a commercial antibody against hFXN (purchased from AbCam), as well as an antibody against β-Actin as a loading control.

Figure 7:
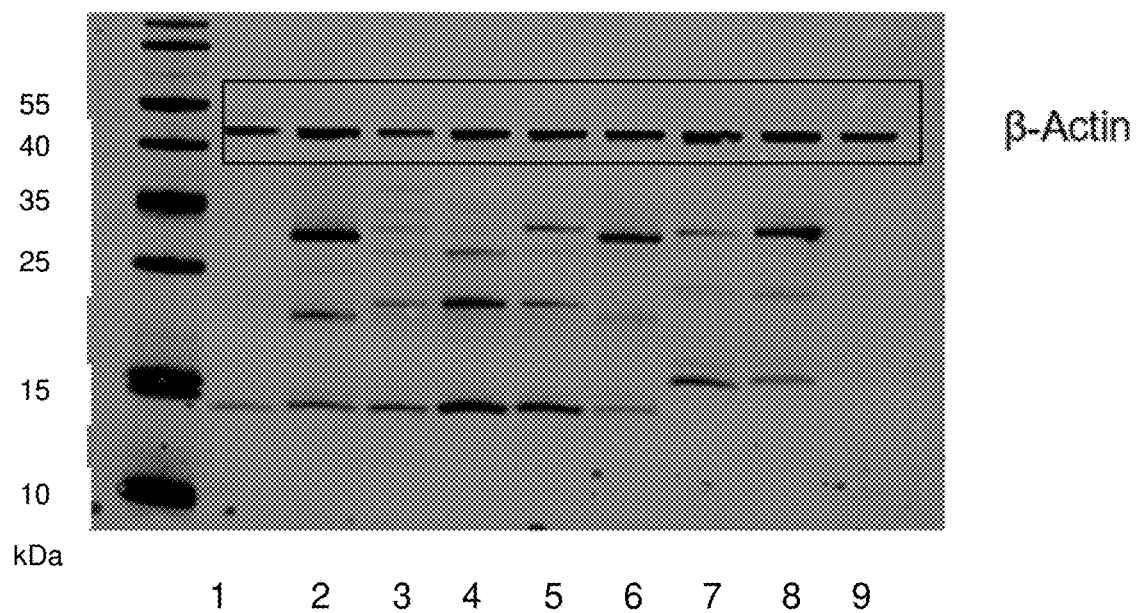
FIG. 7 is a photograph of a Western blot analysis of cell lysates from rat L6 myoblasts transfected with hFXN variants hFXN (Lane 1), a TAT-GG-hFXN fusion protein (Lane 2), TAT-GG-SUMO1-hFXN (Lane 3), TAT-GG-Ubiquitin-hFXN (Lane 4), TAT-GG-EPLFAERK-hFXN (Lane 5), TAT-GG-LLVY-hFXN (Lane 6), TAT-GG-hFXN-NES1 (Lane 7), TAT-GG-hFXN-NES2 (Lane 8) and Mock (Lane 9). The blot was labelled with anti-hFXN antibody and β-actin was used as a control.

The results are presented in FIG. 7. Fully mature hFXN (lane 1, band below 15 kDa marker, ~14.2 kDa) was detected in lysate obtained from cells transfected with hFXN construct. A band corresponding to mature hFXN (~14.2 kDa) was also detected in lysate obtained from cells transfected with a plasmid encoding TAT-GG-hFXN fusion protein (lane 2) and TAT-GG-SUMO1-hFXN (lane 3). Mature hFXN was detected in higher amounts in lysates obtained from cells transfected with TAT-GG-Ubiquitin-hFXN (lane 4), TAT-GG-EPLFAERK-hFXN (lane 5), and TAT-GG-hFXN-NES1 (lane 7, where hFXN-NES1 migrated slower by SDS-PAGE as the appended NES1 increases the molecular weight by ~1 kDa). A band corresponding to mature hFXN was also detected in TAT-GG-LLVY-hFXN (lane 6), and TAT-GG-hFXN-NES2 (lane 8). These results indicate that the novel constructs TAT-GG-Ubiquitin-hFXN, TAT-GG-EPLFAERK-hFXN, and TAT-GG-hFXN-NES1 are proteolytically processed in cells and yield higher amounts of mature hFXN than TAT-GG-hFXN fusion protein.

Example 5

Transduction of Schwann Cells with hFXN Fusion Proteins

The goal of this experiment was to determine and compare the ability of different hFXN fusion proteins to transduce cells.

Figure 8:
FIG. 8 is a schematic representation of the structure of hFXN fusion proteins of the present disclosure tested for their cell transduction ability in Example 5.
Figure 8:
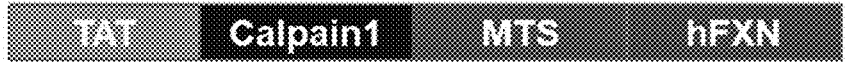
Figure 8:
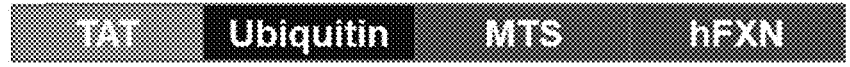
Figure 8:

This experiment utilized the TAT-GG-hFXN fusion protein described in Example 1 and the novel TAT-FXN fusion proteins: TAT-GG-Ubiquitin-hFXN (SEQ ID NO: 56) and TAT-GG-EPLFAERK-hFXN (SEQ ID NO: 58). In TAT-GG-EPLFAERK-hFXN (SEQ ID NO: 58), EPLFAERK (SEQ ID NO: 20) is a Calpain1 sensitive sequence. The schematic structure of the fusion proteins used in the experiment is shown in FIG. 8.

The experiment utilized Schwann cells because these cells grow relatively fast, and are easy to transduce. Also, endogenous levels of hFXN in these cells are below the detection limit and, therefore, are not expected to interfere with the signal produced by the TAT-GG-hFXN fusion proteins.

Schwann cells were plated at a seeding density of 8,000 cells per well in a 96-well plate (Corning 3904) and incubated overnight at 37° C. On day 1, solutions were prepared containing 1.25 µM, 1 µM and 0.5 µM of each TAT-GG-hFXN fusion protein in transduction media containing DMEM, 1% heat inactivated PBS and 20 mM glycerol. Cells were washed with 150 µL of PBS per well, and then 60 µL of TAT-GG-hFXN solution or transduction media alone for negative control were added per well. The cells were incubated at 37° C. for 2 hours, after which 60 µL of complete media containing DMEM, 10% FBS and 1% antibiotic:antymycotic (Gemini bioprodut 400-101) were added per well, and the cells were incubated overnight at 37° C.

The same treatment was repeated on day 2. On day 3, cells in each well were washed with 150 µL of PBS, after which the cells were trypsinized by adding 50 µL of TrypLE (Gibco™ 12604021) to each well and incubating at 37° C. for 5 minutes. After this, the trypsinization reaction was quenched by addition to each well of 50 µL of complete medium. The cells were re-suspended and transferred to a fibronectin-coated glass-bottom plate (Corning 4584) containing 40 µL of complete DMEM per well. The cells were allowed to settle overnight at 37° C.

On day 4, the cells were washed with PBS, after which 50 µL of freshly prepared 4% paraformaldehyde solution was added to each well, and the cells were incubated at room temperature for 10 minutes. Subsequently, the cells were washed twice with 150 µL PBS per well and then 50 µL of blocking buffer (0.3% Triton-X 100, 5% normal goat serum in PBS) was added per well. The cells were incubated at room temperature for 1 hour, after which the blocking buffer was removed, and 50 µL of primary antibody diluted in blocking buffer (Anti-Frataxin Antibody ab110328 from abcam and anti-TOMM20 antibody ab78547 from abcam) was added to each well. The Anti-Frataxin antibody was diluted 1:600, while the TOMM20 antibody was diluted 1:300. The cells were incubated overnight at 4° C.

On day 5, the cells were washed twice with 120 µL of PBS per well, and 50 µL of secondary antibody diluted in blocking buffer was added to each well (Anti-Mouse IgG AlexaFluor594, ab150116 from abcam and Anti-rabbit IgG Alexafluor488, ab150077 from abcam). Each antibody was diluted 1:1000. The cells were incubated at room temperature for one hour, washed with 150 µL of PBS per well, and were stained by adding 50 µL of 300 nM Hoescht 33342 stain per well and incubating for 3 minutes at room temperature. Subsequently, the cells were washed with PBS.

The cells were imaged using a Lionheart microscope. Human FXN was detected using an Alexa-594-labeled goat anti-mouse IgG secondary antibody that bound to the mouse anti-hFXN monoclonal primary antibody. Mitochondrial membrane was detected using an Alexa-488-labelled goat anti-rabbit IgG secondary antibody that bound to the anti-TOMM20 polycolonal primary antibody.

Figure 9:
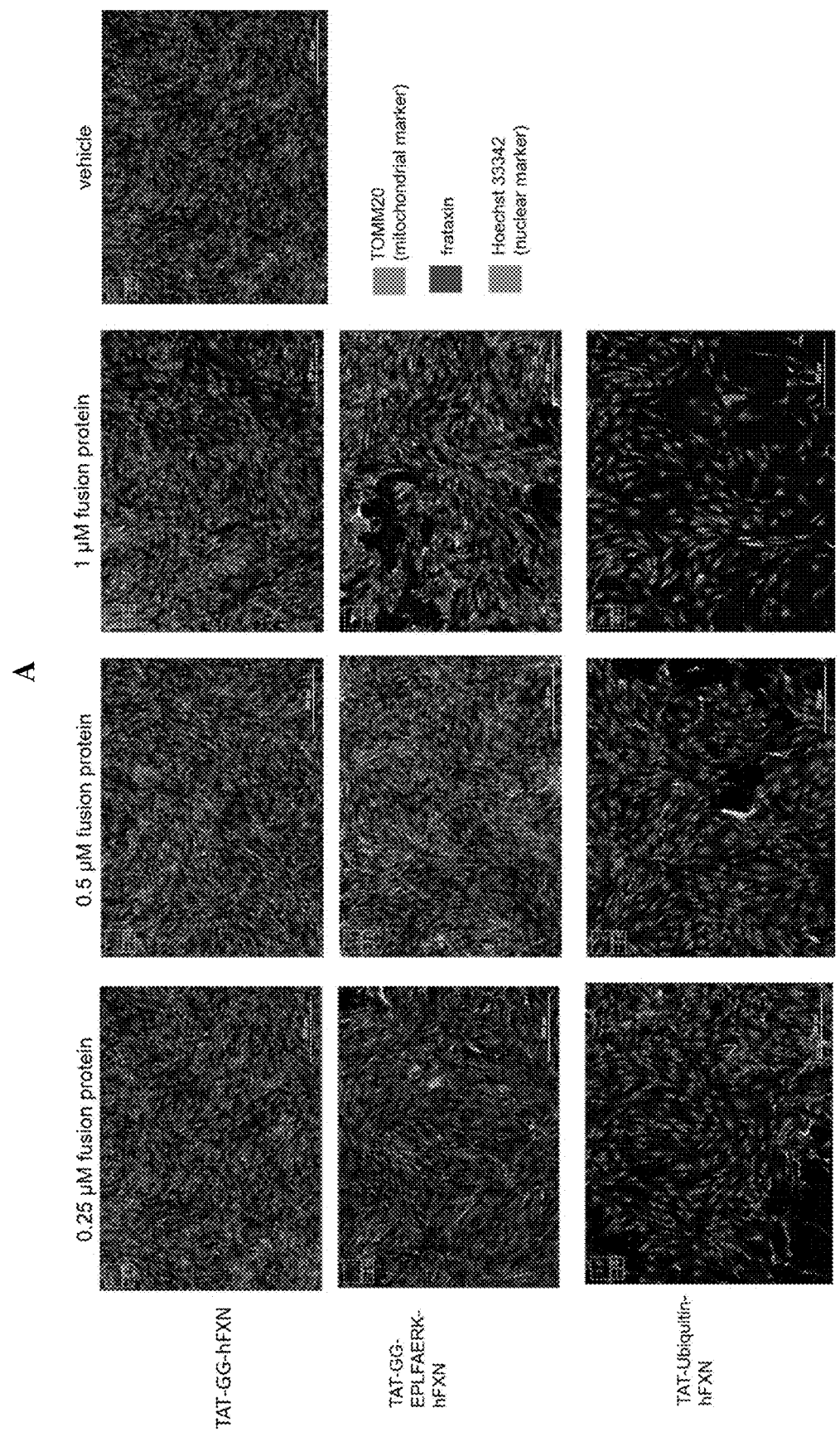
FIG. 9, Panel A is a series of photographs of Schwann cells treated with 0.25 µM, 0.5 µM and 1 µM TAT-GG-hFXN, TAT-GG-EPLFAERK-hFXN, TAT-GG-Ubiquitin-hFXN and vehicle as a negative control. In the photographs, the green color corresponds to the TOMM20 signal as a mitochondrial marker, the red color corresponds to hFXN signal and the blue color corresponds to the Hoechst 33342 dye signal as a nuclear marker.
Figure 9:
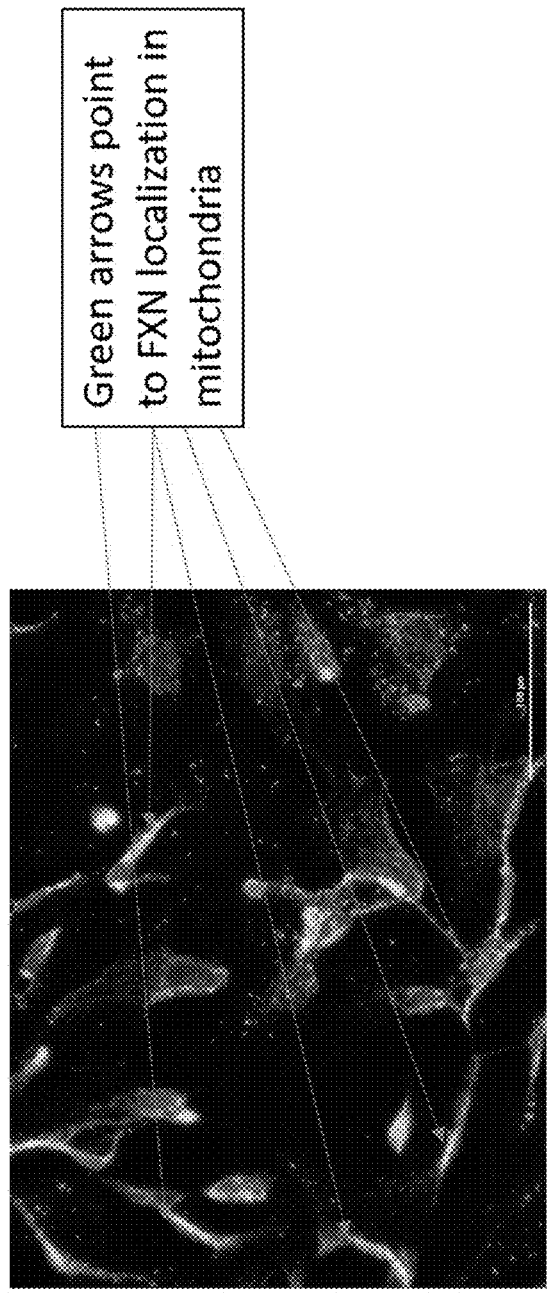
Figure 9:
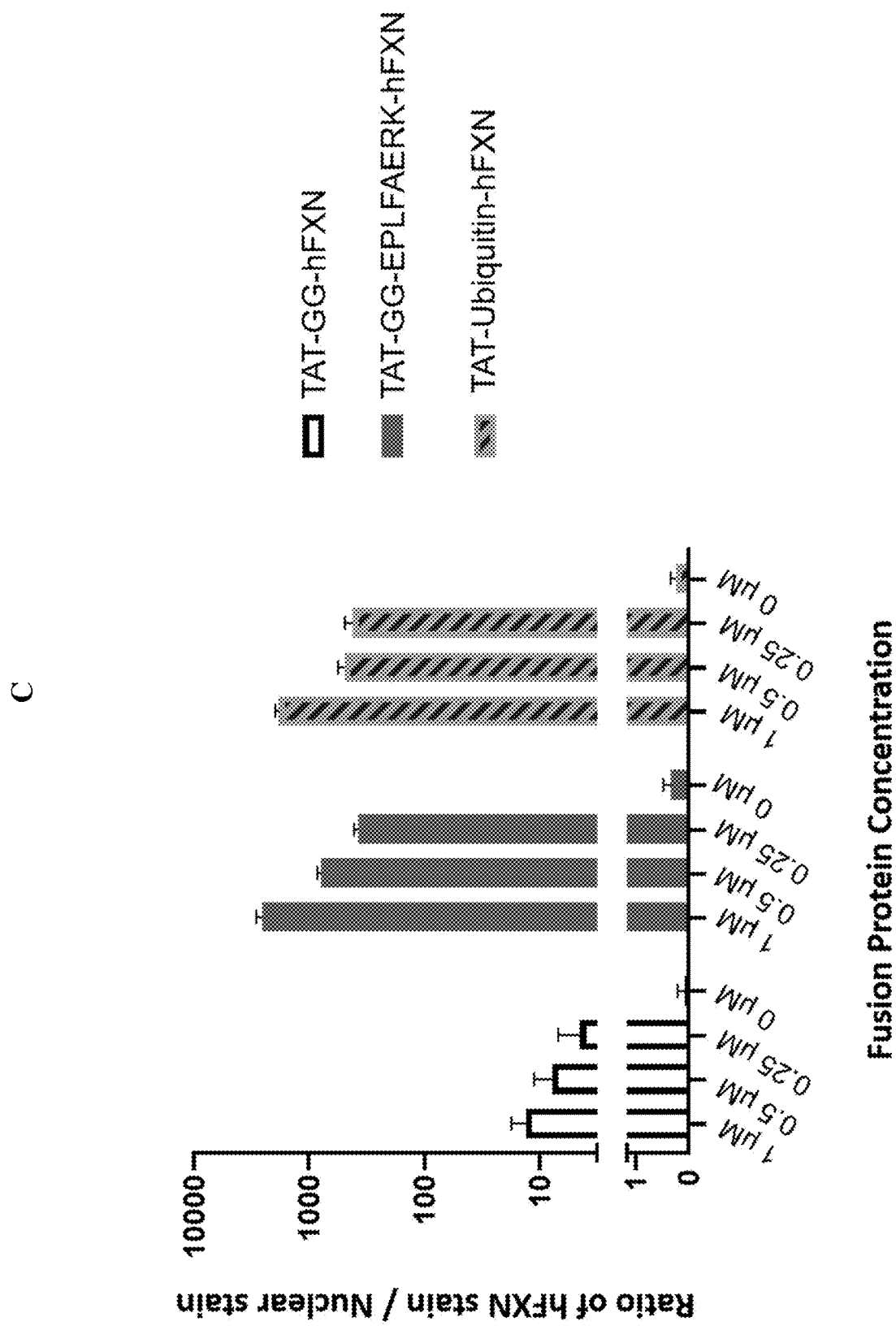
Figure 9:
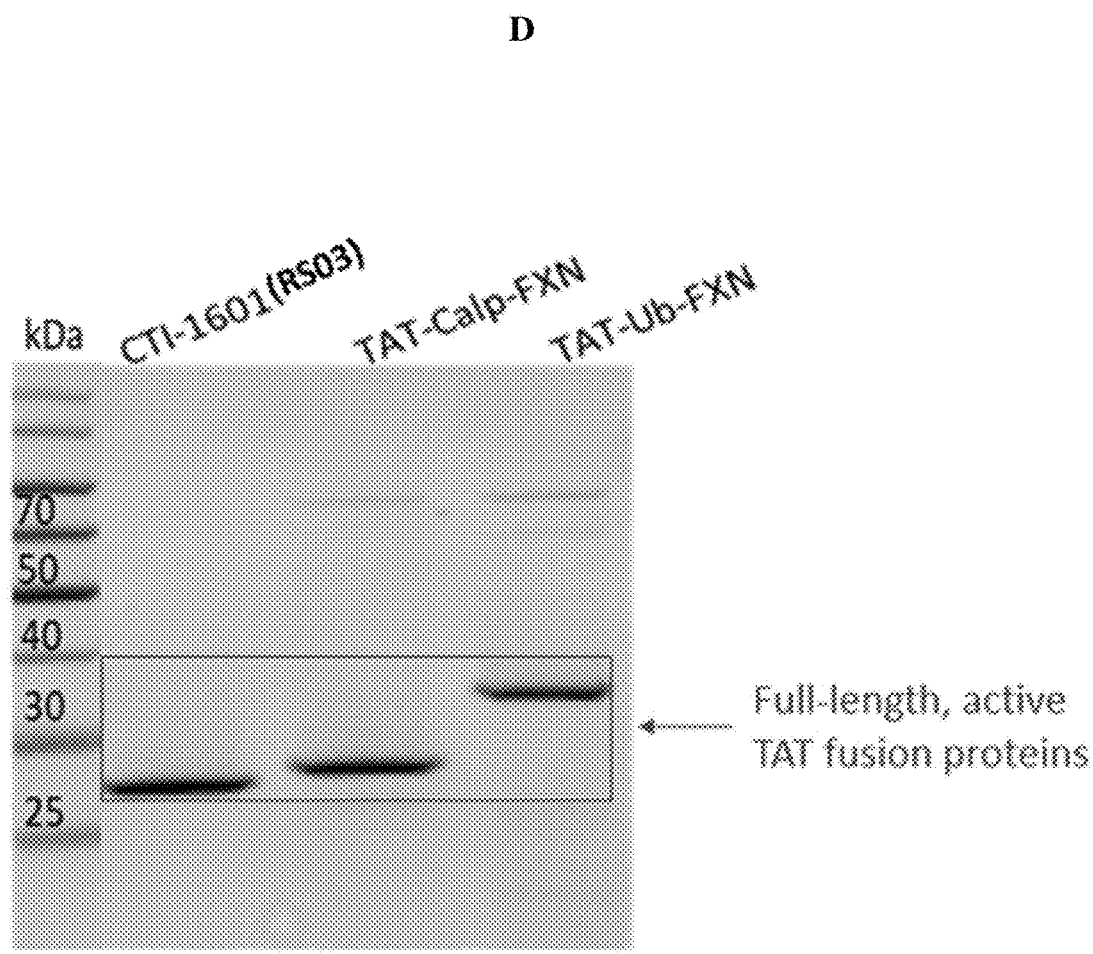

The results of the experiment are presented in FIG. 9. Specifically, FIG. 9, Panel A is a series of photographs of Schwann cells treated with 0.25 µM, 0.5 µM and 1 µM TAT-GG-hFXN, TAT-GG-EPLFAERK-hFXN, TAT-GG-Ubiquitin-hFXN and vehicle as a negative control. In the photographs, the green color corresponds to the TOMM20 signal as a mitochondrial marker, the red color corresponds to hFXN signal and the blue color corresponds to the Hoechst 33342 dye signal as a nuclear marker. Under the imaging conditions, endogenous frataxin levels are not detectable in the Schwann cells. As demonstrated by FIG. 9, Panel A, cells transduced with vehicle showed only nuclear and mitochondrial staining, but not hFXN staining. Cells transduced with TAT-GG-hFXN showed some hFXN staining. In contrast, cells transduced with TAT-GG-EPLFAERK-hFXN and TAT-GG-Ubiquitin-hFXN showed higher levels of hFXN staining at corresponding concentrations.

FIG. 9, Panel B is a high magnification image of cells treated with TAT-GG-Ubiquitin-hFXN fusion protein. This image shows the details of hFXN stain and its localization to mitochondria. This image indicates that in cells treated with novel hFXN fusion proteins, hFXN localizes to mitochondria.

The amount of hFXN signal in the photographs presented in FIG. 9 was quantified by determining the mean intensity of Texas red channel used to detect the signal associated with Alexa 594. The amount of the nuclear signal was quantified by determining the mean intensity of the DAPI channel used to detect the signal associated with the Hoechst 33342 dye.

FIG. 9, Panel C is a bar graph showing the ratios of mean hFXN stain signal to the mean nuclear stain signal for cells treated with various concentrations of TAT-GG-hFXN, TAT-GG-EPLFAERK-hFXN and TAT-GG-Ubiquitin-hFXN. The results presented in FIG. 9, Panel C indicate that the amount of hFXN detected in cells treated with novel fusion proteins of the present disclosure, i.e., TAT-GG-EPLFAERK-hFXN and TAT-GG-Ubiquitin-hFXN, is more than 2 orders of magnitude higher than the amount of hFXN detected in cells treated with TAT-GG-hFXN, at all concentrations studied.

To further ensure accuracy of quantification of hFXN in the microscopy experiments, the purified recombinant hFXN fusion proteins used in for cell transduction experiments were separated on an SDS-PAGE gel and transferred onto a nitrocellulose memtrane. The membrane was stained with a total protein stain and visualized.

FIG. 9, Panel D is a picture of a nitrocellulose membrane following transfer from an SDS-PAGE gel loaded with samples of TAT-GG-hFXN, TAT-GG-EPLFAERK-hFXN, and TAT-GG-Ubiquitin-hFXN used for transduction experiments and stained for total protein. The results presented in FIG. 9, Panel D demonstrate that similar amounts of TAT-GG-hFXN, TAT-GG-EPLFAERK-hFXN and TAT-GG-Ubiquitin-hFXN are found in samples used for transfection. These results demonstrate a lack of fusion protein degradation and confirm that the same amount of each fusion protein was used in transduction experiments. These results also demonstrate that the quantification results seen in the microscopy experiments in FIG. 9, Panels A and B are not due to the differences in the amounts of hFXN fusion proteins added to the cells.

The results presented in FIG. 9, Panels A-D demonstrate that the amount of protein of interest, e.g., hFXN, detected in cells following transduction of cells with novel fusion proteins of the present disclosure comprising CPP and TES is significantly higher than the amount of protein of interest, e.g., hFXN, detected in cells following transduction of cells with fusion protein that comprises CPP but does not comprise TES. The results indicate that introducing TES into a fusion protein comprising CPP, such that the TES is located between CPP and the protein of interest, can significantly increase the amount of protein of interest in a cell.

Example 6

Transduction of Schwann Cells and H9C2 Cells with hFXN Fusion Proteins

The goal of this experiment was to determine and compare the ability of hFXN to localize to mitochondria after transduction of cells with different hFXN fusion proteins.

This experiment utilized Schwann cells and H9C2 myoblast cells and the same hFXN fusion proteins used in Example 5 and illustrated in FIG. 8, i.e., TAT-GG-hFXN, TAT-GG-EPLFAERK-hFXN and TAT-GG-Ubiquitin-hFXN. The experiment utilized the same procedure described in Example 5 to treat the cells with the hFXN fusion proteins at fusion protein concentration of 0, 0.0625 µM, 0.125 µM, 0.25 µM, 0.5 µM. The cells were subsequently stained using an anti-FXN stain, nuclear stain and mitochondrial stain, and analyzed using microscopy as described in Example 5.

Figure 10:
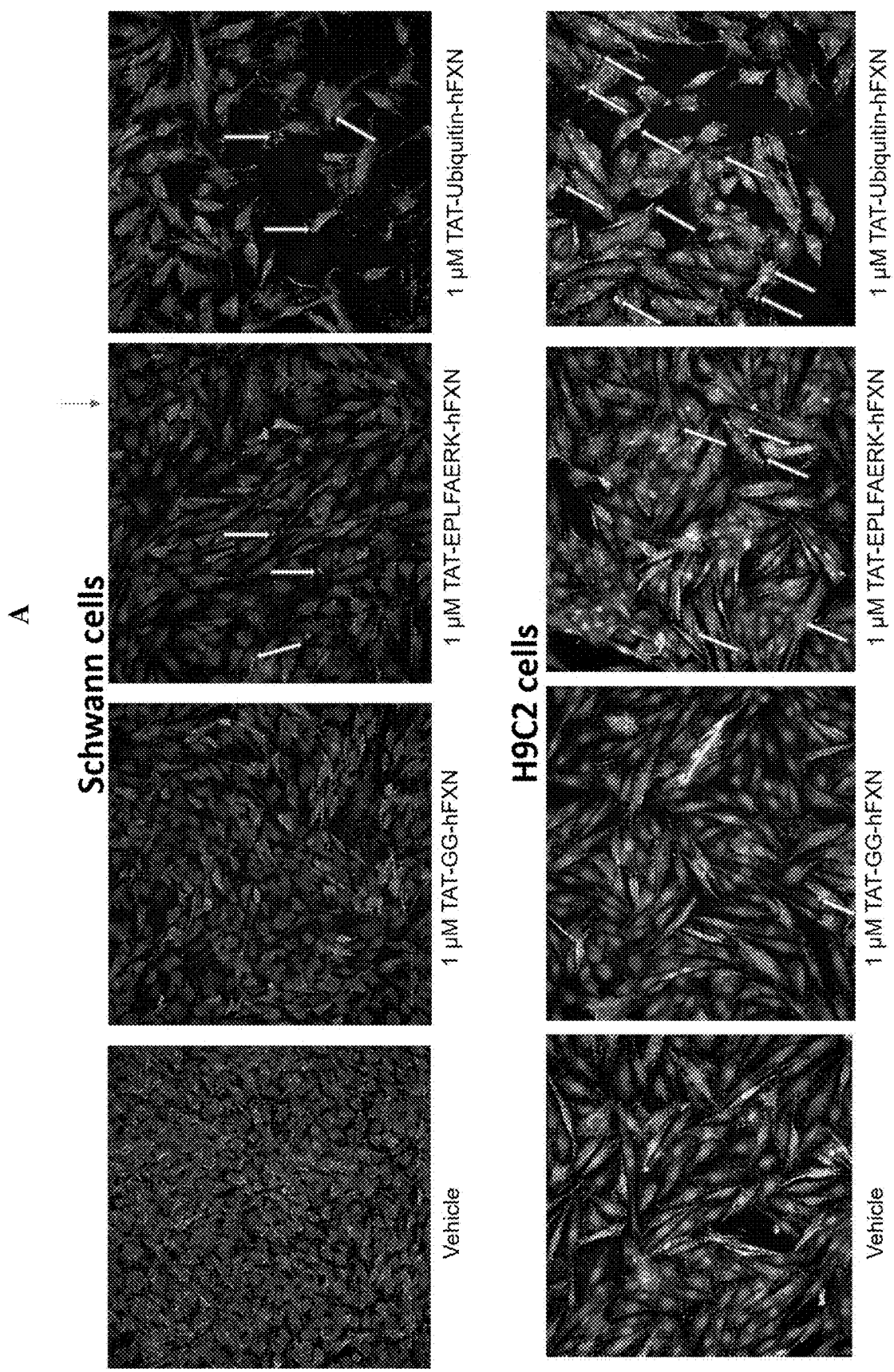
FIG. 10, Panel A is a series of representative photographs of Schwann and H9C2 cells treated with 1 µM hFXN fusion proteins TAT-GG-hFXN, TAT-GG-EPLFAERK-hFXN and TAT-GG-Ubiquitin-hFXN and stained with mitochondrial, nuclear and anti-FXN stains. The white errors show representative localication of hFXN to mitochondria.
Figure 10:
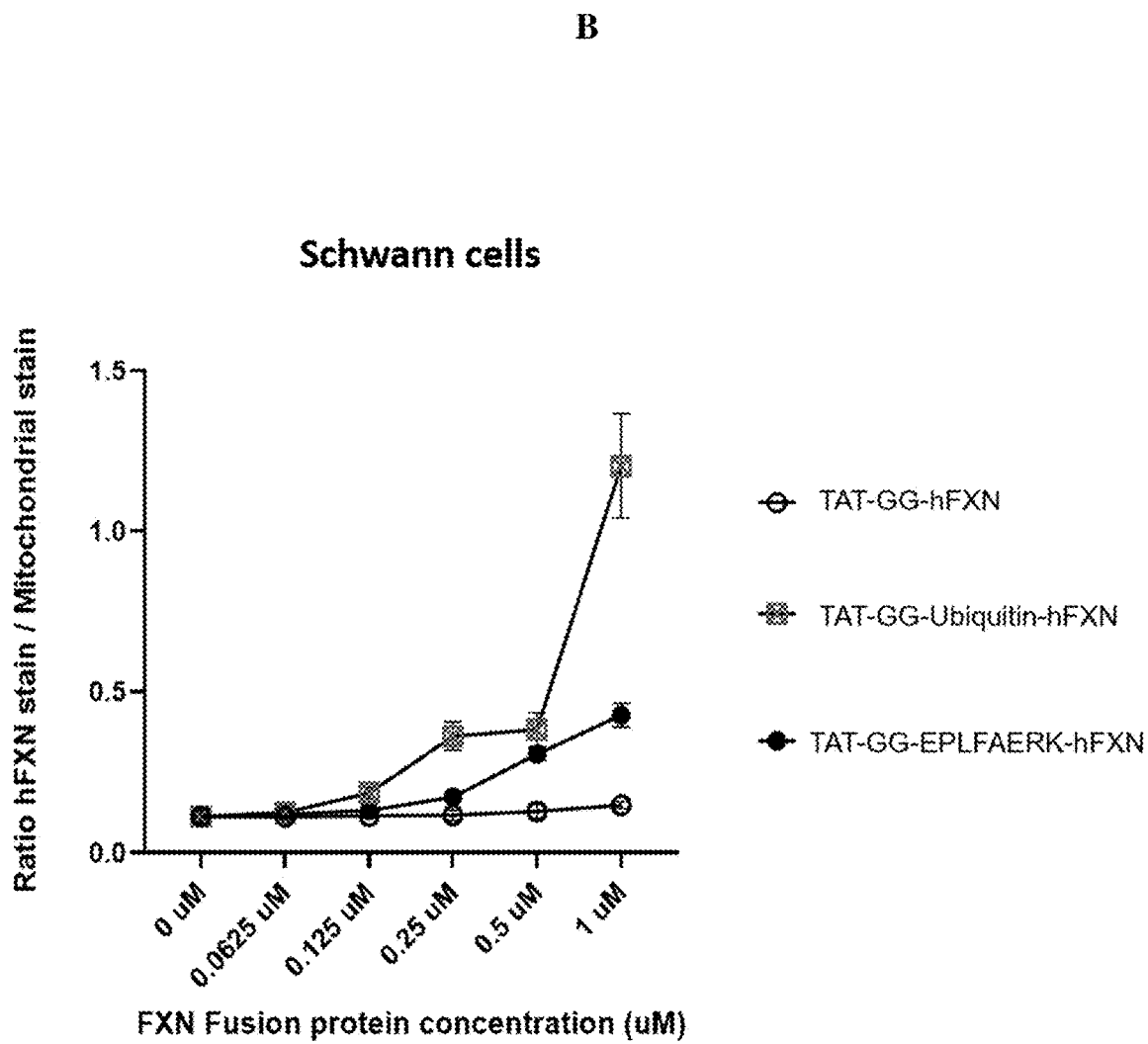
Figure 10:
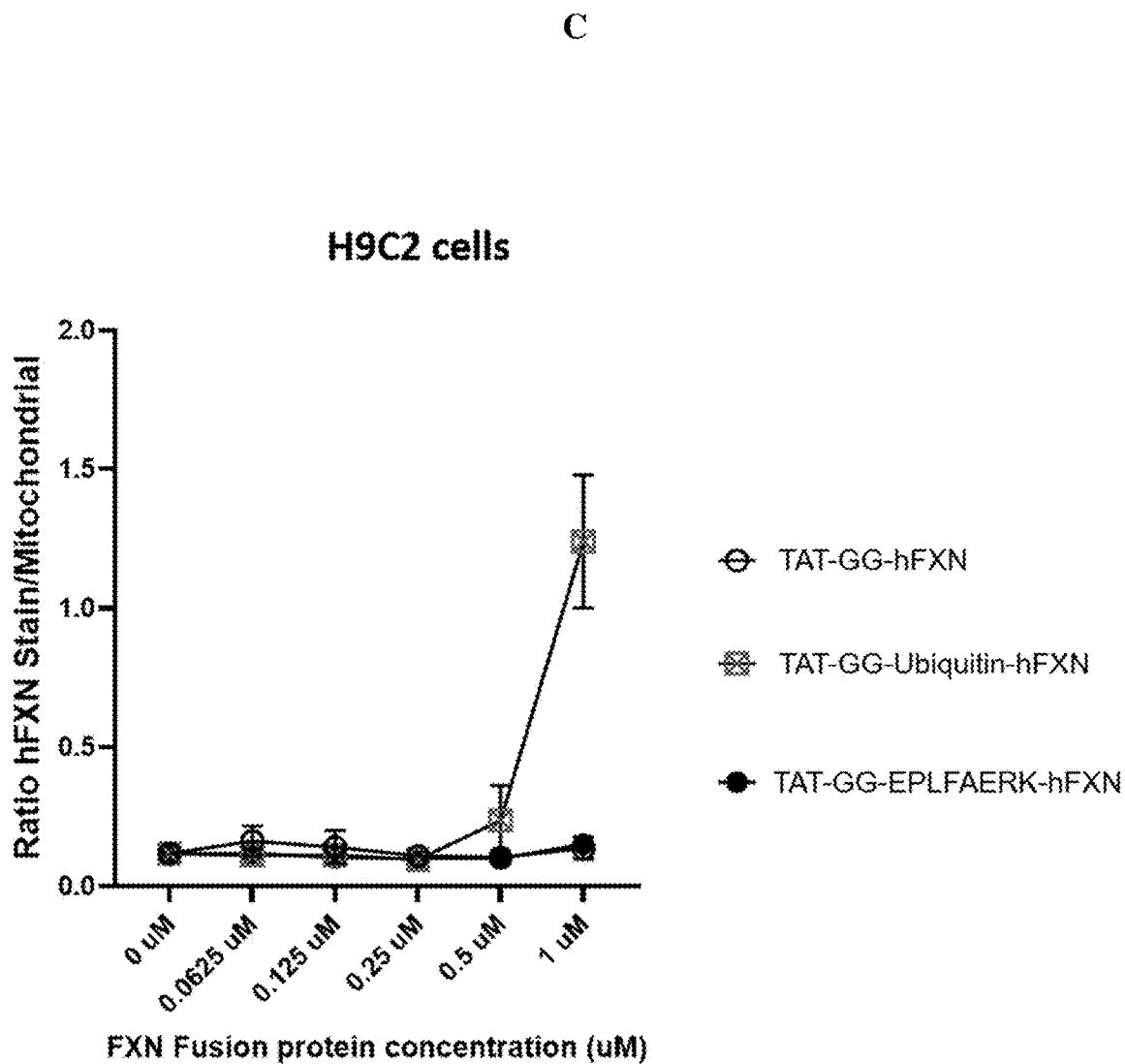
Figure 10:
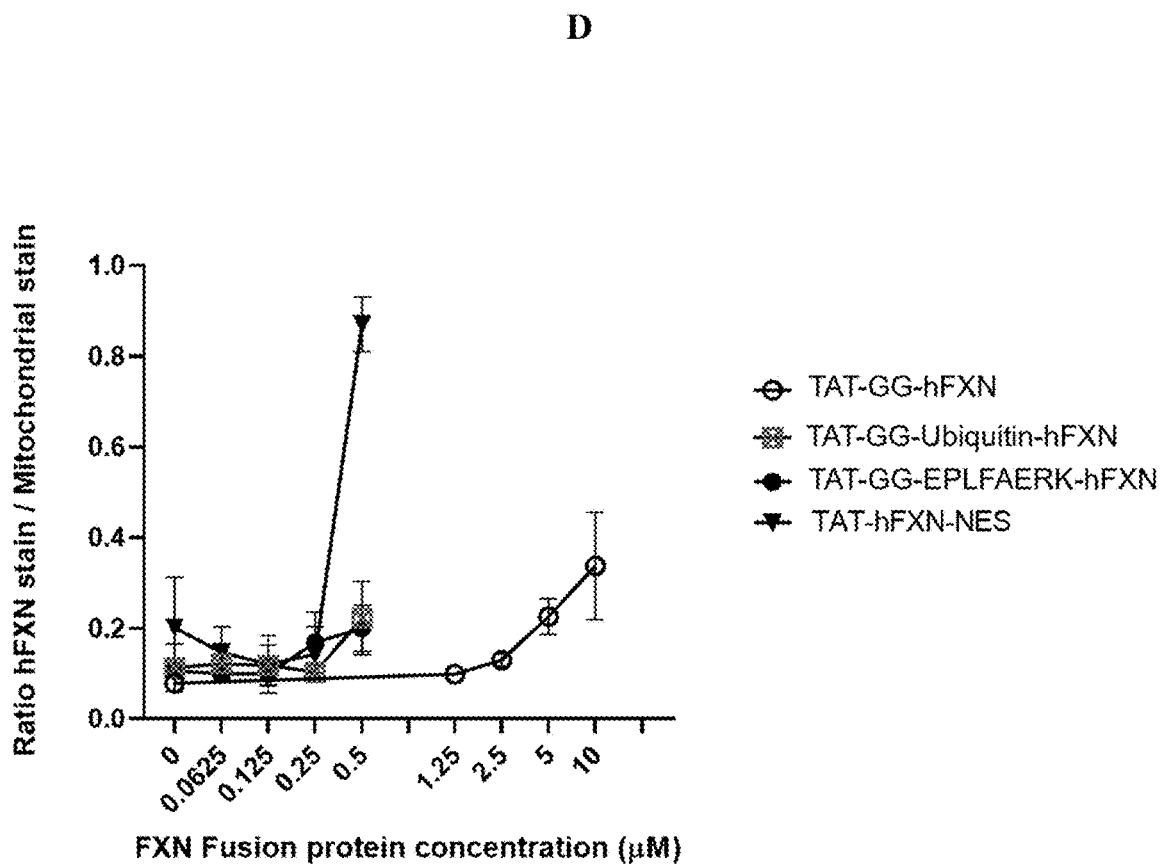

FIG. 10, Panel A is a series of representative photographs of Schwann and H9C2 cells treated with 1 µM hFXN fusion proteins and stained with mitochondrial, nuclear and anti-FXN stains. The white arrows show high level of representative localication of hFXN to mitochondria. The results shown in FIG. 10, Panel A indicate that the amount of hFXN in cells treated with 1 µM TAT-GG-EPLFAERK-hFXN and TAT-GG-Ubiquitin-hFXN is higher than the amount of hFXN in cells treated with TAT-GG-hFXN. The results also indicate that in cells treated with 1 µM TAT-GG-EPLFAERK-hFXN and TAT-GG-Ubiquitin-hFXN, hFXN localizes to mitochondria (see white arrows), while less mitochondrial localization of hFXN is observed in cells treated with 1 µM TAT-GG-hFXN.

The mean anti-FXN stain signal and the mean anti-mitochondrial stain signal were determined for each sample, and the ratio of the mean anti-FXN stain signal to the mean anti-mitochondrial stain signal (TOMM20) was calculated. FIG. 10, Panel B presents the ratio of the mean anti-FXN stain signal to the mean anti-mitochondrial stain signal graphed as a function of hFXN fusion protein concentration in Schwann cells. FIG. 10, Panel C presents the ratio of the mean anti-FXN stain signal to the mean anti-mitochondrial stain signal graphed as a function of hFXN fusion protein concentration in H9C2 cells. The results presented in FIG. 10, Panels B and C demonstrate that higher amounts of hFXN localize to mitochondria in Schwann cells and H9C2 cells treated with GG-EPLFAERK-hFXN and TAT-GG-Ubiquitin-hFXN, as compared to Schwann cells and H9C2 cells treated with TAT-GG-hFXN. Further, the amount of mitochondrial localization in cells treated with GG-EPLFAERK-hFXN and TAT-GG-Ubiquitin-hFXN is dose-dependent.

Another cell transfection experiment was conducted using Schwann cells and hFXN fusion proteins which included: TAT-GG-hFXN, TAT-GG-EPLFAERK-hFXN, TAT-GG-Ubiquitin-hFXN, and TAT-GG-hFXN NES1 (SEQ ID NO: 60 and depicted in FIG. 8). The experimental protocol used for the experiment was the same as described above. FIG. 10, Panel D presents the ratio of the mean anti-FXN stain signal to the mean anti-mitochondrial stain signal graphed as a function of hFXN fusion protein concentration in Schwann cells. The results presented in FIG. 10, Panel D demonstrate that higher amounts of hFXN localize to mitochondria in Schwann cells cells treated with TAT-GG-EPLFAERK-hFXN, TAT-GG-Ubiquitin-hFXN and TAT-GG-hFXN-NES1, as compared to Schwann cells and H9C2 cells treated with TAT-GG-hFXN. The results also demonstrate that at the fusion protein concentration of 0.5 µM, the amount of hFXN localized to mitochondria after treatment with TAT-GG-hFXN-NES1 is significantly higher than the amount of hFXN localized to mitochondria after treatment with TAT-GG-EPLFAERK-hFXN, TAT-GG-Ubiquitin-hFXN. Further, the amount of mitochondrial localization in cells treated with the novel hFXN fusion proteins is dose-dependent.

The results presented in FIG. 10, Panels A-D indicate that higher amounts of hFXN are detected in cells treated with novel fusion proteins of the disclosure, i.e., TAT-GG-EPLFAERK-hFXN, TAT-GG-Ubiquitin-hFXN and TAT-GG-hFXN-NES1, as compared to cells treated with TAT-GG-hFXN. The results also indicate that hFXN in cells treated with novel hFXN fusion proteins of the disclosure localize to mitochondria.

Example 7

Confirmation of Intracellular Processing of Novel hFXN Fusion Proteins

The goal of this experiment was to confirm that the novel hFXN fusion proteins of the present disclosure are correctly processed by cellular machienery to yield the mature FXN protein. This experiment utilized L6 rat myoblast cells and the same hFXN fusion proteins used in Example 5 and illustrated in FIG. 8, i.e., TAT-GG-hFXN, TAT-GG-EPL- FAERK-hFXN and TAT-GG-Ubiquitin-hFXN. This experiment also utilized two additional hFXN fusion proteins as follows: TAT-GG-hFXN-NES1 (SEQ ID NO: 60) and TAT-GG-SUMO-hFXN (SEQ ID NO: 81). The amino acid sequence of TAT-GG-SUMO-hFXN (SEQ ID NO: 81) is shown below:

```
MYGRKKRRQRRRGGSDSEVNQEAKPEVKPEVKPETHINLKVSDGSSEIF
FKIKKTTPLRRLMEAFAKRQGKEMDSLRFLYDGIRIQADQTPEDLDMED
NDIIEAHREQIGGMWTLGRRAVAGLLASPSPAQAQTLTRVPRPAELAPL
CGRRGLRTDIDATCTPRRASSNQRGLNQIWNVKKQSVYLMNLRKSGTLG
HPGSLDETTYERLAEETLDSLAEFFEDLADKPYTFEDYDVSFGSGVLTV
KLGGDLGTYVINKQTPNKQIWLSSPSSGPKRYDWTGKNWVYSHDGVSLH
ELLAAELTKALKTKLDLSSLAYSGKDA.
```

For the experiment, L6 cells were transfected with DNA vectors encoding the hFXN fusion proteins, and the cells were incubated for 24 hours. The cells were collected and processed to isolate total protein which was then separated on an SDS-PAGE gel. After SDS-PAGE separation, frataxin in the gel was analyzed using Western blotting with anti-FXN antibody and anti-β actin antibodies for control.

Figure 11:
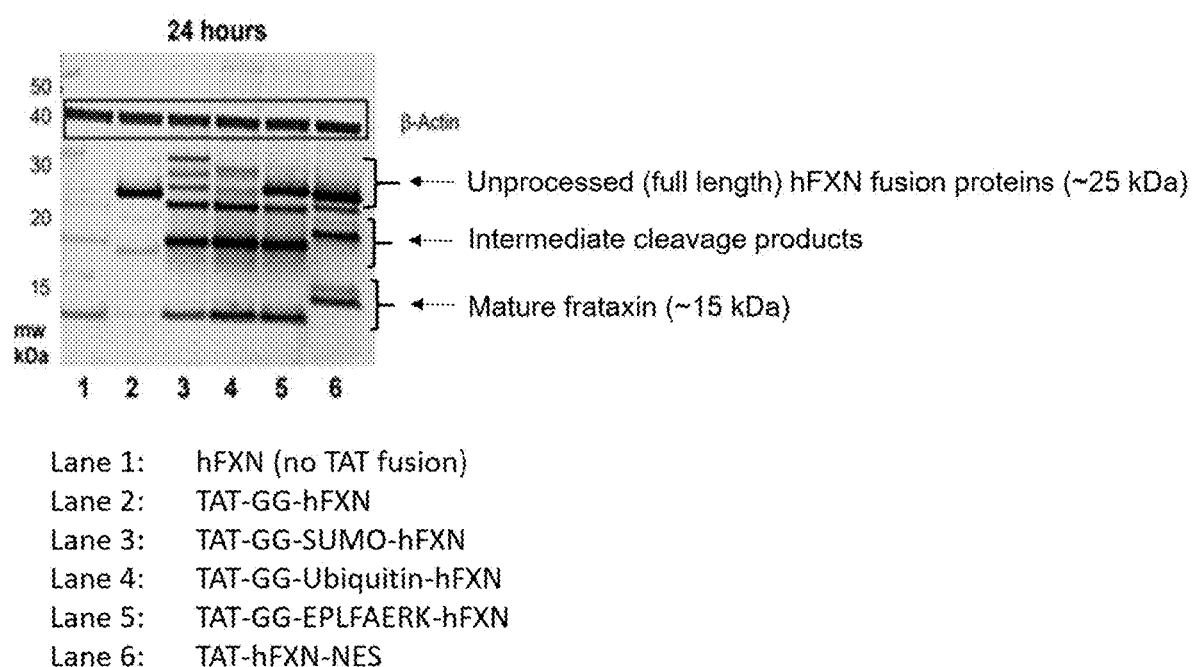
FIG. 11 is a photograph of the Western blot of total protein samples isolated from cells transfected with various hFXN fusion proteins and analyzed using anti-FXN antibody.

FIG. 11 is a photograph of the Western blot of total protein samples isolated from cells transfected with various hFXN fusion proteins and analyzed using anti-FXN antibody. Lane 1 contains a sample of cells transfected with a construct encoding hFXN control without TAT fusion. In this sample, a band of about 15 kDa corresponds to mature, processed hFXN resulting after double cleavage of the MTS sequence by endogenous mitochondrial α- and β-MPP proteases.

Lane 2 corresponds to a sample of cells transfected with a construct encoding TAT-GG-hFXN fusion protein. In this sample, a small amount of hFXN appears as a processed, mature frataxin, however, the majority of hFXN exists as a full length unprocessed fusion protein of about 25 kDa.

Lanes 3, 4 and 5 correspond to samples of cells transfected with constructs encoding, respectively, TAT-SUMO-hFXN, TAT-GG-Ubiquitin-hFXN and TAT-GG-EPLFAERK-hFXN. Under the same experimental conditions, these samples contain higher amounts of mature hFXN than the samples in lanes 1 and 2. Also present in lanes 3-5 are the intermediate cleavage products corresponding to incomplete hFXN processing and to various SUMO cleavages (lane 3).

Lane 6 contains a sample of cells transfected with constructs encoding TAT-GG-hFXN-NES. This sample also contains higher amounts of mature hFXN than samples in lanes 1 and 2. Also present in lane 6 are the intermediate cleavage products corresponding to incomplete hFXN processing. It is noted that the molecular weight of mature hFXN and intermediate cleavage products is higher than the the molecular weight of mature hFXN and intermediate cleavage products in other samples because NES is not cleaved by processing and remains a part of the fusion protein after MTS cleavage.

The results presented in FIG. 11 demonstrate that the novel hFXN fusion proteins of the present disclosure, i.e., TAT-SUMO-hFXN, TAT-GG-Ubiquitin-hFXN, TAT-GG-EPLFAERK-hFXN, and TAT-GG-hFXN-NES are processed in cells to yield mature hFXN. The results also demonstrate that the processing of the novel hFXN fusion proteins to yield mature hFXN is more efficient than processing of TAT-GG-hFXN fusion protein. The more efficient processing of the novel hFXN fusion proteins as compared to processing of TAT-GG-hFXN may, at least partially, be explained by the fact that lower amounts of the novel hFXN fusion proteins localize to the nucleus, as compared to the TAT-GG-hFXN fusion proteins, as shown in FIGS. 4 and 6.

Example 8

Functional Characterization of hFXN Fusion Proteins

The goal of this experiment was to characterize the function of the novel hFXN fusion proteins. Applicant has previously shown that cells deficient in LRPPRC exhibit high levels of cell media acidification and secretion of SYR61 protein into the media. Applicant has also previously shown that treatment of LRPPRC-deficient cells caused a decrease in both cell media acidification and the amount of secreted SYR61 protein (see, e.g., WO 2021/011929, the entire contents of which are hereby incorporated herein by reference). Thus, cell media acidification and the amount of secreted SYR61 protein may be used as a measure of FXN activity in cells.

The present experiment utilized cell line HEK 293 LRPPRC KD (clone 21C), which was previously described, e.g., in WO 2021/011929. Briefly, this cell line is an LRPPRC knockdown cell line, generated by transferring HEK293 cells with LRPPRC shRNA, resulting in gene silencing of LRPPRC. A control cell line transfected with a scramble sequence (Scr-5) was also used in the experiment. This experiment also utilized the same hFXN fusion proteins used in Example 5 and illustrated in FIG. 8, i.e., TAT-GG-hFXN, TAT-GG-EPLFAERK-hFXN and TAT-GG-Ubiquitin-hFXN.

For the experiment, the LRPPRC KD cells and Scr-5 cells were plated at a seeding density of 50,000 cells per well in a 24 well plate in complete DMEM (DMEM, 10% FBS and 1% antibiotic: antimycotic). On day 1, the cells were treated with vehicle, TAT-GG-hFXN, TAT-GG-EPLFAERK-hFXN, orTAT-GG-Ubiquitin-hFXN for 3 hours at 37° C. Treatment of cells with TAT-GG-hFXN fusion protein was conducted at the fusion protein concentrations of 2.5 µM, 5 µM and 10 µM. Treatment of cells with TAT-GG-EPLFAERK-hFXN and TAT-GG-Ubiquitin-hFXN was conducted at the fusion protein concentrations of 0.25 µM, 0.5 µM and 1 µM. After three hours, complete media was added to each well, and the cells were incubated overnight at 37° C.

The same treatment was repeated on day 2, and the cells were incubated overnight at 37° C. On day 3, the cells were incubated in complete medium for additional 48 hours.

After 48 hours, the media was collected. Analysis of CYR61 levels was performed by CYR61 Elisa using Human Cyr61/CCN1 Quantikine ELISA Kit (R & D Systems catalogue # DCYR10). Lactate levels in the media were determined using lactate glo kit (#J5021 Promega Corporation) according to the manufacturer's protocol.

Figure 12:
FIG. 12, Panel A shows a picture of culture plate containing samples of LRPPRC KD cells and Scr-5 cells treated with hFXN fusion proteins of the disclosure.
Figure 12:
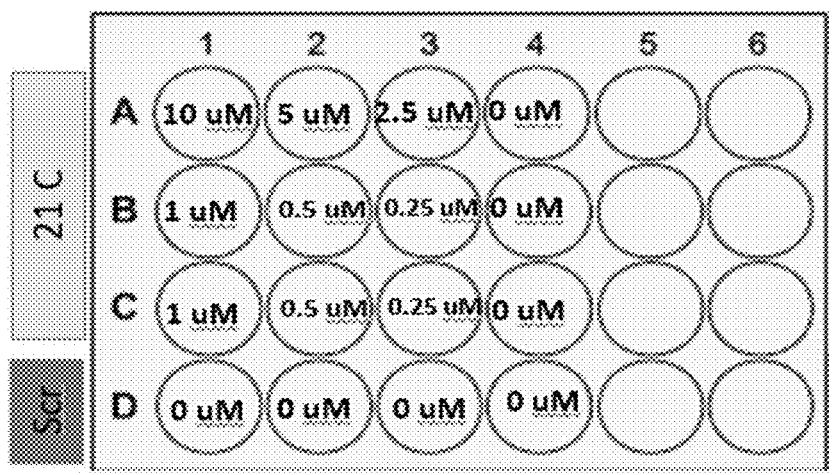
Figure 12:
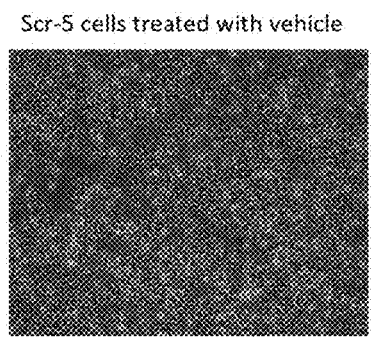
Figure 12:
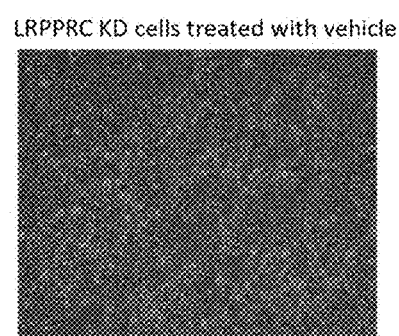
Figure 12:
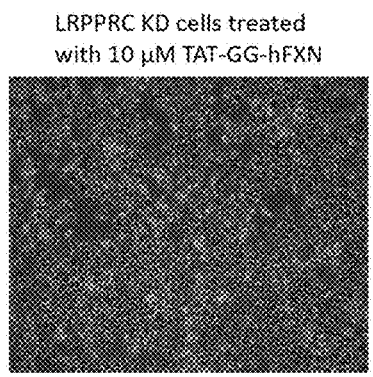
Figure 12:
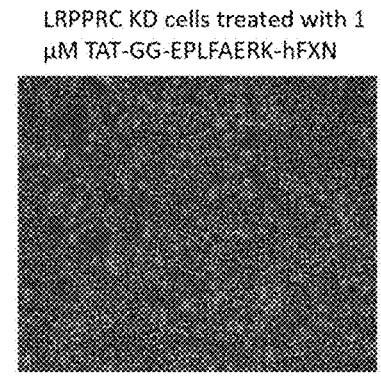
Figure 12:
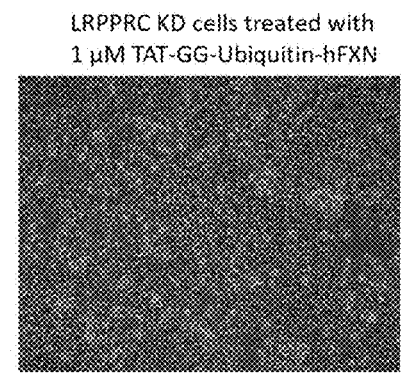
Figure 12:
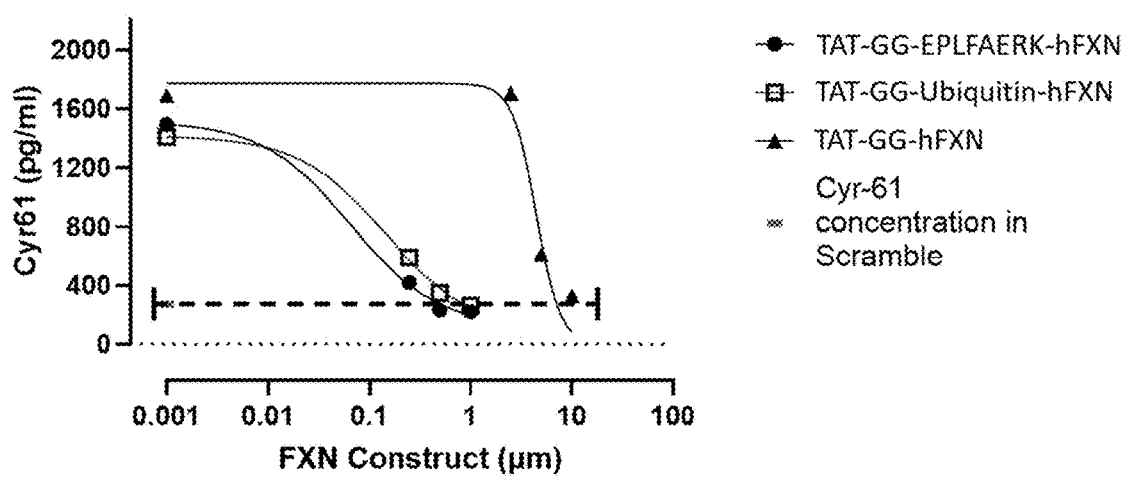
Figure 12:
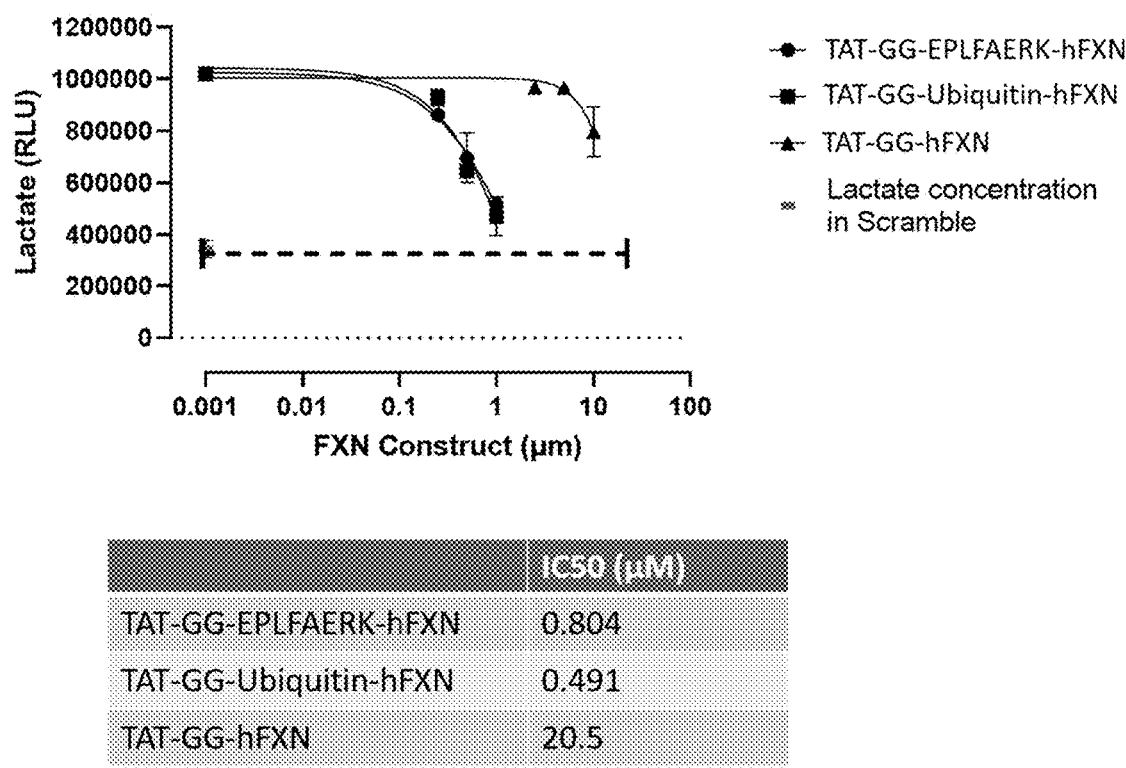

FIG. 12, Panel A shows a picture of a culture plate containing samples of LRPPRC KD cells and Scr-5 cells treated with hFXN fusion proteins of the disclosure. Acidification of the cell culture media is reflected by the changing color of phenol red in the culture media from pink (low acidification) to yellow (high acidification). FIG. 12, Panel A also shows a schematic representation of samples in the cell culture plate shown in the picture.

The results in FIG. 12, Panel A demonstrate that LRPPRC KD cells induce cell media acidification (as demonstrated by the yellow media in the wells of column 4, rows 1-3, of the plate), and that the extent of media acidification decreases in a dose-dependent manner after treatment with the tested hFXN fusion proteins (as demonstrated by: the orange media in the wells in column 3, rows 1-3; the pink media in the wells in column 2, rows 1-3; and the darker pink/red media in the wells in column 1, rows 1-3, of the plate). The results also demonstrate that TAT-GG-hFXN can prevent media acidification at a concentration of 10 µM, while each of TAT-GG-EPLFAERK-hFXN and TAT-GG-Ubiquitin-hFXN can prevent media acification at a significantly lower concentration of 1 µM than TAT-GG-hFXN.

FIG. 12, Panel B is a series of photographs of the LRPPRC KD and Scr-5 control cells treated with the highest tested concentration of each hFXN fusion protein or vehicle. The results in FIG. 12, Panel B demonstrate that acidification of the cell culture media was not due to cell death.

FIG. 12, Panel C is a graph showing the amount of CYR61 in the media of LRPPRC KD cells treated with hFXN fusion proteins. The results in FIG. 12, Panel C demonstrate concentration-dependent inhibition of CYR61 secretion by the LRPPRC KD cells after treatment with hFXN fusion proteins. The results also demonstrate that the inhibitory effect on CYR61 secretion is seen at significantly lower concentrations of TAT-GG-EPLFAERK-hFXN and TAT-GG-Ubiquitin-hFXN as compared to TAT-GG-hFXN. This effect is also reflected in the lower $IC_{50}$ values for CYR61 inhibition of TAT-GG-EPLFAERK-hFXN and TAT-GG-Ubiquitin-hFXN as compared to the $IC_{50}$ value of TAT-GG-hFXN, presented in the table in FIG. 12, Panel C.

FIG. 12, Panel D is a graph showing the amount of lactate in the media of LRPPRC KD cells treated with hFXN fusion proteins. The results in FIG. 12, Panel D demonstrate concentration-dependent inhibition of lactate production by the LRPPRC KD cells after treatment with hFXN fusion proteins. The results also demonstrate that the inhibitory effect on lactate production is seen at significantly lower concentrations of TAT-GG-EPLFAERK-hFXN and TAT-GG-Ubiquitin-hFXN as compared to TAT-GG-hFXN. This effect is also reflected in the lower $IC_{50}$ values for inhibition of lactate production of TAT-GG-EPLFAERK-hFXN and TAT-GG-Ubiquitin-hFXN as compared to the $IC_{50}$ value of TAT-GG-hFXN, presented in the table in FIG. 12, Panel D.

The results presented in FIG. 12, Panels A-D demonstrate that TAT-GG-EPLFAERK-hFXN and TAT-GG-Ubiquitin-hFXN are characterized by higher activity than TAT-GG-hFXN, as measured by the inhibition of lactate production and CYR61 secretion. The results indicate that introducting TES into a fusion protein enhances function of the fusion protein.

Example 9

Design and Synthesis of Novel PARKIN Fusion Constructs

The goal of this experiment was to synthesize novel fusion proteins according to the present disclosure comprising human PARKIN protein (SEQ ID NO: 7).

The design of the PARKIN fusion proteins was similar to the design of the hFXN fusion constructs described in Example 2. Some PARKIN fusion proteins comprised a sequence encoding a cell penetrating peptide (CPP), such as HIV-TAT (YGRKKRRQRRR; SEQ ID NO. 11) peptide, fused to TES, e.g., an amino acid sequence that can be cleaved by an endogenous intracellular protease, and immediately followed by PARKIN as the protein of interest. A di-peptide GG was used as a linker between the CPP and the proteolytic cleavage domain.

Cleavage of TAT-GG from the fusion protein in the cytosol will result in a TAT-free PARKIN protein. The proteolytic cleavage domains used in the PARKIN fusion proteins were ubiquitin (SEQ ID NO: 18) and EPLFAERK (SEQ ID NO: 20).

An alternative PARKIN fusion protein was designed to include a nuclear exportation signal (NES), and in that way avoid accumulation of PARKIN in the cellular nucleus. The construct was designed to include a CPP, linked to PARKIN as a protein of interest, linked to a NES.

Figure 13:
FIG. 13 is a schematic representation of the structure of PARKIN fusion proteins of the present disclosure.
Figure 13:
Figure 13:
Figure 13:

A schematic of the PARKIN fusion proteins is provided in FIG. 13, and a summary of the fusion protein constructs is provided in Table 13.

TABLE 13

Novel TAT-PARKIN fusion proteins.

| Fusion Protein | SEQ ID NO. | CPP | Protease cleavable domain or NES | Protease responsible for cleavage | Protein of interest |
|---|---|---|---|---|---|
| TAT-GG-Ubiquitin-PARKIN | 69 | TAT | Ubiquitin | Deubiquitinase | PARKIN |
| TAT-GG-EPLFAERK-PARKIN | 70 | TAT | EPLFAERK (SEQ ID NO: 20) | Calpain1 | PARKIN |
| TAT-GG-PARKIN-NES1 | 71 | TAT | NES1 | not relevant | PARKIN |
| His6-SUMO-TAT-GG-PARKIN | 82 | TAT | SUMO | SUMO | PARKIN |

The amino acid sequence of His6-SUMO-TAT-GG-PARKIN (SEQ ID NO: 82), which was used as a control, is shown below:

HHHHHHSDSEVNQEAKPEVKPETHINLKVSDGSSEIFFKIKKTTP

LRRLMEAFAKRQGKEMDSLRFLYDGIRIQADQTPEDLDMEDNDIIEAHR

EQIGGMYGRKKRRQRRRGGMIVFVRFNSSHGFPVEVDSDTSIFQLKEVV

AKRQGVPADQLRVIFAGKELRNDWTVQNCDLDQQSIVHIVQRPWRKGQE

MNATGGDDPRNAAGGCEREPQSLTRVDLSSSVLPGDSVGLAVILHTDSR

-continued

KDSPPAGSPAGRSIYNSFYVYCKGPCQRVQPGKLRVQCSTCRQATLTLT

QGPSCWDDVLIPNRMSGECQSPHCPGTSAEFFFKCGAHPTSDKETSVAL

HLIATNSRNITCITCTDVRSPVLVFQCNSRHVICLDCFHLYCVTRLNDR

QFVHDPQLGYSLPCVAGCPNSLIKELHHFRILGEEQYNRYQQYGAEECV

LQMGGVLCPRPGCGAGLLPEPDQRKVTCEGGNGLGCGFAFCRECKEAYH

EGECSAVFEASGTTTQAYRVDERAAEQARWEAASKETIKKTTKPCPRCH

VPVEKNGGCMHMKCPQPQCRLEWCWNCGCEWNRVCMGDHWFDV.

It is noted that in the control fusion protein, His6-SUMO-TAT-GG-PARKIN, the His6-SUMO portion is present solely for the ease of purification. Following purification using the His6 tag (SEQ ID NO: 85), the His6 tag (SEQ ID NO: 85) is removed by the protease-mediated cleavage of the SUMO sequence. Thus, the control fusion protein of SEQ ID NO: 82 does not contain a TES sequence.

Example 10

Transduction Ability of PARKIN Fusion Proteins

The goal of this experiment was to determine the ability of PARKIN fusion proteins to transduce cells and to localize to the mitochondria.

The experiment utilized L6 rat myoblast cells because these cells have low endogenous PARKIN levels and therefore do not interfere with the signal produced by the TAT-GG-hFXN fusion proteins. The experiment also utilized the PARKIN fusion proteins described in Example 9.

For the experiment, L6 cells were plated at a seeding density of 8,000 cells per well in a 96 well plate (corning 3904) in complete DMEM medium (DMEM, 10% PBS and 1% antibiotic: antimycotic) and incubated overnight at 37° C. On day 1, the cells were treated with 0.0625 µM, 0.125 µM, 0.25 µM, 0.5 µM and 1 µM of each PARKIN fusion protein for 2 hours at 37° C. After two hours, same amount of complete media was added per well and incubated overnight at 37° C. The same treatment was repeated on day 2.

On day 3, the cells were washed with PBS, trypsinized, resuspended in the complete cell culture medium, transferred to a fibronectin-coated glass-bottom plate allowed to settle overnight at 37° C. On day 4, the cells were washed with PBS and treated with freshly prepared 4% paraformaldehyde solution at room temperature for 10 minutes. After 10 minutes, the cells were washed twice PBS, and then 50 µL of blocking buffer (0.3% Triton-X 100, 5% normal goat serum in PBS) was added per well and incubated at room temperature for 1 hour. After 1 hour, blocking buffer was aspirated and 50 µL of primary antibody diluted in blocking buffer (Anti-Parkin Antibody, 12235-1-AP (1:100) and anti-TOMM20 antibody, EMD Millipore MABT166 (1:500), was added per well and incubated overnight at 4° C.

On day 5, the cells were washed twice with PBS and 50 µL of secondary antibody diluted in blocking buffer (Anti-Mouse IgG AlexaFluor594, ab150116 abcam (1:1000), Anti-rabbit IgG Alexafluor488, ab150077 abcam (1:1000)) was added to each well. The cells were incubated at room temperature for one hour, after which they were gently washed with PBS, mixed with 50 µL of 300 nM Hoescht 33342 stain and allowed to stand at room temperature for 3 minutes. Subsequently, the cells were washed twice with PBS and imaged. The ratio of PARKIN protein colocolizing with mitochondria was evaluated using Harmony software from Operetta (High Content Imager from Perkin Elmer and plotted as a function of the ratio of PARKIN localizing to mitochondria to concentration of proteins (µM). Specifically, the ratio of the amount of AlexaFluor488 staining (corresponding to PARKIN) to the amount of AlexaFluor 594 staining (corresponding to mitochondria) was calculated and plotted on a graph to compare the transduction efficiency of various PARKIN fusion proteins.

Figure 14:
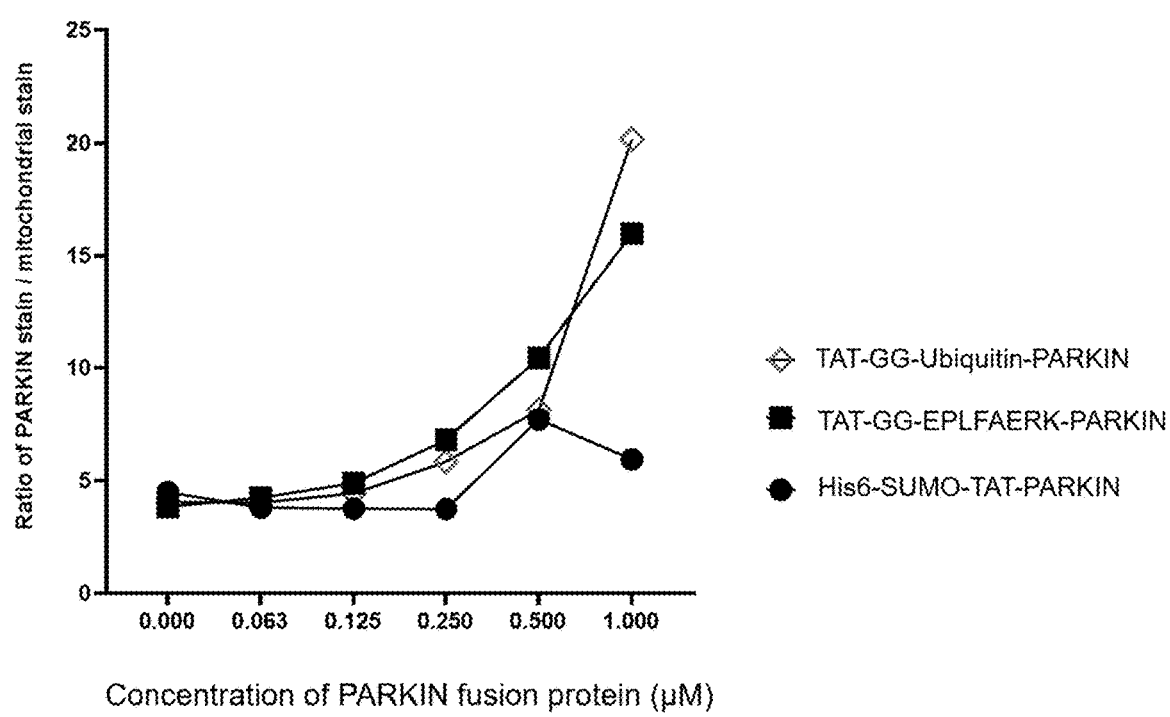
FIG. 14 is a graph showing the ratio of PARKIN stain to the mitochondrial stain as a function of PARKIN fusion protein concentration for cells treated with different concentrations of His6-SUMO-TAT-GG-PARKIN, TAT-GG-EPL-FAERK-PARKIN and TAT-GG-Ubiquitin-PARKIN.

The results of the experiment are presented in FIG. 14. Specifically, FIG. 14 is a graph showing the ratio of PARKIN stain to the mitochondrial stain as a function of PARKIN fusion protein concentration for cells treated with different concentratons of His6-SUMO-TAT-GG-PARKIN, TAT-GG-EPLFAERK-PARKIN and TAT-GG-Ubiquitin-PARKIN. The results presented in FIG. 14 demonstrate that transduction of cells with the PARKIN fusion proteins occurs in a dose dependent manner, with higher ratios indicating higher mitochondria localization. The results indicate that PARKIN fusion proteins containing TES, i.e., TAT-GG-EPLFAERK-PARKIN and TAT-GG-Ubiquitin-PARKIN, have more mitochondrial localization at 1 µM concentration than the control PARKIN fusion protein without TES, His6-SUMO-TAT-GG-PARKIN. The results of this experiment indicate that PARKIN fusion proteins containing TES are transduced into cells and correctly localize to mitochondria in higher amounts than the control His6-SUMO-TAT-PARKIN fusion protein.

Example 11

Activity of PARKIN Fusion Proteins

The goal of this experiment was to test the activity of PARKIN in cells treated with the novel PARKIN fusion proteins. Specifically, the goal of the experiment was to determine if, after treatment of cells with the novel PARKIN fusion proteins, PARKIN localizes to mitochondria to induce mitophagy in the presence of mitochondrial uncoupler, carbonyl cyanide m-chlorophenyl hydrazone (CCCP).

For the experiment, L6 rat myoblast cells were treated with 0 µM, 0.5 µM and 1 µM His6-SUMO-TAT-GG-PARKIN, TAT-GG-EPLFAERK-PARKIN, orTAT-GG-Ubiquitin-PARKIN in the presence and absence of 10 µM CCCP Immunostaining and microscopy were then performed essentially as described in Example 10.

Figure 15:
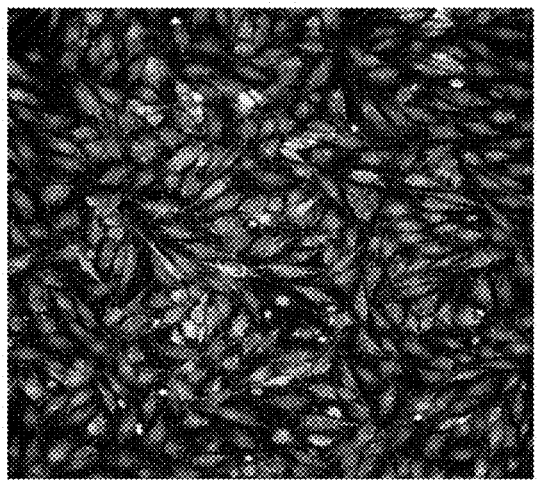
FIG. 15 is a series of phographs of L6 rat myoblast cells treated with 0 µM or 0.5 µM TAT-GG-EPLFAERK-PARKIN in the absence or presence of 10 µM CCCP.
Figure 15:
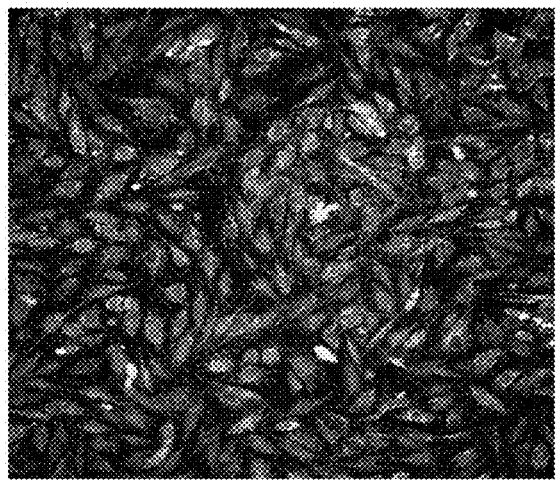
Figure 15:
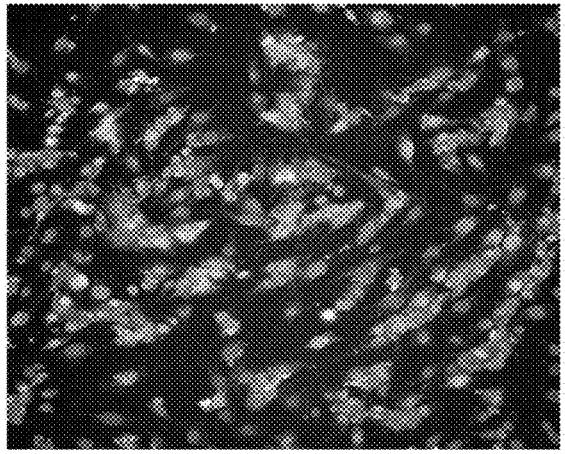
Figure 15:
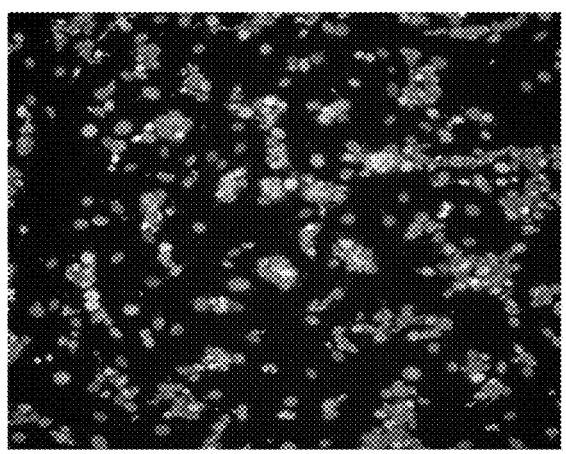

The results of the experiment for TAT-GG-EPLFAERK-PARKIN are shown in FIG. 15. Specifically, FIG. 15 is a series of phographs of L6 rat myoblast cells treated with 0 µM or 0.5 µM TAT-GG-EPLFAERK-PARKIN in the absence or presence of 10 µM CCCP. The results presented in FIG. 15 demonstrate that control L6 rat myoblast cells do not show any morphological differences in the absence or presence of CCCP. Also, FIG. 15 shows that, in the absence of treatment with PARKIN fusion proteins, endogenous PARKIN remains undetectable in L6 cells. The results presented in FIG. 15 also show that in L6 rat myoblast cells treated with TAT-GG-EPLFAERK-PARKIN, localization of PARKIN to mitochondria is observed in the presence of CCCP. This observation is consistent with the known role of endogeouns PARKIN in mitophagy which involves PARKIN mitochondrial relocalization to the mitochondria upon mitochondrial membrane depolarization.

The invention claimed is:

1. A fusion protein, comprising:
a protein of interest to be delivered to a cell;
a cell penetrating peptide (CPP); and
a target enhancing sequence (TES);
wherein the fusion protein comprises:
an amino acid sequence having at least 85% sequence identity to SEQ ID NO: 55;
an amino acid sequence having at least 85% sequence identity to SEQ ID NO: 56;
an amino acid sequence having at least 85% sequence identity to SEQ ID NO: 81;
an amino acid sequence having at least 96% sequence identity to SEQ ID NOs: 58;
an amino acid sequence having at least 97% sequence identity to SEQ ID NOs: 60;
an amino acid sequence having at least 97% sequence identity to SEQ ID NO: 61;
an amino acid sequence having at least 98% sequence identity to SEQ ID NO: 57; or
an amino acid sequence having at least 98% sequence identity to SEQ ID NO: 59.

2. The fusion protein of claim 1, comprising the amino acid sequence of SEQ ID NO: 55.

3. The fusion protein of claim 1, consisting of the amino acid sequence of SEQ ID NO: 55.

4. The fusion protein of claim 1, comprising the amino acid sequence of SEQ ID NO: 56.

5. The fusion protein of claim 1, consisting of the amino acid sequence of SEQ ID NO: 56.

6. The fusion protein of claim 1, comprising the amino acid sequence of SEQ ID NO: 81.

7. The fusion protein of claim 1, consisting of the amino acid sequence of SEQ ID NO: 81.

8. The fusion protein of claim 1, comprising the amino acid sequence of SEQ ID NO: 58.

9. The fusion protein of claim 1, consisting of the amino acid sequence of SEQ ID NO: 58.

10. The fusion protein of claim 1, comprising the amino acid sequence of SEQ ID NO: 60.

11. The fusion protein of claim 1, consisting of the amino acid sequence of SEQ ID NO: 60.

12. The fusion protein of claim 1, comprising the amino acid sequence of SEQ ID NO: 61.

13. The fusion protein of claim 1, consisting of the amino acid sequence of SEQ ID NO: 61.

14. The fusion protein of claim 1, comprising the amino acid sequence of SEQ ID NO: 57.

15. The fusion protein of claim 1, consisting of the amino acid sequence of SEQ ID NO: 57.

16. The fusion protein of claim 1, comprising the amino acid sequence of SEQ ID NO: 59.

17. The fusion protein of claim 1, consisting of the amino acid sequence of SEQ ID NO: 59.

18. A conjugate for intracellular delivery of proteins to non-nuclear organelles comprising the fusion protein of claim 1 and a moiety linked to said fusion protein, wherein said moiety is selected from a group consisting of a radioactive label, a fluorescent label, a small molecule, and a polymeric molecule.

19. A cell comprising the fusion protein of claim 1.

20. A pharmaceutical composition comprising the fusion protein of claim 1.

21. A method of delivering a protein of interest to a cell, said method comprising contacting said cell with the fusion protein of claim 1.

22. A method of intracellular delivery of a protein of interest to a non-nuclear organelle in a cell, said method comprising contacting said cell with the fusion protein of claim 1.

23. The method of claim 22, wherein said non-nuclear organelle is mitochondria.

24. A method for treating a non-nuclear organelle associated disorder, said method comprising administering to a subject in need thereof the fusion protein of claim 1.

25. The method of claim 24, wherein the non-nuclear organelle associated disorder is Friedreich's ataxia (PDRA).

26. The method of claim 24, wherein said subject is a human.

* * * * *

UNITED STATES PATENT AND TRADEMARK OFFICE
CERTIFICATE OF CORRECTION

PATENT NO. : 11,891,420 B2
APPLICATION NO. : 17/214757
DATED : February 6, 2024
INVENTOR(S) : Joan David Bettoun et al.

It is certified that error appears in the above-identified patent and that said Letters Patent is hereby corrected as shown below:

In the Claims

Column 197, Claim 1, Line 67, replace "NOs" with --NO--;

Column 198, Claim 1, Line 55, replace "NOs" with --NO--;

Column 200, Claim 25, Line 23, replace "PDRA" with --FRDA--.

Signed and Sealed this
Seventh Day of May, 2024

Katherine Kelly Vidal
*Director of the United States Patent and Trademark Office*

SEQUENCE LISTING

<160> NUMBER OF SEQ ID NOS: 88

<210> SEQ ID NO 1
<211> LENGTH: 210
<212> TYPE: PRT
<213> ORGANISM: Homo sapiens

<400> SEQUENCE: 1

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
        35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
        115                 120                 125

Ser Gly Val Leu Thr Val Lys Leu Gly Gly Asp Leu Gly Thr Tyr Val
    130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                165                 170                 175

His Asp Gly Val Ser Leu His Glu Leu Leu Ala Ala Glu Leu Thr Lys
            180                 185                 190

Ala Leu Lys Thr Lys Leu Asp Leu Ser Ser Leu Ala Tyr Ser Gly Lys
        195                 200                 205

Asp Ala
    210

<210> SEQ ID NO 2
<211> LENGTH: 130
<212> TYPE: PRT
<213> ORGANISM: Homo sapiens

<400> SEQUENCE: 2

Ser Gly Thr Leu Gly His Pro Gly Ser Leu Asp Glu Thr Thr Tyr Glu
1               5                   10                  15

Arg Leu Ala Glu Glu Thr Leu Asp Ser Leu Ala Glu Phe Phe Glu Asp
            20                  25                  30

Leu Ala Asp Lys Pro Tyr Thr Phe Glu Asp Tyr Asp Val Ser Phe Gly
        35                  40                  45

Ser Gly Val Leu Thr Val Lys Leu Gly Gly Asp Leu Gly Thr Tyr Val
    50                  55                  60

Ile Asn Lys Gln Thr Pro Asn Lys Gln Ile Trp Leu Ser Ser Pro Ser
65                  70                  75                  80

Ser Gly Pro Lys Arg Tyr Asp Trp Thr Gly Lys Asn Trp Val Tyr Ser
                85                  90                  95

His Asp Gly Val Ser Leu His Glu Leu Leu Ala Ala Glu Leu Thr Lys

```
            100             105                 110
Ala Leu Lys Thr Lys Leu Asp Leu Ser Ser Leu Ala Tyr Ser Gly Lys
        115                 120                 125

Asp Ala
    130

<210> SEQ ID NO 3
<211> LENGTH: 292
<212> TYPE: PRT
<213> ORGANISM: Homo sapiens

<400> SEQUENCE: 3

Met Pro Leu His Val Lys Trp Pro Phe Pro Ala Val Pro Pro Leu Thr
1               5                   10                  15

Trp Thr Leu Ala Ser Ser Val Val Met Gly Leu Val Gly Thr Tyr Ser
            20                  25                  30

Cys Phe Trp Thr Lys Tyr Met Asn His Leu Thr Val His Asn Arg Glu
        35                  40                  45

Val Leu Tyr Glu Leu Ile Glu Lys Arg Gly Pro Ala Thr Pro Leu Ile
    50                  55                  60

Thr Val Ser Asn His Gln Ser Cys Met Asp Asp Pro His Leu Trp Gly
65                  70                  75                  80

Ile Leu Lys Leu Arg His Ile Trp Asn Leu Lys Leu Met Arg Trp Thr
                85                  90                  95

Pro Ala Ala Ala Asp Ile Cys Phe Thr Lys Glu Leu His Ser His Phe
            100                 105                 110

Phe Ser Leu Gly Lys Cys Val Pro Val Cys Arg Gly Ala Glu Phe Phe
        115                 120                 125

Gln Ala Glu Asn Glu Gly Lys Gly Val Leu Asp Thr Gly Arg His Met
130                 135                 140

Pro Gly Ala Gly Lys Arg Arg Glu Lys Gly Asp Gly Val Tyr Gln Lys
145                 150                 155                 160

Gly Met Asp Phe Ile Leu Glu Lys Leu Asn His Gly Asp Trp Val His
                165                 170                 175

Ile Phe Pro Glu Gly Lys Val Asn Met Ser Ser Glu Phe Leu Arg Phe
            180                 185                 190

Lys Trp Gly Ile Gly Arg Leu Ile Ala Glu Cys His Leu Asn Pro Ile
        195                 200                 205

Ile Leu Pro Leu Trp His Val Gly Met Asn Asp Val Leu Pro Asn Ser
210                 215                 220

Pro Pro Tyr Phe Pro Arg Phe Gly Gln Lys Ile Thr Val Leu Ile Gly
225                 230                 235                 240

Lys Pro Phe Ser Ala Leu Pro Val Leu Glu Arg Leu Arg Ala Glu Asn
                245                 250                 255

Lys Ser Ala Val Glu Met Arg Lys Ala Leu Thr Asp Phe Ile Gln Glu
            260                 265                 270

Glu Phe Gln His Leu Lys Thr Gln Ala Glu Gln Leu His Asn His Leu
        275                 280                 285

Gln Pro Gly Arg
    290

<210> SEQ ID NO 4
<211> LENGTH: 359
<212> TYPE: PRT
<213> ORGANISM: Homo sapiens
```

<400> SEQUENCE: 4

Met Ala Ala Val Ser Gly Leu Val Arg Arg Pro Leu Arg Glu Val Ser
1               5                   10                  15

Gly Leu Leu Lys Arg Arg Phe His Trp Thr Ala Pro Ala Ala Leu Gln
            20                  25                  30

Val Thr Val Arg Asp Ala Ile Asn Gln Gly Met Asp Glu Glu Leu Glu
        35                  40                  45

Arg Asp Glu Lys Val Phe Leu Leu Gly Glu Val Ala Gln Tyr Asp
    50                  55                  60

Gly Ala Tyr Lys Val Ser Arg Gly Leu Trp Lys Lys Tyr Gly Asp Lys
65                  70                  75                  80

Arg Ile Ile Asp Thr Pro Ile Ser Glu Met Gly Phe Ala Gly Ile Ala
                85                  90                  95

Val Gly Ala Ala Met Ala Gly Leu Arg Pro Ile Cys Glu Phe Met Thr
            100                 105                 110

Phe Asn Phe Ser Met Gln Ala Ile Asp Gln Val Ile Asn Ser Ala Ala
            115                 120                 125

Lys Thr Tyr Tyr Met Ser Gly Leu Gln Pro Val Pro Ile Val Phe
        130                 135                 140

Arg Gly Pro Asn Gly Ala Ser Ala Gly Val Ala Ala Gln His Ser Gln
145                 150                 155                 160

Cys Phe Ala Ala Trp Tyr Gly His Cys Pro Gly Leu Lys Val Val Ser
                165                 170                 175

Pro Trp Asn Ser Glu Asp Ala Lys Gly Leu Ile Lys Ser Ala Ile Arg
            180                 185                 190

Asp Asn Asn Pro Val Val Leu Glu Asn Glu Leu Met Tyr Gly Val
        195                 200                 205

Pro Phe Glu Phe Pro Glu Ala Gln Ser Lys Asp Phe Leu Ile Pro
    210                 215                 220

Ile Gly Lys Ala Lys Ile Glu Arg Gln Gly Thr His Ile Thr Val Val
225                 230                 235                 240

Ser His Ser Arg Pro Val Gly His Cys Leu Glu Ala Ala Val Leu
                245                 250                 255

Ser Lys Glu Gly Val Glu Cys Glu Val Ile Asn Met Arg Thr Ile Arg
            260                 265                 270

Pro Met Asp Met Glu Thr Ile Glu Ala Ser Val Met Lys Thr Asn His
        275                 280                 285

Leu Val Thr Val Glu Gly Gly Trp Pro Gln Phe Gly Val Gly Ala Glu
    290                 295                 300

Ile Cys Ala Arg Ile Met Glu Gly Pro Ala Phe Asn Phe Leu Asp Ala
305                 310                 315                 320

Pro Ala Val Arg Val Thr Gly Ala Asp Val Pro Met Pro Tyr Ala Lys
                325                 330                 335

Ile Leu Glu Asp Asn Ser Ile Pro Gln Val Lys Asp Ile Ile Phe Ala
            340                 345                 350

Ile Lys Lys Thr Leu Asn Ile
        355

<210> SEQ ID NO 5
<211> LENGTH: 1394
<212> TYPE: PRT
<213> ORGANISM: Homo sapiens

<400> SEQUENCE: 5

```
Met Ala Ala Leu Leu Arg Ser Ala Arg Trp Leu Leu Arg Ala Gly Ala
1               5                   10                  15

Ala Pro Arg Leu Pro Leu Ser Leu Arg Leu Pro Gly Gly Pro Gly
            20                  25                  30

Arg Leu His Ala Ala Ser Tyr Leu Pro Ala Arg Ala Gly Pro Val
                35                  40                  45

Ala Gly Gly Leu Leu Ser Pro Ala Arg Leu Tyr Ala Ile Ala Ala Lys
        50                  55                  60

Glu Lys Asp Ile Gln Glu Ser Thr Phe Ser Arg Lys Ile Ser
65                      70                  75                  80

Asn Gln Phe Asp Trp Ala Leu Met Arg Leu Asp Leu Ser Val Arg Arg
                    85                  90                  95

Thr Gly Arg Ile Pro Lys Lys Leu Leu Gln Lys Val Phe Asn Asp Thr
                100                 105                 110

Cys Arg Ser Gly Gly Leu Gly Gly Ser His Ala Leu Leu Leu Leu Arg
            115                 120                 125

Ser Cys Gly Ser Leu Leu Pro Glu Leu Lys Leu Glu Glu Arg Thr Glu
        130                 135                 140

Phe Ala His Arg Ile Trp Asp Thr Leu Gln Lys Leu Gly Ala Val Tyr
145                 150                 155                 160

Asp Val Ser His Tyr Asn Ala Leu Leu Lys Val Tyr Leu Gln Asn Glu
                165                 170                 175

Tyr Lys Phe Ser Pro Thr Asp Phe Leu Ala Lys Met Glu Glu Ala Asn
            180                 185                 190

Ile Gln Pro Asn Arg Val Thr Tyr Gln Arg Leu Ile Ala Ser Tyr Cys
        195                 200                 205

Asn Val Gly Asp Ile Glu Gly Ala Ser Lys Ile Leu Gly Phe Met Lys
    210                 215                 220

Thr Lys Asp Leu Pro Val Thr Glu Ala Val Phe Ser Ala Leu Val Thr
225                 230                 235                 240

Gly His Ala Arg Ala Gly Asp Met Glu Asn Ala Glu Asn Ile Leu Thr
                245                 250                 255

Val Met Arg Asp Ala Gly Ile Glu Pro Gly Pro Asp Thr Tyr Leu Ala
            260                 265                 270

Leu Leu Asn Ala Tyr Ala Glu Lys Gly Asp Ile Asp His Val Lys Gln
        275                 280                 285

Thr Leu Glu Lys Val Glu Lys Ser Glu Leu His Leu Met Asp Arg Asp
    290                 295                 300

Leu Leu Gln Ile Ile Phe Ser Phe Ser Lys Ala Gly Tyr Pro Gln Tyr
305                 310                 315                 320

Val Ser Glu Ile Leu Glu Lys Val Thr Cys Glu Arg Arg Tyr Ile Pro
                325                 330                 335

Asp Ala Met Asn Leu Ile Leu Leu Val Thr Glu Lys Leu Glu Asp
            340                 345                 350

Val Ala Leu Gln Ile Leu Leu Ala Cys Pro Val Ser Lys Glu Asp Gly
        355                 360                 365

Pro Ser Val Phe Gly Ser Phe Phe Leu Gln His Cys Val Thr Met Asn
    370                 375                 380

Thr Pro Val Glu Lys Leu Thr Asp Tyr Cys Lys Lys Leu Lys Glu Val
385                 390                 395                 400

Gln Met His Ser Phe Pro Leu Gln Phe Thr Leu His Cys Ala Leu Leu
                405                 410                 415

Ala Asn Lys Thr Asp Leu Ala Lys Ala Leu Met Lys Ala Val Lys Glu
```

```
            420             425             430
Glu Gly Phe Pro Ile Arg Pro His Tyr Phe Trp Pro Leu Leu Val Gly
            435                 440                 445
Arg Arg Lys Glu Lys Asn Val Gln Gly Ile Ile Glu Ile Leu Lys Gly
            450                 455                 460
Met Gln Glu Leu Gly Val His Pro Asp Gln Glu Thr Tyr Thr Asp Tyr
465                 470                 475                 480
Val Ile Pro Cys Phe Asp Ser Val Asn Ser Ala Arg Ala Ile Leu Gln
                485                 490                 495
Glu Asn Gly Cys Leu Ser Asp Ser Asp Met Phe Ser Gln Ala Gly Leu
            500                 505                 510
Arg Ser Glu Ala Ala Asn Gly Asn Leu Asp Phe Val Leu Ser Phe Leu
            515                 520                 525
Lys Ser Asn Thr Leu Pro Ile Ser Leu Gln Ser Ile Arg Ser Ser Leu
            530                 535                 540
Leu Leu Gly Phe Arg Arg Ser Met Asn Ile Asn Leu Trp Ser Glu Ile
545                 550                 555                 560
Thr Glu Leu Leu Tyr Lys Asp Gly Arg Tyr Cys Gln Glu Pro Arg Gly
                565                 570                 575
Pro Thr Glu Ala Val Gly Tyr Phe Leu Tyr Asn Leu Ile Asp Ser Met
            580                 585                 590
Ser Asp Ser Glu Val Gln Ala Lys Glu Glu His Leu Arg Gln Tyr Phe
            595                 600                 605
His Gln Leu Glu Lys Met Asn Val Lys Ile Pro Glu Asn Ile Tyr Arg
            610                 615                 620
Gly Ile Arg Asn Leu Leu Glu Ser Tyr His Val Pro Glu Leu Ile Lys
625                 630                 635                 640
Asp Ala His Leu Leu Val Glu Ser Lys Asn Leu Asp Phe Gln Lys Thr
                645                 650                 655
Val Gln Leu Thr Ser Ser Glu Leu Glu Ser Thr Leu Glu Thr Leu Lys
            660                 665                 670
Ala Glu Asn Gln Pro Ile Arg Asp Val Leu Lys Gln Leu Ile Leu Val
            675                 680                 685
Leu Cys Ser Glu Glu Asn Met Gln Lys Ala Leu Glu Leu Lys Ala Lys
            690                 695                 700
Tyr Glu Ser Asp Met Val Thr Gly Gly Tyr Ala Ala Leu Ile Asn Leu
705                 710                 715                 720
Cys Cys Arg His Asp Lys Val Glu Asp Ala Leu Asn Leu Lys Glu Glu
                725                 730                 735
Phe Asp Arg Leu Asp Ser Ser Ala Val Leu Asp Thr Gly Lys Tyr Val
            740                 745                 750
Gly Leu Val Arg Val Leu Ala Lys His Gly Lys Leu Gln Asp Ala Ile
            755                 760                 765
Asn Ile Leu Lys Glu Met Lys Glu Lys Asp Val Leu Ile Lys Asp Thr
            770                 775                 780
Thr Ala Leu Ser Phe Phe His Met Leu Asn Gly Ala Ala Leu Arg Gly
785                 790                 795                 800
Glu Ile Glu Thr Val Lys Gln Leu His Glu Ala Ile Val Thr Leu Gly
                805                 810                 815
Leu Ala Glu Pro Ser Thr Asn Ile Ser Phe Pro Leu Val Thr Val His
            820                 825                 830
Leu Glu Lys Gly Asp Leu Ser Thr Ala Leu Glu Val Ala Ile Asp Cys
            835                 840                 845
```

-continued

```
Tyr Glu Lys Tyr Lys Val Leu Pro Arg Ile His Asp Val Leu Cys Lys
    850                 855                 860
Leu Val Glu Lys Gly Glu Thr Asp Leu Ile Gln Lys Ala Met Asp Phe
865                 870                 875                 880
Val Ser Gln Glu Gln Gly Glu Met Val Met Leu Tyr Asp Leu Phe Phe
                    885                 890                 895
Ala Phe Leu Gln Thr Gly Asn Tyr Lys Glu Ala Lys Lys Ile Ile Glu
                900                 905                 910
Thr Pro Gly Ile Arg Ala Arg Ser Ala Arg Leu Gln Trp Phe Cys Asp
            915                 920                 925
Arg Cys Val Ala Asn Asn Gln Val Glu Thr Leu Glu Lys Leu Val Glu
930                 935                 940
Leu Thr Gln Lys Leu Phe Glu Cys Asp Arg Asp Gln Met Tyr Tyr Asn
945                 950                 955                 960
Leu Leu Lys Leu Tyr Lys Ile Asn Gly Asp Trp Gln Arg Ala Asp Ala
                965                 970                 975
Val Trp Asn Lys Ile Gln Glu Glu Asn Val Ile Pro Arg Glu Lys Thr
            980                 985                 990
Leu Arg Leu Leu Ala Glu Ile Leu  Arg Glu Gly Asn  Gln Glu Val Pro
        995                 1000                 1005
Phe Asp Val Pro Glu Leu Trp  Tyr Glu Asp Glu Lys  His Ser Leu
    1010                 1015                 1020
Asn Ser Ser Ser Ala Ser Thr  Thr Glu Pro Asp Phe  Gln Lys Asp
    1025                 1030                 1035
Ile Leu Ile Ala Cys Arg Leu  Asn Gln Lys Lys Gly  Ala Tyr Asp
    1040                 1045                 1050
Ile Phe Leu Asn Ala Lys Glu  Gln Asn Ile Val Phe  Asn Ala Glu
    1055                 1060                 1065
Thr Tyr Ser Asn Leu Ile Lys  Leu Leu Met Ser Glu  Asp Tyr Phe
    1070                 1075                 1080
Thr Gln Ala Met Glu Val Lys  Ala Phe Ala Glu Thr  His Ile Lys
    1085                 1090                 1095
Gly Phe Thr Leu Asn Asp Ala  Ala Asn Ser Arg Leu  Ile Ile Thr
    1100                 1105                 1110
Gln Val Arg Arg Asp Tyr Leu  Lys Glu Ala Val Thr  Thr Leu Lys
    1115                 1120                 1125
Thr Val Leu Asp Gln Gln Gln  Thr Pro Ser Arg Leu  Ala Val Thr
    1130                 1135                 1140
Arg Val Ile Gln Ala Leu Ala  Met Lys Gly Asp Val  Glu Asn Ile
    1145                 1150                 1155
Glu Val Val Gln Lys Met Leu  Asn Gly Leu Glu Asp  Ser Ile Gly
    1160                 1165                 1170
Leu Ser Lys Met Val Phe Ile  Asn Asn Ile Ala Leu  Ala Gln Ile
    1175                 1180                 1185
Lys Asn Asn Asn Ile Asp Ala  Ala Ile Glu Asn Ile  Glu Asn Met
    1190                 1195                 1200
Leu Thr Ser Glu Asn Lys Val  Ile Glu Pro Gln Tyr  Phe Gly Leu
    1205                 1210                 1215
Ala Tyr Leu Phe Arg Lys Val  Ile Glu Glu Gln Leu  Glu Pro Ala
    1220                 1225                 1230
Val Glu Lys Ile Ser Ile Met  Ala Glu Arg Leu Ala  Asn Gln Phe
    1235                 1240                 1245
```

-continued

```
Ala Ile Tyr Lys Pro Val Thr Asp Phe Phe Leu Gln Leu Val Asp
    1250                1255                1260

Ala Gly Lys Val Asp Asp Ala Arg Ala Leu Leu Gln Arg Cys Gly
    1265                1270                1275

Ala Ile Ala Glu Gln Thr Pro Ile Leu Leu Phe Leu Leu Arg
    1280                1285                1290

Asn Ser Arg Lys Gln Gly Lys Ala Ser Thr Val Lys Ser Val Leu
    1295                1300                1305

Glu Leu Ile Pro Glu Leu Asn Glu Lys Glu Ala Tyr Asn Ser
    1310                1315                1320

Leu Met Lys Ser Tyr Val Ser Glu Lys Asp Val Thr Ser Ala Lys
    1325                1330                1335

Ala Leu Tyr Glu His Leu Thr Ala Lys Asn Thr Lys Leu Asp Asp
    1340                1345                1350

Leu Phe Leu Lys Arg Tyr Ala Ser Leu Leu Lys Tyr Ala Gly Glu
    1355                1360                1365

Pro Val Pro Phe Ile Glu Pro Pro Glu Ser Phe Glu Phe Tyr Ala
    1370                1375                1380

Gln Gln Leu Arg Lys Leu Arg Glu Asn Ser Ser
    1385                1390

<210> SEQ ID NO 6
<211> LENGTH: 109
<212> TYPE: PRT
<213> ORGANISM: Homo sapiens

<400> SEQUENCE: 6

Met Ala Ala Ser Ala Ala Arg Gly Ala Ala Ala Leu Arg Arg Ser Ile
1               5                   10                  15

Asn Gln Pro Val Ala Phe Val Arg Arg Ile Pro Trp Thr Ala Ala Ser
                20                  25                  30

Ser Gln Leu Lys Glu His Phe Ala Gln Phe Gly His Val Arg Arg Cys
        35                  40                  45

Ile Leu Pro Phe Asp Lys Glu Thr Gly Phe His Arg Gly Leu Gly Trp
    50                  55                  60

Val Gln Phe Ser Ser Glu Glu Gly Leu Arg Asn Ala Leu Gln Gln Glu
65                  70                  75                  80

Asn His Ile Ile Asp Gly Val Lys Val Gln Val His Thr Arg Arg Pro
                85                  90                  95

Lys Leu Pro Gln Thr Ser Asp Asp Glu Lys Lys Asp Phe
            100                 105

<210> SEQ ID NO 7
<211> LENGTH: 465
<212> TYPE: PRT
<213> ORGANISM: Homo sapiens

<400> SEQUENCE: 7

Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Val Ala Lys
                20                  25                  30

Arg Gln Gly Val Pro Ala Asp Gln Leu Arg Val Ile Phe Ala Gly Lys
        35                  40                  45

Glu Leu Arg Asn Asp Trp Thr Val Gln Asn Cys Asp Leu Asp Gln Gln
    50                  55                  60
```

-continued

```
Ser Ile Val His Ile Val Gln Arg Pro Trp Arg Lys Gly Gln Glu Met
 65                  70                  75                  80

Asn Ala Thr Gly Gly Asp Asp Pro Arg Asn Ala Ala Gly Gly Cys Glu
                 85                  90                  95

Arg Glu Pro Gln Ser Leu Thr Arg Val Asp Leu Ser Ser Val Leu
            100                 105                 110

Pro Gly Asp Ser Val Gly Leu Ala Val Ile Leu His Thr Asp Ser Arg
            115                 120                 125

Lys Asp Ser Pro Pro Ala Gly Ser Pro Ala Gly Arg Ser Ile Tyr Asn
            130                 135                 140

Ser Phe Tyr Val Tyr Cys Lys Gly Pro Cys Gln Arg Val Gln Pro Gly
145                 150                 155                 160

Lys Leu Arg Val Gln Cys Ser Thr Cys Arg Gln Ala Thr Leu Thr Leu
                165                 170                 175

Thr Gln Gly Pro Ser Cys Trp Asp Asp Val Leu Ile Pro Asn Arg Met
            180                 185                 190

Ser Gly Glu Cys Gln Ser Pro His Cys Pro Gly Thr Ser Ala Glu Phe
        195                 200                 205

Phe Phe Lys Cys Gly Ala His Pro Thr Ser Asp Lys Glu Thr Ser Val
210                 215                 220

Ala Leu His Leu Ile Ala Thr Asn Ser Arg Asn Ile Thr Cys Ile Thr
225                 230                 235                 240

Cys Thr Asp Val Arg Ser Pro Val Leu Val Phe Gln Cys Asn Ser Arg
                245                 250                 255

His Val Ile Cys Leu Asp Cys Phe His Leu Tyr Cys Val Thr Arg Leu
            260                 265                 270

Asn Asp Arg Gln Phe Val His Asp Pro Gln Leu Gly Tyr Ser Leu Pro
            275                 280                 285

Cys Val Ala Gly Cys Pro Asn Ser Leu Ile Lys Glu Leu His His Phe
            290                 295                 300

Arg Ile Leu Gly Glu Glu Gln Tyr Asn Arg Tyr Gln Gln Tyr Gly Ala
305                 310                 315                 320

Glu Glu Cys Val Leu Gln Met Gly Gly Val Leu Cys Pro Arg Pro Gly
                325                 330                 335

Cys Gly Ala Gly Leu Leu Pro Glu Pro Asp Gln Arg Lys Val Thr Cys
            340                 345                 350

Glu Gly Gly Asn Gly Leu Gly Cys Gly Phe Ala Phe Cys Arg Glu Cys
            355                 360                 365

Lys Glu Ala Tyr His Glu Gly Glu Cys Ser Ala Val Phe Glu Ala Ser
            370                 375                 380

Gly Thr Thr Thr Gln Ala Tyr Arg Val Asp Glu Arg Ala Ala Glu Gln
385                 390                 395                 400

Ala Arg Trp Glu Ala Ala Ser Lys Glu Thr Ile Lys Lys Thr Thr Lys
                405                 410                 415

Pro Cys Pro Arg Cys His Val Pro Val Glu Lys Asn Gly Gly Cys Met
            420                 425                 430

His Met Lys Cys Pro Gln Pro Gln Cys Arg Leu Glu Trp Cys Trp Asn
            435                 440                 445

Cys Gly Cys Glu Trp Asn Arg Val Cys Met Gly Asp His Trp Phe Asp
            450                 455                 460

Val
465
```

```
<210> SEQ ID NO 8
<211> LENGTH: 581
<212> TYPE: PRT
<213> ORGANISM: Homo sapiens

<400> SEQUENCE: 8
```

| Met | Ala | Val | Arg | Gln | Ala | Leu | Gly | Arg | Gly | Leu | Gln | Leu | Gly | Arg | Ala |
|---|---|---|---|---|---|---|---|---|---|---|---|---|---|---|---|
| 1 | | | | 5 | | | | | 10 | | | | | 15 | |

| Leu | Leu | Leu | Arg | Phe | Thr | Gly | Lys | Pro | Gly | Arg | Ala | Tyr | Gly | Leu | Gly |
|---|---|---|---|---|---|---|---|---|---|---|---|---|---|---|---|
| | | | 20 | | | | | 25 | | | | | 30 | | |

| Arg | Pro | Gly | Pro | Ala | Ala | Gly | Cys | Val | Arg | Gly | Glu | Arg | Pro | Gly | Trp |
|---|---|---|---|---|---|---|---|---|---|---|---|---|---|---|---|
| | | 35 | | | | | 40 | | | | | 45 | | | |

| Ala | Ala | Gly | Pro | Gly | Ala | Glu | Pro | Arg | Arg | Val | Gly | Leu | Gly | Leu | Pro |
|---|---|---|---|---|---|---|---|---|---|---|---|---|---|---|---|
| | 50 | | | | | 55 | | | | | 60 | | | | |

| Asn | Arg | Leu | Arg | Phe | Phe | Arg | Gln | Ser | Val | Ala | Gly | Leu | Ala | Ala | Arg |
|---|---|---|---|---|---|---|---|---|---|---|---|---|---|---|---|
| 65 | | | | | 70 | | | | | 75 | | | | | 80 |

| Leu | Gln | Arg | Gln | Phe | Val | Val | Arg | Ala | Trp | Gly | Cys | Ala | Gly | Pro | Cys |
|---|---|---|---|---|---|---|---|---|---|---|---|---|---|---|---|
| | | | | 85 | | | | | 90 | | | | | 95 | |

| Gly | Arg | Ala | Val | Phe | Leu | Ala | Phe | Gly | Leu | Gly | Leu | Gly | Leu | Ile | Glu |
|---|---|---|---|---|---|---|---|---|---|---|---|---|---|---|---|
| | | | 100 | | | | | 105 | | | | | 110 | | |

| Glu | Lys | Gln | Ala | Glu | Ser | Arg | Arg | Ala | Val | Ser | Ala | Cys | Gln | Glu | Ile |
|---|---|---|---|---|---|---|---|---|---|---|---|---|---|---|---|
| | | 115 | | | | | 120 | | | | | 125 | | | |

| Gln | Ala | Ile | Phe | Thr | Gln | Lys | Ser | Lys | Pro | Gly | Pro | Asp | Pro | Leu | Asp |
|---|---|---|---|---|---|---|---|---|---|---|---|---|---|---|---|
| | 130 | | | | | 135 | | | | | 140 | | | | |

| Thr | Arg | Arg | Leu | Gln | Gly | Phe | Arg | Leu | Glu | Glu | Tyr | Leu | Ile | Gly | Gln |
|---|---|---|---|---|---|---|---|---|---|---|---|---|---|---|---|
| 145 | | | | | 150 | | | | | 155 | | | | | 160 |

| Ser | Ile | Gly | Lys | Gly | Cys | Ser | Ala | Ala | Val | Tyr | Glu | Ala | Thr | Met | Pro |
|---|---|---|---|---|---|---|---|---|---|---|---|---|---|---|---|
| | | | | 165 | | | | | 170 | | | | | 175 | |

| Thr | Leu | Pro | Gln | Asn | Leu | Glu | Val | Thr | Lys | Ser | Thr | Gly | Leu | Leu | Pro |
|---|---|---|---|---|---|---|---|---|---|---|---|---|---|---|---|
| | | | 180 | | | | | 185 | | | | | 190 | | |

| Gly | Arg | Gly | Pro | Gly | Thr | Ser | Ala | Pro | Gly | Glu | Gly | Gln | Glu | Arg | Ala |
|---|---|---|---|---|---|---|---|---|---|---|---|---|---|---|---|
| | | 195 | | | | | 200 | | | | | 205 | | | |

| Pro | Gly | Ala | Pro | Ala | Phe | Pro | Leu | Ala | Ile | Lys | Met | Met | Trp | Asn | Ile |
|---|---|---|---|---|---|---|---|---|---|---|---|---|---|---|---|
| | 210 | | | | | 215 | | | | | 220 | | | | |

| Ser | Ala | Gly | Ser | Ser | Glu | Ala | Ile | Leu | Asn | Thr | Met | Ser | Gln | Glu |
|---|---|---|---|---|---|---|---|---|---|---|---|---|---|---|
| 225 | | | | | 230 | | | | | 235 | | | | | 240 |

| Leu | Val | Pro | Ala | Ser | Arg | Val | Ala | Leu | Ala | Gly | Glu | Tyr | Gly | Ala | Val |
|---|---|---|---|---|---|---|---|---|---|---|---|---|---|---|---|
| | | | | 245 | | | | | 250 | | | | | 255 | |

| Thr | Tyr | Arg | Lys | Ser | Lys | Arg | Gly | Pro | Lys | Gln | Leu | Ala | Pro | His | Pro |
|---|---|---|---|---|---|---|---|---|---|---|---|---|---|---|---|
| | | | 260 | | | | | 265 | | | | | 270 | | |

| Asn | Ile | Ile | Arg | Val | Leu | Arg | Ala | Phe | Thr | Ser | Ser | Val | Pro | Leu | Leu |
|---|---|---|---|---|---|---|---|---|---|---|---|---|---|---|---|
| | 275 | | | | | 280 | | | | | 285 | | | | |

| Pro | Gly | Ala | Leu | Val | Asp | Tyr | Pro | Asp | Val | Leu | Pro | Ser | Arg | Leu | His |
|---|---|---|---|---|---|---|---|---|---|---|---|---|---|---|---|
| 290 | | | | | 295 | | | | | 300 | | | | | |

| Pro | Glu | Gly | Leu | Gly | His | Gly | Arg | Thr | Leu | Phe | Leu | Val | Met | Lys | Asn |
|---|---|---|---|---|---|---|---|---|---|---|---|---|---|---|---|
| 305 | | | | | 310 | | | | | 315 | | | | | 320 |

| Tyr | Pro | Cys | Thr | Leu | Arg | Gln | Tyr | Leu | Cys | Val | Asn | Thr | Pro | Ser | Pro |
|---|---|---|---|---|---|---|---|---|---|---|---|---|---|---|---|
| | | | 325 | | | | | 330 | | | | | 335 | | |

| Arg | Leu | Ala | Ala | Met | Met | Leu | Leu | Gln | Leu | Leu | Glu | Gly | Val | Asp | His |
|---|---|---|---|---|---|---|---|---|---|---|---|---|---|---|---|
| | 340 | | | | | 345 | | | | | 350 | | | | |

| Leu | Val | Gln | Gln | Gly | Ile | Ala | His | Arg | Asp | Leu | Lys | Ser | Asp | Asn | Ile |
|---|---|---|---|---|---|---|---|---|---|---|---|---|---|---|---|
| | | 355 | | | | | 360 | | | | | 365 | | | |

| Leu | Val | Glu | Leu | Asp | Pro | Asp | Gly | Cys | Pro | Trp | Leu | Val | Ile | Ala | Asp |
|---|---|---|---|---|---|---|---|---|---|---|---|---|---|---|---|
| | 370 | | | | | 375 | | | | | 380 | | | | |

```
Phe Gly Cys Cys Leu Ala Asp Glu Ser Ile Gly Leu Gln Leu Pro Phe
385                 390                 395                 400

Ser Ser Trp Tyr Val Asp Arg Gly Gly Asn Gly Cys Leu Met Ala Pro
            405                 410                 415

Glu Val Ser Thr Ala Arg Pro Gly Pro Arg Ala Val Ile Asp Tyr Ser
        420                 425                 430

Lys Ala Asp Ala Trp Ala Val Gly Ala Ile Ala Tyr Glu Ile Phe Gly
    435                 440                 445

Leu Val Asn Pro Phe Tyr Gln Gly Lys Ala His Leu Glu Ser Arg
    450                 455                 460

Ser Tyr Gln Glu Ala Gln Leu Pro Ala Leu Pro Glu Ser Val Pro Pro
465                 470                 475                 480

Asp Val Arg Gln Leu Val Arg Ala Leu Leu Gln Arg Glu Ala Ser Lys
            485                 490                 495

Arg Pro Ser Ala Arg Val Ala Ala Asn Val Leu His Leu Ser Leu Trp
            500                 505                 510

Gly Glu His Ile Leu Ala Leu Lys Asn Leu Lys Leu Asp Lys Met Val
        515                 520                 525

Gly Trp Leu Leu Gln Gln Ser Ala Ala Thr Leu Leu Ala Asn Arg Leu
530                 535                 540

Thr Glu Lys Cys Cys Val Glu Thr Lys Met Lys Met Leu Phe Leu Ala
545                 550                 555                 560

Asn Leu Glu Cys Glu Thr Leu Cys Gln Ala Ala Leu Leu Leu Cys Ser
            565                 570                 575

Trp Arg Ala Ala Leu
            580

<210> SEQ ID NO 9
<211> LENGTH: 189
<212> TYPE: PRT
<213> ORGANISM: Homo sapiens

<400> SEQUENCE: 9

Met Ala Ser Lys Arg Ala Leu Val Ile Leu Ala Lys Gly Ala Glu Glu
1               5                   10                  15

Met Glu Thr Val Ile Pro Val Asp Val Met Arg Arg Ala Gly Ile Lys
            20                  25                  30

Val Thr Val Ala Gly Leu Ala Gly Lys Asp Pro Val Gln Cys Ser Arg
        35                  40                  45

Asp Val Val Ile Cys Pro Asp Ala Ser Leu Glu Asp Ala Lys Lys Glu
    50                  55                  60

Gly Pro Tyr Asp Val Val Val Leu Pro Gly Gly Asn Leu Gly Ala Gln
65                  70                  75                  80

Asn Leu Ser Glu Ser Ala Ala Val Lys Glu Ile Leu Lys Glu Gln Glu
            85                  90                  95

Asn Arg Lys Gly Leu Ile Ala Ala Ile Cys Ala Gly Pro Thr Ala Leu
            100                 105                 110

Leu Ala His Glu Ile Gly Phe Gly Ser Lys Val Thr Thr His Pro Leu
        115                 120                 125

Ala Lys Asp Lys Met Met Asn Gly Gly His Tyr Thr Tyr Ser Glu Asn
    130                 135                 140

Arg Val Glu Lys Asp Gly Leu Ile Leu Thr Ser Arg Gly Pro Gly Thr
145                 150                 155                 160

Ser Phe Glu Phe Ala Leu Ala Ile Val Glu Ala Leu Asn Gly Lys Glu
            165                 170                 175
```

Val Ala Ala Gln Val Lys Ala Pro Leu Val Leu Lys Asp
            180                 185

<210> SEQ ID NO 10
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Gly Leu Arg Thr Asp Ile Asp Ala
            35                  40                  45

Thr Cys Thr Pro Arg Arg Ala Ser Ser Asn Gln Arg Gly Leu Asn Gln
        50                  55                  60

Ile Trp Asn Val Lys Lys Gln Ser Val Tyr Leu Met Asn Leu Arg Lys
65                  70                  75                  80

<210> SEQ ID NO 11
<211> LENGTH: 11
<212> TYPE: PRT
<213> ORGANISM: Human immunodeficiency virus

<400> SEQUENCE: 11

Tyr Gly Arg Lys Lys Arg Arg Gln Arg Arg Arg
1               5                   10

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gly Trp Thr Leu Asn Ser Ala Gly Tyr Leu Leu Gly Pro His Ala Val
1               5                   10                  15

Gly Asn His Arg Ser Phe Ser Asp Lys Asn Gly Leu Thr Ser
            20                  25                  30

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Asn Leu Lys Ala Leu Ala Ala Leu Ala Lys Lys Ile Leu
1               5                   10

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 14

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gln Ile Lys Ile Trp Phe Gln Asn Arg Arg Met Lys Trp Lys Lys
1               5                   10                  15

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Arg Arg Arg Arg Arg Arg Arg Arg
1               5

<210> SEQ ID NO 17
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 18
<211> LENGTH: 76
<212> TYPE: PRT
<213> ORGANISM: Homo sapiens

<400> SEQUENCE: 18

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75
```

<210> SEQ ID NO 19
<211> LENGTH: 4
<212> TYPE: PRT
<213> ORGANISM: Unknown
<220> FEATURE:
<223> OTHER INFORMATION: Description of Unknown:
      caspase cleavage domain sequence

<400> SEQUENCE: 19

Asp Glu Val Asp
1

<210> SEQ ID NO 20
<211> LENGTH: 8
<212> TYPE: PRT
<213> ORGANISM: Unknown
<220> FEATURE:
<223> OTHER INFORMATION: Description of Unknown:
      calpain cleavage domain sequence

<400> SEQUENCE: 20

Glu Pro Leu Phe Ala Glu Arg Lys
1               5

<210> SEQ ID NO 21
<211> LENGTH: 4
<212> TYPE: PRT
<213> ORGANISM: Unknown
<220> FEATURE:
<223> OTHER INFORMATION: Description of Unknown:
      calpain cleavage domain sequence

<400> SEQUENCE: 21

Leu Leu Val Tyr
1

<210> SEQ ID NO 22
<211> LENGTH: 5
<212> TYPE: PRT
<213> ORGANISM: Unknown
<220> FEATURE:
<223> OTHER INFORMATION: Description of Unknown:
      Enterokinase protease cleavage site sequence

<400> SEQUENCE: 22

Asp Asp Asp Asp Lys
1               5

<210> SEQ ID NO 23
<211> LENGTH: 7
<212> TYPE: PRT
<213> ORGANISM: Unknown
<220> FEATURE:
<223> OTHER INFORMATION: Description of Unknown:
      human Rhinovirus protease cleavage site sequence

<400> SEQUENCE: 23

Leu Glu Val Leu Phe Gln Pro
1               5

<210> SEQ ID NO 24
<211> LENGTH: 7
<212> TYPE: PRT
<213> ORGANISM: Tobacco Etch Virus

<400> SEQUENCE: 24

-continued

Leu Glu Val Leu Phe Gly Pro
1               5

<210> SEQ ID NO 25
<211> LENGTH: 7
<212> TYPE: PRT
<213> ORGANISM: Tobacco Etch Virus

<400> SEQUENCE: 25

Glu Asn Leu Tyr Phe Gln Ser
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 26

Glu Xaa Xaa Tyr Xaa Gln Gly
1               5

<210> SEQ ID NO 27
<211> LENGTH: 7
<212> TYPE: PRT
<213> ORGANISM: Tobacco vein mottling virus

<400> SEQUENCE: 27

Glu Thr Val Arg Phe Gln Ser
1               5

<210> SEQ ID NO 28
<211> LENGTH: 4
<212> TYPE: PRT
<213> ORGANISM: Unknown
<220> FEATURE:
<223> OTHER INFORMATION: Description of Unknown:
      Factor Xa protease cleavage site sequence

<400> SEQUENCE: 28

Ile Glu Gly Arg
1

<210> SEQ ID NO 29
<211> LENGTH: 4
<212> TYPE: PRT
<213> ORGANISM: Unknown
<220> FEATURE:
<223> OTHER INFORMATION: Description of Unknown:
      Factor Xa protease cleavage site sequence

<400> SEQUENCE: 29

Ile Asp Gly Arg
1

<210> SEQ ID NO 30
<211> LENGTH: 5
<212> TYPE: PRT

```
<213> ORGANISM: Unknown
<220> FEATURE:
<223> OTHER INFORMATION: Description of Unknown:
      Thrombin cleavage site sequence

<400> SEQUENCE: 30

Leu Val Pro Arg Ser
1               5

<210> SEQ ID NO 31
<211> LENGTH: 5
<212> TYPE: PRT
<213> ORGANISM: Unknown
<220> FEATURE:
<223> OTHER INFORMATION: Description of Unknown:
      Thrombin cleavage site sequence

<400> SEQUENCE: 31

Leu Val Pro Gly Ser
1               5

<210> SEQ ID NO 32
<211> LENGTH: 97
<212> TYPE: PRT
<213> ORGANISM: Unknown
<220> FEATURE:
<223> OTHER INFORMATION: Description of Unknown:
      SUMO1 sequence

<400> SEQUENCE: 32

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Gly
                85                  90                  95

Gly

<210> SEQ ID NO 33
<211> LENGTH: 95
<212> TYPE: PRT
<213> ORGANISM: Unknown
<220> FEATURE:
<223> OTHER INFORMATION: Description of Unknown:
      SUMO2 sequence

<400> SEQUENCE: 33

Met Ala Asp Glu Lys Pro Lys Glu Gly Val Lys Thr Glu Asn Asn Asp
1               5                   10                  15

His Ile Asn Leu Lys Val Ala Gly Gln Asp Gly Ser Val Val Gln Phe
            20                  25                  30

Lys Ile Lys Arg His Thr Pro Leu Ser Lys Leu Met Lys Ala Tyr Cys
        35                  40                  45

Glu Arg Gln Gly Leu Ser Met Arg Gln Ile Arg Phe Arg Phe Asp Gly
    50                  55                  60

Gln Pro Ile Asn Glu Thr Asp Thr Pro Ala Gln Leu Glu Met Glu Asp
```

```
65                  70                  75                  80

Glu Asp Thr Ile Asp Val Phe Gln Gln Gln Thr Gly Gly Val Tyr
                85                  90                  95

<210> SEQ ID NO 34
<211> LENGTH: 103
<212> TYPE: PRT
<213> ORGANISM: Unknown
<220> FEATURE:
<223> OTHER INFORMATION: Description of Unknown:
      SUMO3 sequence

<400> SEQUENCE: 34

Met Ser Glu Glu Lys Pro Lys Glu Gly Val Lys Thr Glu Asn Asp His
1               5                   10                  15

Ile Asn Leu Lys Val Ala Gly Gln Asp Gly Ser Val Val Gln Phe Lys
                20                  25                  30

Ile Lys Arg His Thr Pro Leu Ser Lys Leu Met Lys Ala Tyr Cys Glu
            35                  40                  45

Arg Gln Gly Leu Ser Met Arg Gln Ile Arg Phe Arg Phe Asp Gly Gln
        50                  55                  60

Pro Ile Asn Glu Thr Asp Thr Pro Ala Gln Leu Glu Met Glu Asp Glu
65                  70                  75                  80

Asp Thr Ile Asp Val Phe Gln Gln Gln Thr Gly Gly Val Pro Glu Ser
                85                  90                  95

Ser Leu Ala Gly His Ser Phe
            100

<210> SEQ ID NO 35
<211> LENGTH: 95
<212> TYPE: PRT
<213> ORGANISM: Unknown
<220> FEATURE:
<223> OTHER INFORMATION: Description of Unknown:
      SUMO4 sequence

<400> SEQUENCE: 35

Met Ala Asn Glu Lys Pro Thr Glu Glu Val Lys Thr Glu Asn Asn Asn
1               5                   10                  15

His Ile Asn Leu Lys Val Ala Gly Gln Asp Gly Ser Val Val Gln Phe
                20                  25                  30

Lys Ile Lys Arg Gln Thr Pro Leu Ser Lys Leu Met Lys Ala Tyr Cys
            35                  40                  45

Glu Pro Arg Gly Leu Ser Met Lys Gln Ile Arg Phe Arg Phe Gly Gly
        50                  55                  60

Gln Pro Ile Ser Gly Thr Asp Lys Pro Ala Gln Leu Glu Met Glu Asp
65                  70                  75                  80

Glu Asp Thr Ile Asp Val Phe Gln Gln Pro Thr Gly Gly Val Tyr
                85                  90                  95

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Ala Leu Lys Leu Ala Gly Leu Asp Leu
1               5                   10
```

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Gln Lys Lys Leu Glu Glu Leu Glu Leu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Met Gln Glu Leu Ser Asn Ile Leu Asn Leu
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Pro Pro Leu Glu Arg Leu Thr Leu
1               5

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Cys Gln Ala Phe Ser Asp Val Ile Leu
1               5                   10

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Thr Phe Asp Met His Ser Leu Glu Ser Ser Leu Ile Asp Ile Met
1               5                   10                  15

Arg

<210> SEQ ID NO 42
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 42

Thr Asn Leu Glu Ala Leu Gln Lys Lys Leu Glu Glu Leu Glu Leu Asp
1               5                   10                  15

Glu

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Ser Phe Glu Met Thr Glu Phe Asn Gln Ala Leu Glu Glu Ile Lys
1               5                   10                  15

Gly

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Gly Gly Gly Ser Leu Val Pro Arg Gly Ser Gly Gly Gly Gly Ser
1               5                   10                  15

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Ser Gly Ser Gly Ser
1               5

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Ser Gly Ser Gly Ser Gly Ser Gly Ser Gly Ser Gly Ser Gly Ser
1               5                   10                  15

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47
```

```
Gly Gly Ser Gly Gly His Met Gly Ser Gly Gly
1               5                   10
```

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

```
Gly Gly Ser Gly Gly Ser Gly Gly Ser Gly Gly
1               5                   10
```

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

```
Gly Gly Ser Gly Gly
1               5
```

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

```
Gly Gly Gly Ser Glu Gly Gly Ser Glu Gly Gly Gly Ser Glu Gly
1               5                   10                  15

Gly Gly
```

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

```
Ala Ala Gly Ala Ala Thr Ala Ala
1               5
```

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

```
Gly Gly Gly Gly Gly
1               5
```

<210> SEQ ID NO 53
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 53

Gly Gly Ser Ser Gly
1               5

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ser Gly Gly Gly Thr Gly Gly Gly Ser Gly
1               5                   10

<210> SEQ ID NO 55
<211> LENGTH: 321
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Tyr Gly Arg Lys Lys Arg Gln Arg Arg Gly Gly Met Ser
1               5                   10                  15

Asp Gln Glu Ala Lys Pro Ser Thr Glu Asp Leu Gly Asp Lys Lys Glu
                20                  25                  30

Gly Glu Tyr Ile Lys Leu Lys Val Ile Gly Gln Asp Ser Ser Glu Ile
            35                  40                  45

His Phe Lys Val Lys Met Thr Thr His Leu Lys Lys Leu Lys Glu Ser
        50                  55                  60

Tyr Cys Gln Arg Gln Gly Val Pro Met Asn Ser Leu Arg Phe Leu Phe
65                  70                  75                  80

Glu Gly Gln Arg Ile Ala Asp Asn His Thr Pro Lys Glu Leu Gly Met
                85                  90                  95

Glu Glu Glu Asp Val Ile Glu Val Tyr Gln Glu Gln Thr Gly Gly Met
            100                 105                 110

Trp Thr Leu Gly Arg Arg Ala Val Ala Gly Leu Leu Ala Ser Pro Ser
        115                 120                 125

Pro Ala Gln Ala Gln Thr Leu Thr Arg Val Pro Arg Pro Ala Glu Leu
    130                 135                 140

Ala Pro Leu Cys Gly Arg Arg Gly Leu Arg Thr Asp Ile Asp Ala Thr
145                 150                 155                 160

Cys Thr Pro Arg Arg Ala Ser Ser Asn Gln Arg Gly Leu Asn Gln Ile
                165                 170                 175

Trp Asn Val Lys Lys Gln Ser Val Tyr Leu Met Asn Leu Arg Lys Ser
            180                 185                 190

Gly Thr Leu Gly His Pro Gly Ser Leu Asp Glu Thr Thr Tyr Glu Arg
        195                 200                 205

Leu Ala Glu Glu Thr Leu Asp Ser Leu Ala Glu Phe Phe Glu Asp Leu
    210                 215                 220

Ala Asp Lys Pro Tyr Thr Phe Glu Asp Tyr Asp Val Ser Phe Gly Ser
225                 230                 235                 240
```

```
Gly Val Leu Thr Val Lys Leu Gly Gly Asp Leu Gly Thr Tyr Val Ile
                245                 250                 255

Asn Lys Gln Thr Pro Asn Lys Gln Ile Trp Leu Ser Ser Pro Ser Ser
            260                 265                 270

Gly Pro Lys Arg Tyr Asp Trp Thr Gly Lys Asn Trp Val Tyr Ser His
        275                 280                 285

Asp Gly Val Ser Leu His Glu Leu Leu Ala Ala Glu Leu Thr Lys Ala
    290                 295                 300

Leu Lys Thr Lys Leu Asp Leu Ser Ser Leu Ala Tyr Ser Gly Lys Asp
305                 310                 315                 320

Ala
```

<210> SEQ ID NO 56
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Met Tyr Gly Arg Lys Lys Arg Arg Gln Arg Arg Gly Gly Met Gln
1               5                   10                  15

Ile Phe Val Lys Thr Leu Thr Gly Lys Thr Ile Thr Leu Glu Val Glu
                20                  25                  30

Pro Ser Asp Thr Ile Glu Asn Val Lys Ala Lys Ile Gln Asp Lys Glu
            35                  40                  45

Gly Ile Pro Pro Asp Gln Gln Arg Leu Ile Phe Ala Gly Lys Gln Leu
        50                  55                  60

Glu Asp Gly Arg Thr Leu Ser Asp Tyr Asn Ile Gln Lys Glu Ser Thr
65                  70                  75                  80

Leu His Leu Val Leu Arg Leu Arg Gly Gly Met Trp Thr Leu Gly Arg
                85                  90                  95

Arg Ala Val Ala Gly Leu Leu Ala Ser Pro Ser Pro Ala Gln Ala Gln
                100                 105                 110

Thr Leu Thr Arg Val Pro Arg Pro Ala Glu Leu Ala Pro Leu Cys Gly
            115                 120                 125

Arg Arg Gly Leu Arg Thr Asp Ile Asp Ala Thr Cys Thr Pro Arg Arg
        130                 135                 140

Ala Ser Ser Asn Gln Arg Gly Leu Asn Gln Ile Trp Asn Val Lys Lys
145                 150                 155                 160

Gln Ser Val Tyr Leu Met Asn Leu Arg Lys Ser Gly Thr Leu Gly His
                165                 170                 175

Pro Gly Ser Leu Asp Glu Thr Thr Tyr Glu Arg Leu Ala Glu Glu Thr
            180                 185                 190

Leu Asp Ser Leu Ala Glu Phe Phe Glu Asp Leu Ala Asp Lys Pro Tyr
        195                 200                 205

Thr Phe Glu Asp Tyr Asp Val Ser Phe Gly Ser Gly Val Leu Thr Val
    210                 215                 220

Lys Leu Gly Gly Asp Leu Gly Tyr Val Ile Asn Lys Gln Thr Pro
225                 230                 235                 240

Asn Lys Gln Ile Trp Leu Ser Ser Pro Ser Ser Gly Pro Lys Arg Tyr
                245                 250                 255

Asp Trp Thr Gly Lys Asn Trp Val Tyr Ser His Asp Gly Val Ser Leu
            260                 265                 270
```

His Glu Leu Leu Ala Ala Glu Leu Thr Lys Ala Leu Lys Thr Lys Leu
            275                 280                 285

Asp Leu Ser Ser Leu Ala Tyr Ser Gly Lys Asp Ala
        290                 295                 300

<210> SEQ ID NO 57
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Tyr Gly Arg Lys Lys Arg Gln Arg Arg Gly Gly Asp Glu
1               5                   10                  15

Val Asp Met Trp Thr Leu Gly Arg Arg Ala Val Ala Gly Leu Leu Ala
            20                  25                  30

Ser Pro Ser Pro Ala Gln Ala Gln Thr Leu Thr Arg Val Pro Arg Pro
        35                  40                  45

Ala Glu Leu Ala Pro Leu Cys Gly Arg Gly Leu Arg Thr Asp Ile
    50                  55                  60

Asp Ala Thr Cys Thr Pro Arg Arg Ala Ser Ser Asn Gln Arg Gly Leu
65                  70                  75                  80

Asn Gln Ile Trp Asn Val Lys Lys Gln Ser Val Tyr Leu Met Asn Leu
                85                  90                  95

Arg Lys Ser Gly Thr Leu Gly His Pro Gly Ser Leu Asp Glu Thr Thr
            100                 105                 110

Tyr Glu Arg Leu Ala Glu Glu Thr Leu Asp Ser Leu Ala Glu Phe Phe
        115                 120                 125

Glu Asp Leu Ala Asp Lys Pro Tyr Thr Phe Glu Asp Tyr Asp Val Ser
    130                 135                 140

Phe Gly Ser Gly Val Leu Thr Val Lys Leu Gly Gly Asp Leu Gly Thr
145                 150                 155                 160

Tyr Val Ile Asn Lys Gln Thr Pro Asn Lys Gln Ile Trp Leu Ser Ser
                165                 170                 175

Pro Ser Ser Gly Pro Lys Arg Tyr Asp Trp Thr Gly Lys Asn Trp Val
            180                 185                 190

Tyr Ser His Asp Gly Val Ser Leu His Glu Leu Leu Ala Ala Glu Leu
        195                 200                 205

Thr Lys Ala Leu Lys Thr Lys Leu Asp Leu Ser Ser Leu Ala Tyr Ser
    210                 215                 220

Gly Lys Asp Ala
225

<210> SEQ ID NO 58
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Tyr Gly Arg Lys Lys Arg Gln Arg Arg Gly Gly Glu Pro
1               5                   10                  15

Leu Phe Ala Glu Arg Lys Met Trp Thr Leu Gly Arg Arg Ala Val Ala
            20                  25                  30

```
Gly Leu Leu Ala Ser Pro Ser Pro Ala Gln Ala Gln Thr Leu Thr Arg
            35                  40                  45

Val Pro Arg Pro Ala Glu Leu Ala Pro Leu Cys Gly Arg Arg Gly Leu
 50                  55                  60

Arg Thr Asp Ile Asp Ala Thr Cys Thr Pro Arg Arg Ala Ser Ser Asn
 65                  70                  75                  80

Gln Arg Gly Leu Asn Gln Ile Trp Asn Val Lys Lys Gln Ser Val Tyr
                85                  90                  95

Leu Met Asn Leu Arg Lys Ser Gly Thr Leu Gly His Pro Gly Ser Leu
            100                 105                 110

Asp Glu Thr Thr Tyr Glu Arg Leu Ala Glu Glu Thr Leu Asp Ser Leu
            115                 120                 125

Ala Glu Phe Phe Glu Asp Leu Ala Asp Lys Pro Tyr Thr Phe Glu Asp
130                 135                 140

Tyr Asp Val Ser Phe Gly Ser Gly Val Leu Thr Val Lys Leu Gly Gly
145                 150                 155                 160

Asp Leu Gly Thr Tyr Val Ile Asn Lys Gln Thr Pro Asn Lys Gln Ile
                165                 170                 175

Trp Leu Ser Ser Pro Ser Ser Gly Pro Lys Arg Tyr Asp Trp Thr Gly
            180                 185                 190

Lys Asn Trp Val Tyr Ser His Asp Gly Val Ser Leu His Glu Leu Leu
            195                 200                 205

Ala Ala Glu Leu Thr Lys Ala Leu Lys Thr Lys Leu Asp Leu Ser Ser
210                 215                 220

Leu Ala Tyr Ser Gly Lys Asp Ala
225                 230

<210> SEQ ID NO 59
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Tyr Gly Arg Lys Lys Arg Gln Arg Arg Gly Gly Leu Leu
1                5                  10                  15

Val Tyr Met Trp Thr Leu Gly Arg Arg Ala Val Ala Gly Leu Leu Ala
                20                  25                  30

Ser Pro Ser Pro Ala Gln Ala Gln Thr Leu Thr Arg Val Pro Arg Pro
            35                  40                  45

Ala Glu Leu Ala Pro Leu Cys Gly Arg Arg Gly Leu Arg Thr Asp Ile
 50                  55                  60

Asp Ala Thr Cys Thr Pro Arg Arg Ala Ser Ser Asn Gln Arg Gly Leu
 65                  70                  75                  80

Asn Gln Ile Trp Asn Val Lys Lys Gln Ser Val Tyr Leu Met Asn Leu
                85                  90                  95

Arg Lys Ser Gly Thr Leu Gly His Pro Gly Ser Leu Asp Glu Thr Thr
            100                 105                 110

Tyr Glu Arg Leu Ala Glu Glu Thr Leu Asp Ser Leu Ala Glu Phe Phe
            115                 120                 125

Glu Asp Leu Ala Asp Lys Pro Tyr Thr Phe Glu Asp Tyr Asp Val Ser
130                 135                 140

Phe Gly Ser Gly Val Leu Thr Val Lys Leu Gly Gly Asp Leu Gly Thr
```

```
                145                 150                 155                 160
Tyr Val Ile Asn Lys Gln Thr Pro Asn Lys Gln Ile Trp Leu Ser Ser
                165                 170                 175

Pro Ser Ser Gly Pro Lys Arg Tyr Asp Trp Thr Gly Lys Asn Trp Val
                180                 185                 190

Tyr Ser His Asp Gly Val Ser Leu His Glu Leu Leu Ala Ala Glu Leu
                195                 200                 205

Thr Lys Ala Leu Lys Thr Lys Leu Asp Leu Ser Ser Leu Ala Tyr Ser
                210                 215                 220

Gly Lys Asp Ala
225

<210> SEQ ID NO 60
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Tyr Gly Arg Lys Lys Arg Gln Arg Arg Gly Gly Met Trp
1               5                   10                  15

Thr Leu Gly Arg Arg Ala Val Ala Gly Leu Leu Ala Ser Pro Ser Pro
                20                  25                  30

Ala Gln Ala Gln Thr Leu Thr Arg Val Pro Arg Pro Ala Glu Leu Ala
            35                  40                  45

Pro Leu Cys Gly Arg Arg Gly Leu Arg Thr Asp Ile Asp Ala Thr Cys
        50                  55                  60

Thr Pro Arg Arg Ala Ser Ser Asn Gln Arg Gly Leu Asn Gln Ile Trp
65                  70                  75                  80

Asn Val Lys Lys Gln Ser Val Tyr Leu Met Asn Leu Arg Lys Ser Gly
                85                  90                  95

Thr Leu Gly His Pro Gly Ser Leu Asp Glu Thr Thr Tyr Glu Arg Leu
                100                 105                 110

Ala Glu Glu Thr Leu Asp Ser Leu Ala Glu Phe Phe Glu Asp Leu Ala
            115                 120                 125

Asp Lys Pro Tyr Thr Phe Glu Asp Tyr Asp Val Ser Phe Gly Ser Gly
        130                 135                 140

Val Leu Thr Val Lys Leu Gly Gly Asp Leu Gly Thr Tyr Val Ile Asn
145                 150                 155                 160

Lys Gln Thr Pro Asn Lys Gln Ile Trp Leu Ser Ser Pro Ser Ser Gly
                165                 170                 175

Pro Lys Arg Tyr Asp Trp Thr Gly Lys Asn Trp Val Tyr Ser His Asp
            180                 185                 190

Gly Val Ser Leu His Glu Leu Leu Ala Ala Glu Leu Thr Lys Ala Leu
        195                 200                 205

Lys Thr Lys Leu Asp Leu Ser Ser Leu Ala Tyr Ser Gly Lys Asp Ala
    210                 215                 220

Leu Ala Leu Lys Leu Ala Gly Leu Asp Leu
225                 230

<210> SEQ ID NO 61
<211> LENGTH: 234
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 61

Met Tyr Gly Arg Lys Lys Arg Arg Gln Arg Arg Gly Gly Met Trp
1               5                   10                  15

Thr Leu Gly Arg Arg Ala Val Ala Gly Leu Leu Ala Ser Pro Ser Pro
            20                  25                  30

Ala Gln Ala Gln Thr Leu Thr Arg Val Pro Arg Pro Ala Glu Leu Ala
        35                  40                  45

Pro Leu Cys Gly Arg Arg Gly Leu Arg Thr Asp Ile Asp Ala Thr Cys
    50                  55                  60

Thr Pro Arg Arg Ala Ser Ser Asn Gln Arg Gly Leu Asn Gln Ile Trp
65                  70                  75                  80

Asn Val Lys Lys Gln Ser Val Tyr Leu Met Asn Leu Arg Lys Ser Gly
                85                  90                  95

Thr Leu Gly His Pro Gly Ser Leu Asp Glu Thr Thr Tyr Glu Arg Leu
            100                 105                 110

Ala Glu Glu Thr Leu Asp Ser Leu Ala Glu Phe Phe Glu Asp Leu Ala
        115                 120                 125

Asp Lys Pro Tyr Thr Phe Glu Asp Tyr Asp Val Ser Phe Gly Ser Gly
    130                 135                 140

Val Leu Thr Val Lys Leu Gly Gly Asp Leu Gly Thr Tyr Val Ile Asn
145                 150                 155                 160

Lys Gln Thr Pro Asn Lys Gln Ile Trp Leu Ser Ser Pro Ser Ser Gly
                165                 170                 175

Pro Lys Arg Tyr Asp Trp Thr Gly Lys Asn Trp Val Tyr Ser His Asp
            180                 185                 190

Gly Val Ser Leu His Glu Leu Leu Ala Ala Glu Leu Thr Lys Ala Leu
        195                 200                 205

Lys Thr Lys Leu Asp Leu Ser Ser Leu Ala Tyr Ser Gly Lys Asp Ala
    210                 215                 220

Leu Gln Lys Lys Leu Glu Glu Leu Glu Leu
225                 230

<210> SEQ ID NO 62
<211> LENGTH: 966
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
atgtacggcc gcaagaagcg gagacagagg cgccggggag gaatgtccga ccaggaggcc      60 aagcccctcta ccgaggacct gggcgataag aaggagggcg agtacatcaa gctgaaagtg    120
atcggccagg atagctccga gatccacttc aaggtgaaga tgaccacaca cctgaagaag     180
ctgaaggagt cttattgcca gcggcagggc gtgccaatga acagcctgag attcctgttt     240
gagggccaga ggatcgccga caatcacacc cccaaggagc tgggcatgga ggaggaggat     300
gtgatcgagg tgtatcagga gcagaccggc ggcatgtgga cactgggcag aagggcagtg     360
gcaggcctgc tggcatcccc atctcctgca caggcacaga ccctgacacg cgtgccacgg     420
cccgcagagc tggcaccact gtgcggccgg agaggcctga ggacagacat cgatgccacc     480
tgtacaccta gaagggcctc tagcaaccag cggggcctga accagatctg gaatgtgaag     540

| | | | |
|---|---|---|---|
| aagcagtccg | tgtacctgat | gaatctgaga | aagagcggca ccctgggaca ccctggctcc | 600 |
| ctggacgaga | caacatatga | gaggctggcc | gaggagacac tggattctct ggccgagttc | 660 |
| tttgaggacc | tggccgataa | gccatacacc | ttcgaggact atgatgtgag ctttggctcc | 720 |
| ggcgtgctga | cagtgaagct | gggaggcgac | ctgggcacct acgtgatcaa caagcagaca | 780 |
| cctaataagc | agatctggct | gtcctctcct | agctccggcc caaagcggta cgactggacc | 840 |
| ggcaagaact | gggtgtattc | tcacgatggc | gtgagcctgc acgagctgct ggcagcagag | 900 |
| ctgaccaagg | ccctgaagac | aaagctggac | ctgtctagcc tggcctatag cggcaaggat | 960 |
| gcctga | | | | 966 |

<210> SEQ ID NO 63
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

| | | | |
|---|---|---|---|
| atgtacggcc | ggaagaagcg | gagacagagg | cgccggggag gaatgcagat cttcgtgaag | 60 |
| accctgacag | gcaagaccat | cacactggag | gtggagccct ctgacaccat cgagaacgtg | 120 |
| aaggccaaga | tccaggacaa | ggagggcatc | cccctgatc agcagcgcct gatctttgca | 180 |
| ggcaagcagc | tggaggacgg | acggaccctg | tctgattata atatccagaa ggagagcaca | 240 |
| ctgcacctgg | tgctgaggct | gaggggagga | atgtggaccc tgggcagaag ggcagtggca | 300 |
| ggcctgctgg | cctctccaag | cccagcacag | gcacagaccc tgacaagagt gcctaggcca | 360 |
| gcagagctgg | caccactgtg | cggccggaga | ggcctgagaa cagacatcga tgccacctgt | 420 |
| acacccagaa | gggccagctc | caaccagagg | ggcctgaacc agatctggaa tgtgaagaag | 480 |
| cagagcgtgt | acctgatgaa | tctgaggaag | tccggcaccc tgggcacccc tggctctctg | 540 |
| gacgagacaa | catatgagcg | gctggccgag | agacactgg attccctggc cgagttcttt | 600 |
| gaggacctgg | ccgataagcc | atacaccttc | gaggactatg acgtgagctt cggctctggc | 660 |
| gtgctgacag | tgaagctggg | cggcgatctg | ggcacctacg tgatcaacaa gcagacacct | 720 |
| aataagcaga | tctggctgtc | tagcccctcc | tctggcccta agatacga ctggaccggc | 780 |
| aagaactggg | tgtatagcca | cgatggcgtg | tccctgcacg agctgctggc agcagagctg | 840 |
| accaaggccc | tgaagacaaa | gctggacctg | agctccctgg cctattccgg caaggatgcc | 900 |
| tga | | | | 903 |

<210> SEQ ID NO 64
<211> LENGTH: 687
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

| | | | |
|---|---|---|---|
| atgtacggca | gaaagaagag | gcggcagaga | cgcaggggag gcgacgaggt ggatatgtgg | 60 |
| accctgggcc | ggagagcagt | ggcaggactg | ctggcctctc ccagccctgc ccaggcccag | 120 |
| accctgacac | gcgtgccaag | gccagcagag | ctggcaccac tgtgcggccg caggggcctg | 180 |
| cggacagaca | tcgatgccac | ctgtacacct | cggagagcca gctccaacca gagaggcctg | 240 |
| aaccagatct | ggaatgtgaa | gaagcagtcc | gtgtacctga tgaatctgag gaagtctggc | 300 |

```
accctgggac acccaggcag cctggacgag accacatacg agaggctggc cgaggagaca    360
ctggattctc tggccgagtt ctttgaggac ctggccgata agcccacac cttcgaggac    420 tacgacgtga gcttcggctc tggcgtgctg acagtgaagc tgggcggcga cctgggcacc    480
tacgtgatca acaagcagac acctaataag cagatctggc tgtctagccc ttcctctggc    540
ccaaagaggt acgactggac cggcaagaac tgggtgtaca gccacgatgg cgtgtccctg    600
cacgagctgc tggcagcaga gctgaccaag gccctgaaga caaagctgga cctgagctcc    660
ctggcctaca gcggcaagga tgcctga                                       687
```

<210> SEQ ID NO 65
<211> LENGTH: 699
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
atgtatggaa ggaagaagag acggcagaga cggagaggag gcgagcccct gtttgctgag    60
cggaagatgt ggaccctggg aaggcgggca gtggcaggcc tgctggcaag cccatcccct   120
gcacaggcac agaccctgac aagggtgcca cggcccgcag agctggcacc actgtgcggc   180
aggcggggcc tgagaaccga catcgatgcc acctgtacac ctagaagggc cagctccaac   240
cagaggggcc tgaaccagat ctggaatgtg aagaagcaga gcgtgtacct gatgaatctg   300
aggaagagcg gcaccctggg cacccaggc tccctggacg agacaacata cgagaggctg   360
gccgaggaga cactggattc cctggccgag ttctttgagg acctggccga taagccctac   420
accttcgagg actacgacgt gagcttcggc agcggcgtgc tgacagtgaa gctgggaggc   480
gacctgggca cctacgtgat caacaagcag acacctaata gcagatctg ctgtctagc   540 ccttcctctg gccaaagcg gtacgactgg accggcaaga ctgggtgta ctcccacgat   600 ggcgtgtctc tgcacgagct gctggcagca gagctgacaa agcactgaa aacaaaactg   660 gacctgtcat cactggcata ctctggaaag gacgcataa                          699
```

<210> SEQ ID NO 66
<211> LENGTH: 687
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

```
atgtacggca aaagaagag gcggcagaga cgcaggggag gactgctggt gtacatgtgg    60
accctgggcc ggagagcagt ggcaggactg ctggcctctc ccagccctgc ccaggcccag   120
accctgacac gcgtgccaag gccagcagag ctggcaccac tgtgcggccg caggggcctg   180
cggacagaca tcgatgccac ctgtacacct cggagagcca gctccaacca gagaggcctg   240
aaccagatct ggaatgtgaa gaagcagtcc gtgtacctga tgaatctgag gaagtctggc   300
accctgggac acccaggcag cctggacgag accacatacg agaggctggc cgaggagaca   360
ctggattctc tggccgagtt ctttgaggac ctggccgata agcccacac cttcgaggac    420 tacgacgtga gcttcggctc tggcgtgctg acagtgaagc tgggcggcga cctgggcacc    480
tacgtgatca acaagcagac acctaataag cagatctggc tgtctagccc ttcctctggc    540
```

```
ccaaagaggt acgactggac cggcaagaac tgggtgtaca gccacgatgg cgtgtccctg      600
cacgagctgc tggcagcaga gctgaccaag gccctgaaga caaagctgga cctgagctcc      660
ctggcctaca gcggcaagga tgcctga                                          687
```

```
<210> SEQ ID NO 67
<211> LENGTH: 699
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
atgtatggaa ggaagaagag acggcagaga cggagaggag gcgagcccct gtttgctgag       60
cggaagatgt ggaccctggg aaggcgggca gtggcaggcc tgctggcaag cccatcccct      120
gcacaggcac agaccctgac aagggtgcca cggcccgcag agctggcacc actgtgcggc      180
aggcggggcc tgagaaccga catcgatgcc acctgtacac ctagaaggc cagctccaac      240 cagaggggcc tgaaccagat ctggaatgtg aagaagcaga gcgtgtacct gatgaatctg      300
aggaagagcg gcaccctggg cacccaggc tccctggacg agacaacata cgagaggctg       360
gccgaggaga cactggattc cctggccgag ttctttgagg acctggccga taagccctac       420
accttcgagg actacgacgt gagcttcggc agcggcgtgc tgacagtgaa gctgggaggc      480
gacctgggca cctacgtgat caacaagcag acacctaata gcagatctg ctgtctagc        540 ccttcctctg gcccaaagcg gtacgactgg accggcaaga ctgggtgta ctcccacgat       600 ggcgtgtctc tgcacgagct gctggcagca gagctgacaa agcactgaa aacaaaactg      660 gacctgtcat cactggcata ctctggaaag gacgcataa                             699
```

```
<210> SEQ ID NO 68
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
atgtacggca gaaagaagag gcggcagaga cgcaggggag gaatgtggac cctgggccgg       60
agagcagtgg caggactgct ggcctctccc agccctgccc aggcccagac cctgacacgc      120
gtgccaaggc cagcagagct ggcaccactg tgccgccgca ggggcctgcg acagacatc       180 gatgccacct gtacacctcg agagccagc tccaaccaga gaggcctgaa ccagatctgg       240
aatgtgaaga agcagtccgt gtacctgatg aatctgagga gtctggcac cctgggacac      300 ccaggcagcc tggacgagac cacatacgag aggctggccg aggagacact ggattctctg      360
gccgagttct ttgaggacct ggccgataag ccctacacct cgaggacta cgacgtgagc      420 ttcggctctg gcgtgctgac agtgaagctg ggcggcgacc tgggcaccta cgtgatcaac      480
aagcagacac ctaataagca gatctggctg tctagcccct tcctctggcc aaagaggtac      540
gactggaccg gcaagaactg ggtgtacagc cacgatggcg tgtccctgca cgagctgctg      600
gcagcagagc tgaccaaggc cctgaagaca aagctggacc tgagctccct ggcctacagc      660
ggcaaggatg ccctgcagaa gaagctggag gagctggagc tgtga                      705
```

```
<210> SEQ ID NO 69
<211> LENGTH: 555
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Tyr Gly Arg Lys Lys Arg Arg Gln Arg Arg Gly Gly Met Gln
1               5                   10                  15

Ile Phe Val Lys Thr Leu Thr Gly Lys Thr Ile Thr Leu Glu Val Glu
                20                  25                  30

Pro Ser Asp Thr Ile Glu Asn Val Lys Ala Lys Ile Gln Asp Lys Glu
                35                  40                  45

Gly Ile Pro Pro Asp Gln Gln Arg Leu Ile Phe Ala Gly Lys Gln Leu
50                  55                  60

Glu Asp Gly Arg Thr Leu Ser Asp Tyr Asn Ile Gln Lys Glu Ser Thr
65                  70                  75                  80

Leu His Leu Val Leu Arg Leu Arg Gly Gly Met Ile Val Phe Val Arg
                85                  90                  95

Phe Asn Ser Ser His Gly Phe Pro Val Glu Val Asp Ser Asp Thr Ser
                100                 105                 110

Ile Phe Gln Leu Lys Glu Val Val Ala Lys Arg Gln Gly Val Pro Ala
                115                 120                 125

Asp Gln Leu Arg Val Ile Phe Ala Gly Lys Glu Leu Arg Asn Asp Trp
130                 135                 140

Thr Val Gln Asn Cys Asp Leu Asp Gln Gln Ser Ile Val His Ile Val
145                 150                 155                 160

Gln Arg Pro Trp Arg Lys Gly Gln Glu Met Asn Ala Thr Gly Gly Asp
                165                 170                 175

Asp Pro Arg Asn Ala Ala Gly Gly Cys Glu Arg Glu Pro Gln Ser Leu
                180                 185                 190

Thr Arg Val Asp Leu Ser Ser Ser Val Leu Pro Gly Asp Ser Val Gly
                195                 200                 205

Leu Ala Val Ile Leu His Thr Asp Ser Arg Lys Asp Ser Pro Pro Ala
210                 215                 220

Gly Ser Pro Ala Gly Arg Ser Ile Tyr Asn Ser Phe Tyr Val Tyr Cys
225                 230                 235                 240

Lys Gly Pro Cys Gln Arg Val Gln Pro Gly Lys Leu Arg Val Gln Cys
                245                 250                 255

Ser Thr Cys Arg Gln Ala Thr Leu Thr Leu Thr Gln Gly Pro Ser Cys
                260                 265                 270

Trp Asp Asp Val Leu Ile Pro Asn Arg Met Ser Gly Glu Cys Gln Ser
                275                 280                 285

Pro His Cys Pro Gly Thr Ser Ala Glu Phe Phe Phe Lys Cys Gly Ala
                290                 295                 300

His Pro Thr Ser Asp Lys Glu Thr Ser Val Ala Leu His Leu Ile Ala
305                 310                 315                 320

Thr Asn Ser Arg Asn Ile Thr Cys Ile Thr Cys Thr Asp Val Arg Ser
                325                 330                 335

Pro Val Leu Val Phe Gln Cys Asn Ser Arg His Val Ile Cys Leu Asp
                340                 345                 350

Cys Phe His Leu Tyr Cys Val Thr Arg Leu Asn Asp Arg Gln Phe Val
                355                 360                 365

His Asp Pro Gln Leu Gly Tyr Ser Leu Pro Cys Val Ala Gly Cys Pro
                370                 375                 380
```

```
Asn Ser Leu Ile Lys Glu Leu His His Phe Arg Ile Leu Gly Glu Glu
385                 390                 395                 400

Gln Tyr Asn Arg Tyr Gln Tyr Gly Ala Glu Glu Cys Val Leu Gln
            405                 410                 415

Met Gly Gly Val Leu Cys Pro Arg Pro Gly Cys Gly Ala Gly Leu Leu
        420                 425                 430

Pro Glu Pro Asp Gln Arg Lys Val Thr Cys Glu Gly Gly Asn Gly Leu
        435                 440                 445

Gly Cys Gly Phe Ala Phe Cys Arg Glu Cys Lys Glu Ala Tyr His Glu
    450                 455                 460

Gly Glu Cys Ser Ala Val Phe Glu Ala Ser Gly Thr Thr Thr Gln Ala
465                 470                 475                 480

Tyr Arg Val Asp Glu Arg Ala Ala Glu Gln Ala Arg Trp Glu Ala Ala
                485                 490                 495

Ser Lys Glu Thr Ile Lys Lys Thr Thr Lys Pro Cys Pro Arg Cys His
                500                 505                 510

Val Pro Val Glu Lys Asn Gly Gly Cys Met His Met Lys Cys Pro Gln
            515                 520                 525

Pro Gln Cys Arg Leu Glu Trp Cys Trp Asn Cys Gly Cys Glu Trp Asn
530                 535                 540

Arg Val Cys Met Gly Asp His Trp Phe Asp Val
545                 550                 555

<210> SEQ ID NO 70
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Tyr Gly Arg Lys Lys Arg Arg Gln Arg Arg Gly Gly Glu Pro
1               5                   10                  15

Leu Phe Ala Glu Arg Lys Met Ile Val Phe Val Arg Phe Asn Ser Ser
            20                  25                  30

His Gly Phe Pro Val Glu Val Asp Ser Asp Thr Ser Ile Phe Gln Leu
        35                  40                  45

Lys Glu Val Val Ala Lys Arg Gln Gly Val Pro Ala Asp Gln Leu Arg
    50                  55                  60

Val Ile Phe Ala Gly Lys Glu Leu Arg Asn Asp Trp Thr Val Gln Asn
65                  70                  75                  80

Cys Asp Leu Asp Gln Gln Ser Ile Val His Ile Val Gln Arg Pro Trp
                85                  90                  95

Arg Lys Gly Gln Glu Met Asn Ala Thr Gly Gly Asp Asp Pro Arg Asn
            100                 105                 110

Ala Ala Gly Gly Cys Glu Arg Glu Pro Gln Ser Leu Thr Arg Val Asp
        115                 120                 125

Leu Ser Ser Ser Val Leu Pro Gly Asp Ser Val Gly Leu Ala Val Ile
    130                 135                 140

Leu His Thr Asp Ser Arg Lys Asp Ser Pro Ala Gly Ser Pro Ala
145                 150                 155                 160

Gly Arg Ser Ile Tyr Asn Ser Phe Tyr Val Tyr Cys Lys Gly Pro Cys
                165                 170                 175

Gln Arg Val Gln Pro Gly Lys Leu Arg Val Gln Cys Ser Thr Cys Arg
```

180                 185                 190
Gln Ala Thr Leu Thr Leu Thr Gln Gly Pro Ser Cys Trp Asp Val
                195                 200                 205
Leu Ile Pro Asn Arg Met Ser Gly Glu Cys Gln Ser Pro His Cys Pro
210                 215                 220
Gly Thr Ser Ala Glu Phe Phe Lys Cys Gly Ala His Pro Thr Ser
225                 230                 235                 240
Asp Lys Glu Thr Ser Val Ala Leu His Leu Ile Ala Thr Asn Ser Arg
                245                 250                 255
Asn Ile Thr Cys Ile Thr Cys Thr Asp Val Arg Ser Pro Val Leu Val
                260                 265                 270
Phe Gln Cys Asn Ser Arg His Val Ile Cys Leu Asp Cys Phe His Leu
                275                 280                 285
Tyr Cys Val Thr Arg Leu Asn Asp Arg Gln Phe Val His Asp Pro Gln
                290                 295                 300
Leu Gly Tyr Ser Leu Pro Cys Val Ala Gly Cys Pro Asn Ser Leu Ile
305                 310                 315                 320
Lys Glu Leu His His Phe Arg Ile Leu Gly Glu Gln Tyr Asn Arg
                325                 330                 335
Tyr Gln Gln Tyr Gly Ala Glu Glu Cys Val Leu Gln Met Gly Gly Val
                340                 345                 350
Leu Cys Pro Arg Pro Gly Cys Gly Ala Gly Leu Leu Pro Glu Pro Asp
                355                 360                 365
Gln Arg Lys Val Thr Cys Glu Gly Gly Asn Gly Leu Gly Cys Gly Phe
                370                 375                 380
Ala Phe Cys Arg Glu Cys Lys Glu Ala Tyr His Glu Gly Glu Cys Ser
385                 390                 395                 400
Ala Val Phe Glu Ala Ser Gly Thr Thr Thr Gln Ala Tyr Arg Val Asp
                405                 410                 415
Glu Arg Ala Ala Glu Gln Ala Arg Trp Glu Ala Ala Ser Lys Glu Thr
                420                 425                 430
Ile Lys Lys Thr Thr Lys Pro Cys Pro Arg Cys His Val Pro Val Glu
                435                 440                 445
Lys Asn Gly Gly Cys Met His Met Lys Cys Pro Gln Pro Gln Cys Arg
                450                 455                 460
Leu Glu Trp Cys Trp Asn Cys Gly Cys Glu Trp Asn Arg Val Cys Met
465                 470                 475                 480
Gly Asp His Trp Phe Asp Val
                485

<210> SEQ ID NO 71
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Tyr Gly Arg Lys Lys Arg Arg Gln Arg Arg Gly Gly Met Ile
1               5                   10                  15

Val Phe Val Arg Phe Asn Ser Ser His Gly Phe Pro Val Glu Val Asp
                20                  25                  30

Ser Asp Thr Ser Ile Phe Gln Leu Lys Glu Val Val Ala Lys Arg Gln
                35                  40                  45

```
Gly Val Pro Ala Asp Gln Leu Arg Val Ile Phe Ala Gly Lys Glu Leu
    50                  55                  60

Arg Asn Asp Trp Thr Val Gln Asn Cys Asp Leu Asp Gln Gln Ser Ile
 65                  70                  75                  80

Val His Ile Val Gln Arg Pro Trp Arg Lys Gly Gln Glu Met Asn Ala
                 85                  90                  95

Thr Gly Gly Asp Asp Pro Arg Asn Ala Ala Gly Gly Cys Glu Arg Glu
                100                 105                 110

Pro Gln Ser Leu Thr Arg Val Asp Leu Ser Ser Val Leu Pro Gly
            115                 120                 125

Asp Ser Val Gly Leu Ala Val Ile Leu His Thr Asp Ser Arg Lys Asp
    130                 135                 140

Ser Pro Pro Ala Gly Ser Pro Ala Gly Arg Ser Ile Tyr Asn Ser Phe
145                 150                 155                 160

Tyr Val Tyr Cys Lys Gly Pro Cys Gln Arg Val Gln Pro Gly Lys Leu
                165                 170                 175

Arg Val Gln Cys Ser Thr Cys Arg Gln Ala Thr Leu Thr Leu Thr Gln
                180                 185                 190

Gly Pro Ser Cys Trp Asp Asp Val Leu Ile Pro Asn Arg Met Ser Gly
            195                 200                 205

Glu Cys Gln Ser Pro His Cys Pro Gly Thr Ser Ala Glu Phe Phe Phe
    210                 215                 220

Lys Cys Gly Ala His Pro Thr Ser Asp Lys Glu Thr Ser Val Ala Leu
225                 230                 235                 240

His Leu Ile Ala Thr Asn Ser Arg Asn Ile Thr Cys Ile Thr Cys Thr
                245                 250                 255

Asp Val Arg Ser Pro Val Leu Val Phe Gln Cys Asn Ser Arg His Val
                260                 265                 270

Ile Cys Leu Asp Cys Phe His Leu Tyr Cys Val Thr Arg Leu Asn Asp
            275                 280                 285

Arg Gln Phe Val His Asp Pro Gln Leu Gly Tyr Ser Leu Pro Cys Val
    290                 295                 300

Ala Gly Cys Pro Asn Ser Leu Ile Lys Glu Leu His His Phe Arg Ile
305                 310                 315                 320

Leu Gly Glu Glu Gln Tyr Asn Arg Tyr Gln Gln Tyr Gly Ala Glu Glu
                325                 330                 335

Cys Val Leu Gln Met Gly Gly Val Leu Cys Pro Arg Pro Gly Cys Gly
            340                 345                 350

Ala Gly Leu Leu Pro Glu Pro Asp Gln Arg Lys Val Thr Cys Glu Gly
            355                 360                 365

Gly Asn Gly Leu Gly Cys Gly Phe Ala Phe Cys Arg Glu Cys Lys Glu
    370                 375                 380

Ala Tyr His Glu Gly Glu Cys Ser Ala Val Phe Glu Ala Ser Gly Thr
385                 390                 395                 400

Thr Thr Gln Ala Tyr Arg Val Asp Glu Arg Ala Ala Glu Gln Ala Arg
                405                 410                 415

Trp Glu Ala Ala Ser Lys Glu Thr Ile Lys Lys Thr Thr Lys Pro Cys
            420                 425                 430

Pro Arg Cys His Val Pro Val Glu Lys Asn Gly Gly Cys Met His Met
    435                 440                 445

Lys Cys Pro Gln Pro Gln Cys Arg Leu Glu Trp Cys Trp Asn Cys Gly
450                 455                 460

Cys Glu Trp Asn Arg Val Cys Met Gly Asp His Trp Phe Asp Val Leu
```

-continued

```
               465                 470                 475                 480
Ala Leu Lys Leu Ala Gly Leu Asp Leu
                    485

<210> SEQ ID NO 72
<211> LENGTH: 806
<212> TYPE: PRT
<213> ORGANISM: Homo sapiens

<400> SEQUENCE: 72

Met Gln Phe Phe Gly Arg Leu Val Asn Thr Phe Ser Gly Val Thr Asn
1               5                   10                  15

Leu Phe Ser Asn Pro Phe Arg Val Lys Glu Val Ala Val Ala Asp Tyr
                20                  25                  30

Thr Ser Ser Asp Arg Val Arg Glu Glu Gly Gln Leu Ile Leu Phe Gln
            35                  40                  45

Asn Thr Pro Asn Arg Thr Trp Asp Cys Val Leu Val Asn Pro Arg Asn
        50                  55                  60

Ser Gln Ser Gly Phe Arg Leu Phe Gln Leu Glu Leu Glu Ala Asp Ala
65                  70                  75                  80

Leu Val Asn Phe His Gln Tyr Ser Ser Gln Leu Leu Pro Phe Tyr Glu
                85                  90                  95

Ser Ser Pro Gln Val Leu His Thr Glu Val Leu Gln His Leu Thr Asp
                100                 105                 110

Leu Ile Arg Asn His Pro Ser Trp Ser Val Ala His Leu Ala Val Glu
            115                 120                 125

Leu Gly Ile Arg Glu Cys Phe His His Ser Arg Ile Ile Ser Cys Ala
        130                 135                 140

Asn Cys Ala Glu Asn Glu Glu Gly Cys Thr Pro Leu His Leu Ala Cys
145                 150                 155                 160

Arg Lys Gly Asp Gly Glu Ile Leu Val Glu Leu Val Gln Tyr Cys His
                165                 170                 175

Thr Gln Met Asp Val Thr Asp Tyr Lys Gly Glu Thr Val Phe His Tyr
                180                 185                 190

Ala Val Gln Gly Asp Asn Ser Gln Val Leu Gln Leu Leu Gly Arg Asn
            195                 200                 205

Ala Val Ala Gly Leu Asn Gln Val Asn Asn Gln Gly Leu Thr Pro Leu
        210                 215                 220

His Leu Ala Cys Gln Leu Gly Lys Gln Glu Met Val Arg Val Leu Leu
225                 230                 235                 240

Leu Cys Asn Ala Arg Cys Asn Ile Met Gly Pro Asn Gly Tyr Pro Ile
                245                 250                 255

His Ser Ala Met Lys Phe Ser Gln Lys Gly Cys Ala Glu Met Ile Ile
                260                 265                 270

Ser Met Asp Ser Ser Gln Ile His Ser Lys Asp Pro Arg Tyr Gly Ala
            275                 280                 285

Ser Pro Leu His Trp Ala Lys Asn Ala Glu Met Ala Arg Met Leu Leu
        290                 295                 300

Lys Arg Gly Cys Asn Val Asn Ser Thr Ser Ser Ala Gly Asn Thr Ala
305                 310                 315                 320

Leu His Val Ala Val Met Arg Asn Arg Phe Asp Cys Ala Ile Val Leu
                325                 330                 335

Leu Thr His Gly Ala Asn Ala Asp Ala Arg Gly Glu His Gly Asn Thr
                340                 345                 350
```

-continued

```
Pro Leu His Leu Ala Met Ser Lys Asp Asn Val Glu Met Ile Lys Ala
        355                 360                 365
Leu Ile Val Phe Gly Ala Glu Val Asp Thr Pro Asn Asp Phe Gly Glu
    370                 375                 380
Thr Pro Thr Phe Leu Ala Ser Lys Ile Gly Arg Leu Val Thr Arg Lys
385                 390                 395                 400
Ala Ile Leu Thr Leu Leu Arg Thr Val Gly Ala Glu Tyr Cys Phe Pro
                405                 410                 415
Pro Ile His Gly Val Pro Ala Glu Gln Gly Ser Ala Ala Pro His His
            420                 425                 430
Pro Phe Ser Leu Glu Arg Ala Gln Pro Pro Ile Ser Leu Asn Asn
        435                 440                 445
Leu Glu Leu Gln Asp Leu Met His Ile Ser Arg Ala Arg Lys Pro Ala
    450                 455                 460
Phe Ile Leu Gly Ser Met Arg Asp Glu Lys Arg Thr His Asp His Leu
465                 470                 475                 480
Leu Cys Leu Asp Gly Gly Val Lys Gly Leu Ile Ile Ile Gln Leu
                485                 490                 495
Leu Ile Ala Ile Glu Lys Ala Ser Gly Val Ala Thr Lys Asp Leu Phe
            500                 505                 510
Asp Trp Val Ala Gly Thr Ser Thr Gly Gly Ile Leu Ala Leu Ala Ile
        515                 520                 525
Leu His Ser Lys Ser Met Ala Tyr Met Arg Gly Met Tyr Phe Arg Met
    530                 535                 540
Lys Asp Glu Val Phe Arg Gly Ser Arg Pro Tyr Glu Ser Gly Pro Leu
545                 550                 555                 560
Glu Glu Phe Leu Lys Arg Glu Phe Gly Glu His Thr Lys Met Thr Asp
                565                 570                 575
Val Arg Lys Pro Lys Val Met Leu Thr Gly Thr Leu Ser Asp Arg Gln
            580                 585                 590
Pro Ala Glu Leu His Leu Phe Arg Asn Tyr Asp Ala Pro Glu Thr Val
        595                 600                 605
Arg Glu Pro Arg Phe Asn Gln Asn Val Asn Leu Arg Pro Pro Ala Gln
    610                 615                 620
Pro Ser Asp Gln Leu Val Trp Arg Ala Ala Arg Ser Ser Gly Ala Ala
625                 630                 635                 640
Pro Thr Tyr Phe Arg Pro Asn Gly Arg Phe Leu Asp Gly Gly Leu Leu
                645                 650                 655
Ala Asn Asn Pro Thr Leu Asp Ala Met Thr Glu Ile His Glu Tyr Asn
            660                 665                 670
Gln Asp Leu Ile Arg Lys Gly Gln Ala Asn Lys Val Lys Lys Leu Ser
        675                 680                 685
Ile Val Val Ser Leu Gly Thr Gly Arg Ser Pro Gln Val Pro Val Thr
    690                 695                 700
Cys Val Asp Val Phe Arg Pro Ser Asn Pro Trp Glu Leu Ala Lys Thr
705                 710                 715                 720
Val Phe Gly Ala Lys Glu Leu Gly Lys Met Val Val Asp Cys Cys Thr
                725                 730                 735
Asp Pro Asp Gly Arg Ala Val Asp Arg Ala Arg Ala Trp Cys Glu Met
            740                 745                 750
Val Gly Ile Gln Tyr Phe Arg Leu Asn Pro Gln Leu Gly Thr Asp Ile
        755                 760                 765
Met Leu Asp Glu Val Ser Asp Thr Val Leu Val Asn Ala Leu Trp Glu
```

```
             770                 775                 780
Thr Glu Val Tyr Ile Tyr Glu His Arg Glu Glu Phe Gln Lys Leu Ile
785                 790                 795                 800

Gln Leu Leu Leu Ser Pro
                805
```

<210> SEQ ID NO 73
<211> LENGTH: 752
<212> TYPE: PRT
<213> ORGANISM: Homo sapiens

<400> SEQUENCE: 73

```
Met Gln Phe Phe Gly Arg Leu Val Asn Thr Phe Ser Gly Val Thr Asn
1               5                   10                  15

Leu Phe Ser Asn Pro Phe Arg Val Lys Glu Val Ala Val Ala Asp Tyr
                20                  25                  30

Thr Ser Ser Asp Arg Val Arg Glu Glu Gly Gln Leu Ile Leu Phe Gln
            35                  40                  45

Asn Thr Pro Asn Arg Thr Trp Asp Cys Val Leu Val Asn Pro Arg Asn
50                  55                  60

Ser Gln Ser Gly Phe Arg Leu Phe Gln Leu Glu Leu Ala Asp Ala
65                  70                  75                  80

Leu Val Asn Phe His Gln Tyr Ser Ser Gln Leu Leu Pro Phe Tyr Glu
                85                  90                  95

Ser Ser Pro Gln Val Leu His Thr Glu Val Leu Gln His Leu Thr Asp
            100                 105                 110

Leu Ile Arg Asn His Pro Ser Trp Ser Val Ala His Leu Ala Val Glu
            115                 120                 125

Leu Gly Ile Arg Glu Cys Phe His His Ser Arg Ile Ile Ser Cys Ala
130                 135                 140

Asn Cys Ala Glu Asn Glu Glu Gly Cys Thr Pro Leu His Leu Ala Cys
145                 150                 155                 160

Arg Lys Gly Asp Gly Glu Ile Leu Val Glu Leu Val Gln Tyr Cys His
                165                 170                 175

Thr Gln Met Asp Val Thr Asp Tyr Lys Gly Glu Thr Val Phe His Tyr
            180                 185                 190

Ala Val Gln Gly Asp Asn Ser Gln Val Leu Gln Leu Leu Gly Arg Asn
            195                 200                 205

Ala Val Ala Gly Leu Asn Gln Val Asn Asn Gln Gly Leu Thr Pro Leu
210                 215                 220

His Leu Ala Cys Gln Leu Gly Lys Gln Glu Met Val Arg Val Leu Leu
225                 230                 235                 240

Leu Cys Asn Ala Arg Cys Asn Ile Met Gly Pro Asn Gly Tyr Pro Ile
                245                 250                 255

His Ser Ala Met Lys Phe Ser Gln Lys Gly Cys Ala Glu Met Ile Ile
            260                 265                 270

Ser Met Asp Ser Ser Gln Ile His Ser Lys Asp Pro Arg Tyr Gly Ala
            275                 280                 285

Ser Pro Leu His Trp Ala Lys Asn Ala Glu Met Ala Arg Met Leu Leu
290                 295                 300

Lys Arg Gly Cys Asn Val Asn Ser Thr Ser Ser Ala Gly Asn Thr Ala
305                 310                 315                 320

Leu His Val Ala Val Met Arg Asn Arg Phe Asp Cys Ala Ile Val Leu
                325                 330                 335
```

```
Leu Thr His Gly Ala Asn Ala Asp Ala Arg Gly Glu His Gly Asn Thr
                340                 345                 350

Pro Leu His Leu Ala Met Ser Lys Asp Asn Val Glu Met Ile Lys Ala
        355                 360                 365

Leu Ile Val Phe Gly Ala Glu Val Asp Thr Pro Asn Asp Phe Gly Glu
    370                 375                 380

Thr Pro Thr Phe Leu Ala Ser Lys Ile Gly Arg Gln Leu Gln Asp Leu
385                 390                 395                 400

Met His Ile Ser Arg Ala Arg Lys Pro Ala Phe Ile Leu Gly Ser Met
                405                 410                 415

Arg Asp Glu Lys Arg Thr His Asp His Leu Leu Cys Leu Asp Gly Gly
        420                 425                 430

Gly Val Lys Gly Leu Ile Ile Ile Gln Leu Leu Ile Ala Ile Glu Lys
            435                 440                 445

Ala Ser Gly Val Ala Thr Lys Asp Leu Phe Asp Trp Val Ala Gly Thr
    450                 455                 460

Ser Thr Gly Gly Ile Leu Ala Leu Ala Ile Leu His Ser Lys Ser Met
465                 470                 475                 480

Ala Tyr Met Arg Gly Met Tyr Phe Arg Met Lys Asp Glu Val Phe Arg
                485                 490                 495

Gly Ser Arg Pro Tyr Glu Ser Gly Pro Leu Glu Glu Phe Leu Lys Arg
        500                 505                 510

Glu Phe Gly Glu His Thr Lys Met Thr Asp Val Arg Lys Pro Lys Val
            515                 520                 525

Met Leu Thr Gly Thr Leu Ser Asp Arg Gln Pro Ala Glu Leu His Leu
    530                 535                 540

Phe Arg Asn Tyr Asp Ala Pro Glu Thr Val Arg Glu Pro Arg Phe Asn
545                 550                 555                 560

Gln Asn Val Asn Leu Arg Pro Pro Ala Gln Pro Ser Asp Gln Leu Val
                565                 570                 575

Trp Arg Ala Ala Arg Ser Ser Gly Ala Ala Pro Thr Tyr Phe Arg Pro
        580                 585                 590

Asn Gly Arg Phe Leu Asp Gly Gly Leu Leu Ala Asn Asn Pro Thr Leu
            595                 600                 605

Asp Ala Met Thr Glu Ile His Glu Tyr Asn Gln Asp Leu Ile Arg Lys
    610                 615                 620

Gly Gln Ala Asn Lys Val Lys Lys Leu Ser Ile Val Val Ser Leu Gly
625                 630                 635                 640

Thr Gly Arg Ser Pro Gln Val Pro Val Thr Cys Val Asp Val Phe Arg
                645                 650                 655

Pro Ser Asn Pro Trp Glu Leu Ala Lys Thr Val Phe Gly Ala Lys Glu
        660                 665                 670

Leu Gly Lys Met Val Val Asp Cys Cys Thr Asp Pro Asp Gly Arg Ala
            675                 680                 685

Val Asp Arg Ala Arg Ala Trp Cys Glu Met Val Gly Ile Gln Tyr Phe
    690                 695                 700

Arg Leu Asn Pro Gln Leu Gly Thr Asp Ile Met Leu Asp Glu Val Ser
705                 710                 715                 720

Asp Thr Val Leu Val Asn Ala Leu Trp Glu Thr Glu Val Tyr Ile Tyr
                725                 730                 735

Glu His Arg Glu Glu Phe Gln Lys Leu Ile Gln Leu Leu Leu Ser Pro
        740                 745                 750
```

<210> SEQ ID NO 74
<211> LENGTH: 752
<212> TYPE: PRT
<213> ORGANISM: Homo sapiens

<400> SEQUENCE: 74

```
Met Gln Phe Phe Gly Arg Leu Val Asn Thr Phe Ser Gly Val Thr Asn
1               5                   10                  15

Leu Phe Ser Asn Pro Phe Arg Val Lys Glu Val Ala Val Ala Asp Tyr
            20                  25                  30

Thr Ser Ser Asp Arg Val Arg Glu Glu Gly Gln Leu Ile Leu Phe Gln
        35                  40                  45

Asn Thr Pro Asn Arg Thr Trp Asp Cys Val Leu Val Asn Pro Arg Asn
    50                  55                  60

Ser Gln Ser Gly Phe Arg Leu Phe Gln Leu Glu Leu Glu Ala Asp Ala
65                  70                  75                  80

Leu Val Asn Phe His Gln Tyr Ser Ser Gln Leu Leu Pro Phe Tyr Glu
                85                  90                  95

Ser Ser Pro Gln Val Leu His Thr Glu Val Leu Gln His Leu Thr Asp
            100                 105                 110

Leu Ile Arg Asn His Pro Ser Trp Ser Val Ala His Leu Ala Val Glu
        115                 120                 125

Leu Gly Ile Arg Glu Cys Phe His His Ser Arg Ile Ile Ser Cys Ala
130                 135                 140

Asn Cys Ala Glu Asn Glu Gly Cys Thr Pro Leu His Leu Ala Cys
145                 150                 155                 160

Arg Lys Gly Asp Gly Glu Ile Leu Val Glu Leu Val Gln Tyr Cys His
                165                 170                 175

Thr Gln Met Asp Val Thr Asp Tyr Lys Gly Glu Thr Val Phe His Tyr
            180                 185                 190

Ala Val Gln Gly Asp Asn Ser Gln Val Leu Gln Leu Leu Gly Arg Asn
        195                 200                 205

Ala Val Ala Gly Leu Asn Gln Val Asn Asn Gln Gly Leu Thr Pro Leu
210                 215                 220

His Leu Ala Cys Gln Leu Gly Lys Gln Glu Met Val Arg Val Leu Leu
225                 230                 235                 240

Leu Cys Asn Ala Arg Cys Asn Ile Met Gly Pro Asn Gly Tyr Pro Ile
                245                 250                 255

His Ser Ala Met Lys Phe Ser Gln Lys Gly Cys Ala Glu Met Ile Ile
            260                 265                 270

Ser Met Asp Ser Ser Gln Ile His Ser Lys Asp Pro Arg Tyr Gly Ala
        275                 280                 285

Ser Pro Leu His Trp Ala Lys Asn Ala Glu Met Ala Arg Met Leu Leu
    290                 295                 300

Lys Arg Gly Cys Asn Val Asn Ser Thr Ser Ser Ala Gly Asn Thr Ala
305                 310                 315                 320

Leu His Val Ala Val Met Arg Asn Arg Phe Asp Cys Ala Ile Val Leu
                325                 330                 335

Leu Thr His Gly Ala Asn Ala Asp Ala Arg Gly Glu His Gly Asn Thr
            340                 345                 350

Pro Leu His Leu Ala Met Ser Lys Asp Asn Val Glu Met Ile Lys Ala
        355                 360                 365

Leu Ile Val Phe Gly Ala Glu Val Asp Thr Pro Asn Asp Phe Gly Glu
    370                 375                 380
```

Thr Pro Thr Phe Leu Ala Ser Lys Ile Gly Arg Gln Leu Gln Asp Leu
385                 390                 395                 400

Met His Ile Ser Arg Ala Arg Lys Pro Ala Phe Ile Leu Gly Ser Met
        405                 410                 415

Arg Asp Glu Lys Arg Thr His Asp His Leu Leu Cys Leu Asp Gly Gly
            420                 425                 430

Gly Val Lys Gly Leu Ile Ile Ile Gln Leu Leu Ile Ala Ile Glu Lys
        435                 440                 445

Ala Ser Gly Val Ala Thr Lys Asp Leu Phe Asp Trp Val Ala Gly Thr
    450                 455                 460

Ser Thr Gly Gly Ile Leu Ala Leu Ala Ile Leu His Ser Lys Ser Met
465                 470                 475                 480

Ala Tyr Met Arg Gly Met Tyr Phe Arg Met Lys Asp Glu Val Phe Arg
                485                 490                 495

Gly Ser Arg Pro Tyr Glu Ser Gly Pro Leu Glu Glu Phe Leu Lys Arg
            500                 505                 510

Glu Phe Gly Glu His Thr Lys Met Thr Asp Val Arg Lys Pro Lys Val
        515                 520                 525

Met Leu Thr Gly Thr Leu Ser Asp Arg Gln Pro Ala Glu Leu His Leu
    530                 535                 540

Phe Arg Asn Tyr Asp Ala Pro Glu Thr Val Arg Glu Pro Arg Phe Asn
545                 550                 555                 560

Gln Asn Val Asn Leu Arg Pro Pro Ala Gln Pro Ser Asp Gln Leu Val
                565                 570                 575

Trp Arg Ala Ala Arg Ser Ser Gly Ala Ala Pro Thr Tyr Phe Arg Pro
            580                 585                 590

Asn Gly Arg Phe Leu Asp Gly Gly Leu Leu Ala Asn Asn Pro Thr Leu
        595                 600                 605

Asp Ala Met Thr Glu Ile His Glu Tyr Asn Gln Asp Leu Ile Arg Lys
    610                 615                 620

Gly Gln Ala Asn Lys Val Lys Lys Leu Ser Ile Val Val Ser Leu Gly
625                 630                 635                 640

Thr Gly Arg Ser Pro Gln Val Pro Val Thr Cys Val Asp Val Phe Arg
                645                 650                 655

Pro Ser Asn Pro Trp Glu Leu Ala Lys Thr Val Phe Gly Ala Lys Glu
            660                 665                 670

Leu Gly Lys Met Val Val Asp Cys Cys Thr Asp Pro Asp Gly Arg Ala
        675                 680                 685

Val Asp Arg Ala Arg Ala Trp Cys Glu Met Val Gly Ile Gln Tyr Phe
    690                 695                 700

Arg Leu Asn Pro Gln Leu Gly Thr Asp Ile Met Leu Asp Glu Val Ser
705                 710                 715                 720

Asp Thr Val Leu Val Asn Ala Leu Trp Glu Thr Val Tyr Ile Tyr
                725                 730                 735

Glu His Arg Glu Glu Phe Gln Lys Leu Ile Gln Leu Leu Leu Ser Pro
            740                 745                 750

<210> SEQ ID NO 75
<211> LENGTH: 806
<212> TYPE: PRT
<213> ORGANISM: Homo sapiens

<400> SEQUENCE: 75

Met Gln Phe Phe Gly Arg Leu Val Asn Thr Phe Ser Gly Val Thr Asn
1               5                   10                  15

-continued

```
Leu Phe Ser Asn Pro Phe Arg Val Lys Glu Val Ala Val Asp Tyr
            20              25              30

Thr Ser Ser Asp Arg Val Arg Glu Glu Gly Gln Leu Ile Leu Phe Gln
        35              40              45

Asn Thr Pro Asn Arg Thr Trp Asp Cys Val Leu Val Asn Pro Arg Asn
50              55              60

Ser Gln Ser Gly Phe Arg Leu Phe Gln Leu Glu Leu Glu Ala Asp Ala
65              70              75              80

Leu Val Asn Phe His Gln Tyr Ser Ser Gln Leu Leu Pro Phe Tyr Glu
                85              90              95

Ser Ser Pro Gln Val Leu His Thr Glu Val Leu Gln His Leu Thr Asp
            100             105             110

Leu Ile Arg Asn His Pro Ser Trp Ser Val Ala His Leu Ala Val Glu
            115             120             125

Leu Gly Ile Arg Glu Cys Phe His His Ser Arg Ile Ile Ser Cys Ala
130             135             140

Asn Cys Ala Glu Asn Glu Glu Gly Cys Thr Pro Leu His Leu Ala Cys
145             150             155             160

Arg Lys Gly Asp Gly Glu Ile Leu Val Glu Leu Val Gln Tyr Cys His
            165             170             175

Thr Gln Met Asp Val Thr Asp Tyr Lys Gly Glu Thr Val Phe His Tyr
            180             185             190

Ala Val Gln Gly Asp Asn Ser Gln Val Leu Gln Leu Leu Gly Arg Asn
            195             200             205

Ala Val Ala Gly Leu Asn Gln Val Asn Asn Gln Gly Leu Thr Pro Leu
            210             215             220

His Leu Ala Cys Gln Leu Gly Lys Gln Glu Met Val Arg Val Leu Leu
225             230             235             240

Leu Cys Asn Ala Arg Cys Asn Ile Met Gly Pro Asn Gly Tyr Pro Ile
            245             250             255

His Ser Ala Met Lys Phe Ser Gln Lys Gly Cys Ala Glu Met Ile Ile
            260             265             270

Ser Met Asp Ser Ser Gln Ile His Ser Lys Asp Pro Arg Tyr Gly Ala
            275             280             285

Ser Pro Leu His Trp Ala Lys Asn Ala Glu Met Ala Arg Met Leu Leu
            290             295             300

Lys Arg Gly Cys Asn Val Asn Ser Thr Ser Ser Ala Gly Asn Thr Ala
305             310             315             320

Leu His Val Ala Val Met Arg Asn Arg Phe Asp Cys Ala Ile Val Leu
            325             330             335

Leu Thr His Gly Ala Asn Ala Asp Ala Arg Gly Glu His Gly Asn Thr
            340             345             350

Pro Leu His Leu Ala Met Ser Lys Asp Asn Val Glu Met Ile Lys Ala
            355             360             365

Leu Ile Val Phe Gly Ala Glu Val Asp Thr Pro Asn Asp Phe Gly Glu
            370             375             380

Thr Pro Thr Phe Leu Ala Ser Lys Ile Gly Arg Leu Val Thr Arg Lys
385             390             395             400

Ala Ile Leu Thr Leu Leu Arg Thr Val Gly Ala Glu Tyr Cys Phe Pro
            405             410             415

Pro Ile His Gly Val Pro Ala Glu Gln Gly Ser Ala Ala Pro His His
            420             425             430
```

```
Pro Phe Ser Leu Glu Arg Ala Gln Pro Pro Ile Ser Leu Asn Asn
            435                 440                 445

Leu Glu Leu Gln Asp Leu Met His Ile Ser Arg Ala Arg Lys Pro Ala
450                 455                 460

Phe Ile Leu Gly Ser Met Arg Asp Glu Lys Arg Thr His Asp His Leu
465                 470                 475                 480

Leu Cys Leu Asp Gly Gly Val Lys Gly Leu Ile Ile Gln Leu
                485                 490                 495

Leu Ile Ala Ile Glu Lys Ala Ser Gly Val Ala Thr Lys Asp Leu Phe
                500                 505                 510

Asp Trp Val Ala Gly Thr Ser Thr Gly Gly Ile Leu Ala Leu Ala Ile
            515                 520                 525

Leu His Ser Lys Ser Met Ala Tyr Met Arg Gly Met Tyr Phe Arg Met
530                 535                 540

Lys Asp Glu Val Phe Arg Gly Ser Arg Pro Tyr Glu Ser Gly Pro Leu
545                 550                 555                 560

Glu Glu Phe Leu Lys Arg Glu Phe Gly Glu His Thr Lys Met Thr Asp
                565                 570                 575

Val Arg Lys Pro Lys Val Met Leu Thr Gly Thr Leu Ser Asp Arg Gln
            580                 585                 590

Pro Ala Glu Leu His Leu Phe Arg Asn Tyr Asp Ala Pro Glu Thr Val
            595                 600                 605

Arg Glu Pro Arg Phe Asn Gln Asn Val Asn Leu Arg Pro Pro Ala Gln
            610                 615                 620

Pro Ser Asp Gln Leu Val Trp Arg Ala Ala Arg Ser Ser Gly Ala Ala
625                 630                 635                 640

Pro Thr Tyr Phe Arg Pro Asn Gly Arg Phe Leu Asp Gly Gly Leu Leu
                645                 650                 655

Ala Asn Asn Pro Thr Leu Asp Ala Met Thr Glu Ile His Glu Tyr Asn
                660                 665                 670

Gln Asp Leu Ile Arg Lys Gly Gln Ala Asn Lys Val Lys Lys Leu Ser
            675                 680                 685

Ile Val Val Ser Leu Gly Thr Gly Arg Ser Pro Gln Val Pro Val Thr
690                 695                 700

Cys Val Asp Val Phe Arg Pro Ser Asn Pro Trp Glu Leu Ala Lys Thr
705                 710                 715                 720

Val Phe Gly Ala Lys Glu Leu Gly Lys Met Val Val Asp Cys Cys Thr
                725                 730                 735

Asp Pro Asp Gly Arg Ala Val Asp Arg Ala Arg Ala Trp Cys Glu Met
            740                 745                 750

Val Gly Ile Gln Tyr Phe Arg Leu Asn Pro Gln Leu Gly Thr Asp Ile
            755                 760                 765

Met Leu Asp Glu Val Ser Asp Thr Val Leu Val Asn Ala Leu Trp Glu
770                 775                 780

Thr Glu Val Tyr Ile Tyr Glu His Arg Glu Glu Phe Gln Lys Leu Ile
785                 790                 795                 800

Gln Leu Leu Leu Ser Pro
                805

<210> SEQ ID NO 76
<211> LENGTH: 752
<212> TYPE: PRT
<213> ORGANISM: Homo sapiens

<400> SEQUENCE: 76
```

```
Met Gln Phe Phe Gly Arg Leu Val Asn Thr Phe Ser Gly Val Thr Asn
1               5                   10                  15

Leu Phe Ser Asn Pro Phe Arg Val Lys Glu Val Ala Val Ala Asp Tyr
            20                  25                  30

Thr Ser Ser Asp Arg Val Arg Glu Glu Gly Gln Leu Ile Leu Phe Gln
        35                  40                  45

Asn Thr Pro Asn Arg Thr Trp Asp Cys Val Leu Val Asn Pro Arg Asn
    50                  55                  60

Ser Gln Ser Gly Phe Arg Leu Phe Gln Leu Glu Leu Ala Asp Ala
65              70                  75                  80

Leu Val Asn Phe His Gln Tyr Ser Ser Gln Leu Leu Pro Phe Tyr Glu
                85                  90                  95

Ser Ser Pro Gln Val Leu His Thr Glu Val Leu Gln His Leu Thr Asp
            100                 105                 110

Leu Ile Arg Asn His Pro Ser Trp Ser Val Ala His Leu Ala Val Glu
        115                 120                 125

Leu Gly Ile Arg Glu Cys Phe His His Ser Arg Ile Ile Ser Cys Ala
130                 135                 140

Asn Cys Ala Glu Asn Glu Glu Gly Cys Thr Pro Leu His Leu Ala Cys
145                 150                 155                 160

Arg Lys Gly Asp Gly Glu Ile Leu Val Glu Leu Val Gln Tyr Cys His
                165                 170                 175

Thr Gln Met Asp Val Thr Asp Tyr Lys Gly Glu Thr Val Phe His Tyr
            180                 185                 190

Ala Val Gln Gly Asp Asn Ser Gln Val Leu Gln Leu Leu Gly Arg Asn
        195                 200                 205

Ala Val Ala Gly Leu Asn Gln Val Asn Gln Gly Leu Thr Pro Leu
210                 215                 220

His Leu Ala Cys Gln Leu Gly Lys Gln Glu Met Val Arg Val Leu Leu
225                 230                 235                 240

Leu Cys Asn Ala Arg Cys Asn Ile Met Gly Pro Asn Gly Tyr Pro Ile
            245                 250                 255

His Ser Ala Met Lys Phe Ser Gln Lys Gly Cys Ala Glu Met Ile Ile
        260                 265                 270

Ser Met Asp Ser Ser Gln Ile His Ser Lys Asp Pro Arg Tyr Gly Ala
    275                 280                 285

Ser Pro Leu His Trp Ala Lys Asn Ala Glu Met Ala Arg Met Leu Leu
    290                 295                 300

Lys Arg Gly Cys Asn Val Asn Ser Thr Ser Ser Ala Gly Asn Thr Ala
305                 310                 315                 320

Leu His Val Ala Val Met Arg Asn Arg Phe Asp Cys Ala Ile Val Leu
            325                 330                 335

Leu Thr His Gly Ala Asn Ala Asp Ala Arg Gly Glu His Gly Asn Thr
        340                 345                 350

Pro Leu His Leu Ala Met Ser Lys Asp Asn Val Glu Met Ile Lys Ala
    355                 360                 365

Leu Ile Val Phe Gly Ala Glu Val Asp Thr Pro Asn Asp Phe Gly Glu
370                 375                 380

Thr Pro Thr Phe Leu Ala Ser Lys Ile Gly Arg Gln Leu Gln Asp Leu
385                 390                 395                 400

Met His Ile Ser Arg Ala Arg Lys Pro Ala Phe Ile Leu Gly Ser Met
            405                 410                 415
```

-continued

```
Arg Asp Glu Lys Arg Thr His Asp His Leu Leu Cys Leu Asp Gly Gly
            420                 425                 430

Gly Val Lys Gly Leu Ile Ile Ile Gln Leu Leu Ile Ala Ile Glu Lys
            435                 440                 445

Ala Ser Gly Val Ala Thr Lys Asp Leu Phe Asp Trp Val Ala Gly Thr
        450                 455                 460

Ser Thr Gly Gly Ile Leu Ala Leu Ala Ile Leu His Ser Lys Ser Met
465                 470                 475                 480

Ala Tyr Met Arg Gly Met Tyr Phe Arg Met Lys Asp Glu Val Phe Arg
                485                 490                 495

Gly Ser Arg Pro Tyr Glu Ser Gly Pro Leu Glu Glu Phe Leu Lys Arg
            500                 505                 510

Glu Phe Gly Glu His Thr Lys Met Thr Asp Val Arg Lys Pro Lys Val
        515                 520                 525

Met Leu Thr Gly Thr Leu Ser Asp Arg Gln Pro Ala Glu Leu His Leu
    530                 535                 540

Phe Arg Asn Tyr Asp Ala Pro Glu Thr Val Arg Glu Pro Arg Phe Asn
545                 550                 555                 560

Gln Asn Val Asn Leu Arg Pro Pro Ala Gln Pro Ser Asp Gln Leu Val
                565                 570                 575

Trp Arg Ala Ala Arg Ser Ser Gly Ala Ala Pro Thr Tyr Phe Arg Pro
            580                 585                 590

Asn Gly Arg Phe Leu Asp Gly Gly Leu Leu Ala Asn Asn Pro Thr Leu
        595                 600                 605

Asp Ala Met Thr Glu Ile His Glu Tyr Asn Gln Asp Leu Ile Arg Lys
    610                 615                 620

Gly Gln Ala Asn Lys Val Lys Lys Leu Ser Ile Val Val Ser Leu Gly
625                 630                 635                 640

Thr Gly Arg Ser Pro Gln Val Pro Val Thr Cys Val Asp Val Phe Arg
                645                 650                 655

Pro Ser Asn Pro Trp Glu Leu Ala Lys Thr Val Phe Gly Ala Lys Glu
            660                 665                 670

Leu Gly Lys Met Val Val Asp Cys Cys Thr Asp Pro Asp Gly Arg Ala
        675                 680                 685

Val Asp Arg Ala Arg Ala Trp Cys Glu Met Val Gly Ile Gln Tyr Phe
    690                 695                 700

Arg Leu Asn Pro Gln Leu Gly Thr Asp Ile Met Leu Asp Glu Val Ser
705                 710                 715                 720

Asp Thr Val Leu Val Asn Ala Leu Trp Glu Thr Glu Val Tyr Ile Tyr
                725                 730                 735

Glu His Arg Glu Glu Phe Gln Lys Leu Ile Gln Leu Leu Leu Ser Pro
            740                 745                 750

<210> SEQ ID NO 77
<211> LENGTH: 752
<212> TYPE: PRT
<213> ORGANISM: Homo sapiens

<400> SEQUENCE: 77

Met Gln Phe Phe Gly Arg Leu Val Asn Thr Phe Ser Gly Val Thr Asn
1               5                   10                  15

Leu Phe Ser Asn Pro Phe Arg Val Lys Glu Val Ala Val Ala Asp Tyr
            20                  25                  30

Thr Ser Ser Asp Arg Val Arg Glu Gly Gln Leu Ile Leu Phe Gln
        35                  40                  45
```

-continued

```
Asn Thr Pro Asn Arg Thr Trp Asp Cys Val Leu Val Asn Pro Arg Asn
     50                  55                  60

Ser Gln Ser Gly Phe Arg Leu Phe Gln Leu Glu Leu Glu Ala Asp Ala
 65                  70                  75                  80

Leu Val Asn Phe His Gln Tyr Ser Ser Gln Leu Leu Pro Phe Tyr Glu
                 85                  90                  95

Ser Ser Pro Gln Val Leu His Thr Glu Val Leu Gln His Leu Thr Asp
                100                 105                 110

Leu Ile Arg Asn His Pro Ser Trp Ser Val Ala His Leu Ala Val Glu
            115                 120                 125

Leu Gly Ile Arg Glu Cys Phe His His Ser Arg Ile Ile Ser Cys Ala
        130                 135                 140

Asn Cys Ala Glu Asn Glu Glu Gly Cys Thr Pro Leu His Leu Ala Cys
145                 150                 155                 160

Arg Lys Gly Asp Gly Glu Ile Leu Val Glu Leu Val Gln Tyr Cys His
                165                 170                 175

Thr Gln Met Asp Val Thr Asp Tyr Lys Gly Glu Thr Val Phe His Tyr
            180                 185                 190

Ala Val Gln Gly Asp Asn Ser Gln Val Leu Gln Leu Leu Gly Arg Asn
        195                 200                 205

Ala Val Ala Gly Leu Asn Gln Val Asn Asn Gln Gly Leu Thr Pro Leu
    210                 215                 220

His Leu Ala Cys Gln Leu Gly Lys Gln Glu Met Val Arg Val Leu Leu
225                 230                 235                 240

Leu Cys Asn Ala Arg Cys Asn Ile Met Gly Pro Asn Gly Tyr Pro Ile
                245                 250                 255

His Ser Ala Met Lys Phe Ser Gln Lys Gly Cys Ala Glu Met Ile Ile
            260                 265                 270

Ser Met Asp Ser Ser Gln Ile His Ser Lys Asp Pro Arg Tyr Gly Ala
        275                 280                 285

Ser Pro Leu His Trp Ala Lys Asn Ala Glu Met Ala Arg Met Leu Leu
    290                 295                 300

Lys Arg Gly Cys Asn Val Asn Ser Thr Ser Ser Ala Gly Asn Thr Ala
305                 310                 315                 320

Leu His Val Ala Val Met Arg Asn Arg Phe Asp Cys Ala Ile Val Leu
                325                 330                 335

Leu Thr His Gly Ala Asn Ala Asp Ala Arg Gly Glu His Gly Asn Thr
            340                 345                 350

Pro Leu His Leu Ala Met Ser Lys Asp Asn Val Glu Met Ile Lys Ala
        355                 360                 365

Leu Ile Val Phe Gly Ala Glu Val Asp Thr Pro Asn Asp Phe Gly Glu
    370                 375                 380

Thr Pro Thr Phe Leu Ala Ser Lys Ile Gly Arg Gln Leu Gln Asp Leu
385                 390                 395                 400

Met His Ile Ser Arg Ala Arg Lys Pro Ala Phe Ile Leu Gly Ser Met
                405                 410                 415

Arg Asp Glu Lys Arg Thr His Asp His Leu Leu Cys Leu Asp Gly Gly
            420                 425                 430

Gly Val Lys Gly Leu Ile Ile Ile Gln Leu Leu Ile Ala Ile Glu Lys
        435                 440                 445

Ala Ser Gly Val Ala Thr Lys Asp Leu Phe Asp Trp Val Ala Gly Thr
    450                 455                 460
```

Ser Thr Gly Gly Ile Leu Ala Leu Ala Ile Leu His Ser Lys Ser Met
465                 470                 475                 480

Ala Tyr Met Arg Gly Met Tyr Phe Arg Met Lys Asp Glu Val Phe Arg
            485                 490                 495

Gly Ser Arg Pro Tyr Glu Ser Gly Pro Leu Glu Glu Phe Leu Lys Arg
        500                 505                 510

Glu Phe Gly Glu His Thr Lys Met Thr Asp Val Arg Lys Pro Lys Val
    515                 520                 525

Met Leu Thr Gly Thr Leu Ser Asp Arg Gln Pro Ala Glu Leu His Leu
530                 535                 540

Phe Arg Asn Tyr Asp Ala Pro Glu Thr Val Arg Glu Pro Arg Phe Asn
545                 550                 555                 560

Gln Asn Val Asn Leu Arg Pro Ala Gln Pro Ser Asp Gln Leu Val
                565                 570                 575

Trp Arg Ala Ala Arg Ser Ser Gly Ala Ala Pro Thr Tyr Phe Arg Pro
            580                 585                 590

Asn Gly Arg Phe Leu Asp Gly Gly Leu Ala Asn Asn Pro Thr Leu
        595                 600                 605

Asp Ala Met Thr Glu Ile His Glu Tyr Asn Gln Asp Leu Ile Arg Lys
    610                 615                 620

Gly Gln Ala Asn Lys Val Lys Lys Leu Ser Ile Val Val Ser Leu Gly
625                 630                 635                 640

Thr Gly Arg Ser Pro Gln Val Pro Val Thr Cys Val Asp Val Phe Arg
                645                 650                 655

Pro Ser Asn Pro Trp Glu Leu Ala Lys Thr Val Phe Gly Ala Lys Glu
            660                 665                 670

Leu Gly Lys Met Val Val Asp Cys Cys Thr Asp Pro Asp Gly Arg Ala
        675                 680                 685

Val Asp Arg Ala Arg Ala Trp Cys Glu Met Val Gly Ile Gln Tyr Phe
    690                 695                 700

Arg Leu Asn Pro Gln Leu Gly Thr Asp Ile Met Leu Asp Glu Val Ser
705                 710                 715                 720

Asp Thr Val Leu Val Asn Ala Leu Trp Glu Thr Glu Val Tyr Ile Tyr
                725                 730                 735

Glu His Arg Glu Glu Phe Gln Lys Leu Ile Gln Leu Leu Ser Pro
            740                 745                 750

<210> SEQ ID NO 78
<211> LENGTH: 628
<212> TYPE: PRT
<213> ORGANISM: Homo sapiens

<400> SEQUENCE: 78

Met Asp Val Thr Asp Tyr Lys Gly Glu Thr Val Phe His Tyr Ala Val
1               5                   10                  15

Gln Gly Asp Asn Ser Gln Val Leu Gln Leu Leu Gly Arg Asn Ala Val
                20                  25                  30

Ala Gly Leu Asn Gln Val Asn Asn Gln Gly Leu Thr Pro Leu His Leu
        35                  40                  45

Ala Cys Gln Leu Gly Lys Gln Glu Met Val Arg Val Leu Leu Leu Cys
    50                  55                  60

Asn Ala Arg Cys Asn Ile Met Gly Pro Asn Gly Tyr Pro Ile His Ser
65                  70                  75                  80

Ala Met Lys Phe Ser Gln Lys Gly Cys Ala Glu Met Ile Ile Ser Met
                85                  90                  95

-continued

```
Asp Ser Ser Gln Ile His Ser Lys Asp Pro Arg Tyr Gly Ala Ser Pro
            100                 105                 110
Leu His Trp Ala Lys Asn Ala Glu Met Ala Arg Met Leu Leu Lys Arg
        115                 120                 125
Gly Cys Asn Val Asn Ser Thr Ser Ser Ala Gly Asn Thr Ala Leu His
    130                 135                 140
Val Ala Val Met Arg Asn Arg Phe Asp Cys Ala Ile Val Leu Leu Thr
145                 150                 155                 160
His Gly Ala Asn Ala Asp Ala Arg Gly Glu His Gly Asn Thr Pro Leu
                165                 170                 175
His Leu Ala Met Ser Lys Asp Asn Val Glu Met Ile Lys Ala Leu Ile
            180                 185                 190
Val Phe Gly Ala Glu Val Asp Thr Pro Asn Asp Phe Gly Glu Thr Pro
        195                 200                 205
Thr Phe Leu Ala Ser Lys Ile Gly Arg Leu Val Thr Arg Lys Ala Ile
    210                 215                 220
Leu Thr Leu Leu Arg Thr Val Gly Ala Glu Tyr Cys Phe Pro Pro Ile
225                 230                 235                 240
His Gly Val Pro Ala Glu Gln Gly Ser Ala Ala Pro His His Pro Phe
                245                 250                 255
Ser Leu Glu Arg Ala Gln Pro Pro Ile Ser Leu Asn Asn Leu Glu
            260                 265                 270
Leu Gln Asp Leu Met His Ile Ser Arg Ala Arg Lys Pro Ala Phe Ile
        275                 280                 285
Leu Gly Ser Met Arg Asp Glu Lys Arg Thr His Asp His Leu Leu Cys
    290                 295                 300
Leu Asp Gly Gly Gly Val Lys Gly Leu Ile Ile Ile Gln Leu Leu Ile
305                 310                 315                 320
Ala Ile Glu Lys Ala Ser Gly Val Ala Thr Lys Asp Leu Phe Asp Trp
                325                 330                 335
Val Ala Gly Thr Ser Thr Gly Gly Ile Leu Ala Leu Ala Ile Leu His
            340                 345                 350
Ser Lys Ser Met Ala Tyr Met Arg Gly Met Tyr Phe Arg Met Lys Asp
        355                 360                 365
Glu Val Phe Arg Gly Ser Arg Pro Tyr Glu Ser Gly Pro Leu Glu Glu
    370                 375                 380
Phe Leu Lys Arg Glu Phe Gly Glu His Thr Lys Met Thr Asp Val Arg
385                 390                 395                 400
Lys Pro Lys Val Met Leu Thr Gly Thr Leu Ser Asp Arg Gln Pro Ala
                405                 410                 415
Glu Leu His Leu Phe Arg Asn Tyr Asp Ala Pro Glu Thr Val Arg Glu
            420                 425                 430
Pro Arg Phe Asn Gln Asn Val Asn Leu Arg Pro Pro Ala Gln Pro Ser
        435                 440                 445
Asp Gln Leu Val Trp Arg Ala Ala Arg Ser Ser Gly Ala Ala Pro Thr
    450                 455                 460
Tyr Phe Arg Pro Asn Gly Arg Phe Leu Asp Gly Gly Leu Leu Ala Asn
465                 470                 475                 480
Asn Pro Thr Leu Asp Ala Met Thr Glu Ile His Glu Tyr Asn Gln Asp
                485                 490                 495
Leu Ile Arg Lys Gly Gln Ala Asn Lys Val Lys Lys Leu Ser Ile Val
            500                 505                 510
```

```
Val Ser Leu Gly Thr Gly Arg Ser Pro Gln Val Pro Val Thr Cys Val
            515                 520                 525

Asp Val Phe Arg Pro Ser Asn Pro Trp Glu Leu Ala Lys Thr Val Phe
530                 535                 540

Gly Ala Lys Glu Leu Gly Lys Met Val Val Asp Cys Cys Thr Asp Pro
545                 550                 555                 560

Asp Gly Arg Ala Val Asp Arg Ala Arg Ala Trp Cys Glu Met Val Gly
                565                 570                 575

Ile Gln Tyr Phe Arg Leu Asn Pro Gln Leu Gly Thr Asp Ile Met Leu
                580                 585                 590

Asp Glu Val Ser Asp Thr Val Leu Val Asn Ala Leu Trp Glu Thr Glu
            595                 600                 605

Val Tyr Ile Tyr Glu His Arg Glu Glu Phe Gln Lys Leu Ile Gln Leu
            610                 615                 620

Leu Leu Ser Pro
625

<210> SEQ ID NO 79
<211> LENGTH: 580
<212> TYPE: PRT
<213> ORGANISM: Homo sapiens

<400> SEQUENCE: 79

Met Gly Arg Ser Trp Trp Ser Trp Cys Ser Thr Ala Thr Leu Arg Trp
1               5                   10                  15

Met Ser Pro Thr Thr Arg Glu Arg Pro Ser Ser Ile Met Leu Ser Arg
            20                  25                  30

Val Thr Ile Leu Arg Cys Cys Arg Cys Ala Glu Met Ile Ile Ser Met
            35                  40                  45

Asp Ser Ser Gln Ile His Ser Lys Asp Pro Arg Tyr Gly Ala Ser Pro
50                  55                  60

Leu His Trp Ala Lys Asn Ala Glu Met Ala Arg Met Leu Leu Lys Arg
65                  70                  75                  80

Gly Cys Asn Val Asn Ser Thr Ser Ser Ala Gly Asn Thr Ala Leu His
                85                  90                  95

Val Ala Val Met Arg Asn Arg Phe Asp Cys Ala Ile Val Leu Leu Thr
            100                 105                 110

His Gly Ala Asn Ala Asp Ala Arg Gly Glu His Gly Asn Thr Pro Leu
        115                 120                 125

His Leu Ala Met Ser Lys Asp Asn Val Glu Met Ile Lys Ala Leu Ile
    130                 135                 140

Val Phe Gly Ala Glu Val Asp Thr Pro Asn Asp Phe Gly Glu Thr Pro
145                 150                 155                 160

Thr Phe Leu Ala Ser Lys Ile Gly Arg Leu Val Thr Arg Lys Ala Ile
                165                 170                 175

Leu Thr Leu Leu Arg Thr Val Gly Ala Glu Tyr Cys Phe Pro Pro Ile
            180                 185                 190

His Gly Val Pro Ala Glu Gln Gly Ser Ala Ala Pro His His Pro Phe
        195                 200                 205

Ser Leu Glu Arg Ala Gln Pro Pro Ile Ser Leu Asn Asn Leu Glu
    210                 215                 220

Leu Gln Asp Leu Met His Ile Ser Arg Ala Arg Lys Pro Ala Phe Ile
225                 230                 235                 240

Leu Gly Ser Met Arg Asp Glu Lys Arg Thr His Asp His Leu Leu Cys
                245                 250                 255
```

```
Leu Asp Gly Gly Gly Val Lys Gly Leu Ile Ile Gln Leu Leu Ile
            260                 265                 270

Ala Ile Glu Lys Ala Ser Gly Val Ala Thr Lys Asp Leu Phe Asp Trp
        275                 280                 285

Val Ala Gly Thr Ser Thr Gly Gly Ile Leu Ala Leu Ala Ile Leu His
        290                 295                 300

Ser Lys Ser Met Ala Tyr Met Arg Gly Met Tyr Phe Arg Met Lys Asp
305                 310                 315                 320

Glu Val Phe Arg Gly Ser Arg Pro Tyr Glu Ser Gly Pro Leu Glu Glu
                325                 330                 335

Phe Leu Lys Arg Glu Phe Gly Glu His Thr Lys Met Thr Asp Val Arg
            340                 345                 350

Lys Pro Lys Val Met Leu Thr Gly Thr Leu Ser Asp Arg Gln Pro Ala
        355                 360                 365

Glu Leu His Leu Phe Arg Asn Tyr Asp Ala Pro Glu Thr Val Arg Glu
    370                 375                 380

Pro Arg Phe Asn Gln Asn Val Asn Leu Arg Pro Ala Gln Pro Ser
385                 390                 395                 400

Asp Gln Leu Val Trp Arg Ala Arg Ser Ser Gly Ala Ala Pro Thr
            405                 410                 415

Tyr Phe Arg Pro Asn Gly Arg Phe Leu Asp Gly Gly Leu Leu Ala Asn
        420                 425                 430

Asn Pro Thr Leu Asp Ala Met Thr Glu Ile His Glu Tyr Asn Gln Asp
    435                 440                 445

Leu Ile Arg Lys Gly Gln Ala Asn Lys Val Lys Leu Ser Ile Val
        450                 455                 460

Val Ser Leu Gly Thr Gly Arg Ser Pro Gln Val Pro Val Thr Cys Val
465                 470                 475                 480

Asp Val Phe Arg Pro Ser Asn Pro Trp Glu Leu Ala Lys Thr Val Phe
            485                 490                 495

Gly Ala Lys Glu Leu Gly Lys Met Val Val Asp Cys Cys Thr Asp Pro
        500                 505                 510

Asp Gly Arg Ala Val Asp Arg Ala Arg Ala Trp Cys Glu Met Val Gly
    515                 520                 525

Ile Gln Tyr Phe Arg Leu Asn Pro Gln Leu Gly Thr Asp Ile Met Leu
530                 535                 540

Asp Glu Val Ser Asp Thr Val Leu Val Asn Ala Leu Trp Glu Thr Glu
545                 550                 555                 560

Val Tyr Ile Tyr Glu His Arg Glu Glu Phe Gln Lys Leu Ile Gln Leu
                565                 570                 575

Leu Leu Ser Pro
            580

<210> SEQ ID NO 80
<211> LENGTH: 574
<212> TYPE: PRT
<213> ORGANISM: Homo sapiens

<400> SEQUENCE: 80

Met Asp Val Thr Asp Tyr Lys Gly Glu Thr Val Phe His Tyr Ala Val
1               5                   10                  15

Gln Gly Asp Asn Ser Gln Val Leu Gln Leu Leu Gly Arg Asn Ala Val
            20                  25                  30

Ala Gly Leu Asn Gln Val Asn Asn Gln Gly Leu Thr Pro Leu His Leu
```

```
            35                  40                  45
Ala Cys Gln Leu Gly Lys Gln Glu Met Val Arg Val Leu Leu Leu Cys
 50                  55                  60

Asn Ala Arg Cys Asn Ile Met Gly Pro Asn Gly Tyr Pro Ile His Ser
 65                  70                  75                  80

Ala Met Lys Phe Ser Gln Lys Gly Cys Ala Glu Met Ile Ile Ser Met
                 85                  90                  95

Asp Ser Ser Gln Ile His Ser Lys Asp Pro Arg Tyr Gly Ala Ser Pro
                100                 105                 110

Leu His Trp Ala Lys Asn Ala Glu Met Ala Arg Met Leu Leu Lys Arg
            115                 120                 125

Gly Cys Asn Val Asn Ser Thr Ser Ala Gly Asn Thr Ala Leu His
            130                 135                 140

Val Ala Val Met Arg Asn Arg Phe Asp Cys Ala Ile Val Leu Leu Thr
145                 150                 155                 160

His Gly Ala Asn Ala Asp Ala Arg Gly Glu His Gly Asn Thr Pro Leu
                165                 170                 175

His Leu Ala Met Ser Lys Asp Asn Val Glu Met Ile Lys Ala Leu Ile
            180                 185                 190

Val Phe Gly Ala Glu Val Asp Thr Pro Asn Asp Phe Gly Glu Thr Pro
            195                 200                 205

Thr Phe Leu Ala Ser Lys Ile Gly Arg Gln Leu Gln Asp Leu Met His
            210                 215                 220

Ile Ser Arg Ala Arg Lys Pro Ala Phe Ile Leu Gly Ser Met Arg Asp
225                 230                 235                 240

Glu Lys Arg Thr His Asp His Leu Leu Cys Leu Asp Gly Gly Val
                245                 250                 255

Lys Gly Leu Ile Ile Ile Gln Leu Leu Ile Ala Ile Glu Lys Ala Ser
            260                 265                 270

Gly Val Ala Thr Lys Asp Leu Phe Asp Trp Val Ala Gly Thr Ser Thr
            275                 280                 285

Gly Gly Ile Leu Ala Leu Ala Ile Leu His Ser Lys Ser Met Ala Tyr
            290                 295                 300

Met Arg Gly Met Tyr Phe Arg Met Lys Asp Glu Val Phe Arg Gly Ser
305                 310                 315                 320

Arg Pro Tyr Glu Ser Gly Pro Leu Glu Glu Phe Leu Lys Arg Glu Phe
                325                 330                 335

Gly Glu His Thr Lys Met Thr Asp Val Arg Lys Pro Lys Val Met Leu
            340                 345                 350

Thr Gly Thr Leu Ser Asp Arg Gln Pro Ala Glu Leu His Leu Phe Arg
            355                 360                 365

Asn Tyr Asp Ala Pro Glu Thr Val Arg Glu Pro Arg Phe Asn Gln Asn
            370                 375                 380

Val Asn Leu Arg Pro Pro Ala Gln Pro Ser Asp Gln Leu Val Trp Arg
385                 390                 395                 400

Ala Ala Arg Ser Ser Gly Ala Ala Pro Thr Tyr Phe Arg Pro Asn Gly
                405                 410                 415

Arg Phe Leu Asp Gly Gly Leu Leu Ala Asn Asn Pro Thr Leu Asp Ala
            420                 425                 430

Met Thr Glu Ile His Glu Tyr Asn Gln Asp Leu Ile Arg Lys Gly Gln
            435                 440                 445

Ala Asn Lys Val Lys Lys Leu Ser Ile Val Val Ser Leu Gly Thr Gly
450                 455                 460
```

```
Arg Ser Pro Gln Val Pro Val Thr Cys Val Asp Val Phe Arg Pro Ser
465                 470                 475                 480

Asn Pro Trp Glu Leu Ala Lys Thr Val Phe Gly Ala Lys Glu Leu Gly
            485                 490                 495

Lys Met Val Val Asp Cys Cys Thr Asp Pro Asp Gly Arg Ala Val Asp
        500                 505                 510

Arg Ala Arg Ala Trp Cys Glu Met Val Gly Ile Gln Tyr Phe Arg Leu
            515                 520                 525

Asn Pro Gln Leu Gly Thr Asp Ile Met Leu Asp Glu Val Ser Asp Thr
        530                 535                 540

Val Leu Val Asn Ala Leu Trp Glu Thr Glu Val Tyr Ile Tyr Glu His
545                 550                 555                 560

Arg Glu Glu Phe Gln Lys Leu Ile Gln Leu Leu Leu Ser Pro
                565                 570

<210> SEQ ID NO 81
<211> LENGTH: 321
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Tyr Gly Arg Lys Lys Arg Arg Gln Arg Arg Gly Gly Ser Asp
1               5                   10                  15

Ser Glu Val Asn Gln Glu Ala Lys Pro Glu Val Lys Pro Glu Val Lys
                20                  25                  30

Pro Glu Thr His Ile Asn Leu Lys Val Ser Asp Gly Ser Ser Glu Ile
            35                  40                  45

Phe Phe Lys Ile Lys Lys Thr Thr Pro Leu Arg Arg Leu Met Glu Ala
        50                  55                  60

Phe Ala Lys Arg Gln Gly Lys Glu Met Asp Ser Leu Arg Phe Leu Tyr
65                  70                  75                  80

Asp Gly Ile Arg Ile Gln Ala Asp Gln Thr Pro Glu Asp Leu Asp Met
                85                  90                  95

Glu Asp Asn Asp Ile Ile Glu Ala His Arg Glu Gln Ile Gly Gly Met
            100                 105                 110

Trp Thr Leu Gly Arg Arg Ala Val Ala Gly Leu Leu Ala Ser Pro Ser
        115                 120                 125

Pro Ala Gln Ala Gln Thr Leu Thr Arg Val Pro Arg Pro Ala Glu Leu
    130                 135                 140

Ala Pro Leu Cys Gly Arg Arg Gly Leu Arg Thr Asp Ile Asp Ala Thr
145                 150                 155                 160

Cys Thr Pro Arg Arg Ala Ser Ser Asn Gln Arg Gly Leu Asn Gln Ile
                165                 170                 175

Trp Asn Val Lys Lys Gln Ser Val Tyr Leu Met Asn Leu Arg Lys Ser
            180                 185                 190

Gly Thr Leu Gly His Pro Gly Ser Leu Asp Glu Thr Thr Tyr Glu Arg
        195                 200                 205

Leu Ala Glu Glu Thr Leu Asp Ser Leu Ala Glu Phe Phe Glu Asp Leu
    210                 215                 220

Ala Asp Lys Pro Tyr Thr Phe Glu Asp Tyr Asp Val Ser Phe Gly Ser
225                 230                 235                 240

Gly Val Leu Thr Val Lys Leu Gly Gly Asp Leu Gly Thr Tyr Val Ile
```

```
                    245                 250                 255
Asn Lys Gln Thr Pro Asn Lys Gln Ile Trp Leu Ser Ser Pro Ser Ser
                260                 265                 270

Gly Pro Lys Arg Tyr Asp Trp Thr Gly Lys Asn Trp Val Tyr Ser His
            275                 280                 285

Asp Gly Val Ser Leu His Glu Leu Leu Ala Ala Glu Leu Thr Lys Ala
        290                 295                 300

Leu Lys Thr Lys Leu Asp Leu Ser Ser Leu Ala Tyr Ser Gly Lys Asp
305                 310                 315                 320

Ala

<210> SEQ ID NO 82
<211> LENGTH: 582
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

His His His His His Ser Asp Ser Glu Val Asn Gln Glu Ala Lys
1               5                   10                  15

Pro Glu Val Lys Pro Glu Val Lys Pro Glu Thr His Ile Asn Leu Lys
                20                  25                  30

Val Ser Asp Gly Ser Ser Glu Ile Phe Phe Lys Ile Lys Lys Thr Thr
            35                  40                  45

Pro Leu Arg Arg Leu Met Glu Ala Phe Ala Lys Arg Gln Gly Lys Glu
        50                  55                  60

Met Asp Ser Leu Arg Phe Leu Tyr Asp Gly Ile Arg Ile Gln Ala Asp
65                  70                  75                  80

Gln Thr Pro Glu Asp Leu Asp Met Glu Asp Asn Asp Ile Ile Glu Ala
                85                  90                  95

His Arg Glu Gln Ile Gly Gly Met Tyr Gly Arg Lys Lys Arg Arg Gln
            100                 105                 110

Arg Arg Arg Gly Gly Met Ile Val Phe Val Arg Phe Asn Ser Ser His
        115                 120                 125

Gly Phe Pro Val Glu Val Asp Ser Asp Thr Ser Ile Phe Gln Leu Lys
130                 135                 140

Glu Val Val Ala Lys Arg Gln Gly Val Pro Ala Asp Gln Leu Arg Val
145                 150                 155                 160

Ile Phe Ala Gly Lys Glu Leu Arg Asn Asp Trp Thr Val Gln Asn Cys
                165                 170                 175

Asp Leu Asp Gln Gln Ser Ile Val His Ile Val Gln Arg Pro Trp Arg
            180                 185                 190

Lys Gly Gln Glu Met Asn Ala Thr Gly Gly Asp Asp Pro Arg Asn Ala
        195                 200                 205

Ala Gly Gly Cys Glu Arg Glu Pro Gln Ser Leu Thr Arg Val Asp Leu
    210                 215                 220

Ser Ser Ser Val Leu Pro Gly Asp Ser Val Gly Leu Ala Val Ile Leu
225                 230                 235                 240

His Thr Asp Ser Arg Lys Asp Ser Pro Ala Gly Ser Pro Ala Gly
                245                 250                 255

Arg Ser Ile Tyr Asn Ser Phe Tyr Val Tyr Cys Lys Gly Pro Cys Gln
            260                 265                 270

Arg Val Gln Pro Gly Lys Leu Arg Val Gln Cys Ser Thr Cys Arg Gln
```

```
            275                 280                 285
Ala Thr Leu Thr Leu Thr Gln Gly Pro Ser Cys Trp Asp Asp Val Leu
    290                 295                 300

Ile Pro Asn Arg Met Ser Gly Glu Cys Gln Ser Pro His Cys Pro Gly
305                 310                 315                 320

Thr Ser Ala Glu Phe Phe Lys Cys Gly Ala His Pro Thr Ser Asp
                    325                 330                 335

Lys Glu Thr Ser Val Ala Leu His Leu Ile Ala Thr Asn Ser Arg Asn
                340                 345                 350

Ile Thr Cys Ile Thr Cys Thr Asp Val Arg Ser Pro Val Leu Val Phe
            355                 360                 365

Gln Cys Asn Ser Arg His Val Ile Cys Leu Asp Cys Phe His Leu Tyr
        370                 375                 380

Cys Val Thr Arg Leu Asn Asp Arg Gln Phe Val His Asp Pro Gln Leu
385                 390                 395                 400

Gly Tyr Ser Leu Pro Cys Val Ala Gly Cys Pro Asn Ser Leu Ile Lys
                405                 410                 415

Glu Leu His His Phe Arg Ile Leu Gly Glu Glu Gln Tyr Asn Arg Tyr
                420                 425                 430

Gln Gln Tyr Gly Ala Glu Glu Cys Val Leu Gln Met Gly Gly Val Leu
            435                 440                 445

Cys Pro Arg Pro Gly Cys Gly Ala Gly Leu Leu Pro Glu Pro Asp Gln
        450                 455                 460

Arg Lys Val Thr Cys Glu Gly Gly Asn Gly Leu Gly Cys Gly Phe Ala
465                 470                 475                 480

Phe Cys Arg Glu Cys Lys Glu Ala Tyr His Glu Gly Glu Cys Ser Ala
                485                 490                 495

Val Phe Glu Ala Ser Gly Thr Thr Thr Gln Ala Tyr Arg Val Asp Glu
                500                 505                 510

Arg Ala Ala Glu Gln Ala Arg Trp Glu Ala Ala Ser Lys Glu Thr Ile
            515                 520                 525

Lys Lys Thr Thr Lys Pro Cys Pro Arg Cys His Val Pro Val Glu Lys
        530                 535                 540

Asn Gly Gly Cys Met His Met Lys Cys Pro Gln Pro Gln Cys Arg Leu
545                 550                 555                 560

Glu Trp Cys Trp Asn Cys Gly Cys Glu Trp Asn Arg Val Cys Met Gly
                565                 570                 575

Asp His Trp Phe Asp Val
                580

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Met Tyr Gly Arg Lys Lys Arg Arg Gln Arg Arg Arg
1               5                   10

<210> SEQ ID NO 84
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 84

Glu Xaa Xaa Tyr Xaa Gln Ser
1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 85

His His His His His His
1               5

<210> SEQ ID NO 86
<211> LENGTH: 1665
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
atgtacggcc ggaagaagcg gcggcagcgt cggagaggcg gcatgcagat cttcgtgaaa      60
acattaaccg gcaagaccat caccctggaa gtggaaccta gcgacaccat cgagaacgtg     120
aaggccaaga tccaggacaa ggaaggcatc cctcctgatc agcagcgact gattttcgct     180
ggaaagcagc tggaagatgg cagaaccctg agcgactaca acatccagaa ggagagcaca     240
ctgcacctgg tgctgaggct gcggggcggc atgatcgtgt cgtgagatt caacagcagc     300 cacggcttcc ccgtcgaggt ggattctgac accagcatct ttcaactgaa ggaagtggtg     360
gcaaagagac agggcgtgcc cgccgatcaa ctgcgggtaa tcttcgccgg aaaagagctg     420
agaaatgact ggacagtgca gaactgcgac ctggatcagc aaagcattgt gcacatcgtg     480
cagcggcctt gcggaaagg ccaggagatg aacgccaccg cggagatga tcctagaaat      540 gctgctggcg gctgcgagcg ggaaccccag agcctgacca gagtggacct gtccagctct     600
gtgctaccag cgacagcgt gggcctggcc gtgatcctgc acacagattc agaaaggac      660 agcccacctg ccggcagccc ggccggaagg tccatctaca actccttcta cgtgtactgc     720 aagggcccctt gccagagagt gcaacctggc aaactgagag ttcagtgctc tacatgtaga     780
caagccacac tgacactgac ccagggcccc agctgttggg acgacgtgct gatccccaac     840
agaatgagcg cgagtgcca aagcccccac tgccctggca ccagcgccga gttcttcttt     900
aagtgtggag ctcaccccac ctccgacaag gaaaccagct ggccctgca tctgatcgcc     960 accaacagca gaaacatcac ctgtatcaca tgcaccgacg tcagaagccc tgtgcttgtg    1020
tttcagtgta atagccggca cgtgatctgc tggactgct tccacctgta ctgcgtgacc    1080
agactgaacg acagacagtt tgtgcacgac cctcagctgg gctactcgct gccttgtgtg    1140
```

```
gccggctgtc ctaactctct gatcaaggaa ctgcatcact tcagaatcct gggcgaggaa    1200
cagtacaacc ggtaccagca gtacggcgcc gaggaatgcg tgctgcagat gggcggagtg    1260
ctgtgcccta gacccggatg tggagccgga ctgctgcctg agcccgacca gcggaaagtg    1320
acctgcgagg gaggcaacgg cctcggctgc ggtttcgcct tctgcagaga atgtaaagaa    1380
gcttaccacg aggggagtg ttctgccgtg ttcgaggcct ctggcacaac cacccaggct    1440
tatagagtgg acgagagagc cgccgagcag gccagatggg aggccgccag caaggagaca    1500
atcaagaaga ccacaaagcc ttgcccacgc tgccacgtgc ctgtggaaaa aacggcggc    1560 tgtatgcaca tgaagtgccc tcagcctcag tgcagactgg aatggtgctg gaactgcggc    1620
tgcgagtgga atagagtctg catgggcgat cactggttcg acgtt    1665
```

<210> SEQ ID NO 87
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87

```
atgtacggca gaaagaaaag acgccagaga cggcggggcg gcgagcctct gttcgccgaa      60
agaaagatga ttgtgtttgt cagatttaat tcttcacacg gatttcccgt cgaagtggat     120
tcagacacca gtattttca gcttaaggag gtcgtagcca agcggcaggg cgtgcccgcc     180
gaccaattga gagtgatctt tgctggaaaa gaattgagga atgattggac tgtccagaac     240
tgcgatttgg atcagcagtc tatcgtgcat atagttcagc gaccatggcg caagggacag     300
gagatgaatg caaccggagg cgacgaccca cggaatgcag ccggagggtg tgagagagag     360
ccccagagtt tgactcgggt cgatctgagc tctagcgtac tcccagggga ttcagtggga     420
ctcgcagtta tcctgcatac tgactccaga aaggactcac cgcccgcgg gagtccggcc     480 ggaagatcaa tttataatag cttttacgtt tattgtaagg gaccctgtca gagagtacag     540
cccggcaagt tgagggtgca atgtagtacc tgccgccagg ccacgctgac actcacacag     600
ggaccatcct gttgggacga cgtgcttatc cccaacagga tgtccggtga gtgtcaatcc     660
cctcactgcc ctgggacaag cgccgaattc ttcttcaaat gtggtgccca ccccacatcc     720
gacaaggaga cttccgtcgc cctgcacctg atcgcaacta acagccggaa tatcacgtgc     780
atcacctgca cggatgtgcg gtcccctgtg ctggtctttc agtgtaattc tcggcacgtg     840
atctgccttg actgcttcca cctgtactgc gttacgacg tgaacgacag gcagttcgtg     900
catgaccctc agcttgggta ctctcttcca tgtgttgccg ggtgtcctaa ctcattgatc     960
aaggagctcc accacttcag gatttggggg gaggagcaat ataaccgata ccagcagtac    1020
ggcgccgagg agtgtgtgct gcagatggga ggagtacttt gtccacgccc gggatgtgga    1080
gcaggcctgc tcccagaacc agatcaacgc aaggtgacgt gtgagggagg aaatgggctc    1140
ggctgcgggt tcgcctttg cagggagtgt aaggaggcct atcatgaagg tgaatgctcc    1200
gctgtgttcg aggcctctgg tactaccact caggcctata ggtcgacga gagagctgct    1260 gagcaagccc gatgggaggc tgcaagcaaa gaaaccatca agaaaactac gaagccatgc    1320
cctcgctgcc atgtgcccgt cgagaagaac ggtggctgca tgcacatgaa gtgtccacag    1380
ccccagtgcc ggttgaatg gtgttggaat tgcggatgcg aatggaaccg cgtctgcatg    1440
ggcgatcact ggttcgacgt t    1461
```

<210> SEQ ID NO 88
<211> LENGTH: 1467
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

```
atgtacggaa gaaaaaagcg gagacagaga agaagaggcg ggatgatcgt gttcgtgcgg      60
ttcaacagca gccacggctt tccagtcgag gtggactctg acacctccat cttccagctg     120
aaggaggtgg tggccaagcg gcagggcgtg cctgccgatc agctgagggt gatctttgcc     180
gggaaggagc tgcggaatga ctggaccgta cagaactgcg acctggacca gcaatctatc     240
gtgcacatcg tgcagcgacc ttggcggaag ggccaggaga tgaacgctac aggcggcgac     300
gaccctagaa atgccgccgg cggatgtgaa cgggaacctc aatctctgac acgggtggat     360
ctgagctcta gcgtgctccc cggagactct gtgggcctgg ccgtgatcct gcacaccgac     420
agcaggaagg acagcccccc cgccggaagt cctgccggca gatccatcta caactctttc     480
tacgtgtact gcaaaggccc ttgccagcgc gtgcagcctg gcaagctgag agtgcaatgt     540
agcacctgta gacaggccac actgacactg acccagggac ctagctgctg ggatgatgtg     600
ctgattccta acagaatgag cggcgagtgc cagagcctc actgcccgg cacaagcgcc      660 gaattcttct tcaagtgcgg cgcccaccct accagcgaca aggagacaag cgtggccctg     720
catctaatcg ccactaacag cagaaacatc acctgtatca cctgcaccga cgtcagaagc     780
ccagtgctcg tgtttcagtg caacagccgg cacgtgatct gcctggattg cttccacctg     840
tactgtgtca ccagactgaa cgatagacag ttcgtgcatg atccacagct gggctacagc     900
ctgccctgcg ttgccggctg tcctaactcc ctgatcaagg aactgcacca cttccggatc     960
ctgggcgagg aacagtacaa ccgctaccag cagtacggcg ccgaggaatg cgtgctgcag    1020
atgggaggag tgctgtgccc cagacctgga tgcggtgctg gactgctgcc tgagcccgac    1080
caaagaaagg tgacctgcga gggcggcaac ggcctgggct gtggcttcgc cttctgcaga    1140
gagtgcaagg aagcctatca cgagggcgaa tgcagcgccg tgtttgaggc ttctggcacc    1200
accacccagg cttatagagt cgacgagcgg gccgctgagc aggccagatg ggaggctgcc    1260
agcaaggaaa ccatcaagaa aacaacaaag ccctgcccta gatgtcacgt gccagttgag    1320
aagaacggcg gctgcatgca catgaaatgt cctcagcctc agtgcagact ggaatggtgc    1380
tggaattgcg gctgtgaatg gaatcgggtg tgcatgggcg accactggtt cgatgtgctg    1440
gccctgaaac tggcaggcct ggacctg                                         1467
```